(12) United States Patent
Andersen et al.

(10) Patent No.: US 7,432,099 B2
(45) Date of Patent: Oct. 7, 2008

(54) AMYLASE VARIANTS

(75) Inventors: Carsten Andersen, Værløse (DK);
Torben Vedel Borchert, Birkerød (DK);
Bjarne Rønfeldt Nielsen, Virum (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/925,576

(22) Filed: Aug. 9, 2001

(65) Prior Publication Data

US 2003/0129718 A1   Jul. 10, 2003

Related U.S. Application Data

(63) Continuation of application No. PCT/DK01/00144, filed on Mar. 4, 2001.

(60) Provisional application No. 60/271,382, filed on Feb. 26, 2001, provisional application No. 60/189,857, filed on Mar. 15, 2000.

(30) Foreign Application Priority Data

Mar. 8, 2000 (DK) .............................. 2000 00376
Feb. 23, 2001 (DK) .............................. 2001 00303

(51) Int. Cl.
*C12N 9/26* (2006.01)
*C12N 9/28* (2006.01)
*C07H 21/04* (2006.01)

(52) U.S. Cl. .................... 435/201; 435/202; 536/23.2
(58) Field of Classification Search .............. 435/4, 435/6, 69.1, 183, 200, 201, 252.3, 320.1; 536/23.2; 530/350
See application file for complete search history.

(56) References Cited

U.S. PATENT DOCUMENTS

| | | | | |
|---|---|---|---|---|
| 5,824,531 A | * | 10/1998 | Outtrup et al. | 435/202 |
| 5,856,164 A | * | 1/1999 | Outtrup et al. | 435/202 |
| 6,093,562 A | * | 7/2000 | Bisgård-Frantzen et al. | 435/202 |
| 6,187,576 B1 | * | 2/2001 | Svendsen et al. | 435/202 |
| 6,197,565 B1 | * | 3/2001 | Svendsen et al. | 435/202 |
| 6,204,232 B1 | * | 3/2001 | Borchert et al. | 510/226 |
| 6,287,826 B1 | * | 9/2001 | Norman et al. | 435/99 |
| 6,297,038 B1 | * | 10/2001 | Bisgård-Frantzen et al. | 435/202 |
| 6,361,989 B1 | * | 3/2002 | Svendsen et al. | 435/202 |
| 6,486,113 B1 | * | 11/2002 | Hatada et al. | 510/392 |
| 6,528,298 B1 | * | 3/2003 | Svendsen et al. | 435/202 |
| 6,673,589 B2 | * | 1/2004 | Borchert et al. | 435/202 |
| 6,867,031 B2 | * | 3/2005 | Bisgard-Frantzen et al. | 435/202 |
| 6,887,986 B1 | * | 5/2005 | Svendsen et al. | 536/23.2 |

FOREIGN PATENT DOCUMENTS

| | | |
|---|---|---|
| WO | WO 96/23874 | 8/1996 |
| WO | WO 97/41213 | 11/1997 |
| WO | WO 99/19467 | 4/1999 |

OTHER PUBLICATIONS

Igarashi et al. ( Database SPTREMBL, Accession No. O82839, Nov. 1998).*

* cited by examiner

*Primary Examiner*—Elizabeth Slobodyansky
(74) *Attorney, Agent, or Firm*—Michael N. Krenicky

(57) ABSTRACT

The present invention relates to variants (mutants) of polypeptides, in particular Termamyl-like alpha-amylases, which variant has alpha-amylase activity and exhibits an alteration in at least one of the following properties relative to said parent alpha-amylase: substrate specificity, substrate binding, substrate cleavage pattern, thermal stability, pH/activity profile, pH/stability profile, stability towards oxidation, $Ca^{2+}$ dependency, specific activity, and solubility, in particular under production conditions.

7 Claims, 5 Drawing Sheets

```
       1                                                         50
1    HHNGTNGTMM  QYFEWHLPND  GNHWNRLRDD  ASNLRNRGIT  AIWIPPAWKG
2    HHNGTNGTMM  QYFEWYLPND  GNHWNRLRDD  AANLKSKGIT  AVWIPPAWKG
3    ....VNGTLM  QYFEWYTPND  GQHWKRLQND  AEHLSDIGIT  AVWIPPAYKG
4    ..ANLNGTLM  QYFEWYMPND  GQHWRRLQND  SAYLAEHGIT  AVWIPPAYKG
5    .AAPFNGTMM  QYFEWYLPDD  GTLWTKVANE  ANNLSSLGIT  ALWLPPAYKG 51                                                        100
1    TSQNDVGYGA  YDLYDLGEFN  QKGTVRTKYG  TRSQLESAIH  ALKNNGVQVY
2    TSQNDVGYGA  YDLYDLGEFN  QKGTVRTKYG  TRNQLQAAVT  SLKNNGIQVY
3    LSQSDNGYGP  YDLYDLGEFQ  QKGTVRTKYG  TKSELQDAIG  SLHSRNVQVY
4    TSQADVGYGA  YDLYDLGEFH  QKGTVRTKYG  TKGELQSAIK  SLHSRDINVY
5    TSRSDVGYGV  YDLYDLGEFN  QKGTVRTKYG  TKAQYLQAIQ  AAHAAGMQVY 101                                                       150
1    GDVVMNHKGG  ADATENVLAV  EVNPNNRNQE  ISGDYTIEAW  TKFDFPGRGN
2    GDVVMNHKGG  ADGTEIVNAV  EVNRSNRNQE  TSGEYAIEAW  TKFDFPGRGN
3    GDVVLNHKAG  ADATEDVTAV  EVNPANRNQE  TSEEYQIKAW  TDFRFPGRGN
4    GDVVINHKGG  ADATEDVTAV  EVDPADRNRV  ISGEHLIKAW  THFHFPGRGS
5    ADVVFDHKGG  ADGTEWVDAV  EVNPSDRNQE  ISGTYQIQAW  TKFDFPGRGN 151                                                       200
1    TYSDFKWRWY  HFDGVDWDQS  RQFQNRIYKF  RGDGKAWDWE  VDSENGNYDY
2    NHSSFKWRWY  HFDGTDWDQS  RQLQNKIYKF  RGTGKAWDWE  VDTENGNYDY
3    TYSDFKWHWY  HFDGADWDES  RKI.SRIFKF  RGEGKAWDWE  VSSENGNYDY
4    TYSDFKWHWY  HFDGTDWDES  RKL.NRIYKF  ..QGKAWDWE  VSNENGNYDY
5    TYSSFKWRWY  HFDGVDWDES  RKL.SRIYKF  RGIGKAWDWE  VDTENGNYDY
```

Fig. 1A

```
      201                                                            250
1    LMYADVDMDH  PEVVNELRRW  GEWYTNTLNL  DGFRIDAVKH  IKYSFTRDWL
2    LMYADVDMDH  PEVIHELRNW  GVWYTNTLNL  DGFRIDAVKH  IKYSFTRDWL
3    LMYADVDYDH  PDVVAETKKW  GIWYANELSL  DGFRIDAAKH  IKFSFLRDWV
4    LMYADIDYDH  PDVAAEIKRW  GTWYANELQL  DGFRLDAVKH  IKFSFLRDWV
5    LMYADLDMDH  PEVVTELKNW  GKWYVNTTNI  DGFRLDAVKH  IKFSFFPDWL 251                                                            300
1    THVRNATGKE  MFAVAEFWKN  DLGALENYLN  KTNWNHSVFD  VPLHYNLYNA
2    THVRNTTGKP  MFAVAEFWKN  DLGAIENYLN  KTSWNHSAFD  VPLHYNLYNA
3    QAVRQATGKE  MFTVAEYWQN  NAGKLENYLN  KTSFNQSVFD  VPLHFNLQAA
4    NHVREKTGKE  MFTVAEYWQN  DLGALENYLN  KTNFNHSVFD  VPLHYQFHAA
5    SYVRSQTGKP  LFTVGEYWSY  DINKLHNYIT  KTDGTMSLFD  APLHNKFYTA 301                                                            350
1    SNSGGNYDMA  KLLNGTVVQK  HPMHAVTFVD  NHDSQPGESL  ESFVQEWFKP
2    SNSGGYYDMR  NILNGSVVQK  HPTHAVTFVD  NHDSQPGEAL  ESFVQQWFKP
3    SSQGGGYDMR  RLLDGTVVSR  HPEKAVTFVE  NHDTQPGQSL  ESTVQTWFKP
4    STQGGGYDMR  KLLNGTVVSK  HPLKSVTFVD  NHDTQPGQSL  ESTVQTWFKP
5    SKSGGAFDMR  TLMTNTLMKD  QPTLAVTFVD  NHDTEPGQAL  QSWVDPWFKP 351                                                            400
1    LAYALILTRE  QGYPSVFYGD  YYGIPTHS..  .VPAMKAKID  PILEARQNFA
2    LAYALVLTRE  QGYPSVFYGD  YYGIPTHG..  .VPAMKSKID  PLLQARQTFA
3    LAYAFILTRE  SGYPQVFYGD  MYGTKGTSPK  EIPSLKDNIE  PILKARKEYA
4    LAYAFILTRE  SGYPQVFYGD  MYGTKGDSQR  EIPALKHKIE  PILKARKQYA
5    LAYAFILTRQ  EGYPCVFYGD  YYGIPQYN..  .IPSLKSKID  PLLIARRDYA 401                                                            450
1    YGTQHDYFDH  HNIIGWTREG  NTTHPNSGLA  TIMSDGPGGE  KWMYVGQNKA
2    YGTQHDYFDH  HDIIGWTREG  NSSHPNSGLA  TIMSDGPGGN  KWMYVGKNKA
3    YGPQHDYIDH  PDVIGWTREG  DSSAAKSGLA  ALITDGPGGS  KRMYAGLKNA
4    YGAQHDYFDH  HDIVGWTREG  DSSVANSGLA  ALITDGPGGA  KRMYVGRQNA
5    YGTQHDYLDH  SDIIGWTREG  GTEKPGSGLA  ALITDGPGGS  KWMYVGKQHA
```

Fig. 1B

```
      451                                                         500
1    GQVWHDITGN KPGTVTINAD GWANFSVNGG SVSIWVKR.. ..........
2    GQVWRDITGN RTGTVTINAD GWGNFSVNGG SVSVWVKQ.. ..........
3    GETWYDITGN RSDTVKIGSD GWGEFHVNDG SVSIYVQ... ..........
4    GETWHDITGN RSEPVVINSE GWGEFHVNGG SVSIYVQR.. ..........
5    GKVFYDLTGN RSDTVTINSD GWGEFKVNGG SVSVWVPRKT TVSTIARPIT 501                519
1    .......... .........
2    .......... .........
3    .......... .........
4    .......... .........
5    TRPWTGEFVR WTEPRLVAW
```

Fig. 1C

SEQUENCE LISTING

<160> NUMBER OF SEQ ID NOS: 20

<210> SEQ ID NO 1
<211> LENGTH: 1455
<212> TYPE: DNA
<213> ORGANISM: Bacillus sp.
<220> FEATURE:
<221> NAME/KEY: CDS
<222> LOCATION: (1)..(1455)
<223> OTHER INFORMATION: SP690

<400> SEQUENCE: 1

```
cat cat aat gga aca aat ggt act atg atg caa tat ttc gaa tgg tat        48
His His Asn Gly Thr Asn Gly Thr Met Met Gln Tyr Phe Glu Trp Tyr
1               5                   10                  15 ttg cca aat gac ggg aat cat tgg aac agg ttg agg gat gac gca gct        96
Leu Pro Asn Asp Gly Asn His Trp Asn Arg Leu Arg Asp Asp Ala Ala
                20                  25                  30 aac tta aag agt aaa ggg ata aca gct gta tgg atc cca cct gca tgg       144
Asn Leu Lys Ser Lys Gly Ile Thr Ala Val Trp Ile Pro Pro Ala Trp
            35                  40                  45 aag ggg act tcc cag aat gat gta ggt tat gga gcc tat gat tta tat       192
Lys Gly Thr Ser Gln Asn Asp Val Gly Tyr Gly Ala Tyr Asp Leu Tyr
        50                  55                  60 gat ctt gga gag ttt aac cag aag ggg acg gtt cgt aca aaa tat gga       240
Asp Leu Gly Glu Phe Asn Gln Lys Gly Thr Val Arg Thr Lys Tyr Gly
65                  70                  75                  80 aca cgc aac cag cta cag gct gcg gtg acc tct tta aaa aat aac ggc       288
Thr Arg Asn Gln Leu Gln Ala Ala Val Thr Ser Leu Lys Asn Asn Gly
                85                  90                  95 att cag gta tat ggt gat gtc gtc atg aat cat aaa ggt gga gca gat       336
Ile Gln Val Tyr Gly Asp Val Val Met Asn His Lys Gly Gly Ala Asp
            100                 105                 110 ggt acg gaa att gta aat gcg gta gaa gtg aat cgg agc aac cga aac       384
Gly Thr Glu Ile Val Asn Ala Val Glu Val Asn Arg Ser Asn Arg Asn
        115                 120                 125 cag gaa acc tca gga gag tat gca ata gaa gcg tgg aca aag ttt gat       432
Gln Glu Thr Ser Gly Glu Tyr Ala Ile Glu Ala Trp Thr Lys Phe Asp
    130                 135                 140 ttt cct gga aga gga aat aac cat tcc agc ttt aag tgg cgc tgg tat       480
Phe Pro Gly Arg Gly Asn Asn His Ser Ser Phe Lys Trp Arg Trp Tyr
145                 150                 155                 160 cat ttt gat ggg aca gat tgg gat cag tca cgc cag ctt caa aac aaa       528
His Phe Asp Gly Thr Asp Trp Asp Gln Ser Arg Gln Leu Gln Asn Lys
                165                 170                 175 ata tat aaa ttc agg gga aca ggc aag gcc tgg gac tgg gaa gtc gat       576
Ile Tyr Lys Phe Arg Gly Thr Gly Lys Ala Trp Asp Trp Glu Val Asp
            180                 185                 190 aca gag aat ggc aac tat gac tat ctt atg tat gca gac gtg gat atg       624
Thr Glu Asn Gly Asn Tyr Asp Tyr Leu Met Tyr Ala Asp Val Asp Met
        195                 200                 205 gat cac cca gaa gta ata cat gaa ctt aga aac tgg gga gtg tgg tat       672
Asp His Pro Glu Val Ile His Glu Leu Arg Asn Trp Gly Val Trp Tyr
    210                 215                 220 acg aat aca ctg aac ctt gat gga ttt aga ata gat gca gtg aaa cat       720
Thr Asn Thr Leu Asn Leu Asp Gly Phe Arg Ile Asp Ala Val Lys His
225                 230                 235                 240 ata aaa tat agc ttt acg aga gat tgg ctt aca cat gtg cgt aac acc       768
Ile Lys Tyr Ser Phe Thr Arg Asp Trp Leu Thr His Val Arg Asn Thr
                245                 250                 255
```

```
aca ggt aaa cca atg ttt gca gtg gct gag ttt tgg aaa aat gac ctt      816
Thr Gly Lys Pro Met Phe Ala Val Ala Glu Phe Trp Lys Asn Asp Leu
        260                 265                 270 ggt gca att gaa aac tat ttg aat aaa aca agt tgg aat cac tcg gtg      864
Gly Ala Ile Glu Asn Tyr Leu Asn Lys Thr Ser Trp Asn His Ser Val
275                 280                 285 ttt gat gtt cct ctc cac tat aat ttg tac aat gca tct aat agc ggt      912
Phe Asp Val Pro Leu His Tyr Asn Leu Tyr Asn Ala Ser Asn Ser Gly
        290                 295                 300 ggt tat tat gat atg aga aat att tta aat ggt tct gtg gtg caa aaa      960
Gly Tyr Tyr Asp Met Arg Asn Ile Leu Asn Gly Ser Val Val Gln Lys
305                 310                 315                 320 cat cca aca cat gcc gtt act ttt gtt gat aac cat gat tct cag ccc     1008
His Pro Thr His Ala Val Thr Phe Val Asp Asn His Asp Ser Gln Pro
                325                 330                 335 ggg gaa gca ttg gaa tcc ttt gtt caa caa tgg ttt aaa cca ctt gca     1056
Gly Glu Ala Leu Glu Ser Phe Val Gln Gln Trp Phe Lys Pro Leu Ala
            340                 345                 350 tat gca ttg gtt ctg aca agg gaa caa ggt tat cct tcc gta ttt tat     1104
Tyr Ala Leu Val Leu Thr Arg Glu Gln Gly Tyr Pro Ser Val Phe Tyr
        355                 360                 365 ggg gat tac tac ggt atc cca acc cat ggt gtt ccg gct atg aaa tct     1152
Gly Asp Tyr Tyr Gly Ile Pro Thr His Gly Val Pro Ala Met Lys Ser
370                 375                 380 aaa ata gac cct ctt ctg cag gca cgt caa act ttt gcc tat ggt acg     1200
Lys Ile Asp Pro Leu Leu Gln Ala Arg Gln Thr Phe Ala Tyr Gly Thr
385                 390                 395                 400 cag cat gat tac ttt gat cat cat gat att atc ggt tgg aca aga gag     1248
Gln His Asp Tyr Phe Asp His His Asp Ile Ile Gly Trp Thr Arg Glu
                405                 410                 415 gga aat agc tcc cat cca aat tca ggc ctt gcc acc att atg tca gat     1296
Gly Asn Ser Ser His Pro Asn Ser Gly Leu Ala Thr Ile Met Ser Asp
            420                 425                 430 ggt cca ggt ggt aac aaa tgg atg tat gtg ggg aaa aat aaa gcg gga     1344
Gly Pro Gly Gly Asn Lys Trp Met Tyr Val Gly Lys Asn Lys Ala Gly
        435                 440                 445 caa gtt tgg aga gat att acc gga aat agg aca ggc acc gtc aca att     1392
Gln Val Trp Arg Asp Ile Thr Gly Asn Arg Thr Gly Thr Val Thr Ile
450                 455                 460 aat gca gac gga tgg ggt aat ttc tct gtt aat gga ggg tcc gtt tcg     1440
Asn Ala Asp Gly Trp Gly Asn Phe Ser Val Asn Gly Gly Ser Val Ser
465                 470                 475                 480 gtt tgg gtg aag caa                                                  1455
Val Trp Val Lys Gln
            485

<210> SEQ ID NO 2
<211> LENGTH: 485
<212> TYPE: PRT
<213> ORGANISM: Bacillus sp.

<400> SEQUENCE: 2

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
```

-continued

```
                  50                   55                   60
Asp Leu Gly Glu Phe Asn Gln Lys Gly Thr Val Arg Thr Lys Tyr Gly
 65                  70                   75                   80

Thr Arg Asn Gln Leu Gln Ala Ala Val Thr Ser Leu Lys Asn Asn Gly
                 85                   90                   95

Ile Gln Val Tyr Gly Asp Val Val Met Asn His Lys Gly Gly Ala Asp
            100                  105                  110

Gly Thr Glu Ile Val Asn Ala Val Glu Val Asn Arg Ser Asn Arg Asn
        115                  120                  125

Gln Glu Thr Ser Gly Glu Tyr Ala Ile Glu Ala Trp Thr Lys Phe Asp
130                  135                  140

Phe Pro Gly Arg Gly Asn Asn His Ser Ser Phe Lys Trp Arg Trp Tyr
145                  150                  155                  160

His Phe Asp Gly Thr Asp Trp Asp Gln Ser Arg Gln Leu Gln Asn Lys
                165                  170                  175

Ile Tyr Lys Phe Arg Gly Thr Gly Lys Ala Trp Asp Trp Glu Val Asp
            180                  185                  190

Thr Glu Asn Gly Asn Tyr Asp Tyr Leu Met Tyr Ala Asp Val Asp Met
        195                  200                  205

Asp His Pro Glu Val Ile His Glu Leu Arg Asn Trp Gly Val Trp Tyr
210                  215                  220

Thr Asn Thr Leu Asn Leu Asp Gly Phe Arg Ile Asp Ala Val Lys His
225                  230                  235                  240

Ile Lys Tyr Ser Phe Thr Arg Asp Trp Leu Thr His Val Arg Asn Thr
                245                  250                  255

Thr Gly Lys Pro Met Phe Ala Val Ala Glu Phe Trp Lys Asn Asp Leu
            260                  265                  270

Gly Ala Ile Glu Asn Tyr Leu Asn Lys Thr Ser Trp Asn His Ser Val
        275                  280                  285

Phe Asp Val Pro Leu His Tyr Asn Leu Tyr Asn Ala Ser Asn Ser Gly
290                  295                  300

Gly Tyr Tyr Asp Met Arg Asn Ile Leu Asn Gly Ser Val Val Gln Lys
305                  310                  315                  320

His Pro Thr His Ala Val Thr Phe Val Asp Asn His Asp Ser Gln Pro
                325                  330                  335

Gly Glu Ala Leu Glu Ser Phe Val Gln Gln Trp Phe Lys Pro Leu Ala
            340                  345                  350

Tyr Ala Leu Val Leu Thr Arg Glu Gln Gly Tyr Pro Ser Val Phe Tyr
        355                  360                  365

Gly Asp Tyr Tyr Gly Ile Pro Thr His Gly Val Pro Ala Met Lys Ser
370                  375                  380

Lys Ile Asp Pro Leu Leu Gln Ala Arg Gln Thr Phe Ala Tyr Gly Thr
385                  390                  395                  400

Gln His Asp Tyr Phe Asp His His Asp Ile Ile Gly Trp Thr Arg Glu
                405                  410                  415

Gly Asn Ser Ser His Pro Asn Ser Gly Leu Ala Thr Ile Met Ser Asp
            420                  425                  430

Gly Pro Gly Gly Asn Lys Trp Met Tyr Val Gly Lys Asn Lys Ala Gly
        435                  440                  445

Gln Val Trp Arg Asp Ile Thr Gly Asn Arg Thr Gly Thr Val Thr Ile
        450                  455                  460

Asn Ala Asp Gly Trp Gly Asn Phe Ser Val Asn Gly Gly Ser Val Ser
465                  470                  475                  480
```

```
Val Trp Val Lys Gln
            485

<210> SEQ ID NO 3
<211> LENGTH: 1455
<212> TYPE: DNA
<213> ORGANISM: Bacillus sp.
<220> FEATURE:
<221> NAME/KEY: CDS
<222> LOCATION: (1)..(1455)
<223> OTHER INFORMATION: SP722

<400> SEQUENCE: 3 cat cat aat ggg aca aat ggg acg atg atg caa tac ttt gaa tgg cac      48
His His Asn Gly Thr Asn Gly Thr Met Met Gln Tyr Phe Glu Trp His
1               5                  10                  15 ttg cct aat gat ggg aat cac tgg aat aga tta aga gat gat gct agt      96
Leu Pro Asn Asp Gly Asn His Trp Asn Arg Leu Arg Asp Asp Ala Ser
                20                  25                  30 aat cta aga aat aga ggt ata acc gct att tgg att ccg cct gcc tgg     144
Asn Leu Arg Asn Arg Gly Ile Thr Ala Ile Trp Ile Pro Pro Ala Trp
            35                  40                  45 aaa ggg act tcg caa aat gat gtg ggg tat gga gcc tat gat ctt tat     192
Lys Gly Thr Ser Gln Asn Asp Val Gly Tyr Gly Ala Tyr Asp Leu Tyr
        50                  55                  60 gat tta ggg gaa ttt aat caa aag ggg acg gtt cgt act aag tat ggg     240
Asp Leu Gly Glu Phe Asn Gln Lys Gly Thr Val Arg Thr Lys Tyr Gly
65                  70                  75                  80 aca cgt agt caa ttg gag tct gcc atc cat gct tta aag aat aat ggc     288
Thr Arg Ser Gln Leu Glu Ser Ala Ile His Ala Leu Lys Asn Asn Gly
                85                  90                  95 gtt caa gtt tat ggg gat gta gtg atg aac cat aaa gga gga gct gat     336
Val Gln Val Tyr Gly Asp Val Val Met Asn His Lys Gly Gly Ala Asp
                100                 105                 110 gct aca gaa aac gtt ctt gct gtc gag gtg aat cca aat aac cgg aat     384
Ala Thr Glu Asn Val Leu Ala Val Glu Val Asn Pro Asn Asn Arg Asn
            115                 120                 125 caa gaa ata tct ggg gac tac aca att gag gct tgg act aag ttt gat     432
Gln Glu Ile Ser Gly Asp Tyr Thr Ile Glu Ala Trp Thr Lys Phe Asp
        130                 135                 140 ttt cca ggg agg ggt aat aca tac tca gac ttt aaa tgg cgt tgg tat     480
Phe Pro Gly Arg Gly Asn Thr Tyr Ser Asp Phe Lys Trp Arg Trp Tyr
145                 150                 155                 160 cat ttc gat ggt gta gat tgg gat caa tca cga caa ttc caa aat cgt     528
His Phe Asp Gly Val Asp Trp Asp Gln Ser Arg Gln Phe Gln Asn Arg
                165                 170                 175 atc tac aaa ttc cga ggt gat ggt aag gca tgg gat tgg gaa gta gat     576
Ile Tyr Lys Phe Arg Gly Asp Gly Lys Ala Trp Asp Trp Glu Val Asp
                180                 185                 190 tcg gaa aat gga aat tat gat tat tta atg tat gca gat gta gat atg     624
Ser Glu Asn Gly Asn Tyr Asp Tyr Leu Met Tyr Ala Asp Val Asp Met
            195                 200                 205 gat cat ccg gag gta gta aat gag ctt aga aga tgg gga gaa tgg tat     672
Asp His Pro Glu Val Val Asn Glu Leu Arg Arg Trp Gly Glu Trp Tyr
        210                 215                 220 aca aat aca tta aat ctt gat gga ttt agg atc gat gcg gtg aag cat     720
Thr Asn Thr Leu Asn Leu Asp Gly Phe Arg Ile Asp Ala Val Lys His
225                 230                 235                 240 att aaa tat agc ttt aca cgt gat tgg ttg acc cat gta aga aac gca     768
Ile Lys Tyr Ser Phe Thr Arg Asp Trp Leu Thr His Val Arg Asn Ala
                245                 250                 255
```

```
acg gga aaa gaa atg ttt gct gtt gct gaa ttt tgg aaa aat gat tta    816
Thr Gly Lys Glu Met Phe Ala Val Ala Glu Phe Trp Lys Asn Asp Leu
        260                 265                 270 ggt gcc ttg gag aac tat tta aat aaa aca aac tgg aat cat tct gtc    864
Gly Ala Leu Glu Asn Tyr Leu Asn Lys Thr Asn Trp Asn His Ser Val
    275                 280                 285 ttt gat gtc ccc ctt cat tat aat ctt tat aac gcg tca aat agt gga    912
Phe Asp Val Pro Leu His Tyr Asn Leu Tyr Asn Ala Ser Asn Ser Gly
290                 295                 300 ggc aac tat gac atg gca aaa ctt ctt aat gga acg gtt gtt caa aag    960
Gly Asn Tyr Asp Met Ala Lys Leu Leu Asn Gly Thr Val Val Gln Lys
305                 310                 315                 320 cat cca atg cat gcc gta act ttt gtg gat aat cac gat tct caa cct   1008
His Pro Met His Ala Val Thr Phe Val Asp Asn His Asp Ser Gln Pro
                325                 330                 335 ggg gaa tca tta gaa tca ttt gta caa gaa tgg ttt aag cca ctt gct   1056
Gly Glu Ser Leu Glu Ser Phe Val Gln Glu Trp Phe Lys Pro Leu Ala
            340                 345                 350 tat gcg ctt att tta aca aga gaa caa ggc tat ccc tct gtc ttc tat   1104
Tyr Ala Leu Ile Leu Thr Arg Glu Gln Gly Tyr Pro Ser Val Phe Tyr
        355                 360                 365 ggt gac tac tat gga att cca aca cat agt gtc cca gca atg aaa gcc   1152
Gly Asp Tyr Tyr Gly Ile Pro Thr His Ser Val Pro Ala Met Lys Ala
    370                 375                 380 aag att gat cca atc tta gag gcg cgt caa aat ttt gca tat gga aca   1200
Lys Ile Asp Pro Ile Leu Glu Ala Arg Gln Asn Phe Ala Tyr Gly Thr
385                 390                 395                 400 caa cat gat tat ttt gac cat cat aat ata atc gga tgg aca cgt gaa   1248
Gln His Asp Tyr Phe Asp His His Asn Ile Ile Gly Trp Thr Arg Glu
                405                 410                 415 gga aat acc acg cat ccc aat tca gga ctt gcg act atc atg tcg gat   1296
Gly Asn Thr Thr His Pro Asn Ser Gly Leu Ala Thr Ile Met Ser Asp
            420                 425                 430 ggg cca ggg gga gag aaa tgg atg tac gta ggg caa aat aaa gca ggt   1344
Gly Pro Gly Gly Glu Lys Trp Met Tyr Val Gly Gln Asn Lys Ala Gly
        435                 440                 445 caa gtt tgg cat gac ata act gga aat aaa cca gga aca gtt acg atc   1392
Gln Val Trp His Asp Ile Thr Gly Asn Lys Pro Gly Thr Val Thr Ile
    450                 455                 460 aat gca gat gga tgg gct aat ttt tca gta aat gga gga tct gtt tcc   1440
Asn Ala Asp Gly Trp Ala Asn Phe Ser Val Asn Gly Gly Ser Val Ser
465                 470                 475                 480 att tgg gtg aaa cga                                                1455
Ile Trp Val Lys Arg
                485

<210> SEQ ID NO 4
<211> LENGTH: 485
<212> TYPE: PRT
<213> ORGANISM: Bacillus sp.

<400> SEQUENCE: 4

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
                20                  25                  30

Asn Leu Arg Asn Arg Gly Ile Thr Ala Ile Trp Ile Pro Pro Ala Trp
            35                  40                  45

Lys Gly Thr Ser Gln Asn Asp Val Gly Tyr Gly Ala Tyr Asp Leu Tyr
```

-continued

```
                 50                  55                  60
Asp Leu Gly Glu Phe Asn Gln Lys Gly Thr Val Arg Thr Lys Tyr Gly
 65                  70                  75                  80

Thr Arg Ser Gln Leu Glu Ser Ala Ile His Ala Leu Lys Asn Asn Gly
                 85                  90                  95

Val Gln Val Tyr Gly Asp Val Val Met Asn His Lys Gly Gly Ala Asp
                100                 105                 110

Ala Thr Glu Asn Val Leu Ala Val Glu Val Asn Pro Asn Asn Arg Asn
            115                 120                 125

Gln Glu Ile Ser Gly Asp Tyr Thr Ile Glu Ala Trp Thr Lys Phe Asp
130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
            195                 200                 205

Asp His Pro Glu Val Val Asn Glu Leu Arg Arg Trp Gly Glu Trp Tyr
210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
            245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
            275                 280                 285

Phe Asp Val Pro Leu His Tyr Asn Leu Tyr Asn Ala Ser Asn Ser Gly
290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
            355                 360                 365

Gly Asp Tyr Tyr Gly Ile Pro Thr His Ser Val Pro Ala Met Lys Ala
370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
            405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
            435                 440                 445

Gln Val Trp His Asp Ile Thr Gly Asn Lys Pro Gly Thr Val Thr Ile
            450                 455                 460

Asn Ala Asp Gly Trp Ala Asn Phe Ser Val Asn Gly Gly Ser Val Ser
465                 470                 475                 480
```

```
Ile Trp Val Lys Arg
            485

<210> SEQ ID NO 5
<211> LENGTH: 1548
<212> TYPE: DNA
<213> ORGANISM: Bacillus stearothermophilus
<220> FEATURE:
<221> NAME/KEY: CDS
<222> LOCATION: (1)..(1548)
<223> OTHER INFORMATION: BSG

<400> SEQUENCE: 5 gcc gca ccg ttt aac ggc acc atg atg cag tat ttt gaa tgg tac ttg      48
Ala Ala Pro Phe Asn Gly Thr Met Met Gln Tyr Phe Glu Trp Tyr Leu
1               5                   10                  15 ccg gat gat ggc acg tta tgg acc aaa gtg gcc aat gaa gcc aac aac      96
Pro Asp Asp Gly Thr Leu Trp Thr Lys Val Ala Asn Glu Ala Asn Asn
            20                  25                  30 tta tcc agc ctt ggc atc acc gct ctt tgg ctg ccg ccc gct tac aaa     144
Leu Ser Ser Leu Gly Ile Thr Ala Leu Trp Leu Pro Pro Ala Tyr Lys
        35                  40                  45 gga aca agc cgc agc gac gta ggg tac gga gta tac gac ttg tat gac     192
Gly Thr Ser Arg Ser Asp Val Gly Tyr Gly Val Tyr Asp Leu Tyr Asp
    50                  55                  60 ctc ggc gaa ttc aat caa aaa ggg acc gtc cgc aca aaa tac gga aca     240
Leu Gly Glu Phe Asn Gln Lys Gly Thr Val Arg Thr Lys Tyr Gly Thr
65                  70                  75                  80 aaa gct caa tat ctt caa gcc att caa gcc gcc cac gcc gct gga atg     288
Lys Ala Gln Tyr Leu Gln Ala Ile Gln Ala Ala His Ala Ala Gly Met
                85                  90                  95 caa gtg tac gcc gat gtc gtg ttc gac cat aaa ggc ggc gct gac ggc     336
Gln Val Tyr Ala Asp Val Val Phe Asp His Lys Gly Gly Ala Asp Gly
            100                 105                 110 acg gaa tgg gtg gac gcc gtc gaa gtc aat ccg tcc gac cgc aac caa     384
Thr Glu Trp Val Asp Ala Val Glu Val Asn Pro Ser Asp Arg Asn Gln
        115                 120                 125 gaa atc tcg ggc acc tat caa atc caa gca tgg acg aaa ttt gat ttt     432
Glu Ile Ser Gly Thr Tyr Gln Ile Gln Ala Trp Thr Lys Phe Asp Phe
    130                 135                 140 ccc ggg cgg ggc aac acc tac tcc agc ttt aag tgg cgc tgg tac cat     480
Pro Gly Arg Gly Asn Thr Tyr Ser Ser Phe Lys Trp Arg Trp Tyr His
145                 150                 155                 160 ttt gac ggc gtt gat tgg gac gaa agc cga aaa ttg agc cgc att tac     528
Phe Asp Gly Val Asp Trp Asp Glu Ser Arg Lys Leu Ser Arg Ile Tyr
                165                 170                 175 aaa ttc cgc ggc atc ggc aaa gcg tgg gat tgg gaa gta gac acg gaa     576
Lys Phe Arg Gly Ile Gly Lys Ala Trp Asp Trp Glu Val Asp Thr Glu
            180                 185                 190 aac gga aac tat gac tac tta atg tat gcc gac ctt gat atg gat cat     624
Asn Gly Asn Tyr Asp Tyr Leu Met Tyr Ala Asp Leu Asp Met Asp His
        195                 200                 205 ccc gaa gtc gtg acc gag ctg aaa aac tgg ggg aaa tgg tat gtc aac     672
Pro Glu Val Val Thr Glu Leu Lys Asn Trp Gly Lys Trp Tyr Val Asn
    210                 215                 220 aca acg aac att gat ggg ttc cgg ctt gat gcc gtc aag cat att aag     720
Thr Thr Asn Ile Asp Gly Phe Arg Leu Asp Ala Val Lys His Ile Lys
225                 230                 235                 240 ttc agt ttt ttt cct gat tgg ttg tcg tat gtg cgt tct cag act ggc     768
Phe Ser Phe Phe Pro Asp Trp Leu Ser Tyr Val Arg Ser Gln Thr Gly
                245                 250                 255
```

| | | | | | | | | | | | | | | | |
|---|---|---|---|---|---|---|---|---|---|---|---|---|---|---|---|
| aag | ccg | cta | ttt | acc | gtc | ggg | gaa | tat | tgg | agc | tat | gac | atc | aac | aag | 816 |
| Lys | Pro | Leu | Phe | Thr | Val | Gly | Glu | Tyr | Trp | Ser | Tyr | Asp | Ile | Asn | Lys | |
| | | | 260 | | | | | 265 | | | | | 270 | | | |

```
aag ccg cta ttt acc gtc ggg gaa tat tgg agc tat gac atc aac aag    816
Lys Pro Leu Phe Thr Val Gly Glu Tyr Trp Ser Tyr Asp Ile Asn Lys
            260                 265                 270 ttg cac aat tac att acg aaa aca gac gga acg atg tct ttg ttt gat    864
Leu His Asn Tyr Ile Thr Lys Thr Asp Gly Thr Met Ser Leu Phe Asp
            275                 280                 285 gcc ccg tta cac aac aaa ttt tat acc gct tcc aaa tca ggg ggc gca    912
Ala Pro Leu His Asn Lys Phe Tyr Thr Ala Ser Lys Ser Gly Gly Ala
            290                 295                 300 ttt gat atg cgc acg tta atg acc aat act ctc atg aaa gat caa ccg    960
Phe Asp Met Arg Thr Leu Met Thr Asn Thr Leu Met Lys Asp Gln Pro
305                 310                 315                 320 aca ttg gcc gtc acc ttc gtt gat aat cat gac acc gaa ccc ggc caa   1008
Thr Leu Ala Val Thr Phe Val Asp Asn His Asp Thr Glu Pro Gly Gln
            325                 330                 335 gcg ctg cag tca tgg gtc gac cca tgg ttc aaa ccg ttg gct tac gcc   1056
Ala Leu Gln Ser Trp Val Asp Pro Trp Phe Lys Pro Leu Ala Tyr Ala
            340                 345                 350 ttt att cta act cgg cag gaa gga tac ccg tgc gtc ttt tat ggt gac   1104
Phe Ile Leu Thr Arg Gln Glu Gly Tyr Pro Cys Val Phe Tyr Gly Asp
            355                 360                 365 tat tat ggc att cca caa tat aac att cct tcg ctg aaa agc aaa atc   1152
Tyr Tyr Gly Ile Pro Gln Tyr Asn Ile Pro Ser Leu Lys Ser Lys Ile
370                 375                 380 gat ccg ctc ctc atc gcg cgc agg gat tat gct tac gga acg caa cat   1200
Asp Pro Leu Leu Ile Ala Arg Arg Asp Tyr Ala Tyr Gly Thr Gln His
385                 390                 395                 400 gat tat ctt gat cac tcc gac atc atc ggg tgg aca agg gaa ggg ggc   1248
Asp Tyr Leu Asp His Ser Asp Ile Ile Gly Trp Thr Arg Glu Gly Gly
            405                 410                 415 act gaa aaa cca gga tcc gga ctg gcc gca ctg atc acc gat ggg ccg   1296
Thr Glu Lys Pro Gly Ser Gly Leu Ala Ala Leu Ile Thr Asp Gly Pro
            420                 425                 430 gga gga agc aaa tgg atg tac gtt ggc aaa caa cac gct gga aaa gtg   1344
Gly Gly Ser Lys Trp Met Tyr Val Gly Lys Gln His Ala Gly Lys Val
            435                 440                 445 ttc tat gac ctt acc ggc aac cgg agt gac acc gtc acc atc aac agt   1392
Phe Tyr Asp Leu Thr Gly Asn Arg Ser Asp Thr Val Thr Ile Asn Ser
450                 455                 460 gat gga tgg ggg gaa ttc aaa gtc aat ggc ggt tcg gtt tcg gtt tgg   1440
Asp Gly Trp Gly Glu Phe Lys Val Asn Gly Gly Ser Val Ser Val Trp
465                 470                 475                 480 gtt cct aga aaa acg acc gtt tct acc atc gct cgg ccg atc aca acc   1488
Val Pro Arg Lys Thr Thr Val Ser Thr Ile Ala Arg Pro Ile Thr Thr
            485                 490                 495 cga ccg tgg act ggt gaa ttc gtc cgt tgg acc gaa cca cgg ttg gtg   1536
Arg Pro Trp Thr Gly Glu Phe Val Arg Trp Thr Glu Pro Arg Leu Val
            500                 505                 510 gca tgg cct tga                                                   1548
Ala Trp Pro
        515
```

<210> SEQ ID NO 6
<211> LENGTH: 515
<212> TYPE: PRT
<213> ORGANISM: Bacillus stearothermophilus

<400> SEQUENCE: 6

```
Ala Ala Pro Phe Asn Gly Thr Met Met Gln Tyr Phe Glu Trp Tyr Leu
1               5                   10                  15
```

-continued

Pro Asp Asp Gly Thr Leu Trp Thr Lys Val Ala Asn Glu Ala Asn Asn
              20                  25                  30

Leu Ser Ser Leu Gly Ile Thr Ala Leu Trp Leu Pro Pro Ala Tyr Lys
             35                  40                  45

Gly Thr Ser Arg Ser Asp Val Gly Tyr Gly Val Tyr Asp Leu Tyr Asp
         50                  55                  60

Leu Gly Glu Phe Asn Gln Lys Gly Thr Val Arg Thr Lys Tyr Gly Thr
 65                  70                  75                  80

Lys Ala Gln Tyr Leu Gln Ala Ile Gln Ala Ala His Ala Ala Gly Met
                 85                  90                  95

Gln Val Tyr Ala Asp Val Val Phe Asp His Lys Gly Gly Ala Asp Gly
             100                 105                 110

Thr Glu Trp Val Asp Ala Val Glu Val Asn Pro Ser Asp Arg Asn Gln
         115                 120                 125

Glu Ile Ser Gly Thr Tyr Gln Ile Gln Ala Trp Thr Lys Phe Asp Phe
     130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asp Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Gly
                405                 410                 415

Thr Glu Lys Pro Gly Ser Gly Leu Ala Ala Leu Ile Thr Asp Gly Pro
            420                 425                 430

```
Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
        450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515

<210> SEQ ID NO 7
<211> LENGTH: 1920
<212> TYPE: DNA
<213> ORGANISM: Bacillus licheniformis
<220> FEATURE:
<221> NAME/KEY: CDS
<222> LOCATION: (421)..(1872)
<223> OTHER INFORMATION: Termamyl

<400> SEQUENCE: 7
```

| | |
|---|---:|
| cggaagattg gaagtacaaa aataagcaaa agattgtcaa tcatgtcatg agccatgcgg | 60 |
| gagacggaaa aatcgtctta atgcacgata tttatgcaac gttcgcagat gctgctgaag | 120 |
| agattattaa aaagctgaaa gcaaaaggct atcaattggt aactgtatct cagcttgaag | 180 |
| aagtgaagaa gcagagaggc tattgaataa atgagtagaa gcgccatatc ggcgcttttc | 240 |
| ttttggaaga aaatataggg aaaatggtac ttgttaaaaa ttcggaatat ttatacaaca | 300 |
| tcatatgttt cacattgaaa ggggaggaga atcatgaaac aacaaaaacg gctttacgcc | 360 |
| cgattgctga cgctgttatt tgcgctcatc ttcttgctgc ctcattctgc agcagcggcg | 420 |

```
gca aat ctt aat ggg acg ctg atg cag tat ttt gaa tgg tac atg ccc      468
Ala Asn Leu Asn Gly Thr Leu Met Gln Tyr Phe Glu Trp Tyr Met Pro
1               5                   10                  15 aat gac ggc caa cat tgg agg cgt ttg caa aac gac tcg gca tat ttg      516
Asn Asp Gly Gln His Trp Arg Arg Leu Gln Asn Asp Ser Ala Tyr Leu
            20                  25                  30 gct gaa cac ggt att act gcc gtc tgg att ccc ccg gca tat aag gga      564
Ala Glu His Gly Ile Thr Ala Val Trp Ile Pro Pro Ala Tyr Lys Gly
        35                  40                  45 acg agc caa gcg gat gtg ggc tac ggt gct tac gac ctt tat gat tta      612
Thr Ser Gln Ala Asp Val Gly Tyr Gly Ala Tyr Asp Leu Tyr Asp Leu
    50                  55                  60 ggg gag ttt cat caa aaa ggg acg gtt cgg aca aag tac gga aca aaa      660
Gly Glu Phe His Gln Lys Gly Thr Val Arg Thr Lys Tyr Gly Thr Lys
65                  70                  75                  80 gga gag ctg caa tct gcg atc aaa agt ctt cat tcc cgc gac att aac      708
Gly Glu Leu Gln Ser Ala Ile Lys Ser Leu His Ser Arg Asp Ile Asn
                85                  90                  95 gtt tac ggg gat gtg gtc atc aac cac aaa ggc ggc gct gat gcg acc      756
Val Tyr Gly Asp Val Val Ile Asn His Lys Gly Gly Ala Asp Ala Thr
            100                 105                 110 gaa gat gta acc gcg gtt gaa gtc gat ccc gct gac cgc aac cgc gta      804
Glu Asp Val Thr Ala Val Glu Val Asp Pro Ala Asp Arg Asn Arg Val
        115                 120                 125 att tca gga gaa cac cta att aaa gcc tgg aca cat ttt cat ttt ccg      852
Ile Ser Gly Glu His Leu Ile Lys Ala Trp Thr His Phe His Phe Pro
    130                 135                 140
```

| | |
|---|---|
| ggg cgc ggc agc aca tac agc gat ttt aaa tgg cat tgg tac cat ttt<br>Gly Arg Gly Ser Thr Tyr Ser Asp Phe Lys Trp His Trp Tyr His Phe<br>145                      150                    155                160 | 900 |
| gac gga acc gat tgg gac gag tcc cga aag ctg aac cgc atc tat aag<br>Asp Gly Thr Asp Trp Asp Glu Ser Arg Lys Leu Asn Arg Ile Tyr Lys<br>                165                    170                    175 | 948 |
| ttt caa gga aag gct tgg gat tgg gaa gtt tcc aat gaa aac ggc aac<br>Phe Gln Gly Lys Ala Trp Asp Trp Glu Val Ser Asn Glu Asn Gly Asn<br>          180                    185                    190 | 996 |
| tat gat tat ttg atg tat gcc gac atc gat tat gac cat cct gat gtc<br>Tyr Asp Tyr Leu Met Tyr Ala Asp Ile Asp Tyr Asp His Pro Asp Val<br>                195                    200                    205 | 1044 |
| gca gca gaa att aag aga tgg ggc act tgg tat gcc aat gaa ctg caa<br>Ala Ala Glu Ile Lys Arg Trp Gly Thr Trp Tyr Ala Asn Glu Leu Gln<br>210                      215                    220 | 1092 |
| ttg gac ggt ttc cgt ctt gat gct gtc aaa cac att aaa ttt tct ttt<br>Leu Asp Gly Phe Arg Leu Asp Ala Val Lys His Ile Lys Phe Ser Phe<br>225                      230                    235                240 | 1140 |
| ttg cgg gat tgg gtt aat cat gtc agg gaa aaa acg ggg aag gaa atg<br>Leu Arg Asp Trp Val Asn His Val Arg Glu Lys Thr Gly Lys Glu Met<br>                    245                    250                    255 | 1188 |
| ttt acg gta gct gaa tat tgg cag aat gac ttg ggc gcg ctg gaa aac<br>Phe Thr Val Ala Glu Tyr Trp Gln Asn Asp Leu Gly Ala Leu Glu Asn<br>          260                    265                    270 | 1236 |
| tat ttg aac aaa aca aat ttt aat cat tca gtg ttt gac gtg ccg ctt<br>Tyr Leu Asn Lys Thr Asn Phe Asn His Ser Val Phe Asp Val Pro Leu<br>                275                    280                    285 | 1284 |
| cat tat cag ttc cat gct gca tcg aca cag gga ggc ggc tat gat atg<br>His Tyr Gln Phe His Ala Ala Ser Thr Gln Gly Gly Gly Tyr Asp Met<br>290                      295                    300 | 1332 |
| agg aaa ttg ctg aac ggt acg gtc gtt tcc aag cat ccg ttg aaa tcg<br>Arg Lys Leu Leu Asn Gly Thr Val Val Ser Lys His Pro Leu Lys Ser<br>305                      310                    315                320 | 1380 |
| gtt aca ttt gtc gat aac cat gat aca cag ccg ggg caa tcg ctt gag<br>Val Thr Phe Val Asp Asn His Asp Thr Gln Pro Gly Gln Ser Leu Glu<br>                325                    330                    335 | 1428 |
| tcg act gtc caa aca tgg ttt aag ccg ctt gct tac gct ttt att ctc<br>Ser Thr Val Gln Thr Trp Phe Lys Pro Leu Ala Tyr Ala Phe Ile Leu<br>          340                    345                    350 | 1476 |
| aca agg gaa tct gga tac cct cag gtt ttc tac ggg gat atg tac ggg<br>Thr Arg Glu Ser Gly Tyr Pro Gln Val Phe Tyr Gly Asp Met Tyr Gly<br>                355                    360                    365 | 1524 |
| acg aaa gga gac tcc cag cgc gaa att cct gcc ttg aaa cac aaa att<br>Thr Lys Gly Asp Ser Gln Arg Glu Ile Pro Ala Leu Lys His Lys Ile<br>370                      375                    380 | 1572 |
| gaa ccg atc tta aaa gcg aga aaa cag tat gcg tac gga gca cag cat<br>Glu Pro Ile Leu Lys Ala Arg Lys Gln Tyr Ala Tyr Gly Ala Gln His<br>385                      390                    395                400 | 1620 |
| gat tat ttc gac cac cat gac att gtc ggc tgg aca agg gaa ggc gac<br>Asp Tyr Phe Asp His His Asp Ile Val Gly Trp Thr Arg Glu Gly Asp<br>                405                    410                    415 | 1668 |
| agc tcg gtt gca aat tca ggt ttg gcg gca tta ata aca gac gga ccc<br>Ser Ser Val Ala Asn Ser Gly Leu Ala Ala Leu Ile Thr Asp Gly Pro<br>          420                    425                    430 | 1716 |
| ggt ggg gca aag cga atg tat gtc ggc cgg caa aac gcc ggt gag aca<br>Gly Gly Ala Lys Arg Met Tyr Val Gly Arg Gln Asn Ala Gly Glu Thr<br>                435                    440                    445 | 1764 |
| tgg cat gac att acc gga aac cgt tcg gag ccg gtt gtc atc aat tcg<br>Trp His Asp Ile Thr Gly Asn Arg Ser Glu Pro Val Val Ile Asn Ser | 1812 |

```
                    450                455                460
gaa ggc tgg gga gag ttt cac gta aac ggc ggg tcg gtt tca att tat   1860
Glu Gly Trp Gly Glu Phe His Val Asn Gly Gly Ser Val Ser Ile Tyr
465                470                475                480 gtt caa aga tag aagagcagag aggacggatt tcctgaagga aatccgtttt       1912
Val Gln Arg
tttattt                                                            1920

<210> SEQ ID NO 8
<211> LENGTH: 483
<212> TYPE: PRT
<213> ORGANISM: Bacillus licheniformis

<400> SEQUENCE: 8

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
```

-continued

```
                325                 330                 335
Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
            355                 360                 365

Thr Lys Gly Asp Ser Gln Arg Glu Ile Pro Ala Leu Lys His Lys Ile
            370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
                420                 425                 430

Gly Gly Ala Lys Arg Met Tyr Val Gly Arg Gln Asn Ala Gly Glu Thr
            435                 440                 445

Trp His Asp Ile Thr Gly Asn Arg Ser Glu Pro Val Val Ile Asn Ser
            450                 455                 460

Glu Gly Trp Gly Glu Phe His Val Asn Gly Gly Ser Val Ser Ile Tyr
465                 470                 475                 480

Val Gln Arg

<210> SEQ ID NO 9
<211> LENGTH: 2084
<212> TYPE: DNA
<213> ORGANISM: Bacillus amyloliquefaciens
<220> FEATURE:
<221> NAME/KEY: CDS
<222> LOCATION: (343)..(1794)
<223> OTHER INFORMATION: BAN

<400> SEQUENCE: 9
gccccgcaca tacgaaaaga ctggctgaaa acattgagcc tttgatgact gatgatttgg      60
ctgaagaagt ggatcgattg tttgagaaaa gaagaagacc ataaaaatac cttgtctgtc     120
atcagacagg gtattttta tgctgtccag actgtccgct gtgtaaaaat aaggaataaa      180 gggggggttgt tattatttta ctgatatgta aaatataatt tgtataagaa aatgagaggg    240
agaggaaaca tgattcaaaa acgaaagcgg acagtttcgt tcagacttgt gcttatgtgc     300
acgctgttat ttgtcagttt gccgattaca aaacatcag cc gta aat ggc acg         354
                                                Val Asn Gly Thr
                                                1 ctg atg cag tat ttt gaa tgg tat acg ccg aac gac ggc cag cat tgg       402
Leu Met Gln Tyr Phe Glu Trp Tyr Thr Pro Asn Asp Gly Gln His Trp
5                   10                  15                  20 aaa cga ttg cag aat gat gcg gaa cat tta tcg gat atc gga atc act       450
Lys Arg Leu Gln Asn Asp Ala Glu His Leu Ser Asp Ile Gly Ile Thr
                25                  30                  35 gcc gtc tgg att cct ccc gca tac aaa gga ttg agc caa tcc gat aac       498
Ala Val Trp Ile Pro Pro Ala Tyr Lys Gly Leu Ser Gln Ser Asp Asn
            40                  45                  50 gga tac gga cct tat gat ttg tat gat tta gga gaa ttc cag caa aaa       546
Gly Tyr Gly Pro Tyr Asp Leu Tyr Asp Leu Gly Glu Phe Gln Gln Lys
        55                  60                  65 ggg acg gtc aga acg aaa tac ggc aca aaa tca gag ctt caa gat gcg       594
Gly Thr Val Arg Thr Lys Tyr Gly Thr Lys Ser Glu Leu Gln Asp Ala
    70                  75                  80 atc ggc tca ctg cat tcc cgg aac gtc caa gta tac gga gat gtg gtt       642
Ile Gly Ser Leu His Ser Arg Asn Val Gln Val Tyr Gly Asp Val Val
```

```
                85                  90                  95                  100 ttg aat cat aag gct ggt gct gat gca aca gaa gat gta act gcc gtc         690
Leu Asn His Lys Ala Gly Ala Asp Ala Thr Glu Asp Val Thr Ala Val
                    105                 110                 115 gaa gtc aat ccg gcc aat aga aat cag gaa act tcg gag gaa tat caa         738
Glu Val Asn Pro Ala Asn Arg Asn Gln Glu Thr Ser Glu Glu Tyr Gln
                120                 125                 130 atc aaa gcg tgg acg gat ttt cgt ttt ccg ggc cgt gga aac acg tac         786
Ile Lys Ala Trp Thr Asp Phe Arg Phe Pro Gly Arg Gly Asn Thr Tyr
                    135                 140                 145 agt gat ttt aaa tgg cat tgg tat cat ttc gac gga gcg gac tgg gat         834
Ser Asp Phe Lys Trp His Trp Tyr His Phe Asp Gly Ala Asp Trp Asp
                150                 155                 160 gaa tcc cgg aag atc agc cgc atc ttt aag ttt cgt ggg gaa gga aaa         882
Glu Ser Arg Lys Ile Ser Arg Ile Phe Lys Phe Arg Gly Glu Gly Lys
165                 170                 175                 180 gcg tgg gat tgg gaa gta tca agt gaa aac ggc aat tat gac tat tta         930
Ala Trp Asp Trp Glu Val Ser Ser Glu Asn Gly Asn Tyr Asp Tyr Leu
                    185                 190                 195 atg tat gct gat gtt gac tac gac cac cct gat gtc gtg gca gag aca         978
Met Tyr Ala Asp Val Asp Tyr Asp His Pro Asp Val Val Ala Glu Thr
                200                 205                 210 aaa aaa tgg ggt atc tgg tat gcg aat gaa ctg tca tta gac ggc ttc        1026
Lys Lys Trp Gly Ile Trp Tyr Ala Asn Glu Leu Ser Leu Asp Gly Phe
                    215                 220                 225 cgt att gat gcc gcc aaa cat att aaa ttt tca ttt ctg cgt gat tgg        1074
Arg Ile Asp Ala Ala Lys His Ile Lys Phe Ser Phe Leu Arg Asp Trp
230                 235                 240 gtt cag gcg gtc aga cag gcg acg gga aaa gaa atg ttt acg gtt gcg        1122
Val Gln Ala Val Arg Gln Ala Thr Gly Lys Glu Met Phe Thr Val Ala
245                 250                 255                 260 gag tat tgg cag aat aat gcc ggg aaa ctc gaa aac tac ttg aat aaa        1170
Glu Tyr Trp Gln Asn Asn Ala Gly Lys Leu Glu Asn Tyr Leu Asn Lys
                    265                 270                 275 aca agc ttt aat caa tcc gtg ttt gat gtt ccg ctt cat ttc aat tta        1218
Thr Ser Phe Asn Gln Ser Val Phe Asp Val Pro Leu His Phe Asn Leu
                280                 285                 290 cag gcg gct tcc tca caa gga ggc gga tat gat atg agg cgt ttg ctg        1266
Gln Ala Ala Ser Ser Gln Gly Gly Gly Tyr Asp Met Arg Arg Leu Leu
                    295                 300                 305 gac ggt acc gtt gtg tcc agg cat ccg gaa aag gcg gtt aca ttt gtt        1314
Asp Gly Thr Val Val Ser Arg His Pro Glu Lys Ala Val Thr Phe Val
310                 315                 320 gaa aat cat gac aca cag ccg gga cag tca ttg gaa tcg aca gtc caa        1362
Glu Asn His Asp Thr Gln Pro Gly Gln Ser Leu Glu Ser Thr Val Gln
325                 330                 335                 340 act tgg ttt aaa ccg ctt gca tac gcc ttt att ttg aca aga gaa tcc        1410
Thr Trp Phe Lys Pro Leu Ala Tyr Ala Phe Ile Leu Thr Arg Glu Ser
                    345                 350                 355 ggt tat cct cag gtg ttc tat ggg gat atg tac ggg aca aaa ggg aca        1458
Gly Tyr Pro Gln Val Phe Tyr Gly Asp Met Tyr Gly Thr Lys Gly Thr
                360                 365                 370 tcg cca aag gaa att ccc tca ctg aaa gat aat ata gag ccg att tta        1506
Ser Pro Lys Glu Ile Pro Ser Leu Lys Asp Asn Ile Glu Pro Ile Leu
                    375                 380                 385 aaa gcg cgt aag gag tac gca tac ggg ccc cag cac gat tat att gac        1554
Lys Ala Arg Lys Glu Tyr Ala Tyr Gly Pro Gln His Asp Tyr Ile Asp
                390                 395                 400 cac ccg gat gtg atc gga tgg acg agg gaa ggt gac agc tcc gcc gcc        1602
His Pro Asp Val Ile Gly Trp Thr Arg Glu Gly Asp Ser Ser Ala Ala
```

```
His Pro Asp Val Ile Gly Trp Thr Arg Glu Gly Asp Ser Ser Ala Ala
405                 410                 415                 420 aaa tca ggt ttg gcc gct tta atc acg gac gga ccc ggc gga tca aag    1650
Lys Ser Gly Leu Ala Ala Leu Ile Thr Asp Gly Pro Gly Gly Ser Lys
                425                 430                 435 cgg atg tat gcc ggc ctg aaa aat gcc ggc gag aca tgg tat gac ata    1698
Arg Met Tyr Ala Gly Leu Lys Asn Ala Gly Glu Thr Trp Tyr Asp Ile
                440                 445                 450 acg ggc aac cgt tca gat act gta aaa atc gga tct gac ggc tgg gga    1746
Thr Gly Asn Arg Ser Asp Thr Val Lys Ile Gly Ser Asp Gly Trp Gly
            455                 460                 465 gag ttt cat gta aac gat ggg tcc gtc tcc att tat gtt cag aaa taa    1794
Glu Phe His Val Asn Asp Gly Ser Val Ser Ile Tyr Val Gln Lys
            470                 475                 480 ggtaataaaa aaacacctcc aagctgagtg cgggtatcag cttggaggtg cgtttatttt   1854
ttcagccgta tgacaaggtc ggcatcaggt gtgacaaata cggtatgctg gctgtcatag   1914
gtgacaaatc cgggttttgc gccgtttggc ttttcacat gtctgatttt tgtataatca    1974
acaggcacgg agccggaatc tttcgccttg gaaaaataag cggcgatcgt agctgcttcc   2034
aatatggatt gttcatcggg atcgctgctt ttaatcacaa cgtgggatcc              2084

<210> SEQ ID NO 10
<211> LENGTH: 483
<212> TYPE: PRT
<213> ORGANISM: Bacillus amyloliquefaciens

<400> SEQUENCE: 10

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
                20                  25                  30

Ile Gly Ile Thr Ala Val Trp Ile Pro Pro Ala Tyr Lys Gly Leu Ser
            35                  40                  45

Gln Ser Asp Asn Gly Tyr Gly Pro Tyr Asp Leu Tyr Asp Leu Gly Glu
        50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Glu Thr Ser
        115                 120                 125

Glu Glu Tyr Gln Ile Lys Ala Trp Thr Asp Phe Arg Phe Pro Gly Arg
130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
            180                 185                 190

Tyr Asp Tyr Leu Met Tyr Ala Asp Val Asp Tyr Asp His Pro Asp Val
        195                 200                 205

Val Ala Glu Thr Lys Lys Trp Gly Ile Trp Tyr Ala Asn Glu Leu Ser
    210                 215                 220
```

```
Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
            245                 250                 255

Phe Thr Val Ala Glu Tyr Trp Gln Asn Asn Ala Gly Lys Leu Glu Asn
                260                 265                 270

Tyr Leu Asn Lys Thr Ser Phe Asn Gln Ser Val Phe Asp Val Pro Leu
            275                 280                 285

His Phe Asn Leu Gln Ala Ala Ser Ser Gln Gly Gly Tyr Asp Met
        290                 295                 300

Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Thr Ser Pro Lys Glu Ile Pro Ser Leu Lys Asp Asn Ile
    370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
                405                 410                 415

Ser Ser Ala Ala Lys Ser Gly Leu Ala Ala Leu Ile Thr Asp Gly Pro
            420                 425                 430

Gly Gly Ser Lys Arg Met Tyr Ala Gly Leu Lys Asn Ala Gly Glu Thr
        435                 440                 445

Trp Tyr Asp Ile Thr Gly Asn Arg Ser Asp Thr Val Lys Ile Gly Ser
    450                 455                 460

Asp Gly Trp Gly Glu Phe His Val Asn Asp Gly Ser Val Ser Ile Tyr
465                 470                 475                 480

Val Gln Lys

<210> SEQ ID NO 11
<211> LENGTH: 1458
<212> TYPE: DNA
<213> ORGANISM: Bacillus sp.
<220> FEATURE:
<221> NAME/KEY: CDS
<222> LOCATION: (1)..(1458)
<223> OTHER INFORMATION: AA560

<400> SEQUENCE: 11 cac cat aat ggt acg aac ggc aca atg atg cag tac ttt gaa tgg tat      48
His His Asn Gly Thr Asn Gly Thr Met Met Gln Tyr Phe Glu Trp Tyr
1               5                   10                  15 cta cca aat gac gga aac cat tgg aat aga tta agg tct gat gca agt      96
Leu Pro Asn Asp Gly Asn His Trp Asn Arg Leu Arg Ser Asp Ala Ser
            20                  25                  30 aac cta aaa gat aaa ggg atc tca gcg gtt tgg att cct cct gca tgg     144
Asn Leu Lys Asp Lys Gly Ile Ser Ala Val Trp Ile Pro Pro Ala Trp
        35                  40                  45 aag ggt gcc tct caa aat gat gtg ggg tat ggt gct tat gat ctg tat     192
Lys Gly Ala Ser Gln Asn Asp Val Gly Tyr Gly Ala Tyr Asp Leu Tyr
    50                  55                  60 gat tta gga gaa ttc aat caa aaa gga acc att cgt aca aaa tat gga     240
```

```
                                -continued

Asp Leu Gly Glu Phe Asn Gln Lys Gly Thr Ile Arg Thr Lys Tyr Gly
 65                  70                  75                  80 acg cgc aat cag tta caa gct gca gtt aac gcc ttg aaa agt aat gga       288
Thr Arg Asn Gln Leu Gln Ala Ala Val Asn Ala Leu Lys Ser Asn Gly
                 85                  90                  95 att caa gtg tat ggc gat gtt gta atg aat cat aaa ggg gga gca gac       336
Ile Gln Val Tyr Gly Asp Val Val Met Asn His Lys Gly Gly Ala Asp
            100                 105                 110 gct acc gaa atg gtt agg gca gtt gaa gta aac ccg aat aat aga aat       384
Ala Thr Glu Met Val Arg Ala Val Glu Val Asn Pro Asn Asn Arg Asn
        115                 120                 125 caa gaa gtg tcc ggt gaa tat aca att gag gct tgg aca aag ttt gac       432
Gln Glu Val Ser Gly Glu Tyr Thr Ile Glu Ala Trp Thr Lys Phe Asp
    130                 135                 140 ttt cca gga cga ggt aat act cat tca aac ttc aaa tgg aga tgg tat       480
Phe Pro Gly Arg Gly Asn Thr His Ser Asn Phe Lys Trp Arg Trp Tyr
145                 150                 155                 160 cac ttt gat gga gta gat tgg gat cag tca cgt aag ctg aac aat cga       528
His Phe Asp Gly Val Asp Trp Asp Gln Ser Arg Lys Leu Asn Asn Arg
                165                 170                 175 att tat aaa ttt aga ggt gat gga aaa ggg tgg gat tgg gaa gtc gat       576
Ile Tyr Lys Phe Arg Gly Asp Gly Lys Gly Trp Asp Trp Glu Val Asp
            180                 185                 190 aca gaa aac ggt aac tat gat tac cta atg tat gca gat att gac atg       624
Thr Glu Asn Gly Asn Tyr Asp Tyr Leu Met Tyr Ala Asp Ile Asp Met
        195                 200                 205 gat cac cca gag gta gtg aat gag cta aga aat tgg ggt gtt tgg tat       672
Asp His Pro Glu Val Val Asn Glu Leu Arg Asn Trp Gly Val Trp Tyr
    210                 215                 220 acg aat aca tta ggc ctt gat ggt ttt aga ata gat gca gta aaa cat       720
Thr Asn Thr Leu Gly Leu Asp Gly Phe Arg Ile Asp Ala Val Lys His
225                 230                 235                 240 ata aaa tac agc ttt act cgt gat tgg att aat cat gtt aga agt gca       768
Ile Lys Tyr Ser Phe Thr Arg Asp Trp Ile Asn His Val Arg Ser Ala
                245                 250                 255 act ggc aaa aat atg ttt gcg gtt gcg gaa ttt tgg aaa aat gat tta       816
Thr Gly Lys Asn Met Phe Ala Val Ala Glu Phe Trp Lys Asn Asp Leu
            260                 265                 270 ggt gct att gaa aac tat tta aac aaa aca aac tgg aac cat tca gtc       864
Gly Ala Ile Glu Asn Tyr Leu Asn Lys Thr Asn Trp Asn His Ser Val
        275                 280                 285 ttt gat gtt ccg ctg cac tat aac ctc tat aat gct tca aaa agc gga       912
Phe Asp Val Pro Leu His Tyr Asn Leu Tyr Asn Ala Ser Lys Ser Gly
    290                 295                 300 ggg aat tat gat atg agg caa ata ttt aat ggt aca gtc gtg caa aga       960
Gly Asn Tyr Asp Met Arg Gln Ile Phe Asn Gly Thr Val Val Gln Arg
305                 310                 315                 320 cat cca atg cat gct gtt aca ttt gtt gat aat cat gat tcg caa cct      1008
His Pro Met His Ala Val Thr Phe Val Asp Asn His Asp Ser Gln Pro
                325                 330                 335 gaa gaa gct tta gag tct ttt gtt gaa gaa tgg ttc aaa cca tta gcg      1056
Glu Glu Ala Leu Glu Ser Phe Val Glu Glu Trp Phe Lys Pro Leu Ala
            340                 345                 350 tat gct ttg aca tta aca cgt gaa caa ggc tac cct tct gta ttt tat      1104
Tyr Ala Leu Thr Leu Thr Arg Glu Gln Gly Tyr Pro Ser Val Phe Tyr
        355                 360                 365 gga gat tat tat ggc att cca acg cat ggt gta cca gcg atg aaa tcg      1152
Gly Asp Tyr Tyr Gly Ile Pro Thr His Gly Val Pro Ala Met Lys Ser
    370                 375                 380
```

```
aaa att gac ccg att cta gaa gcg cgt caa aag tat gca tat gga aga      1200
Lys Ile Asp Pro Ile Leu Glu Ala Arg Gln Lys Tyr Ala Tyr Gly Arg
385                 390                 395                 400 caa aat gac tac tta gac cat cat aat atc atc ggt tgg aca cgt gaa      1248
Gln Asn Asp Tyr Leu Asp His His Asn Ile Ile Gly Trp Thr Arg Glu
            405                 410                 415 ggg aat aca gca cac ccc aac tcc ggt tta gct act atc atg tcc gat      1296
Gly Asn Thr Ala His Pro Asn Ser Gly Leu Ala Thr Ile Met Ser Asp
        420                 425                 430 ggg gca gga gga aat aag tgg atg ttt gtt ggg cgt aat aaa gct ggt      1344
Gly Ala Gly Gly Asn Lys Trp Met Phe Val Gly Arg Asn Lys Ala Gly
    435                 440                 445 caa gtt tgg acc gat atc act gga aat cgt gca ggt act gtt acg att      1392
Gln Val Trp Thr Asp Ile Thr Gly Asn Arg Ala Gly Thr Val Thr Ile
450                 455                 460 aat gct gat gga tgg ggt aat ttt tct gta aat gga gga tca gtt tct      1440
Asn Ala Asp Gly Trp Gly Asn Phe Ser Val Asn Gly Gly Ser Val Ser
465                 470                 475                 480 att tgg gta aac aaa taa                                              1458
Ile Trp Val Asn Lys
                485

<210> SEQ ID NO 12
<211> LENGTH: 485
<212> TYPE: PRT
<213> ORGANISM: Bacillus sp.

<400> SEQUENCE: 12

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
```

```
            225                 230                 235                 240
Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
                260                 265                 270

Gly Ala Ile Glu Asn Tyr Leu Asn Lys Thr Asn Trp Asn His Ser Val
                275                 280                 285

Phe Asp Val Pro Leu His Tyr Asn Leu Tyr Asn Ala Ser Lys Ser Gly
                290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
                340                 345                 350

Tyr Ala Leu Thr Leu Thr Arg Glu Gln Gly Tyr Pro Ser Val Phe Tyr
                355                 360                 365

Gly Asp Tyr Tyr Gly Ile Pro Thr His Gly Val Pro Ala Met Lys Ser
370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
                420                 425                 430

Gly Ala Gly Gly Asn Lys Trp Met Phe Val Gly Arg Asn Lys Ala Gly
                435                 440                 445

Gln Val Trp Thr Asp Ile Thr Gly Asn Arg Ala Gly Thr Val Thr Ile
                450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 13
<211> LENGTH: 485
<212> TYPE: PRT
<213> ORGANISM: bacillus sp. 707

<400> SEQUENCE: 13

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
                20                  25                  30

Asn Leu Lys Ser Lys Gly Ile Thr Ala Val Trp Ile Pro Pro Ala Trp
                35                  40                  45

Lys Gly Ala Ser Gln Asn Asp Val Gly Tyr Gly Ala Tyr Asp Leu Tyr
                50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
                100                 105                 110
```

-continued

Ala Thr Glu Met Val Arg Ala Val Glu Val Asn Pro Asn Arg Asn
            115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
    195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
    275                 280                 285

Phe Asp Val Pro Leu His Tyr Asn Leu Tyr Asn Ala Ser Lys Ser Gly
290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
    355                 360                 365

Gly Asp Tyr Tyr Gly Ile Pro Thr His Gly Val Pro Ala Met Arg Ser
370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
    435                 440                 445

Gln Val Trp Ser Asp Ile Thr Gly Asn Arg Thr Gly Thr Val Thr Ile
450                 455                 460

Asn Ala Asp Gly Trp Gly Asn Phe Ser Val Asn Gly Gly Ser Val Ser
465                 470                 475                 480

Ile Trp Val Asn Lys
            485

<210> SEQ ID NO 14
<211> LENGTH: 60
<212> TYPE: DNA
<213> ORGANISM: Artificial Sequence
<220> FEATURE:
<223> OTHER INFORMATION: Primer -continued

<400> SEQUENCE: 14
caaaatcgta tctacaaatt cmrkrsyarg dvktgggatt sggaagtaga ttcggaaaat    60

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
gaatttgtag atacgatttt g    21

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
cgattgctga cgctgttatt tgcg    24

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
cttgttccct tgtcagaacc aatg    24

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
gtcatagttg ccgaaatctg tatcgacttc    30

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
gacctgcagt caggcaacta    20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
tagagtcgac ctgcaggcat    20

AMYLASE VARIANTS

CROSS-REFERENCE TO RELATED APPLICATIONS

This application is a continuation of PCT/DK01/00144 filed Mar. 4, 2001 (the international application was published under PCT Article 21(2) in English) and claims, under 35 U.S.C. 119, priority or the benefit of Danish application nos. PA 2000 00376 and PA 2001 00303 filed Mar. 8, 2000 and Feb. 23, 2001, respectively, and U.S. provisional application Nos. 60/189,857, and 60/271,382 filed Mar. 15, 2000 and Feb. 26, 2001, the contents of which are fully incorporated herein by reference.

FIELD OF THE INVENTION

The present invention relates to variants (mutants) of parent Termamyl-like alpha-amylases, which variant has alpha-amylase activity and exhibits an alteration in at least one of the following properties relative to said parent alpha-amylase: substrate specificity, substrate binding, substrate cleavage pattern, thermal stability pH, /activity profile, pH/stability profile, stability towards oxidation, $Ca^{2+}$ dependency, specific activity, and solubility in particular under production and application conditions.

BACKGROUND OF THE INVENTION

Alpha-Amylases (alpha-1,4-glucan-4-glucanohydrolases, E.C. 3.2.1.1) constitute a group of enzymes, which catalyze hydrolysis of starch and other linear and branched 1,4-glucosidic oligo- and polysaccharides.

In modern and industrial biotechnology high protein concentrations are achieved during fermentation, purification, recovery and in product formulation.

During the fermentation the protein concentration depend on the host cell used. In industrial processes the protein concentration typically lies from above 0.1 g/liter fermentation broth. For high yield recombinant production of alpha-amylases in *Bacillus* sp. the protein concentration may be as high as 250 g/liter fermentation broth. After purification the protein concentration may reach levels of about 1000 g/liter.

Such high concentrations leads to an undesirable precipitation resulting in lose of active protein. The tendency today is towards products of increasing strength, which make the ability to maintain the enzyme in solution of increasing importance. Often up-concentration of a protein solutions results in protein precipitates, which are difficult to dissolve into active protein.

Thus, it is the object of this application to provide alpha-amylases with altered properties as defined below, in particular increased solubility.

BRIEF DESCRIPTION OF THE INVENTION

The object of the present invention is to provide Termamyl-like amylases which variants in comparison to the corresponding parent alpha-amylase, i.e., un-mutated alpha-amylase, has alpha-amylase activity and exhibits an alteration in at least one of the following properties relative to said parent alpha-amylase: substrate specificity, substrate binding, substrate cleavage pattern, thermal stability, pH/activity profile, pH/stability profile, stability towards oxidation, $Ca^{2+}$ dependency, specific activity, and solubility, in particular increased solubility under production conditions.

Nomenclature

In the present description and claims, the conventional one-letter and three-letter codes for amino acid residues are used. For ease of reference, alpha-amylase variants of the invention are described by use of the following nomenclature:

Original amino acid(s): position(s): substituted amino acid(s)
According to this nomenclature, for instance the substitution of alanine for asparagine in position 30 is shown as:
Ala30Asn or A30N a deletion of alanine in the same position is shown as:
Ala30* or A30* and insertion of an additional amino acid residue, such as lysine, is shown as:
Ala30AlaLys or A30AK A deletion of a consecutive stretch of amino acid residues, such as amino acid residues 30-33, is indicated as (30-33)* or Δ(A30-N33).

Where a specific alpha-amylase contains a "deletion" in comparison with other alpha-amylases and an insertion is made in such a position this is indicated as:
*36Asp or *36D for insertion of an aspartic acid in position 36.
Multiple mutations are separated by plus signs, i.e.:
Ala30Asp+Glu34Ser or A30N+E34S representing mutations in positions 30 and 34 substituting alanine and glutamic acid for asparagine and serine, respectively.

When one or more alternative amino acid residues may be inserted in a given position it is indicated as
A30N,E or
A30N or A30E Furthermore, when a position suitable for modification is identified herein without any specific modification being suggested, it is to be understood that any amino acid residue may be substituted for the amino acid residue present in the position. Thus, for instance, when a modification of an alanine in position 30 is mentioned, but not specified, it is to be understood that the alanine may be deleted or substituted for any other amino acid, i.e., any one of:
R,N,D,A,C,Q,E,G,H,I,L,K,M,F,P,S,T,W,Y,V.

Further, "A30X" means any one of the following substitutions:
A30R, A30N, A30D, A30C, A30Q, A30E, A30G, A30H, A30I, A30L, A30K, A30M, A30F, A30P, A30S, A30T, A30W, A30Y, or A30 V; or in short: A30R,N,D,C,Q,E,G, H,I,L,K,M,F,P,S,T,W,Y,V.

BRIEF DESCRIPTION OF THE DRAWINGS

FIGS. 1A, 1B and 1C show an alignment of the amino acid sequences of five parent Termamyl-like alpha-amylases. The numbers on the extreme left designate the respective amino acid sequences as follows:
1: SEQ ID NO: 4 (SP722)
2: SEQ ID NO: 2 (SP690)
3: SEQ ID NO: 10 (BAN)
4: SEQ ID NO: 8 (BLA)
5: SEQ ID NO: 6 (BSG).

DETAILED DISCLOSURE OF THE INVENTION

Figure 2:
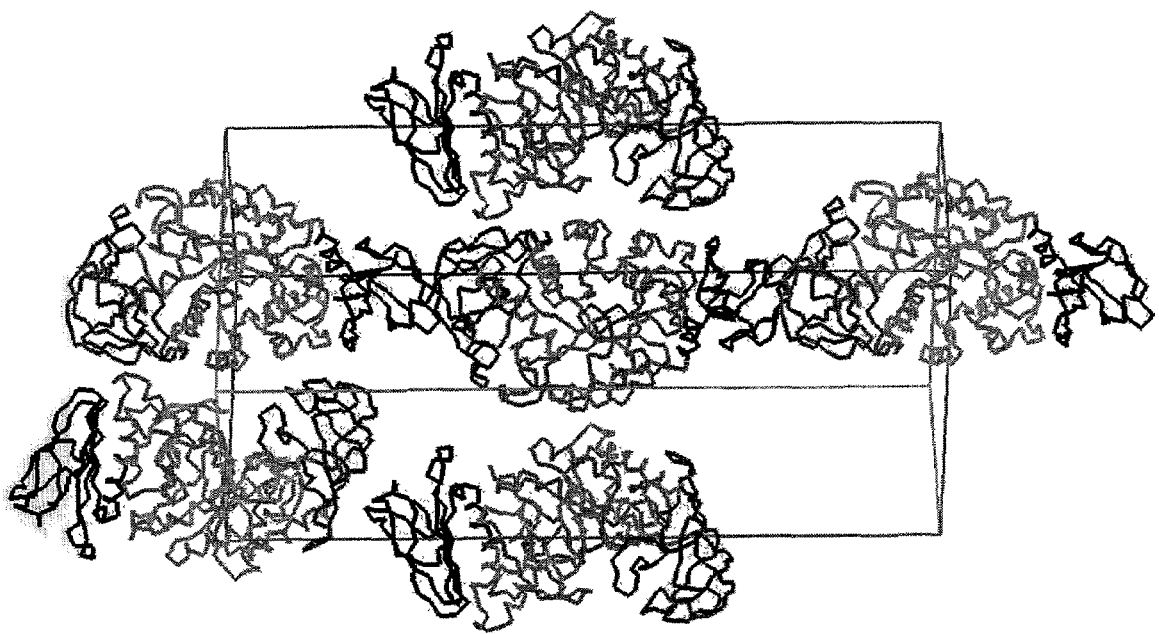
FIG. 2 shows a site-view of the unit cell of 4 enzyme molecules. Each molecule has 8 interacting zones.

The object of the present invention is to provide polypeptides, such as enzymes, in particular alpha-amylases, with an alteration in at least one of the following properties relative to said parent polypeptide: substrate specificity, substrate binding, substrate cleavage pattern, thermal stability, pH/activity profile, pH/stability profile, stability towards oxidation, $Ca^{2+}$ dependency, specific activity, and solubility, in particular under production conditions. The properties will be defined further below.

Polypeptide

Polypeptides according to the invention include proteins with biological activity, antimicrobial activity, and enzymatic activity.

Contemplated enzyme activities include proteases, amylases, CGTases, mannanases, maltogenic amylases, glucoamylases, carbohydrases, transferases, lyases, oxidoreductases, lipases.

In one preferred embodiment the enzyme is an alpha-amylase, in particular a *Bacillus* or *Aspergillus* alpha-amylase. In a preferred embodiment the *Bacillus* alpha-amylase is a Termamyl-like amylases.

Polypeptides with biological activity include, EPO, TPO, growth hormones, regulatory peptides, blood coagulation factors, antibodies etc.

Polypeptide with Altered Solubility

A protein (polypeptide) crystal is built up of systematic ordered identical units closely packed together in 3 dimensions. The unit cells may contain one or more protein molecules and a significant amount of water. Also ions like Calcium, Sodium, Chloride, Sulphate and larger molecules such as surfactants and substrates—present during crystal growth—can be identified in the tertiary structure. Although the single molecules and the single atoms are very small, the repeating array of identical units facilitates X-ray scattering and thus provide structure information, which can be used for protein engineering purposes.

Relative to crystals, precipitates and aggregates are smaller units and the single molecules are more disordered than in the crystals. Nevertheless some of the intermolecular interactions are the same as found in a well ordered crystals and thus can the tertiary structure (3D structure) and intermolecular information be used for designing protein engineered alpha-amylase variants with altered properties, in particular with reduced tendency of precipitating, i.e., variant with increased solubility.

Due to the spherical and often irregular surface structures of proteins, large holes in the unit cell exist, which are occupied by more disordered solvents like water. In fact, the large majority of the protein surface is covered with layers of water, which is one reason why structures of proteins solved by X-ray crystallography are the same as those for proteins in solution. Only at a few areas the protein molecules are in direct contact with each other, but also solvent mediated contacts function as the "glue" that binds the crystal together.

In general the solubility of proteins is affected by organic solvents, salts like ammonium sulphate, NaCl and $CaCl_2$, and by pH change altering the surface charge of the molecule. These factors are considered both for enzyme production to keep the enzyme in solution and for crystallography experiment to grow useful crystals. Large symmetric crystals are grown by slow increase in protein concentration or by altering the protein surface thereby enhancing the inter-molecular contacts.

Not all proteins crystallise in a form useful for X-ray crystallography determination methods, but based on existing tertiary structure accurate models can be build if the homology between the template molecule and the molecule of interest is high enough.

When homologous polypeptides, such as enzymes, in particular Termamyl-like alpha-amylases (defined below), are compared on a tertiary structural basis, the large majority of differences are found on the surface of the molecule.

Despite that, the inventors found that surface residues identified to be involved—directly or indirectly through water molecules—in crystal formations for the Termamyl-like amylase (SP722 disclosed in SEQ ID NO: 4) is also playing a key role for crystallisation of other Termamyl-like amylases (defined below).

Below is described one example of modeling a tertialy structure of one Termamyl-like alpha-alpha from another Termamyl-like alpha-amiase structure (SP722 structure disclosed in APPENDIX 1).

It is to be understood that the concept of the invention and the below described modeling method according to the invention can generally be extrapolated to all polypeptides, proteins, in particular enzymes, such as alpha-amylases.

The Tertiary Structure of SP722 and Modeling the Tertiary Structures of Another Termamyl-Like Alpha-Aylase.

Mutants of alpha-amylases of the present invention have been found based on the tertiary structure shown in APPENDIX 1 of SP722 (SEQ ID NO: 4). Mutants of other polypeptides may be found based on other tertiary structures.

Crystals of the alkaline Termamyl-like alpha-amylase (SP722) (shown in SEQ ID NO: 4 and also disclosed in U.S. Pat. No. 5,824,531) were obtained by the hanging drop method (well-known in the art), and the tertiary structure (3D-structure) is disclosed in APPENDIX 1.

Figure 3:
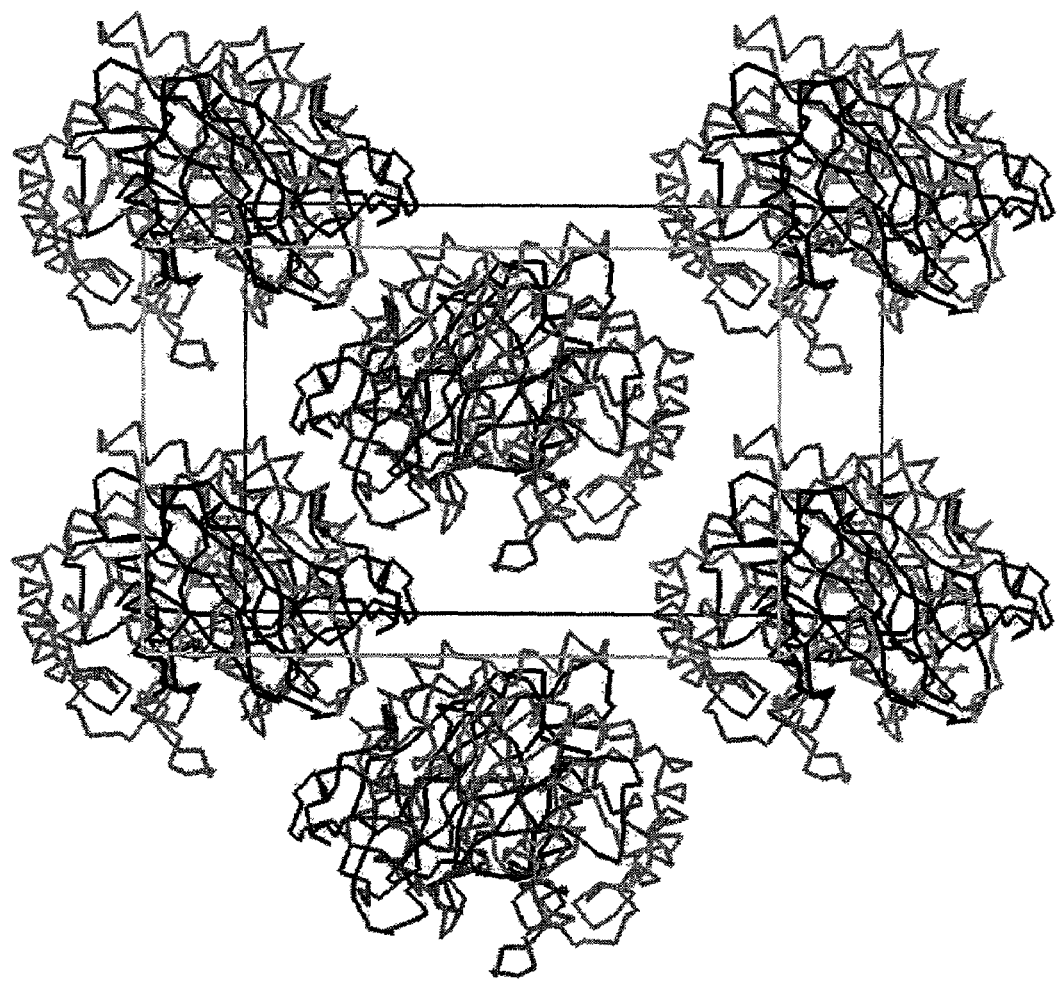
FIG. 3 shows a top-view of the unit cell of 4 enzyme molecules.

The unit cell was found to contain 4 enzyme molecules and each molecule has 8 interacting zones (see FIGS. 2 and 3). Two zones have been identified on the side of the enzyme surrounding the active site and one large area is found on the backside of the alpha-amylase relative to the active site. There are further two interaction zones on the sides and an interaction side at the bottom and one at the top of the molecule making top-to-bottom interactions.

As can be seen from FIG. 2 the two interaction zones surrounding the active site is interacting with the same two areas on an anti-parallel neighbour molecule. Likewise the backside zone is in contact with the backside zone on a third anti-parallel amylase molecule although all contacts here water mediated. It can also be seen from the FIGS. 2 and 3 that the interacting areas are spread all over the molecule.

A model of another alkaline Termamyl-like amylase, AA560 has been build based on the SP722 tertiary structure disclosed in APPENDIX 1. AA560 alpha-amylase is about 87% identical to the template amylase (SP722) and the alignment contains no insertion or deletions. Due to the high homology (identity), the same symmetry and the same crystal interactions, the same interaction zones on the protein surface are involved in crystallization and precipitation at the increasing protein concentrations, which are reached during production, i.e., starting from Trio fermentation stage through the purification stage (see Background section).

Mutations in these interaction zones were constructed, the enzyme expressed and purified, and the protein solubility was measured under different conditions as described in Example 8 and 9 using the method described in the "Materials and Methods" section.

The findings of the present invention may be applied on Termamyl-like amylases being at least 60% identical, preferably at least 70% identical, more preferably 80% identical, even more preferably 85% identical, even more preferably 90% identical, even more 95% identical, even more 97% identical, even more 99% identical to the Termamyl-like alpha-amylase shown in SEQ ID NO: 12. In a preferably the findings may be used on alkaline Termamyl-like alpha-amylases, especially alkaline alpha-amylases of the same length, without additional amino residues or gaps in an aligned primary structure in comparison to SP722 (SEQ ID NO: 4 shown as number 1 in the alignment in FIG. 1). Especially, the finding may be used on the following alkaline Termamyl-like alpha-amylases: SP690 (SEQ ID NO: 2), SP722 (SEQ ID NO: 4), AA560 (SEQ ID NO: 12), #707 alpha-amylase (SEQ ID NO: 13), the KSM APE 1378 alpha-amylase disclosed in KSM AP1378 alpha-amylase is disclosed in WO 97/00324, or fragment or truncated forms thereof. The latter mentioned alkaline alpha-amylases have very similar tertiary crystal structure around the above-mentioned interactions zones, and have the same primary structure length 485 amino acids.

Contrary hereto, for instance, Termamyl (shown as sequence number 4 in the alignment in FIG. 1) lacks two amino acid residues (positions 1 and 2); has gaps in positions 174 and 181-182; and has three additional amino acid residues in positions 378-381 when aligned with SP722.

BAN (shown as sequence number 3 in the alignment in FIG. 1) lacks five amino acid residues (positions 1-4 and 488); has gaps in positions 174 and 181-182; and has three additional amino acid residues in positions 378-381 if aligned with SP722.

BSG (shown as sequence number 5 in the alignment in FIG. 1) lacks one amino acid residues (position 1); and has 31 additional amino acid residues in positions 489-519 if aligned with SP722.

KSM-K36 and KSM-K38 (EP 1,022,334-A) lack five amino acid residues (positions 1 and 2) and has gaps in positions 174 and 181-182 when aligned with SP722.

AA180, AA20 and Amrk385 (Danish patent application no. PA 2000 00347 or PCT/DK01/00133) have one additional amino acid in position 261 when aligned with SP722.

Below it is described how to model a Termamyl-like alpha-amylase from another alpha-amylase. In Example 4 the modeling of AA560 from SP722 is described. This method can be exprepolated to other polypetides as for instance the above-mentioned.

Modeling of Termamyl-Like Alpha-amylases

WO 96/23874 provides the tertiary structure (3D Structure), X-ray crystal structural data for a Termamyl-like alpha-amylase, which consists of the 300 N-terminal amino acid residues of the B. amyloliquefaciens alpha-amylase (BAN™) and amino acids 301-483 of the C-terminal end of the B. licheniformis alpha-amylase (SEQ ID NO: 8). WO 96/23874 further describes methodology for designing (modeling), on the basis of an analysis of the structure of a parent Termamyl-like alpha-amylase, variants of the parent Termamyl-like alpha-amylase which exhibit altered properties relative to the parent.

Other Termamyl-like structures may be modeled in accordance with WO 96/23874, which is hereby incorporated by reference.

In connection with obtaining variant of the present invention the AA560 tertiary structure was designed (modeled) based on the tertiary structure of SP722 (disclosed in APPENDIX 1) as described in Example 1. The structure of other Termamyl-like alpha-amylases (e.g., those disclosed herein) may be built analogously.

Termamyl-Like Alpha-amylases

A number of alpha-amylases produced by *Bacillus* spp. are highly homologous (identical) on the amino acid level.

The identity of a number of *Bacillus* alpha-amylases can be found in the below Table 1:

TABLE 1

| | Percent identity | | | | | | | |
|---|---|---|---|---|---|---|---|---|
| | 707 | AP1378 | BAN | BSG | SP690 | SP722 | AA560 | Termamyl |
| 707 | 100.0 | 86.4 | 66.9 | 66.5 | 87.6 | 86.2 | 95.5 | 68.1 |
| AP1378 | 86.4 | 100.0 | 67.1 | 68.1 | 95.1 | 86.6 | 86.0 | 69.4 |
| BAN | 66.9 | 67.1 | 100.0 | 65.6 | 67.1 | 68.8 | 66.9 | 80.7 |
| BSG | 66.5 | 68.1 | 65.6 | 100.0 | 67.9 | 67.1 | 66.3 | 65.4 |
| SP690 | 87.6 | 95.1 | 67.1 | 67.9 | 100.0 | 87.2 | 87.0 | 69.2 |
| SP722 | 86.2 | 86.6 | 68.8 | 67.1 | 87.2 | 100.0 | 86.8 | 70.8 |
| AA560 | 95.5 | 86.0 | 66.9 | 66.3 | 87.0 | 86.8 | 100.0 | 68.3 |
| Termamyl | 68.1 | 69.4 | 80.7 | 65.4 | 69.2 | 70.8 | 68.3 | 100.0 |

For instance, the B. licheniformis alpha-amylase comprising the amino acid sequence shown in SEQ ID NO: 8 (commercially available as Termamyl™) has been found to be about 81% homologous with the B. amyloliquefaciens alpha-amylase comprising the amino acid sequence shown in SEQ ID NO: 10 and about 65% homologous with the B. stearothermophilus alpha-amylase comprising the amino acid sequence shown in SEQ ID NO: 6. Further homologous alpha-amylases include SP690 and SP722 disclosed in WO 95/26397 and further depicted in SEQ ID NO: 2 and SEQ ID NO: 4, respectively. Other amylases are the AA560 alpha-amylase derived from *Bacillus* sp. and shown in SEQ ID NO: 12, and the #707 alpha-amylase derived from *Bacillus* sp., shown in SEQ ID NO: 13 and described by Tsukamoto et al., *Biochemical and Biophysical Research Communications*, 151 (1988), pp. 25-31.

The KSM AP1378 alpha-amylase is disclosed in WO 97/00324 (from KAO Corporation). Also the K38 and K38 alpha-amylases disclosed in EP 1,022,334 are contemplated according to the invention.

Still further homologous alpha-amylases include the alpha-amylase produced by the *B. licheniformis* strain described in EP 0252666 (ATCC 27811), and the alpha-amylases identified in WO 91/00353 and WO 94/18314. Other commercial Termamyl-like alpha-amylases are comprised in the products sold under the following tradenames: Optitherm™ and Takatherm™ (available from Solvay);

Maxamyl™ (available from Gist-brocades/Genencor), Spezym AA™ and Spezyme Delta AA™ (available from Genencor), and Keistase™ (available from Daiwa), Purastar™ ST 5000E, PURASTRA™ HPAM L (from Genencor Int.).

Because of the substantial homology found between these alpha-amylases, they are considered to belong to the same class of alpha-amylases, namely the class of "Termamyl-like alpha-amylases".

Accordingly, in the present context, the term "Termamyl-like alpha-amylase" is intended to indicate an alpha-amylase, which, at the amino acid level, exhibits a substantial identity to Termamyl™, i.e., the *B. licheniformis* alpha-amylase having the amino acid sequence shown in SEQ ID NO: 8.

In other words, all the following alpha-amylases, which has the amino acid sequences shown in SEQ ID NOS: 2, 4, 6, 8, 10, 12 and 13 are considered to be "Termamyl-like alpha-amylase". Other Termamyl-like alpha-amylases are alpha-amylases i) which displays at least 60%, such as at least 70%, e.g., at least 75%, or at least 80%, at least 85%, at least 90%, at least 95%, at least 97%, at least 99% homology with at least one of said amino acid sequences shown in SEQ ID NOS: 2, 4, 6, 8, 10, 12, and 13, and/or ii) is encoded by a DNA sequence which hybridizes to the DNA sequences encoding the above-specified alpha-amylases which are apparent from SEQ ID NOS: 1, 3, 5, 7, 9 and of the present specification (which encoding sequences encode the amino acid sequences shown in SEQ ID NOS: 2, 4, 6, 8, 10 and 12, respectively).

In connection with property i), the homology may be determined as the degree of identity between the two sequences indicating a derivation of the first sequence from the second. The homology may suitably be determined by means of computer programs known in the art such as GAP provided in the GCG program package (described above). Thus, Gap GCGv8 may be used with the following default parameters: GAP creation penalty of 5.0 and GAP extension penalty of 0.3, default scoring matrix, for nucleic sequences and 3.0 and 0.1, respectively, from protein sequences. GAP uses the method of Needleman/Wunsch/Sellers to make alignments.

A structural alignment between Termamyl (SEQ ID NO: 8) and another Termamyl-like alpha-amylase may be used to identify equivalent/corresponding positions in other Termamyl-like alpha-amylases. One method of obtaining said structural alignment is to use the Pile Up programme from the GCG package using default values of gap penalties, i.e., a gap creation penalty of 3.0 and gap extension penalty of 0.1. Other structural alignment methods include the hydrophobic cluster analysis (Gaboriaud et al., (1987), FEBS LETTERS 224, pp. 149-155) and reverse threading (Huber, T; Torda, A E, PROTEIN SCIENCE Vol. 7, No.1 pp. 142-149 (1998).

Hybridisation

The oligonucleotide probe used in the characterisation of the polypeptide, such as the Termamyl-like alpha-amylase in accordance with property ii) above may suitably be prepared on the basis of the full or partial nucleotide or amino acid sequence of the alpha-amylase in question.

Suitable conditions for testing hybridisation involve presoaking in 5×SSC and prehybridizing for 1 hour at ~40° C. in a solution of 20% formamide, 5×Denhardt's solution, 50 mM sodium phosphate, pH 6.8, and 50 mg of denatured sonicated calf thymus DNA, followed by hybridisation in the same solution supplemented with 100 mM ATP for 18 hours at ~40° C., is followed by three times washing of the filter in 2×SSC, 0.2% SDS at 40° C. for 30 minutes (low stringency), preferred at 50° C. (medium stringency), more preferably at 65° C. (high stringency), even more preferably at ~75° C. (very high stringency). More details about the hybridisation method can be found in Sambrook et al., Molecular_Cloning: A Laboratory Manual, 2nd Ed., Cold Spring Harbor, 1989.

In the present context, "derived from" is intended not only to indicate an alpha-amylase produced or producible by a strain of the organism in question, but also an alpha-amylase encoded by a DNA sequence isolated from such strain and produced in a host organism transformed with said DNA sequence. Finally, the term is intended to indicate an alpha-amylase, which is encoded by a DNA sequence of synthetic and/or cDNA origin and which has the identifying characteristics of the alpha-amylase in question. The term is also intended to indicate that the parent alpha-amylase may be a variant of a naturally occurring alpha-amylase, i.e., a variant, which is the result of a modification (insertion, substitution, deletion) of one or more amino acid residues of the naturally occurring alpha-amylase.

Parent Termamyl-Like Alpha-amylases

According to the invention all Termamy-like alpha-amylases, as defined above, may be used as the parent (i.e., backbone) alpha-amylase. In a preferred embodiment of the invention the parent alpha-amylase is derived from *B. licheniformis*, e.g., one of those referred to above, such as the *B. licheniformis* alpha-amylase having the amino acid sequence shown in SEQ ID NO: 10. Especially preferred parent alpha-amylases are the SP722 alpha-amylase and the AA560 alpha-amylase. In one embodiment the parent alpha-amyase has one or more of the following mutations/substitutions: Delta (R81-G182); Delta (D183-G184); Delta (D183-G184)+N195F; RR181 Q+N445Q+K446N; Delta (D183-G184)+R181Q.

Parent Hybrid Termamyl-Like Alpha-amylases

The parent alpha-amylase (i.e., backbone alpha-amylase) may also be a hybrid alpha-amylase, i.e., an alpha-amylase, which comprises a combination of partial amino acid sequences derived from at least two alpha-amylases.

The parent hybrid alpha-amylase may be one, which on the basis of amino acid homology (identity) and/or DNA hybridization (as defined above) can be determined to belong to the Termamyl-like alpha-amylase family. In this case, the hybrid alpha-amylase is typically composed of at least one part of a Termamyl-like alpha-amylase and part(s) of one or more other alpha-amylases selected from Termamyl-like alpha-amylases or non-Termamyl-like alpha-amylases of microbial (bacterial or fungal) and/or mammalian origin.

Thus, the parent hybrid alpha-amylase may comprise a combination of partial amino acid sequences deriving from at least two Termamyl-like alpha-amylases, or from at least one Termamyl-like and at least one non-Termamyl-like bacterial alpha-amylase, or from at least one Termamyl-like and at least one fungal alpha-amylase. The Termamyl-like alpha-amylase from which a partial amino acid sequence derives, may be any of those specific Termamyl-like alpha-amylase referred to herein.

For instance, the parent alpha-amylase may comprise a C-terminal part of an alpha-amylase derived from a strain of *B. licheniformis*, and a N-terminal part of an alpha-amylase derived from a strain of *B. amyloliquefaciens* or from a strain of *B. stearothermophilus*. For instance, the parent α-amylase may comprise at least 430 amino acid residues of the C-terminal part of the *B. licheniformis* alpha-amylase, and may, e.g., comprise a) an amino acid segment corresponding to the 37 N-terminal amino acid residues of the *B. amyloliquefaciens* alpha-amylase having the amino acid sequence shown in SEQ ID NO: 10 and an amino acid segment corresponding to the 445 C-terminal amino acid residues of the *B. licheni-*

*formis* alpha-amylase having the amino acid sequence shown in SEQ ID NO: 8, or a hybrid Termamyl-like alpha-amylase being identical to the Termamyl sequence, i.e., the *Bacillus licheniformis* alpha-amylase shown in SEQ ID NO: 8, except that the N-terminal 35 amino acid residues (of the mature protein) has been replaced by the N-terminal 33 residues of BAN (mature protein), i.e., the *Bacillus amyloliquefaciens* alpha-amylase shown in SEQ ID NO: 10; or b) an amino acid segment corresponding to the 68 N-terminal amino acid residues of the *B. stearothermnophilus* α-amylase having the amino acid sequence shown in SEQ ID NO: 6 and an amino acid segment corresponding to the 415 C-terminal amino acid residues of the *B. licheniformis* alpha-amylase having the amino acid sequence shown in SEQ ID NO: 8.

Another suitable parent hybrid alpha-amylase is the one previously described in WO 96/23874 (from Novo Nordisk) constituting the N-terminus of BAN, *Bacillus amyloliquefaciens* alpha-amylase (amino acids 1-300 of the mature protein) and the C-terminus from Termamyl (amino acids 301-483 of the mature protein).

Altered Properties

The following discusses the relationship between mutations, which are present in variants of the invention, and desirable alterations in properties (relative to those a parent Termamyl-like alpha-amylase), which may result therefrom.

As mentioned above the invention relates to Termamyl-like alpha-amylases with altered properties, in particular under production conditions.

Parent Termamyl-like alpha-amylase specifically contemplated in connection with going through the specifically contemplated altered properties are the above mentioned parent Termamyl-like alpha-amylase and parent hydrid Termamyl-like alpha-amylases. The SP722 alpha-amylase is used as the starting point, but corresponding positions in, e.g., the Termamyl, BSG, BAN, AA560, SP690, AA180, KSM AP1378, and #707, K38, and K36 should be understood as disclosed too.

In a preferred embodiment the variant of the invention has increased solubility, in particular under washing or cleaning conditions.

In an aspect the invention relates to variant with altered properties as mentioned above.

In the first aspect a variant of a parent Termamyl-like alpha-amylase, comprising an alteration at one or more positions (using SEQ ID NO: 12 for the amino acid numbering) selected from the group consisting of:
R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, and N484, wherein
(a) the alteration(s) are independently
(i) an insertion of an amino acid downstream of the amino acid which occupies the position,
(ii) a deletion of the amino acid which occupies the position, or
(iii) a substitution of the amino acid which occupies the position with a different amino acid,
(b) the variant has alpha-amylase activity and
(c) each position corresponds to a position of the amino acid sequence of SEQ ID NO: 12.

In SP722 (SEQ ID NO: 4) such corresponding positions are: R28; N94; L118; N125; Q174; R181; G182; D183; G184; A186; W189; N195, M202, Y298; N299; N302; S303; N306; A310; N314; K320; H324; Q345; F396, T400, W439, Q444; N445, K446, Q449, K458; N471, and K484.

In a preferred embodiment the variant of the invention (using SEQ ID NO: 12 for the numbering) has one or more of the following mutations/substitutions:
Delta G184; Delta (R181-G182); Delta (D183-G184); R28N, K; S94K; R118K; N125A,R,K; N174D; R181Q,E,K; G186R; W189R,K; N195F; M202L; Y298H,F; N299A; K302R, S303Q, N306G,D,R,K; R310A,K,Q,E,H,D,N; N314D; R320K; H324K; E345R,D,K,N; Y396F; R400T, K; W439R; R444K; N445K,Q; K446N; Q449E; R458K; N471 E; N484Q.

Preferred double, triple and multi-mutations—using SEQ ID NO: 12 as the basis for the numbering—include:
Delta(D183-G184)+R181Q;
Delta(D183-G184)+G186R;
Delta(D183-G184)+N195F;
Delta(D183-G184)+M202L;
Delta(D183-G184)+G186R+N195F;
Delta(D183-G184)+N195F+R400T;
Delta(D183-G184)+N195F+W439R;
Delta(D183-G184)+N195F+Q449E;
Delta(D183-G184)+N195F+N484Q;
Delta(D183-G184)+N195F+K446N;
Delta(D183-G184)+N195F+N445Q+K446N+N484E;
Delta(D183-G184)+N195F+N445Q+K446N+Q449E;
Delta(D183-G184)+N195F+N471E;
Delta(D183-G184)+N195F+H324K;
Delta(D183-G184)+N195F+Y396F;
Delta(D183-G184)+N195F+K446D;
Delta(D183-G184)+N195F+R181Q;
Delta(D183-G184)+N195F+R181E;
Delta(D183-G184)+N195F+N445Q+K446N;
N445Q+K446N;
N445Q+K446N+N484E;
N445Q+K446N+Q449E;
Delta (D183-G184)+N195F+R181Q+N445Q+K446N;
Delta (D183-G184)+N195F+R181Q+K446N;
Delta (D183-G184)+N195F+R181Q+N445Q+K446N+N484E;
Delta (D183-G184)+N195F+R181E+N445Q+K446N;
Delta (D183-G184)+N195F+R181E+K446N;
Delta (D183-G184)+N195F+R181E+N445Q+K446N+N484E;
Delta (D183-G184)+N195F+N445Q+K446N+Y243F;
Delta (D183-G184)+N195F+N445Q+K446N+V209I;
Delta (D183-G184)+N195F+E212R;
Delta (D183-G184)+N195F+M116R;
Delta (D183-G184)+N195F+K142H+D144H+R158H;
Delta (D183-G184)+N195F+K142H+D144H;
Delta (D183-G184)+N195F+R158H;
Delta (D183-G184)+N195F+E345R;
Delta (D183-G184)+N195F+W189R;
Delta (D183-G184)+N195F+Y298H;
Delta (D183-G184)+N195F+N299A;
Delta (D183-G184)+N195F+K302R+S303Q;
Delta (D183-G184)+N195F+N306G;
Delta (D183-G184)+N195F+Y298H+N299A+K302R+S303Q+N306G;
Delta (D183-G184)+N195F+N125A;
Delta (D183-G184)+N195F+N125R;
Delta (D183-G184)+N195F+R181Q+N445Q+K446N+R310A;
Delta (D183-G184)+N195F+R181Q+N445Q+K446N+R310A+Q311N;
Delta (D183-G184)+N195F+R181Q+N445Q+K446N+R320K;
Delta (D183-G184)+N195F+R181Q+N445Q+K446N+Q319K+R320D;

Delta (D183-G184)+N195F+R181Q+N445Q+K446N+ N306A; 5Delta (D183-G184)+N195F+R181Q+N445Q+ K446N+K302N;
Delta (D183-G184)+N195F+R181Q+N445Q+K446N+ E345N;
Delta (D183-G184)+N195F+R181Q+N445Q+K446N+ Y298F;
Delta (D183-G184)+N195F+R181Q+N445Q+K446N+ R28N;
Delta (D183-G184)+N195F+R181Q+N445Q+K446N+ R28N+R310A;
Delta (D183-G184)+N195F+R181Q+N445Q+K446N+ N128D+N306D;
Delta (D183-G184)+N195F+R181Q+N445Q+K446N+ N128D;
Delta (D183-G184)+N195F+R181Q+N445Q+K446N+ N306D;
N174D+N314D;
Delta (D183-G184)+N195F+N306D+R310H+E345D;
Delta(D183-G184)+R181Q+N195F+W189R+S94K;
Delta(D183-G184)+R181Q+W189R+S94K;
Delta(D183-G184)+N195F+R181Q+S94K;
Delta(D183-G184)+N195F+R181K+N125R;
Delta(D183-G184)+N195F+R181K+N125K;
Delta(D183-G184)+N195F+R118K+R320K+R458K;
Delta(D183-G184)+R181Q+N195F+R118K+R320K+ R458K;
Delta(D183-G184)+N195F+R181Q+N306G;
Delta(D183-G184)+N195F+R181Q+W189R;
Delta(D183-G184)+R181Q+N195F+R118K+N125K+ R444K+N445K
Delta(D183-G184)+R181Q+N195F+R118K+N125K+ R320K+R458K;
Delta(D183-G184)+R181Q+N195F+R118K+N125R+ R320K+R458K;
Delta(D183-G184)+R181Q+N195F+S94K+R118K+ R320K+R458K;
Delta(D183-G184)+R181Q+N195F+R118K+N306R+ R320K+R458K;
Delta(D183-G184)+N195F+R118K+R320K+R458K+ R444K+N445K;
Delta(D183-G184)+N195F+S94K+R118K+N306R+ R320K+R458K;

Contemplated variants include the specific ones mentioned in the examples and the above mention mutations in further combination with one or more of the mutations/substitution: Delta (D183-G184); N195F; R181Q; G186R; M202L; V206F,L,M; N193S,T,P Increased Solubility All the above-mentioned mutations result in Termamyl-like alpha-amylase variants with altered solubility when used in any alpha-amylase within the group of Termamyl-like alpha-amylase as defined above.

Thus, in a preferred embodiment the variant of the invention is a variant of a parent Termamyl-like alpha-amylase, which has increased solubility (as defined) in comparison to the parent Termemyl-like alpha-amylase, comprising an alteration at one or more positions (using SEQ ID NO: 12 for the amino acid numbering) selected from the group of:
R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484, wherein
(a) the alteration(s) are independently
  (i) an insertion of an amino acid downstream of the amino acid which occupies the position,
  (ii) a deletion of the amino acid which occupies the position, or
  (iii) a substitution of the amino acid which occupies the position with a different amino acid,
(b) the variant has alpha-amylase activity and
(c) each position corresponds to a position of the amino acid sequence of SEQ ID NO: 12.

In a preferred embodiment a variant of the invention with increased solubility in comparison to the parent alpha-amylase has one or more of the following substitutions:
Delta G184; Delta (R181-G182); Delta (D183-G184); R28N, K; S94K; R118K; N125A,R,K; N174D; R181Q,E,K; G186R; W189R,K; N195F; M202L; Y298H,F; N299A; K302R, S303Q, N306G,D,R,K; R310A,K,Q,E,H,D,N; N314D; R320K; H324K; E345R,D,K,N; Y396F; R400T, K; W439R; R444K; N445K,Q; K446N; Q449E; R458K; N471E; N484Q.

In a more preferred embodiment variant of the invention with increased solubility (determined using one of the methods described in the "Materials and Methods" section)— using SEQ ID NO: 12 as the basis for the numbering— include:
Delta(D183-G184)+R181Q;
Delta(D183-G184)+G186R;
Delta(D183-G184)+N195F;
Delta(D183-G184)+M202L;
Delta(D183-G184)+G186R+N195F;
Delta(D183-G184)+N195F+R400T;
Delta(D183-G184)+N195F+W439R;
Delta(D183-G184)+N195F+Q449E;
Delta(D183-G184)+N195F+N484Q;
Delta(D183-G184)+N195F+K446N;
Delta(D183-G184)+N195F+N445Q+K446N+N484E;
Delta(D183-G184)+N195F+N445Q+K446N+Q449E;
Delta(D183-G184)+N195F+N471E;
Delta(D183-G184)+N195F+H324K;
Delta(D183-G184)+N195F+Y396F;
Delta(D183-G184)+N195F+K446D;
Delta(D183-G184)+N195F+R181Q;
Delta(D183-G184)+N195F+R181E;
Delta(D183-G184)+N195F+N445Q+K446N;
N445Q+K446N;
N445Q+K446N+N484E;
N445Q+K446N+Q449E;
Delta (D183-G184)+N195F+R181Q+N445Q+K446N;
Delta (D183-G184)+N195F+R181Q+K446N;
Delta (D183-G184)+N195F+R181Q+N445Q+K446N+ N484E;
Delta (D183-G184)+N195F+R181E+N445Q+K446N;
Delta (D183-G184)+N195F+R181E+K446N;
Delta (D183-G184)+N195F+R181E+N445Q+K446N+ N484E;
Delta (D183-G184)+N195F+N445Q+K446N+Y243F;
Delta (D183-G184)+N195F+N445Q+K446N+V209I;
Delta (D183-G184)+N195F+E212R;
Delta (D183-G184)+N195F+M116R;
Delta (D183-G184)+N195F+K142H+D144H+R158H;
Delta (D183-G184)+N195F+K142H+D144H;
Delta (D183-G184)+N195F+R158H;
Delta (D183-G184)+N195F+E345R;
Delta (D183-G184)+N195F+W189R;
Delta (D183-G184)+N195F+Y298H;
Delta (D183-G184)+N195F+N299A;

Delta (D183-G184)+N195F+K302R+S303Q;
Delta (D183-G184)+N195F+N306G;
Delta (D183-G184)+N195F+Y298H+N299A+K302R+S303Q+N306G;
Delta (D183-G184)+N195F+N125A;
Delta (D183-G184)+N195F+N125R;
Delta (D183-G184)+N195F+R181Q+N445Q+K446N+R310A;
Delta (D183-G184)+N195F+R181Q+N445Q+K446N+R310A+Q311N;
Delta (D183-G184)+N195F+R181Q+N445Q+K446N+R320K;
Delta (D183-G184)+N195F+R181Q+N445Q+K446N+Q319K+R320D;
Delta (D183-G184)+N195F+R181Q+N445Q+K446N+N306A;
Delta (D183-G184)+N195F+R181Q+N445Q+K446N+K302N;
Delta (D183-G184)+N195F+R181Q+N445Q+K446N+E345N;
Delta (D183-G184)+N195F+R181Q+N445Q+K446N+Y298F;
Delta (D183-G184)+N195F+R181Q+N445Q+K446N+R28N;
Delta (D183-G184)+N195F+R181Q+N445Q+K446N+R28N+R310A;
Delta (D183-G184)+N195F+R181Q+N445Q+K446N+NR28D+N306D;
Delta (D183-G184)+N195F+R181Q+N445Q+K446N+N128D;
Delta (D183-G184)+N195F+R181Q+N445Q+K446N+N306D;
N174D+N314D;
Delta (D183-G184)+N195F+N306D+R310H+E345D;
Delta(D183-G184)+R181Q+N195F+W189R+S94K;
Delta(D183-G184)+R181Q+W189R+S94K;
Delta(D183-G184)+N195F+R181Q+S94K;
Delta(D183-G184)+N195F+R181K+N125R;
Delta(D183-G184)+N195F+R181K+N125K;
Delta(D183-G184)+N195F+R118K+R320K+R458K;
Delta(D183-G184)+R181Q+N195F+R118K+R320K+R458K;
Delta(D183-G184)+N195F+R181Q+N306G;
Delta(D183-G184)+N195F+R181Q+W189R;
Delta(D183-G184)+R181Q+N195F+R118K+N125K+R444K+N445K
Delta(D183-G184)+R181Q+N195F+R118K+N125K+R320K+R458K;
Delta(D183-G184)+R181Q+N195F+R118K+N125R+R320K+R458K;
Delta(D183-G184)+R181Q+N195F+S94K+R118K+R320K+R458K;
Delta(D183-G184)+R181Q+N195F+R118K+N306R+R320K+R458K;
Delta(D183-G184)+N195F+R118K+R320K+R458K+R444K+N445K;
Delta(D183-G184)+N195F+S94K+R118K+N306R+R320K+R458K;

Other combinations according to the invention include the specific one mentioned in the examples and one or more of the following substitutions: N195F; R181Q; G186R; M202L; V206F,L,M, N193P.

Stability

In the context of the present invention, mutations (including amino acid substitutions and deletions) of importance with respect to achieving altered stability, in particular improved stability (i.e., higher or lower), at especially high pH (i.e., pH 8-10.5) include any of the mutations listed in the in "Altered properties" section.

$Ca^{2+}$ Stability

Altered $Ca^{2+}$ stability means the stability of the enzyme under $Ca^{2+}$ depletion has been improved, i.e., higher or lower stability. In the context of the present invention, mutations (including amino acid substitutions and deletions) of importance with respect to achieving altered $Ca^{2+}$ stability, in particular improved $Ca^{2+}$ stability, i.e., higher or lower stability, at especially high pH (i.e., pH 8-10.5) include any of the mutations listed in the in "Altered properties" section.

Specific Activity

In a further aspect of the present invention, important mutations (including amino acid substitutions and deletions) with respect to obtaining variants exhibiting altered specific activity, in particular increased or decreased specific activity, especially at temperatures from 10-60° C., preferably 20-50° C., especially 30-40° C., include any of the mutations listed in the in "Altered properties" section.

General Mutations in Variants of the Invention

The particularly interesting mutations (including amino acid substitutions and deletions) are those that increase the mobility around the active site of the enzyme. This is accomplished by changes that disrupt stabilizing interaction in the vicinity of the active site, i.e., within preferably 10 Å or 8 Å or 6 Å or 4 Å from any of the residues constituting the active site.

Examples are mutations that reduce the size of side chains, such as

Ala to Gly,
Val to Ala or Gly,
Ile or Leu to Val, Ala, or Gly
Thr to Ser.

Such mutations are expected to cause increased flexibility in the active site region either by the introduction of cavities or by the structural rearrangements that fill the space left by the mutation.

It may be preferred that a variant of the invention comprises one or more modifications in addition to those outlined above. Thus, it may be advantageous that one or more Proline residues present in the part of the alpha-amylase variant which is modified is/are replaced with a non-Proline residue which may be any of the possible, naturally occurring non-Proline residues, and which preferably is an Alanine, Glycine, Serine, Threonine, Valine or Leucine.

Analogously, it may be preferred that one or more Cysteine residues present among the amino acid residues with which the parent alpha-amylase is modified is/are replaced with a non-Cysteine residue such as Serine, Alanine, Threonine, Glycine, Valine or Leucine.

Furthermore, a variant of the invention may—either as the only modification or in combination with any of the above outlined modifications—be modified so that one or more Asp and/or Glu present in an amino acid fragment corresponding to the amino acid fragment 185-209 of SEQ ID NO: 10 is replaced by an Asn and/or Gln, respectively. Also of interest is the replacement, in the Termamyl-like alpha-amylase, of one or more of the Lys residues present in an amino acid fragment corresponding to the amino acid fragment 185-209 of SEQ ID NO: 10 by an Arg.

It will be understood that the present invention encompasses variants incorporating two or more of the above outlined modifications.

Furthermore, it may be advantageous to introduce mutations in one or more of the following positions (using SEQ ID NO: 10 (Termamyl™) for the numbering): M15, V128, A111, H133, W138, T149, M197, N188, A209, A210, H405, T412, in particular the following single, double or triple or multi mutations:

M15X, in particular M15T,L;
V128X, in particular V128E;
H133X, in particular H133Y;
N188X, in particular N188S,T,P;
M197X, in particular M197T,L;
A209X, in particular A209V;
M197T/W138F; M197T/W138Y; M15T/H133Y/N188S;
M15N128E/H133Y/N188S; E119C/S130C; D124C/R127C; H133Y/T149I;
G475R, H133Y/S187D; H133Y/A209V;

In AA560 this corresponds to
L17X, in particular L17T;
E130X;
Y135X;
W140X, In particular W140F,Y;
T193X; in particular S,P;
M202X, in particular M202T,L;
V214X;

Contemplated combinations thereof, include
M202T/W140F; M202T/W140Y; L17T/T193S;
L17T/N193P; E121C/S132C; N126C/Q129C; T151I;
G480R.

Methods for Preparing Alpha-amylase Variants of the Invention

Several methods for introducing mutations into genes are known in the art. After a brief discussion of the cloning of alpha-amylase-encoding DNA sequences, methods for generating mutations at specific sites within the alpha-amylase-encoding sequence will be discussed.

Cloning a DNA Sequence Encoding an Alpha-amylase

The DNA sequence encoding a parent alpha-amylase may be isolated from any cell or microorganism producing the alpha-amylase in question, using various methods well known in the art. First, a genomic DNA and/or cDNA library should be constructed using chromosomal DNA or messenger RNA from the organism that produces the alpha-amylase to be studied. Then, if the amino acid sequence of the alpha-amylase is known, homologous, labeled oligonucleotide probes may be synthesized and used to identify alpha-amylase-encoding clones from a genomic library prepared from the organism in question. Alternatively, a labeled oligonucleotide probe containing sequences homologous to a known alpha-amylase gene could be used as a probe to identify alpha-amylase-encoding clones, using hybridization and washing conditions of lower stringency.

Yet another method for identifying alpha-amylase-encoding clones would involve inserting fragments of genomic DNA into an expression vector, such as a plasmid, transforming alpha-amylase-negative bacteria with the resulting genomic DNA library, and then plating the transformed bacteria onto agar containing a substrate for alpha-amylase, thereby allowing clones expressing the alpha-amylase to be identified.

Alternatively, the DNA sequence encoding the enzyme may be prepared synthetically by established standard methods, e.g., the phosphoroamidite method described by S. L. Beaucage and M. H. Caruthers, *Tetrahedron Letters* 22, 1981, pp. 1859-1869 or the method described by Matthes et al., *The EMBO J.* 3, 1984, pp. 801-805. In the phosphoroamidite method, oligonucleotides are synthesized, e.g., in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al., *Science* 239, 1988, pp. 487-491.

Expression of Alpha-amylase Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding an alpha-amylase variant of the invention may be any vector that may conveniently be subjected to recombinant DNA procedures, and the choice of vector will often depend on the host cell into which it is to be introduced. Thus, the vector may be an autonomously replicating vector, i.e., a vector which exists as an extrachromosomal entity, the replication of which is independent of chromosomal replication, e.g., a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the DNA sequence encoding an alpha-amylase variant of the invention, especially in a bacterial host, are the promoter of the lac operon of *E. coli*, the *Streptomyces coelicolor* agarase gene dagA promoters, the promoters of the *Bacillus licheniformis* alpha-amylase gene (amyL), the promoters of the *Bacillus stearothermophilus* maltogenic amylase gene (amyM), the promoters of the *Bacillus amyloliquefaciens* alpha-amylase (amyQ), the promoters of the *Bacillus subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral alpha-amylase, *A. niger* acid stable alpha-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding the alpha-amylase variant of the invention. Termination and polyadenylation sequences may suitably be derived from the same sources as the promoter.

The vector may further comprise a DNA sequence enabling the vector to replicate in the host cell in question.

Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation, e.g., as described in WO 91/17243.

While intracellular expression may be advantageous in some respects, e.g., when using certain bacteria as host cells, it is generally preferred that the expression is extracellular. In general, the *Bacillus* α-amylases mentioned herein comprises a preregion permitting secretion of the expressed protease into the culture medium. If desirable, this preregion may be replaced by a different preregion or signal sequence, conveniently accomplished by substitution of the DNA sequences encoding the respective preregions.

The procedures used to ligate the DNA construct of the invention encoding an alpha-amylase variant, the promoter, terminator and other elements, respectively, and to insert them into suitable vectors containing the information necessary for replication, are well known to persons skilled in the art (cf., for instance, Sambrook et al., Molecular Cloning: A Laboratory Manual, 2nd Ed., Cold Spring Harbor, 1989).

The cell of the invention, either comprising a DNA construct or an expression vector of the invention as defined above, is advantageously used as a host cell in the recombinant production of an alpha-amylase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g., a bacterial or a fungal (including yeast) cell. Examples of suitable bacteria are Gram-positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis*, or *Streptomyces lividans* or *Streptomyces murinus*, or gramnegative bacteria such as *E. coli*. The transformation of the bacteria may, for instance, be effected by protoplast transformation or by using competent cells in a manner known per se.

The yeast organism may favorably be selected from a species of *Saccharomyces* or *Schizosaccharomyces*, e.g. *Saccharomyces cerevisiae*. The filamentous fungus may advantageously belong to a species of *Aspergillus*, e.g., *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of *Aspergillus* host cells is described in EP 238 023.

In a yet further aspect, the present invention relates to a method of producing an alpha-amylase variant of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the alpha-amylase variant of the invention. Suitable media are available from commercial suppliers or may be prepared according to published recipes (e.g., as described in catalogues of the American Type Culture Collection).

The alpha-amylase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Industrial Applications

The alpha-amylase variants of this invention possess valuable properties allowing for a variety of industrial applications. In particular, enzyme variants of the invention are applicable as a component in washing, dishwashing and hard surface cleaning detergent compositions. Variant of the invention with altered properties may be used for starch processes, in particular starch conversion, especially liquefaction of starch (see, e.g., U.S. Pat. No. 3,912,590, EP patent publications Nos. 252 730 and 63 909, and WO 99/19467.

Further, variants of the invention are also particularly useful in the production of sweeteners and ethanol from starch, and/or for textile desizing.

Composition

In an aspect the invention relates to a composition comprising a variant of the invention. In an embodiment the composition of the invention comprises one or more other enzymes, including one or more selected from the group of such as a lipase, cutinase, protease, cellulase, mannanase, maltogenic amylase, CGTase, glucoamylase, peroxidase or laccase, and/or another alpha-amylase.

Detergent Compositions

As mentioned above, variants of the invention may suitably be incorporated in detergent compositions. Reference is made, for example, to WO 96/23874 and WO 97/07202 for further details concerning relevant ingredients of detergent compositions (such as laundry or dishwashing detergents), appropriate methods of formulating the variants in such detergent compositions, and for examples of relevant types of detergent compositions.

Detergent compositions comprising a variant of the invention may additionally comprise one or more other enzymes, such as a lipase, cutinase, protease, cellulase, mannanase, maltogenic amylase, CGTase, glucoamylase, peroxidase or laccase, and/or another alpha-amylase.

Alpha-amylase variants of the invention may be incorporated in detergents at conventionally employed concentrations. It is at present contemplated that a variant of the invention may be incorporated in an amount corresponding to 0.00001-10 mg (calculated as pure, active enzyme protein) of alpha-amylase per liter of wash/dishwash liquor using conventional dosing levels of detergent.

The invention also relates to a method of providing alpha-amylases with altered properties relative to the parent alpha-amylase, in particular solubility, especially increased solubility, substrate specificity, substrate binding, substrate cleavage pattern, temperature stability, pH dependence of enzymatic activity, pH dependence of stability, stability towards oxidation, $Ca^{2+}$-dependency and specific activity, comprising the following steps:

(a) modeling the parent alpha-amylase on the three-dimensional structure of SEQ ID NO:4 depicted in the Appendix 1 to produce a three-dimensional structure of the parent alpha-amylase;

(b) identifying in the three-dimensional structure obtained in step (a) at least one structural part of the parent wherein an alteration in said structural part is predicted to result in said altered property;

(c) modifying the sequence of a nucleic acid encoding the parent alpha-amylase to produce a nucleic acid encoding a deletion, insertion, or substitution of one or more amino acids at a position corresponding to said structural part; and (d) expressing the modified nucleic acid in a host cell to produce the variant alpha-amylase, wherein the variant has alpha-amylase enzymatic activity and has at least one altered property relative to the parent.

In an embodiment the method is a method of constructing a variant of a parent alpha-amylase having an altered property relative to the parent, wherein the parent alpha-amylase has the sequence of SEQ ID NOS: 2, 4, 6, 8, 10, 12 or 13 or has a sequence at least 60% identity (determined as described above) to said sequence, said method comprising:

(a) modeling the parent alpha-amylase on the three-dimensional structure of SEQ ID NO:4 depicted in the Appendix 1 to produce a three-dimensional structure of the parent alpha-amylase;

(b) comparing the three-dimensional structure obtained in step (a) with a three-dimensional structure of an unrelated alpha-amylase, wherein the unrelated alpha-amylase differs from the parent alpha-amylase in said property;

(c) identifying a structural part of the three-dimensional structure obtained in step (a) which is different from the three-dimensional structure of the unrelated alpha-amylase and which is predicted to be relevant to said property, (d) modifying the sequence of a nucleic acid encoding the parent alpha-amylase to produce a nucleic acid encoding a deletion, insertion, or substitution of one or more amino acids at a position corresponding to said structural part; and (e) expressing the modified nucleic acid in a host cell to produce the variant alpha-amylase, wherein the variant has alpha-amylase activity and has one or more altered properties as compared to the parent alpha-amylase.

The Termamyl-like alpha-amylases contemplated are the ones described above.

Method of Increasing the Solubility of Polypeptides

The present invention also relates to a method of increasing the solubility of polypeptides, such as enzymes, in particular Termamyl-like alpha-amylases.

The method of this invention comprises substitutions, insertions and/or deletion of one or more amino acid residue(s), which residue(s) hold a position close to a neighbour polypeptide molecule located in the protein crystal. In the context of this invention, a polypeptide amino acid residue holding a position close to the neighbour molecule indicates an amino acid residue located within the polypeptide in a way that it is within a potential intermolecular interactive distance from an amino acid residue located at a neighbour enzyme molecule in the crystal or precipitate.

Examples of potential intermolecular interactions include, but are not limited to hydrogen bonding, salt bridge formation, polar interactions, hydrophobic interactions and aromatic interactions.

The term "neighboring" means in the context of the present invention the shortest distance between two positions in a crystal structure being prepared, e.g., as described in "Protein Crystallization Techniques, Strategies, and Tips", A Laboratory Manual by Terese M. Bergfors), or as describe on the Internet on the site: hamptonresearch.com.

Thus, in this aspect the invention relates to a method of increasing the solubility of enzyme crystals, wherein one or more amino acid residue(s), 1) located within a distance of 6.0 Å of a neighbouring polyptide molecule in the tertiary crystal structure, and 2) interacting with said neighbouring polypeptide molecule, are mutated, e.g., by substitution or deletion.

In a preferred embodiment the amino acid residues to be mutated are located with 3.5 Å of a neighbouring polypeptide.

Contemplated polypeptides include antimicrobial polypeptides, polypeptides with biological activity, such as insulin, growth hormone, EPO, TPO, Factor VII, Factor VIII.

Contemplated enzyme activities include protease, amylase, CGTase, carbohydrase, transferase, lyase, oxidoreductase, lipase, cellulase, cutinase, pectate lyase, mannanase, maltogenic amylase, glucoamylase, pectin lyase activity.

In a preferred embodiment the enzyme is an amylase, preferably an alpha-amylase, especially a Termamyl-like alpha-amylase as will be described further below.

An amino acid position "close" to the substrate indicates a distance less than 6 Å (angstrom) corresponding to a protein-protein interaction mediated by a single water molecule. In a preferred embodiment an amino acid position close to the substrate indicates a distance less than 3.5 Å (angstrom) corresponding to a direct protein-protein interaction.

Method of Increasing the Solubility of Termamyl-Like Alpha-amylases

In this aspect the invention relates to a method of increasing the solubility of Termamyl-like alpha-amylase crystals, wherein one or more amino acid residue(s), 1) located within a distance of 6.0 Å of a neighbouring Termamyl-like alpha-amylase molecule in the tertiary crystal structure, and 2) interacting with said neighbouring Termamyl-like alpha-amylase molecule, are mutated, e.g., by substitution or deletion.

In a preferred embodiment the amino acid residues to be mutated are located with 3.5 Å of a neighbouring Termamyl-like alpha-amylase. The crystal structure of SP722 depicted in APPENDIX 1 may be used as the reference (fix-point) for determining the distance between neighbouring alpha-amylases.

However, it is within the scope of the invention that the reference (fix-point) crystal structure is a structure modelled (as described above or in WO 96/23874) from SP722 depicted in APPENDIX 1.

Preferred Termamyl-like alpha-amylases include *Bacillus* alpha-amylase selected from the group consisting of alpha-amylase derived from a strain of *B. licheniformis, B. amyloliquefaciens, B. stearothermophilus, Bacillus* sp. NCIB 12289, NCIB 12512, NCIB 12513 or DSM 9375, or DSMZ no. 12649, KSM AP1378.

Termamyl-like alpha-amylase may be any of the alpha-amylases selected from the group depicted in SEQ ID NOS: 2, 4, 6, 8, 10, 12, and 13, or Termamyl-like alpha-amylase having an amino acid sequence which has a degree of identity to SEQ ID NO: 4 of at least 60%, preferably 70%, more preferably at least 80%, even more preferably at least about 90%, even more preferably at least 95%, even more preferably at least 97%, and even more preferably at least 99%, or Termamyl-like alpha-amylase encoded by a nucleic acid sequence, which hydridizes under low, preferably medium, preferred high stringency conditions, with the nucleic acid sequence of SEQ ID NO: 11. The conditions are described in further details above.

Termamyl-like alpha-amylase amino acid residues being less than 6.0 Å from the nearest neighbour amylase molecule are the following (using the SP722 numbering): 19, 20, 21, 22, 25, 28, 29, 53, 76, 84, 87, 90, 93, 94, 124, 125, 126, 128, 142, 144, 156, 157, 158, 159, 160, 161, 170, 171, 172, 173, 174, 175, 183, 184, 185, 186, 187, 188, 189, 190, 193, 195, 196, 197, 209, 212, 226, 229, 256, 257, 258, 259, 280, 281, 298, 299, 300, 302, 303, 304, 305, 306, 310, 311, 314, 319, 320, 321, 322, 341, 345, 405, 406, 408, 444, 447, 448, 449, 463, 464, 465, 466, 467.

Termamyl-like alpha-amylase amino acid residues being less than 3.5 Å from the nearest neighbour amylase molecule are the following (using the SP722 numbering): 22, 25, 28, 76, 94, 125, 128, 158, 160, 171, 173, 174, 184, 189, 209, 226, 229, 298, 299, 302, 306, 310, 314, 320, 345, 405, 447, 466.

The amino acid residues being less than 6.0 Å from the nearest neighboring amylase molecule are the following positions identified in the model structure of the SP722 amylase: ASN 19, ASP 20, GLY 21, GLN 22, ASN 25, ARG 28, ASP 29, GLN 53, ARG 76, GLN 84, SER 87, HIS 90, LYS 93, ASN 94, ASN 125, ASN 126, ASN 128, LYS 142, ASP 144, LYS 156, TRP 157, ARG 158, TRP 159, TYR 160, HIS 161, PHE 173, GLN 174, ASN 175, ASP 183, GLY 184, LYS 185, ALA 186, TRP 187, ASP 188, TRP 189, GLU 190, SER 193, GLY 196, ASN 197, ASP 209, GLU 212, ASN 226, ASN 229, ALA 256, THR 257, GLY 258, LYS 259, ASN 280, LYS 281, TYR 298, ASN 299, ALA 300, ASN 302, SER 303, GLY 304, GLY 305, ASN 306, ALA 310, ASN 314, GLN 319, LYS 320, HIS 321, PRO 322, GLU 341, GLN 345, PHE 405, ASP 406, HIS 408, GLN 444, ALA 447, GLY 448, GLN 449, THR 463, ILE 464, ASN 465, ALA 466, ASP 467.

The amino acid residues being less than 3.5 Å from the nearest neighboring amylase molecule are the following positions identified in the model structure of the SP722 amylase: GLN 22, ASN 25, ARG 28, ARG 76, ASN 94, ASN 125, ASN 128, ARG 158, TYR 160, PHE 173, GLN 174, GLY 184, TRP 189, ASP 209, ASN 226, ASN 229, TYR 298, ASN 299, ASN 302, ASN 306, ASN 314, LYS 320, GLN 345, PHE 405, ALA 447, ALA 466.

The amino acid residues being less than 6.0 Å from the nearest neighboring amylase molecule are the following positions identified in the model structure of the AA560 amylase: ASN 19, ASP 20, ASN 22, ASN 25, ARG 28, SER 29, GLN 53, ARG 76, GLN 84, ALA 87, ASN 90, LYS 93, SER 94, PRO 124, ASN 125, ASN 126, ASN 128, LYS 142, ASP 144, LYS 156, TRP 157, ARG 158, TRP 159, TYR 160, HIS 161, SER 170, ARG 171, LYS 172, LEU 173, ASN 174, ASN 175, ASP 183, GLY 184, LYS 185, GLY 186, TRP 187, ASP 188, TRP 189, GLU 190, THR 193, ASN 195, GLY 196, ASN 197, ASP 209, GLU 212, ASN 226, GLY 229, ALA 256, THR 257, GLY 258, LYS 259, LYS 281, TYR 298, ASN 299, ALA 300, LYS 302, SER 303, GLY 304, ASN 306, ARG 310, GLN 311, ASN 314, GLN 319, ARG 320, HIS 321, PRO 322, GLU 341, GLU 345, LEU 405, HIS 408, ARG 444, ALA 447, GLY 448, GLN 449, THR 463, ILE 464, ASN 465, ALA 466, ASP 467.

The amino acid residues being less than 3.5 Å from the nearest neighboring amylase molecule are the following positions identified in the model structure of the AA560 amylase: ARG 28, ASN 125, ASN 128, ARG 158, TYR 160, ARG 171, LEU 173, ASN 174, GLY 184, TRP 189, GLY 196, ASP 209, ASN 226, TYR 298, ASN 299, LYS 302, ASN 306, ARG 310, ASN 314, ARG 320, GLU 345, ALA 447, ALA 466.

Substitutions in Alpha-amylases Leading to Higher Solubility and Thus to Higher Performance In general, any substitutions disturbing or destroying a protein-protein interaction of any kind will lead to higher solubility and thus to higher performance in a particular application. An amino acid residue participating in protein-protein interaction may thus be changed to a larger, a smaller, more hydrophobic, more hydrophilic, to a charged or to an uncharged amino acid leading to higher solubility.

A larger amino acid residue is capable of making a steric hindance for the interaction and a smaller amino acid residue makes the distance between the interacting residues to large, weaking the interaction. Polar interaction and in particular saltbridges are destroyed by changing at least one of the involved residues to a hydrophobic residues, by changing at least one of the involved residues to a smaller residue making the distance for a strong interaction to large, or by changing at least one of the involved residues to a larger residue which make sterical hindrance. Hydrophobic interactions are effectively disturbed by changing one of the interacting amino acids to hydrophilic amino acid residues but also smaller or larger hydrophobic residues can destroy this kind of interaction. Aromatic interactions can be prevented by changing to a hydrophilic residue or to a small hydrophobic residue.

Materials and Methods

Enzymes

SP722: SEQ ID NO: 4, available from Novozymes, and disclosed in WO 95/26397.

AA560: SEQ ID NO: 12; disclosed in WO 00/60060 and available from Novozymes A/S; disclosed in Danish patent application no. PA 1999 00490; deposited on Jan. 25, 1999 at DSMZ and assigned the DSMZ no. 12649.

AA560 was deposited under the terms of the Budapest Treaty on the International Recognition of the Deposit of Microorganisms for the Purposes of Patent Procedure at Deutshe summmlung von Microorganismen und Zelikulturen GmbH (DSMZ), Mascheroder Weg 1b, D-38124 Braunschweig DE.

*Bacillus subtilis* SHA273: see WO 95/10603

Plasmids pJE1 contains the gene encoding a variant of SP722 alpha-amylase (SEQ ID NO: 4): viz. deletion of 6 nucleotides corresponding to amino acids D183-G184 in the mature protein. Transcription of the JE1 gene is directed from the amyL promoter. The plasmid further more contains the origin of replication and cat-gene conferring resistance towards kanamycin obtained from plasmid pUB110 (Gryczan, T J et al. (1978), J. Bact. 134:318-329).

Methods

Modelbuilding

Protein structure databases, such as "The Protein Data Bank (PDB) pdb.bnl.gov/"or "The Brookhaven databank at Brookhaven National Laboratory, US" are search for proteins similar to the molecule in question that a model are to be build of. The amino acid sequences are aligned taking structurally conserved regions into consideration and the coordinates are copied from the reference protein to the subject protein. The coordinates for regions with insertions and deletions are assigned either from other proteins having similar amino acid sequence, or by using the random structure generator function found In most 3D software packages, eg. in Homology from Blosym, MSI.

When coordinates have been assigned to all amino acids of the subjective protein and the fragments have been linked together, example by the commands END REPAIR and SPLICE REPAIR, in the Discover program from Biosym, MSI, the model are to be refined. The energy of the model is minimised first by relaxing the molecule (RELAX command in the Discover program) and second minimised by molecular dynamics.

References can be found in and in the manuals of homology building software, eg. Homology from Biosym, MSI.

Construction of Library Vector pDorK101

The *E. coli/Bacillus* shuttle vector pDorK101 (described below) can be used to introduce mutations without expression of alpha-amylase in *E. coli* and then be modified in such way that the alpha-amylase is active in *Bacillus*. The vector was constructed as follows: The JE1 encoding gene (SP722 with the deletion of D183-G184) was inactivated in pJE1 by gene interruption in the PstI site in the 5' coding region of SEQ ID NO: 4: SP722 by a 1.2 kb fragment containing an *E. coli* origin of replication. This fragment was PCR amplified from the pUC19 (GenBank Accession #:X02514) using the forward primer: 5'-gacctgcagtcaggcaacta-3' (SEQ ID NO: 19) and the reverse primer: 5'-tagagtcgacctgcaggcat-3' (SEQ ID NO: 20). The PCR amplicon and the pJE1 vector were digested with PstI at 37° C. for 2 hours. The pJE1 vector fragment and the PCR fragment were ligated at room temperature for 1 hour and transformed in *E. coli* by electrotransformation. The resulting vector is designated pDorK101.

Filter Screening Assays

The assay can be used to screening of Termamyl-like α-amylase variants having an improved stability at high pH compared to the parent enzyme and Termamyl-like α-amylase variants having an improved stability at high pH and medium temperatures compared to the parent enzyme depending of the screening temperature setting.

High pH Filter Assay

*Bacillus* libraries are plated on a sandwich of cellulose acetate (OE 67, Schleicher & Schuell, Dassel, Germany)— and nitrocellulose filters (Protran-Ba 85, Schleicher & Schuell, Dassel, Germany) on TY agar plates with 10 µg/ml kanamycin at 37° C. for at least 21 hours. The cellulose acetate layer is located on the TY agar plate.

Each filter sandwich is specifically marked with a needle after plating, but before incubation in order to be able to localize positive variants on the filter and the nitrocellulose filter with bound variants is transferred to a container with glycin-NaOH buffer, pH 8.6-10.6 and incubated at room temperature (can be altered from 10°-60° C.) for 15 min. The cellulose acetate filters with colonies are stored on the TY-plates at room temperature until use. After incubation, residual activity is detected on plates containing 1% agarose, 0.2% starch in glycin-NaOH buffer, pH 8.6-10.6. The assay plates with nitrocellulose filters are marked the same way as the filter sandwich and incubated for 2 hours. at room temperature. After removal of the filters the assay plates are stained with 10% Lugol solution. Starch degrading variants are detected as white spots on dark blue background and then identified on the storage plates. Positive variants are rescreened twice under the same conditions as the first screen.

Low Calcium Filter Assay

The *Bacillus* library are plated on a sandwich of cellulose acetate (OE 67, Schleicher & Schuell, Dassel, Germany)— and nitrocellulose filters (Protran-Ba 85, Schleicher & Schuell, Dassel, Germany) on TY agar plates with a relevant antibiotic, e.g., kanamycin or chloramphenicol, at 37° C. for at least 21 hours. The cellulose acetate layer is located on the TY agar plate.

Each filter sandwich is specifically marked with a needle after plating, but before incubation in order to be able to localize positive variants on the filter and the nitrocellulose filter with bound variants is transferred to a container with carbonate/bicarbonate buffer pH 8.5-10 and with different EDTA concentrations (0.001 mM-100 mM). The filters are incubated at room temperature for 1 hour. The cellulose acetate filters with colonies are stored on the TY-plates at room temperature until use. After incubation, residual activity is detected on plates containing 1% agarose, 0.2% starch in carbonate/bicarbonate buffer pH 8.5-10. The assay plates with nitrocellulose filters are marked the same way as the filter sandwich and incubated for 2 hours. at room temperature. After removal of the filters the assay plates are stained with 10% Lugol solution. Starch degrading variants are detected as white spots on dark blue background and then identified on the storage plates. Positive variants are rescreened twice under the same conditions as the first screen.

Method for Obtaining the Regions of Interest

There are three known 3D structures of bacterial α-amylases. Two of *B. licheniformis* α-amylase, Brookhaven database 1BPL (Machius et al. (1995), J. Mol. Biol. 246, p. 545-559) and 1VJS (Song et al. (1996), Enzymes for Carbohydrate 163 Engineering (Prog. Biotechnol. V 12). These two structures are lacking an important piece of the structure from the so-called B-domain, in the area around the two Calcium ions and one Sodium ion binding sites. We have therefore used a 3D structure of an alpha-amylase BA2 (WO 96/23874 which is a hybrid between BAN™ (SEQ ID NO: 5) and *B. licheniformis* alpha-amylase (SEQ ID NO: 4). On basis of the structure a model of *B. licheniformis* alpha amylase and the SP722 (α-amylase has been built.

Fermentation and Purification of α-amylase Variants

Fermentation and purification may be performed by methods well known in the art.

Stability Determination

All stability trials are made using the same set up. The method is as follows:

The enzyme is incubated under the relevant conditions (1-4). Samples are taken at various time points, e.g., after 0, 5, 10, 15 and 30 minutes and diluted 25 times (same dilution for all taken samples) in assay buffer (0.1 M 50 mM Britton buffer pH 7.3) and the activity is measured using the Phadebas assay (Pharmacia) under standard conditions pH 7.3, 37° C.

The activity measured before incubation (0 minutes) is used as reference (100%). The decline in percent is calculated as a function of the incubation time. The table shows the residual activity after, e.g., 30 minutes of incubation.

Specific Activity Determination

The specific activity is determined using the Phadebas assay (Pharmacia) as activity/mg enzyme. The manufacturer's instructions are followed (see also below under "Assay for α-amylase activity").

Solubility Determination I

Purified enzyme is dialyzed against a selected buffer overnight. Standard conditions are 0.02 M Tris-HCl, 0.15 M NaCl, pH 7.5, room temperature. A preparation, containing approximately 40 mg enzyme is concentrated on an amicon cell using Millepore ultrafiltration membranes, YM10, NMWL: 10,000. Measuring $A_{280}$ before and during the process followed concentration of the enzyme. The concentration step is stopped when precipitation started to occur. Measurement of activity in the supernatant is made to ensure that the precipitate actually is amylase. The precipitate is then dissolved again by adding buffer at room temperature and the protein concentration is measured.

Solubility Determination II

Purified enzyme is dialyzed against a selected buffer overnight. Standard conditions are 0.01 M Boric acid, 0.01 M KCl, 0.002 M $CaCl_2$, 0.15 M NaCl pH 7.5. A preparation, containing approximately 40 mg enzyme is concentrated on an amicon cell using Millepore ultrafiltration hi membranes, YM10, NMWL: 10,000. Measuring $A_{280}$ before and during the process followed concentration of the enzyme. The concentration step is stopped when precipitation started to occur. Measurement of activity in the supernatant is made to ensure that the precipitate actually is amylase. The precipitate is then dissolved again by adding buffer at room temperature and the protein concentration is measured.

Assays for Alpha-Amylase Activity

1. Phadebas Assay

Alpha-amylase activity is determined by a method employing Phadebas® tablets as substrate. Phadebas tablets (Phadebas® Amylase Test, supplied by Pharmacia Diagnostic) contain a cross-linked insoluble blue-colored starch polymer, which has been mixed with bovine serum albumin and a buffer substance and tabletted.

For every single measurement one tablet is suspended in a tube containing 5 ml 50 mM Britton-Robinson buffer (50 mM acetic acid, 50 mM phosphoric acid, 50 mM boric acid, 0.1 mM $CaCl_2$, pH adjusted to the value of interest with NaOH). The test is performed in a water bath at the temperature of interest. The alpha-amylase to be tested is diluted in x ml of 50 mM Britton-Robinson buffer. 1 ml of this alpha-amylase solution is added to the 5 ml 50 mM Britton-Robinson buffer. The starch is hydrolyzed by the alpha-amylase giving soluble blue fragments. The absorbance of the resulting blue solution, measured spectrophotometrically at 620 nm, is a function of the alpha-amylase activity.

It is important that the measured 620 nm absorbance after 10 or 15 minutes of incubation (testing time) is in the range of 0.2 to 2.0 absorbance units at 620 nm. In this absorbance range there is linearity between activity and absorbance (Lambert-Beer law). The dilution of the enzyme must therefore be adjusted to fit this criterion. Under a specified set of conditions (temp., pH, reaction time, buffer conditions) 1 mg of a given alpha-amylase will hydrolyze a certain amount of substrate and a blue colour will be produced. The colour intensity is measured at 620 nm. The measured absorbance is directly proportional to the specific activity (activity/mg of pure alpha-amylase protein) of the alpha-amylase in question under the given set of conditions.

2. Alternative Method

Alpha-amylase activity is determined by a method employing the PNP-G7 substrate. PNP-G7 which is a abbreviation for p-nitrophenyl-alpha,D-maltoheptaoside is a blocked oligosaccharide which can be cleaved by an endoamylase. Following the cleavage, the alpha-Glucosidase included in the kit digest the substrate to liberate a free PNP molecule which has a yellow colour and thus can be measured by visible spectophometry at $\lambda$=405 nm. (400-420 nm). Kits containing PNP-G7 substrate and alpha-Glucosidase is manufactured by Boehringer-Mannheim (cat. No. 1054635).

To prepare the substrate one bottle of substrate (BM 1442309) is added to 5 ml buffer (BM1442309). To prepare the α-Glucosidase one bottle of alpha-Glucosidase (BM 1462309) is added to 45 ml buffer (BM1442309). The working solution is made by mixing 5 ml alpha-Glucosidase solution with 0.5 ml substrate.

The assay is performed by transforming 20 μl enzyme solution to a 96 well microtitre plate and incubating at 25° C. 200 μl working solution, 25° C. is added. The solution is mixed and pre-incubated 1 minute and absorption is measured every 15 sec. over 3 minutes at OD 405 nm.

The slope of the time dependent absorption-curve is directly proportional to the specific activity (activity per mg enzyme) of the alpha-amylase in question under the given set of conditions.

General Method for Random Mutagenesis by Use of the DOPE Program

The random mutagenesis may be carried out as follows:

1. Select regions of interest for modification in the parent enzyme
2. Decide on mutation sites and non-mutated sites in the selected region
3. Decide on which kind of mutations should be carried out, e.g. with respect to the desired stability and/or performance of the variant to be constructed
4. Select structurally reasonable mutations.
5. Adjust the residues selected by step 3 with regard to step 4.
6. Analyze by use of a suitable dope algorithm the nucleotide distribution.
7. If necessary, adjust the wanted residues to genetic code realism (e.g., taking into account constraints resulting from the genetic code (e.g. in order to avoid introduction of stop codons))(the skilled person will be aware that some codon combinations cannot be used in practice and will need to be adapted)
8. Make primers
9. Perform random mutagenesis by use of the primers
10. Select resulting α-amylase variants by screening for the desired improved properties.

Suitable dope algorithms for use in step 6 are well known in the art. One algorithm is described by Tomandl, D. et al., Journal of Computer-Aided Molecular Design, 11 (1997), pp. 29-38). Another algorithm, DOPE, is described in the following:

The Dope Program

The "DOPE" program is a computer algorithm useful to optimize the nucleotide composition of a codon triplet in such a way that it encodes an amino acid distribution which resembles most the wanted amino acid distribution. In order to assess which of the possible distributions is the most similar to the wanted amino acid distribution, a scoring function is needed. In the "Dope" program the following function was found to be suited:

$$s \equiv \prod_{i=1}^{N} \left( \frac{x_i^{y_i}(1-x_i)^{1-y_i}}{y_i^{y_i}(1-y_i)^{1-y_i}} \right)^{w_i},$$

where the $x_i$'s are the obtained amounts of amino acids and groups of amino acids as calculated by the program, $y_i$'s are the wanted amounts of amino acids and groups of amino acids as defined by the user of the program (e.g. specify which of the 20 amino acids or stop codons are wanted to be introduced, e.g. with a certain percentage (e.g. 90% Ala, 3% Ile, 7% Val), and $w_i$'s are assigned weight factors as defined by the user of the program (e.g., depending on the importance of having a specific amino acid residue inserted into the position in question). N is 21 plus the number of amino acid groups as defined by the user of the program. For purposes of this function $0^0$ is defined as being 1.

A Monte-Carlo algorithm (one example being the one described by Valleau, J. P. & Whittington, S. G. (1977) A guide to Mont Carlo for statistical mechanics: 1 Highways. In "Stastistical Mechanics, Part A" Equlibrium Techniqeues ed. B. J. Berne, New York: Plenum) is used for finding the maximum value of this function. In each iteration the following steps are performed:

1. A new random nucleotide composition is chosen for each base, where the absolute difference between the current and the new composition is smaller than or equal to d for each of the four nucleotides G,A,T,C in all three positions of the codon (see below for definition of d).
2. The scores of the new composition and the current composition are compared by the is use of the function s as described above. If the new score is higher or equal to the score of the current composition, the new composition is kept and the current composition is changed to the new one. If the new score is smaller, the probability of keeping the new composition is exp(1000(new_score−current_score)).

A cycle normally consists of 1000 iterations as described above in which d is decreasing linearly from 1 to 0. One hundred or more cycles are performed in an optimization process. The nucleotide composition resulting in the highest score is finally presented.

EXAMPLES

Example 1

Method of Extracting Important Regions and Amino Acid Residues for Identifying SP722 Alpha-amylase Variants with Altered Properties The tertiary structure of the SP722 alpha-amylase was displayed on a UNIX computer station running Insight and all hydrogens and water molecules were deleted. For this minimized amylase structure, all the symetri related amylase molecules were displayed, according to the crystal parameters and the spacegroup determined in the pdb-structure file (Appendix 1). A small computer program was made to calculate the distance from each atom in the mother alpha-amylase to any atom in the symetri related amylase structures. Setting the distance cut-off to 3.5 Å and 6.0 Å, respectively resulted in the lists below:

The amino acid residues being less than 6.0 Å from the nearest neighboring amylase molecule are the following positions identified in the model structure of the SP722 amylase: ASN 19, ASP 20, GLY 21, GLN 22, ASN 25, ARG 28, ASP 29, GLN 53, ARG 76, GLN 84, SER 87, HIS 90, LYS 93, ASN 94, ASN 125, ASN 126, ASN 128, LYS 142, ASP 144, LYS 156, TRP 157, ARG 158, TRP 159, TYR 160, HIS 161, PHE 173, GLN 174, ASN 175, ASP 183, GLY 184, LYS 185, ALA 186, TRP 187, ASP 188, TRP 189, GLU 190, SER 193, GLY 196, ASN 197, ASP 209, GLU 212, ASN 226, ASN 229, ALA 256, THR 257, GLY 258, LYS 259, ASN 280, LYS 281, TYR 298, ASN 299, ALA 300, ASN 302, SER 303, GLY 304, GLY 305, ASN 306, ALA 310, ASN 314, GLN 319, LYS 320, HIS 321, PRO 322, GLU 341, GLN 345, PHE 405, ASP 406, HIS 408, GLN 444, ALA 447, GLY 448, GLN 449, THR 463, ILE 464, ASN 465, ALA 466, ASP 467.

The amino acid residues being less than 3.5 Å from the nearest neighboring amylase molecule are the following positions identified in the model structure of the SP722 amylase: GLN 22, ASN 25, ARG 28, ARG 76, ASN 94, ASN 125, ASN 128, ARG 158, TYR 160, PHE 173, GLN 174, GLY 184, TRP 189, ASP 209, ASN 226, ASN 229, TYR 298, ASN 299, ASN 302, ASN 306, ASN 314, LYS 320, GLN 345, PHE 405, ALA 447, ALA 466.

Example 2

Alternative Method of Extracting Important Regions and Amino Acid Residues for Identifying SP722 Alpha-amylase Variants with Altered Properties The tertiary structure of the SP722 alpha-amylase was displayed on a UNIX computer station running Insight and all hydrogen and water molecules were deleted. This minimized amylase structure was imported ("getmol") into the WHAT IF software (G. Vriend, J. Mol. Graph. (1990) 8, 52-56) and all the symmetry related amylase molecules within 6 angstrom were added to the soup ("symtry, symspg, sympar 6, soushl, soup). A new coordinate file for SP722 including the symmetry molecules was written (makmol, tot 0). The center SP722 amylase was then deleted from the structure file, and a new file including the surrounding molecules was written. A small computer program was made to calculate the distance from each atom in the mother alpha-amylase (original SP72 structure file without water molecules and Hydrogen atoms) to any atom in the symmetry related amylase file. Setting the distance cut-off to 3.5 Å and 6.0 Å, respectively resulted in identification of the position referred to in the description.

What If commands:

| | |
|---|---|
| >>Whatif<< | Starts WHAT IF |
| >>Getmol sp722_HOH.pdb<< | import the water and H-depleted SP722 structure file into the WHAT IF sotware |
| >>symtry<< | Go to symmetry menu |
| >>symspg<< | Reads symmetry related information in structure file |

-continued

| | |
|---|---|
| >>sympar 6<< | Makes symmetry related residues within 6 A distance |
| >>soushl<< | Adds the symmetry molecules to the soup |
| >>soup<< | Go to soup menu |
| >>makmol, "sp722_wi6.pdb", tot 0<< writes the "sp722_wi6" pdb file including all atoms in the soup (SP722 and the symmetry molecules within 6 Å). | |

Example 3

Homology Building of AA560 from SP722 Tertiary Structure

The overall homology of the AA560 alpha-amylase (SEQ ID NO: 12) to SP722 (SEQ ID NO: 4) is about 87% as described above. Sequence alignment of AA560 and SP722 shows there to be no insertion or deletions, which can also be seen in FIG. 1.

The tertiary structure of the AA560 alpha-amylase was model build on the structure disclosed in Appendix 1 using the method "Modelbuiling" described in the "Materials & Methods"-section.

The structure of SP722 was displayed on a UNIX work staion running Insight and Homology software from BIOSYM, MSI. The amino acid sequences were aligned and the Sp722 coordinated assigned to the AA560 amino acids. The coordinates of the first four amino acids in AA560, which are missing in the SP722 structure, were assigned by the "END REPAIR" function.

The AA560 model was refined by first relaxing the amino acid side changes, using the "RELAX" command and then running molecular dynamics to minimise the energy of the 3D model. Default parameters from Insight 95, MSI were chosen for both relaxation molecular dynamics.

Finally the spacegroup and the unit cell dimentions are copied from the SP722 pdb file to the AA560 model file.

Example 4

Method of Extracting Important Regions for Identifying AA560 Alpha-amylase Variants with Altered Properties The model build structure of AA560 was subjected to the same calculations as was SP722 in Example 1. Because the homology of the two alpha-amylases is as high as about 87% identity, the crystal interactions of AA560 are expected to similar to those of SP722, i.e., AA560 crystalize in the same spacegroup as SP722 and with the similar unity cell parameter.

The tertiary structure of the AA560 alpha-amylase was displayed on a UNIX computer station running Insight and all hydrogens and water molecules were deleted. For this minimized amylase structure, all the symetri related amylase molecules were displayed, according to the crystal parameters and the spacegroup for SP722 (Appendix 1). A small computer program was made to calculate the distance from each atom in the "mother" alpha-amylase to any atom in the symetri related amylase structures. Setting the distance cut-off to 3.5 Å and 6.0 Å, respectively resulted in the lists below:

The amino acid residues being less than 6.0 Å from the nearest neighboring amylase molecule are the following positions identified in the model structure of the AA560 amylase: ASN 19, ASP 20, ASN 22, ASN 25, ARG 28, SER 29, GLN 53, ARG 76, GLN 84, ALA 87, ASN 90, LYS 93, SER 94, PRO 124, ASN 125, ASN 126, ASN 128, LYS 142, ASP 144, LYS 156, TRP 157, ARG 158, TRP 159, TYR 160, HIS 161,SER 170, ARG 171, LYS 172, LEU 173, ASN 174, ASN 175, ASP 183, GLY 184, LYS 185, GLY 186, TRP 187, ASP 188, TRP 189, GLU 190, THR 193, ASN 195, GLY 196, ASN 197, ASP 209, GLU 212, ASN 226, GLY 229, ALA 256, THR 257, GLY 258, LYS 259, LYS 281, TYR 298, ASN 299, ALA 300, LYS 302, SER 303, GLY 304, ASN 306, ARG 310, GLN 311, ASN 314, GLN 319, ARG 320, HIS 321, PRO 322, GLU 341, GLU 345, LEU 405, HIS 408, ARG 444, ALA 447, GLY 448, GLN 449, THR 463, ILE 464, ASN 465, ALA 466, ASP 467.

The amino acid residues being less than 3.5 Å from the nearest neighboring amylase molecule are the following positions identified in the model structure of the AA560 amylase: ARG 28, ASN 125, ASN 128, ARG 158, TYR 160, ARG 171, LEU 173, ASN 174, GLY 184, TRP 189, GLY 196, ASP 209, ASN 226, TYR 298, ASN 299, LYS 302, ASN 306, ARG 310, ASN 314, ARG 320, GLU 345, ALA 447, ALA 466.

Example 5

Construction, by Localized Random, Doped Mutagenesis, of AA560 Alpha-amylase Variants Having Increased Solubility in Comparison to the Parent Enzyme To increase the solubility of the AA560 alpha-amylase random mutagenesis in pre-selected region was performed as described in the following.

| Region: | Residue: |
|---|---|
| SA1: | R181-W189 |

The DOPE software (see "Materials and Methods") was used to determine spiked codons for each suggested change in the SA1 region minimizing the amount of stop codons (see table 1). The exact distribution of nucleotides was calculated in the three positions of the codon to give the suggested population of amino acid changes. The doped regions were doped specifically in the indicated positions to have a high chance of getting the desired residues, but still allow other possibilities.

TABLE 1

Distribution of amino acid residues for each position

R181: 72% R, 2% N, 7% Q, 4% H, 4% K, 11% S
G182: 73% G, 13% A, 12% S, 2% T
K185: 95% K, 5% R
G186: 50% A, 4% N, 6% D, 1% E, 1% G, 1% K, 5% S, 31% T
W187: 100% W
D188: 100% D
W189: 92% W, 8% S

The resulting doped oligonucleotide strand is shown in table 2 as sense strand: with the wild type nucleotide and amino acid sequences and the distribution of nucleotides for each doped position.

TABLE 2

| Position | 181 | 182 | 185 | 186 | 187 | 188 | 189 | |
|---|---|---|---|---|---|---|---|---|
| Amino acid seq. | Arg | Gly | Lys | Gly | Trp | Asp | Trp | (SEQ ID NO: 12) |
| Wt nuc. seq. | aga | ggt | aaa | ggg | tgg | gat | tgg | (SEQ ID NO: 11) |

Forward primer (SEQ ID NO: 14)

FSA: 5'-caa aat cgt atc tac aaa ttc 123 456 a7g 8910 tgg gat tllg gaa gta gat tcg gaa aat-3'

Distribution of nucleotides for each doped Position

1: 35% A, 65% C
2: 83% G, 17% A
3: 63% G, 37% T
4: 86% G, 14% A
5: 85% G, 15% C
6: 50% T, 50% C
7: 95% A, 5% G
8: 58% G, 37% A, 5% T
9: 86% C, 13% A, 1% G
10: 83% T, 17% G
11: 92% G, 8% C

Reverse primer (SEQ ID NO: 15)

RSA 5'-gaa ttt gta gat acg att ttg-3'

Random Mutagenesis

The spiked oligonucleotides apparent from Table 2 (which by a common term is designated FSA) and reverse primers RSA for the SA1 region and specific SEQ ID NO: 12: AA560 primers covering the SacII and the DraIII sites are used to generate PCR-library-fragments by the overlap extension method (Horton et al., Gene, 77 (1989), pp. 61-68) with an overlap of 21 base pairs. Plasmid pJE1 is template for the Polymerase Chain Reaction. The PCR fragments are cloned in the *E. coli/Bacillus* shuttle vector pDork101 (see "Materials and Methods" section) enabling mutagenesis in *E. coli* and immediate expression in *Bacillus subtilis* preventing lethal accumulation of amylases in *E. coli*. After establishing the cloned PCR fragments in *E. coli*, a modified pUC19 fragment is digested out of the plasmid and the promoter and the mutated Termamyl gene is physically connected and expression can take place in *Bacillus*.

Screening

The library may be screened in the low calcium filter assays described in the "Material and Methods" section above.

Example 6

Construction of Variants of AA560

The gene encoding the AA560 alpha-amylase shown in SEQ ID NO: 12 is located in a plasmid pTVB223. The amylase is expressed from the amyL promoter in this construct in *Bacillus subtilis*.

A variant of the invention with delta(D183-G184) mutations was constructed by the mega-primer method as described by Sarkar and Sommer, (1990), BioTechniques 8: 404-407.

Gene specific primer B1 (SEQ ID NO: 16) and mutagenic primer 101458 (SEQ ID NO: 18) were used to amplify by PCR an approximately 645 bp DNA fragment from a pTVB223 plasmid encoding AA560 shown in SEQ ID NO: 12).

The 645 bp fragment was purified from an agarose gel and used as a mega-primer together with primer Y2 (SEQ ID NO: 17) in a second PCR carried out on the same template.

The resulting approximately 1080 bp fragment was digested with restriction enzymes BstEII and AflIII and the resulting approximately 510 bp DNA fragment was purified and ligated with the pTVB223 plasmid digested with the same enzymes. Competent *Bacillus subtilis* SHA273 (amylase and protease low) cells were transformed with the ligation and Chlorampenicol resistant transformants and was checked by DNA sequencing to verify the presence of the correct mutations on the plasmid.

```
primer B1:                          (SEQ ID NO: 16)
5' CGA TTG CTG ACG CTG TTA TTT GCG 3' primer Y2:                          (SEQ ID NO: 17)
5' CTT GTT CCC TTG TCA GAA CCA ATG 3' primer 101458                       (SEQ ID NO: 18)
5' GT CAT AGT TGC CGA AAT CTG TAT CGA CTT C 3'
```

The resulting plasmid encoding the AA560 amylase with delta(D183-G184)+N195F was named pTVB232.

The construction of the other variants of the invention was carried out in a similar manner.

Example 7

Determination of Solubility of AA560 and SP722 Variants

AA560 variant was constructed as described above. The solubility was determined as descred in the "Material and Methods" section as Solubility Determination I

| Variant | Solubility (mg/ml) |
|---|---|
| Wild-type AA560 | 2 mg/ml |
| AA560 delta(D183–G184) + N195F + N445Q + N446N(AX23) | more than 6 mg/ml |

0.02 M Tris-HCl, 0.15 M NaCl, pH 7.5, room temperature

The concentration step was started with a protein amount of 40 mg and in general, 50% of the amylases were lost during the process. This loss of protein occurred for all enzymes in the initial phase of the process and full recovery of the enzymes were obtained in the terminating phase where the volumes are become very limited. Loss of enzymes was due to adsorption to the membrane.

Example 8

Determination of Solubility of AA560 Variants

AA560 variants were constructed as described above, using the wild-type AA560 as template. The solubility was determined as described in the "Material and Methods" section under Solubility Determination II

| Mutations | Solubility (g/L) |
|---|---|
| Wild type AA560 | 2.8 |
| AA560 + N125A | 9 |
| AA560 + N125R | 9 |
| AA560 + N306R | 7 |
| AA560 + Y298H + N299A + K302R + S303Q + N306G | 12 |
| AA560 + delta(D183 + G184) + R181Q + E345R | 12 |
| AA560 + delta(D183 + G184) + R181Q + W189R | 4.5 |
| AA560 + delta(D183 + G184) + R181Q + S94K + W189R | 7 |
| AA560 + delta(D183 + G184) + N195F + R118K + R320K + R458K | 10 |
| AA560 + delta(D183 + G184) + N195F + W189K + N306K + N445K | 10 |
| AA560 + delta(D183 + G184) + N195F + R118K + N125K + R444K + N445K | 3 |
| AA560 + delta(D183 + G184) + N195F + W189K + N445K | 12 |
| AA560 + delta(D183 + G184) + N195F + R400T | 4 |
| AA560 + delta(D183 + G184) + N195F + W439R | 5.5 |
| AA560 + delta(D183 + G184) + N195F + Q449E | 3.4 |
| AA560 + delta(D183 + G184) + N195F + N484Q | 4.3 |
| AA560 + delta(D183 + G184) + N195F + R181Q + N445Q + K446N + N484E | 4.15 |
| AA560 + delta(D183 + G184) + N195F + R181E + N445Q + K446N | 3.5 |
| AA560 + delta(D183 + G184) + N195F + R181E + K446N | 5.2 |
| AA560 + delta(D183 + G184) + N195F + R310A + R181Q + N445Q + K446N | 5 |
| AA560 + delta(D183 + G184) + N195F + R320K + R181Q + N445Q + K446N | 6.9 |
| AA560 + delta(D183 + G184) + N195F + Q319K + R320D + R181Q + N445Q + K446N | 4 |
| AA560 + delta(D183 + G184) + N195F + N306A + R181Q + N445Q + K446N | 5.5 |
| AA560 + delta(D183 + G184) + N195F + K302N + R181Q + N445Q + K446N | 8 |
| AA560 + delta(D183 + G184) + N195F + E345N + R181Q + N445Q + K446N | 3.5 |
| AA560 + delta(D183 + G184) + N195F + Y298F + R181Q + N445Q + K446N | 5 |
| AA560 + delta(D183 + G184) + N195F + R28N + R181Q + N445Q + K446N | 4.5 |
| AA560 + delta(D183 + G184) + N195F + R28N + R310A + R181Q + N445Q + K446N | 11 |
| AA560 + delta(D183 + G184) + N195F + N128D + N306D + R181Q + N445Q + K446N | 5.3 |

APPENDIX 1

```
CRYST1   48.180   75.847  155.230  90.00   90.00   90.00 P 21 21 21
SCALE1    0.02076  0.00000  0.00000       0.00000
SCALE2    0.00000  0.01318  0.00000       0.00000
SCALE3    0.00000  0.00000  0.00644       0.00000
ATOM      1  N   THR A   5       7.992  45.862  57.008  1.00 44.97           7
ATOM      2  CA  THR A   5       9.424  45.847  57.375  1.00 44.28           6
ATOM      3  C   THR A   5       9.791  44.763  58.368  1.00 42.47           6
ATOM      4  O   THR A   5       9.118  44.516  59.385  1.00 44.78           8
ATOM      5  CB  THR A   5       9.859  47.256  57.794  1.00 53.11           6
ATOM      6  OG1 THR A   5       8.936  48.132  57.101  1.00 57.19           8
ATOM      7  CG2 THR A   5      11.285  47.524  57.327  1.00 53.46           6
ATOM      8  N   ASN A   6      10.798  43.965  58.016  1.00 37.90           7
ATOM      9  CA  ASN A   6      11.182  42.796  58.794  1.00 32.63           6
ATOM     10  C   ASN A   6      11.930  43.205  60.065  1.00 30.68           6
ATOM     11  O   ASN A   6      12.814  44.059  60.030  1.00 29.58           8
ATOM     12  CB  ASN A   6      12.053  41.919  57.914  1.00 30.63           6
ATOM     13  CG  ASN A   6      11.382  41.198  56.759  1.00 17.30           6
ATOM     14  OD1 ASN A   6      10.296  40.687  56.891  1.00 20.22           8
ATOM     15  ND2 ASN A   6      12.101  41.145  55.643  1.00 32.47           7
ATOM     16  N   GLY A   7      11.603  42.548  61.186  1.00 28.09           7
ATOM     17  CA  GLY A   7      12.292  42.881  62.451  1.00 22.75           6
ATOM     18  C   GLY A   7      13.597  42.146  62.640  1.00 19.14           6
ATOM     19  O   GLY A   7      13.695  40.965  62.333  1.00 16.06           8
ATOM     20  N   THR A   8      14.624  42.823  63.147  1.00 18.17           7
ATOM     21  CA  THR A   8      15.896  42.176  63.458  1.00 19.10           6
ATOM     22  C   THR A   8      16.482  42.662  64.779  1.00 17.43           6
ATOM     23  O   THR A   8      16.638  43.853  64.952  1.00 15.95           8
ATOM     24  CB  THR A   8      16.979  42.465  62.372  1.00 26.45           6
ATOM     25  OG1 THR A   8      16.351  42.055  61.153  1.00 24.27           8
ATOM     26  CG2 THR A   8      18.194  41.568  62.558  1.00 15.46           6
ATOM     27  N   MET A   9      16.841  41.711  65.650  1.00 16.99           7
ATOM     28  CA  MET A   9      17.410  42.149  66.957  1.00 16.54           6
ATOM     29  C   MET A   9      18.908  42.032  66.891  1.00 14.09           6
ATOM     30  O   MET A   9      19.450  41.117  66.285  1.00 16.28           8
ATOM     31  CB  MET A   9      16.903  41.092  67.986  1.00 20.39           6
ATOM     32  CG  MET A   9      17.005  41.347  69.462  1.00 34.30           6
ATOM     33  SD  MET A   9      16.749  39.831  70.439  1.00 29.87          16
ATOM     34  CE  MET A   9      15.299  39.172  69.801  1.00 10.47           6
ATOM     35  N   MET A  10      19.658  42.840  67.617  1.00 12.91           7
ATOM     36  CA  MET A  10      21.063  42.531  67.806  1.00 15.03           6
ATOM     37  C   MET A  10      21.371  42.281  69.316  1.00 15.55           6
ATOM     38  O   MET A  10      20.968  43.127  70.123  1.00 16.31           8
ATOM     39  CB  MET A  10      21.918  43.731  67.392  1.00  8.10           6
ATOM     40  CG  MET A  10      23.386  43.336  67.340  1.00 18.96           6
ATOM     41  SD  MET A  10      24.227  44.719  66.507  1.00 26.55          16
ATOM     42  CE  MET A  10      25.899  44.253  66.714  1.00 22.28           6
ATOM     43  N   GLN A  11      22.169  41.302  69.642  1.00 15.64           7
ATOM     44  CA  GLN A  11      22.676  41.141  70.997  1.00 16.62           6
ATOM     45  C   GLN A  11      23.900  42.031  71.121  1.00 14.80           6
ATOM     46  O   GLN A  11      24.973  41.754  70.591  1.00 15.68           8
ATOM     47  CB  GLN A  11      23.021  39.672  71.257  1.00 21.35           6
ATOM     48  CG  GLN A  11      23.790  39.566  72.563  1.00  9.63           6
ATOM     49  CD  GLN A  11      24.190  38.189  72.982  1.00 16.22           6
ATOM     50  OE1 GLN A  11      24.002  37.196  72.298  1.00 19.21           8
ATOM     51  NE2 GLN A  11      24.789  38.087  74.175  1.00 11.66           7
ATOM     52  N   TYR A  12      23.760  43.191  71.741  1.00 14.58           7
ATOM     53  CA  TYR A  12      24.863  44.157  71.774  1.00 14.52           6
ATOM     54  C   TYR A  12      25.913  43.966  72.861  1.00 16.45           6
ATOM     55  O   TYR A  12      26.204  44.903  73.648  1.00 18.06           8
ATOM     56  CB  TYR A  12      24.206  45.550  71.733  1.00 13.22           6
ATOM     57  CG  TYR A  12      25.138  46.568  71.112  1.00 19.25           6
ATOM     58  CD1 TYR A  12      25.099  46.777  69.714  1.00 21.72           6
```

| ATOM | 59 | CD2 | TYR | A | 12 | 26.042 | 47.309 | 71.833 | 1.00 | 21.37 | 6 |
| ATOM | 60 | CE1 | TYR | A | 12 | 25.939 | 47.688 | 69.119 | 1.00 | 23.24 | 6 |
| ATOM | 61 | CE2 | TYR | A | 12 | 26.857 | 48.237 | 71.237 | 1.00 | 25.94 | 6 |
| ATOM | 62 | CZ | TYR | A | 12 | 26.807 | 48.431 | 69.845 | 1.00 | 25.18 | 6 |
| ATOM | 63 | OH | TYR | A | 12 | 27.689 | 49.335 | 69.287 | 1.00 | 25.31 | 8 |
| ATOM | 64 | N | PHE | A | 13 | 26.564 | 42.818 | 72.979 | 1.00 | 13.34 | 7 |
| ATOM | 65 | CA | PHE | A | 13 | 27.685 | 42.656 | 73.887 | 1.00 | 16.82 | 6 |
| ATOM | 66 | C | PHE | A | 13 | 28.274 | 41.290 | 73.605 | 1.00 | 14.75 | 6 |
| ATOM | 67 | O | PHE | A | 13 | 27.546 | 40.479 | 73.068 | 1.00 | 14.38 | 8 |
| ATOM | 68 | CB | PHE | A | 13 | 27.294 | 42.776 | 75.388 | 1.00 | 15.66 | 6 |
| ATOM | 69 | CG | PHE | A | 13 | 26.320 | 41.755 | 75.919 | 1.00 | 12.49 | 6 |
| ATOM | 70 | CD1 | PHE | A | 13 | 24.961 | 41.920 | 75.789 | 1.00 | 13.73 | 6 |
| ATOM | 71 | CD2 | PHE | A | 13 | 26.743 | 40.643 | 76.601 | 1.00 | 14.47 | 6 |
| ATOM | 72 | CE1 | PHE | A | 13 | 24.033 | 41.007 | 76.282 | 1.00 | 12.15 | 6 |
| ATOM | 73 | CE2 | PHE | A | 13 | 25.835 | 39.720 | 77.121 | 1.00 | 19.40 | 6 |
| ATOM | 74 | CZ | PHE | A | 13 | 24.466 | 39.875 | 76.958 | 1.00 | 11.64 | 6 |
| ATOM | 75 | N | GLU | A | 14 | 29.485 | 41.003 | 74.010 | 1.00 | 14.36 | 7 |
| ATOM | 76 | CA | GLU | A | 14 | 30.034 | 39.676 | 74.020 | 1.00 | 16.15 | 6 |
| ATOM | 77 | C | GLU | A | 14 | 30.746 | 39.519 | 75.403 | 1.00 | 17.45 | 6 |
| ATOM | 78 | O | GLU | A | 14 | 30.913 | 40.533 | 76.085 | 1.00 | 17.41 | 8 |
| ATOM | 79 | CB | GLU | A | 14 | 31.054 | 39.352 | 72.923 | 1.00 | 16.10 | 6 |
| ATOM | 80 | CG | GLU | A | 14 | 32.102 | 40.433 | 72.801 | 1.00 | 14.02 | 6 |
| ATOM | 81 | CD | GLU | A | 14 | 33.463 | 39.876 | 73.166 | 1.00 | 19.45 | 6 |
| ATOM | 82 | OE1 | GLU | A | 14 | 33.542 | 38.730 | 73.659 | 1.00 | 17.76 | 8 |
| ATOM | 83 | OE2 | GLU | A | 14 | 34.460 | 40.577 | 72.944 | 1.00 | 24.92 | 8 |
| ATOM | 84 | N | TRP | A | 15 | 31.209 | 38.352 | 75.765 | 1.00 | 16.89 | 7 |
| ATOM | 85 | CA | TRP | A | 15 | 31.732 | 38.068 | 77.068 | 1.00 | 19.25 | 6 |
| ATOM | 86 | C | TRP | A | 15 | 32.947 | 38.939 | 77.396 | 1.00 | 20.43 | 6 |
| ATOM | 87 | O | TRP | A | 15 | 33.110 | 39.478 | 78.488 | 1.00 | 19.09 | 8 |
| ATOM | 88 | CB | TRP | A | 15 | 32.101 | 36.576 | 77.206 | 1.00 | 20.93 | 6 |
| ATOM | 89 | CG | TRP | A | 15 | 32.291 | 36.259 | 78.669 | 1.00 | 23.04 | 6 |
| ATOM | 90 | CD1 | TRP | A | 15 | 33.453 | 36.102 | 79.356 | 1.00 | 31.96 | 6 |
| ATOM | 91 | CD2 | TRP | A | 15 | 31.235 | 36.075 | 79.620 | 1.00 | 19.31 | 6 |
| ATOM | 92 | NE1 | TRP | A | 15 | 33.198 | 35.828 | 80.689 | 1.00 | 25.07 | 7 |
| ATOM | 93 | CE2 | TRP | A | 15 | 31.847 | 35.794 | 80.866 | 1.00 | 26.64 | 6 |
| ATOM | 94 | CE3 | TRP | A | 15 | 29.844 | 36.098 | 79.535 | 1.00 | 18.13 | 6 |
| ATOM | 95 | CZ2 | TRP | A | 15 | 31.099 | 35.552 | 82.018 | 1.00 | 22.00 | 6 |
| ATOM | 96 | CZ3 | TRP | A | 15 | 29.110 | 35.874 | 80.702 | 1.00 | 29.43 | 6 |
| ATOM | 97 | CH2 | TRP | A | 15 | 29.738 | 35.616 | 81.937 | 1.00 | 13.19 | 6 |
| ATOM | 98 | N | HIS | A | 16 | 33.835 | 39.011 | 76.425 | 1.00 | 18.44 | 7 |
| ATOM | 99 | CA | HIS | A | 16 | 35.061 | 39.722 | 76.562 | 1.00 | 17.90 | 6 |
| ATOM | 100 | C | HIS | A | 16 | 35.149 | 41.187 | 76.257 | 1.00 | 17.37 | 6 |
| ATOM | 101 | O | HIS | A | 16 | 36.293 | 41.637 | 76.074 | 1.00 | 19.01 | 8 |
| ATOM | 102 | CB | HIS | A | 16 | 36.185 | 38.908 | 75.918 | 1.00 | 25.12 | 6 |
| ATOM | 103 | CG | HIS | A | 16 | 36.354 | 37.568 | 76.564 | 1.00 | 22.79 | 6 |
| ATOM | 104 | ND1 | HIS | A | 16 | 36.995 | 37.436 | 77.791 | 1.00 | 31.80 | 7 |
| ATOM | 105 | CD2 | HIS | A | 16 | 35.974 | 36.324 | 76.195 | 1.00 | 30.13 | 6 |
| ATOM | 106 | CE1 | HIS | A | 16 | 37.007 | 36.145 | 78.108 | 1.00 | 36.35 | 6 |
| ATOM | 107 | NE2 | HIS | A | 16 | 36.391 | 35.434 | 77.169 | 1.00 | 28.59 | 7 |
| ATOM | 108 | N | LEU | A | 17 | 34.102 | 41.977 | 76.290 | 1.00 | 16.37 | 7 |
| ATOM | 109 | CA | LEU | A | 17 | 34.310 | 43.400 | 76.062 | 1.00 | 17.67 | 6 |
| ATOM | 110 | C | LEU | A | 17 | 35.251 | 43.901 | 77.175 | 1.00 | 23.03 | 6 |
| ATOM | 111 | O | LEU | A | 17 | 35.367 | 43.325 | 78.258 | 1.00 | 20.48 | 8 |
| ATOM | 112 | CB | LEU | A | 17 | 32.998 | 44.133 | 76.231 | 1.00 | 19.00 | 6 |
| ATOM | 113 | CG | LEU | A | 17 | 31.936 | 43.825 | 75.166 | 1.00 | 23.04 | 6 |
| ATOM | 114 | CD1 | LEU | A | 17 | 30.602 | 44.392 | 75.618 | 1.00 | 15.57 | 6 |
| ATOM | 115 | CD2 | LEU | A | 17 | 32.423 | 44.488 | 73.857 | 1.00 | 16.06 | 6 |
| ATOM | 116 | N | PRO | A | 18 | 36.031 | 44.902 | 76.847 | 1.00 | 23.78 | 7 |
| ATOM | 117 | CA | PRO | A | 18 | 36.979 | 45.490 | 77.777 | 1.00 | 24.94 | 6 |
| ATOM | 118 | C | PRO | A | 18 | 36.187 | 46.159 | 78.903 | 1.00 | 24.27 | 6 |
| ATOM | 119 | O | PRO | A | 18 | 35.132 | 46.765 | 78.711 | 1.00 | 23.28 | 8 |
| ATOM | 120 | CB | PRO | A | 18 | 37.748 | 46.610 | 77.012 | 1.00 | 24.47 | 6 |
| ATOM | 121 | CG | PRO | A | 18 | 36.813 | 46.841 | 75.862 | 1.00 | 25.71 | 6 |
| ATOM | 122 | CD | PRO | A | 18 | 35.984 | 45.606 | 75.564 | 1.00 | 24.09 | 6 |
| ATOM | 123 | N | ASN | A | 19 | 36.761 | 46.106 | 80.092 | 1.00 | 26.70 | 7 |

| | ATOM | 124 | CA  | ASN A | 19 | 36.172 | 46.812 | 81.251 | 1.00 | 27.71 | 6 |
|---|------|-----|-----|-------|----|--------|--------|--------|------|-------|---|
| | ATOM | 125 | C   | ASN A | 19 | 36.645 | 48.255 | 81.184 | 1.00 | 28.45 | 6 |
| | ATOM | 126 | O   | ASN A | 19 | 37.608 | 48.592 | 81.900 | 1.00 | 28.72 | 8 |
| | ATOM | 127 | CB  | ASN A | 19 | 36.642 | 46.133 | 82.547 | 1.00 | 27.29 | 6 |
| 5 | ATOM | 128 | CG  | ASN A | 19 | 36.225 | 46.903 | 83.794 | 1.00 | 29.44 | 6 |
| | ATOM | 129 | OD1 | ASN A | 19 | 35.232 | 47.640 | 83.776 | 1.00 | 22.52 | 8 |
| | ATOM | 130 | ND2 | ASN A | 19 | 37.044 | 46.750 | 84.839 | 1.00 | 25.06 | 7 |
| | ATOM | 131 | N   | ASP A | 20 | 35.986 | 49.096 | 80.377 | 1.00 | 28.38 | 7 |
| | ATOM | 132 | CA  | ASP A | 20 | 36.539 | 50.454 | 80.270 | 1.00 | 27.78 | 6 |
| 10 | ATOM | 133 | C   | ASP A | 20 | 35.449 | 51.479 | 80.504 | 1.00 | 28.07 | 6 |
| | ATOM | 134 | O   | ASP A | 20 | 35.640 | 52.659 | 80.210 | 1.00 | 28.77 | 8 |
| | ATOM | 135 | CB  | ASP A | 20 | 37.177 | 50.655 | 78.893 | 1.00 | 26.77 | 6 |
| | ATOM | 136 | CG  | ASP A | 20 | 36.200 | 50.561 | 77.731 | 1.00 | 33.87 | 6 |
| | ATOM | 137 | OD1 | ASP A | 20 | 34.974 | 50.296 | 77.873 | 1.00 | 24.14 | 8 |
| 15 | ATOM | 138 | OD2 | ASP A | 20 | 36.728 | 50.764 | 76.603 | 1.00 | 37.81 | 8 |
| | ATOM | 139 | N   | GLY A | 21 | 34.244 | 51.012 | 80.822 | 1.00 | 26.21 | 7 |
| | ATOM | 140 | CA  | GLY A | 21 | 33.162 | 51.940 | 81.081 | 1.00 | 27.22 | 6 |
| | ATOM | 141 | C   | GLY A | 21 | 32.691 | 52.722 | 79.860 | 1.00 | 26.93 | 6 |
| | ATOM | 142 | O   | GLY A | 21 | 31.815 | 53.590 | 80.016 | 1.00 | 25.54 | 8 |
| 20 | ATOM | 143 | N   | GLN A | 22 | 33.064 | 52.279 | 78.654 | 1.00 | 27.07 | 7 |
| | ATOM | 144 | CA  | GLN A | 22 | 32.703 | 53.030 | 77.462 | 1.00 | 27.36 | 6 |
| | ATOM | 145 | C   | GLN A | 22 | 31.641 | 52.404 | 76.590 | 1.00 | 27.67 | 6 |
| | ATOM | 146 | O   | GLN A | 22 | 31.360 | 52.911 | 75.502 | 1.00 | 28.65 | 8 |
| | ATOM | 147 | CB  | GLN A | 22 | 33.992 | 53.128 | 76.602 | 1.00 | 34.67 | 6 |
| 25 | ATOM | 148 | CG  | GLN A | 22 | 34.972 | 54.171 | 77.137 | 1.00 | 48.07 | 6 |
| | ATOM | 149 | CD  | GLN A | 22 | 34.124 | 55.372 | 77.568 | 1.00 | 58.84 | 6 |
| | ATOM | 150 | OE1 | GLN A | 22 | 33.337 | 55.865 | 76.748 | 1.00 | 55.38 | 8 |
| | ATOM | 151 | NE2 | GLN A | 22 | 34.273 | 55.691 | 78.848 | 1.00 | 68.48 | 7 |
| | ATOM | 152 | N   | HIS A | 23 | 31.171 | 51.248 | 77.026 | 1.00 | 25.72 | 7 |
| 30 | ATOM | 153 | CA  | HIS A | 23 | 30.218 | 50.491 | 76.306 | 1.00 | 24.66 | 6 |
| | ATOM | 154 | C   | HIS A | 23 | 28.930 | 51.227 | 76.079 | 1.00 | 26.24 | 6 |
| | ATOM | 155 | O   | HIS A | 23 | 28.425 | 51.142 | 74.940 | 1.00 | 26.09 | 8 |
| | ATOM | 156 | CB  | HIS A | 23 | 29.944 | 49.132 | 76.924 | 1.00 | 27.50 | 6 |
| | ATOM | 157 | CG  | HIS A | 23 | 29.459 | 48.262 | 75.783 | 1.00 | 30.42 | 6 |
| 35 | ATOM | 158 | ND1 | HIS A | 23 | 28.124 | 47.891 | 75.695 | 1.00 | 26.32 | 7 |
| | ATOM | 159 | CD2 | HIS A | 23 | 30.139 | 47.735 | 74.731 | 1.00 | 18.69 | 6 |
| | ATOM | 160 | CE1 | HIS A | 23 | 28.009 | 47.109 | 74.625 | 1.00 | 24.30 | 6 |
| | ATOM | 161 | NE2 | HIS A | 23 | 29.197 | 46.996 | 74.051 | 1.00 | 25.74 | 7 |
| | ATOM | 162 | N   | TRP A | 24 | 28.389 | 51.936 | 77.058 | 1.00 | 24.06 | 7 |
| 40 | ATOM | 163 | CA  | TRP A | 24 | 27.164 | 52.668 | 76.740 | 1.00 | 24.62 | 6 |
| | ATOM | 164 | C   | TRP A | 24 | 27.436 | 53.777 | 75.708 | 1.00 | 26.89 | 6 |
| | ATOM | 165 | O   | TRP A | 24 | 26.551 | 54.069 | 74.901 | 1.00 | 27.55 | 8 |
| | ATOM | 166 | CB  | TRP A | 24 | 26.500 | 53.227 | 77.983 | 1.00 | 23.57 | 6 |
| | ATOM | 167 | CG  | TRP A | 24 | 26.098 | 52.223 | 79.031 | 1.00 | 29.81 | 6 |
| 45 | ATOM | 168 | CD1 | TRP A | 24 | 26.275 | 52.395 | 80.378 | 1.00 | 33.41 | 6 |
| | ATOM | 169 | CD2 | TRP A | 24 | 25.403 | 50.979 | 78.874 | 1.00 | 26.85 | 6 |
| | ATOM | 170 | NE1 | TRP A | 24 | 25.740 | 51.334 | 81.064 | 1.00 | 25.62 | 7 |
| | ATOM | 171 | CE2 | TRP A | 24 | 25.192 | 50.446 | 80.180 | 1.00 | 33.54 | 6 |
| | ATOM | 172 | CE3 | TRP A | 24 | 24.920 | 50.239 | 77.790 | 1.00 | 19.92 | 6 |
| 50 | ATOM | 173 | CZ2 | TRP A | 24 | 24.573 | 49.204 | 80.388 | 1.00 | 20.29 | 6 |
| | ATOM | 174 | CZ3 | TRP A | 24 | 24.285 | 49.021 | 77.982 | 1.00 | 18.51 | 6 |
| | ATOM | 175 | CH2 | TRP A | 24 | 24.113 | 48.505 | 79.295 | 1.00 | 28.71 | 6 |
| | ATOM | 176 | N   | ASN A | 25 | 28.591 | 54.418 | 75.710 | 1.00 | 26.59 | 7 |
| | ATOM | 177 | CA  | ASN A | 25 | 28.968 | 55.488 | 74.809 | 1.00 | 26.82 | 6 |
| 55 | ATOM | 178 | C   | ASN A | 25 | 29.058 | 54.937 | 73.374 | 1.00 | 26.47 | 6 |
| | ATOM | 179 | O   | ASN A | 25 | 28.457 | 55.583 | 72.526 | 1.00 | 27.54 | 8 |
| | ATOM | 180 | CB  | ASN A | 25 | 30.302 | 56.133 | 75.214 | 1.00 | 26.92 | 6 |
| | ATOM | 181 |     | ARG A | 26 | 29.669 | 53.786 | 73.166 | 1.00 | 25.06 | 7 |
| | ATOM | 185 | CA  | ARG A | 26 | 29.742 | 53.064 | 71.909 | 1.00 | 24.34 | 6 |
| 60 | ATOM | 186 | C   | ARG A | 26 | 28.350 | 52.795 | 71.364 | 1.00 | 26.26 | 6 |
| | ATOM | 187 | O   | ARG A | 26 | 27.987 | 53.129 | 70.211 | 1.00 | 28.46 | 8 |
| | ATOM | 188 | CB  | ARG A | 26 | 30.437 | 51.710 | 71.988 | 1.00 | 18.01 | 6 |
| | ATOM | 189 | CG  | ARG A | 26 | 31.918 | 51.719 | 72.254 | 1.00 | 30.32 | 6 |
| | ATOM | 190 | CD  | ARG A | 26 | 34.441 | 50.556 | 74.746 | 1.00 | 30.68 | 7 |
| 65 | ATOM | 194 | NH2 | ARG A | 26 | 33.265 | 48.804 | 75.596 | 1.00 | 35.01 | 7 |

| | ATOM | 195 | N | LEU A | 27 | 27.459 | 52.258 | 72.208 | 1.00 | 25.01 | 7 |
|---|---|---|---|---|---|---|---|---|---|---|---|
| | ATOM | 196 | CA | LEU A | 27 | 25.274 | 51.387 | 72.868 | 1.00 | 15.58 | 6 |
| | ATOM | 200 | CG | LEU A | 27 | 23.794 | 51.142 | 72.617 | 1.00 | 21.63 | 6 |
| | ATOM | 201 | CD1 | LEU A | 27 | 23.655 | 50.255 | 71.361 | 1.00 | 22.69 | 6 |
| 5 | ATOM | 202 | CD2 | ARG A | 28 | 25.475 | 56.144 | 70.282 | 1.00 | 29.78 | 6 |
| | ATOM | 206 | O | ARG A | 28 | 24.697 | 56.631 | 69.479 | 1.00 | 28.83 | 8 |
| | ATOM | 207 | CB | ARG A | 28 | 25.466 | 56.807 | 72.651 | 1.00 | 31.86 | 6 |
| | ATOM | 208 | CG | ARG A | 28 | 24.876 | 58.145 | 72.269 | 1.00 | 37.49 | 6 |
| | ATOM | 209 | CD | ARG A | 28 | 25.164 | 59.255 | 73.228 | 1.00 | 44.67 | 6 |
| 10 | ATOM | 210 | NE | ARG A | 28 | 26.521 | 59.652 | 73.443 | 1.00 | 61.34 | 7 |
| | ATOM | 211 | CZ | ARG A | 28 | 27.711 | 59.325 | 73.002 | 1.00 | 66.92 | 6 |
| | ATOM | 212 | NH1 | ARG A | 28 | 27.919 | 58.379 | 72.101 | 1.00 | 72.14 | 7 |
| | ATOM | 213 | NH2 | ARG A | 28 | 28.775 | 59.959 | 73.482 | 1.00 | 73.55 | 7 |
| | ATOM | 214 | N | ASP A | 29 | 26.776 | 56.044 | 70.052 | 1.00 | 30.37 | 7 |
| 15 | ATOM | 215 | CA | ASP A | 29 | 27.415 | 56.397 | 68.797 | 1.00 | 31.81 | 6 |
| | ATOM | 216 | C | ASP A | 29 | 26.957 | 55.556 | 67.596 | 1.00 | 31.24 | 6 |
| | ATOM | 217 | O | ASP A | 29 | 26.834 | 56.080 | 66.507 | 1.00 | 32.51 | 8 |
| | ATOM | 218 | CB | ASP A | 29 | 28.924 | 56.146 | 68.920 | 1.00 | 37.35 | 6 |
| | ATOM | 219 | CG | ASP A | 29 | 29.654 | 57.288 | 69.578 | 1.00 | 59.15 | 6 |
| 20 | ATOM | 220 | OD1 | ASP A | 29 | 29.044 | 58.378 | 69.658 | 1.00 | 70.33 | 8 |
| | ATOM | 221 | OD2 | ASP A | 29 | 30.815 | 57.073 | 70.001 | 1.00 | 68.87 | 8 |
| | ATOM | 222 | N | ASP A | 30 | 26.669 | 54.287 | 67.733 | 1.00 | 29.14 | 7 |
| | ATOM | 223 | CA | ASP A | 30 | 26.201 | 53.368 | 66.728 | 1.00 | 28.11 | 6 |
| | ATOM | 224 | C | ASP A | 30 | 24.732 | 53.414 | 66.407 | 1.00 | 26.63 | 6 |
| 25 | ATOM | 225 | O | ASP A | 30 | 24.254 | 52.741 | 65.481 | 1.00 | 25.59 | 8 |
| | ATOM | 226 | CB | ASP A | 30 | 26.522 | 51.957 | 67.270 | 1.00 | 28.11 | 6 |
| | ATOM | 227 | CG | ASP A | 30 | 27.095 | 51.000 | 66.268 | 1.00 | 40.59 | 6 |
| | ATOM | 228 | OD1 | ASP A | 30 | 27.215 | 51.364 | 65.080 | 1.00 | 36.45 | 8 |
| | ATOM | 229 | OD2 | ASP A | 30 | 27.418 | 49.858 | 66.666 | 1.00 | 33.26 | 8 |
| 30 | ATOM | 230 | N | ALA A | 31 | 23.951 | 54.167 | 67.177 | 1.00 | 26.99 | 7 |
| | ATOM | 231 | CA | ALA A | 31 | 22.500 | 54.152 | 67.001 | 1.00 | 29.43 | 6 |
| | ATOM | 232 | C | ALA A | 31 | 22.008 | 54.304 | 65.557 | 1.00 | 31.37 | 6 |
| | ATOM | 233 | O | ALA A | 31 | 21.093 | 53.581 | 65.107 | 1.00 | 29.31 | 8 |
| | ATOM | 234 | CB | ALA A | 31 | 21.876 | 55.193 | 67.930 | 1.00 | 24.51 | 6 |
| 35 | ATOM | 235 | N | SER A | 32 | 22.536 | 55.287 | 64.829 | 1.00 | 30.92 | 7 |
| | ATOM | 236 | CA | SER A | 32 | 22.120 | 55.571 | 63.454 | 1.00 | 31.74 | 6 |
| | ATOM | 237 | C | SER A | 32 | 22.581 | 54.499 | 62.471 | 1.00 | 30.97 | 6 |
| | ATOM | 238 | O | SER A | 32 | 21.755 | 54.063 | 61.679 | 1.00 | 31.18 | 8 |
| | ATOM | 239 | CB | SER A | 32 | 22.718 | 56.917 | 63.029 | 1.00 | 39.56 | 6 |
| 40 | ATOM | 240 | OG | SER A | 32 | 22.235 | 57.819 | 64.035 | 1.00 | 51.56 | 8 |
| | ATOM | 241 | N | ASN A | 33 | 23.815 | 54.048 | 62.624 | 1.00 | 29.10 | 7 |
| | ATOM | 242 | CA | ASN A | 33 | 24.326 | 52.942 | 61.839 | 1.00 | 31.79 | 6 |
| | ATOM | 243 | C | ASN A | 33 | 23.438 | 51.724 | 61.953 | 1.00 | 31.25 | 6 |
| | ATOM | 244 | O | ASN A | 33 | 22.833 | 51.264 | 60.966 | 1.00 | 33.18 | 8 |
| 45 | ATOM | 245 | CB | ASN A | 33 | 25.756 | 52.589 | 62.274 | 1.00 | 48.26 | 6 |
| | ATOM | 246 | CG | ASN A | 33 | 26.695 | 53.755 | 62.031 | 1.00 | 68.29 | 6 |
| | ATOM | 247 | OD1 | ASN A | 33 | 27.868 | 53.733 | 62.424 | 1.00 | 77.59 | 8 |
| | ATOM | 248 | ND2 | ASN A | 33 | 26.213 | 54.813 | 61.370 | 1.00 | 73.87 | 7 |
| | ATOM | 249 | N | LEU A | 34 | 23.210 | 51.247 | 63.171 | 1.00 | 30.16 | 7 |
| 50 | ATOM | 250 | CA | LEU A | 34 | 22.367 | 50.067 | 63.396 | 1.00 | 29.45 | 6 |
| | ATOM | 251 | C | LEU A | 34 | 21.034 | 50.177 | 62.686 | 1.00 | 28.51 | 6 |
| | ATOM | 252 | O | LEU A | 34 | 20.556 | 49.220 | 62.044 | 1.00 | 29.66 | 8 |
| | ATOM | 253 | CB | LEU A | 34 | 22.161 | 49.834 | 64.927 | 1.00 | 27.74 | 6 |
| | ATOM | 254 | CG | LEU A | 34 | 23.413 | 49.499 | 65.719 | 1.00 | 20.61 | 6 |
| 55 | ATOM | 255 | CD1 | LEU A | 34 | 23.209 | 49.686 | 67.215 | 1.00 | 29.04 | 6 |
| | ATOM | 256 | CD2 | LEU A | 34 | 23.890 | 48.078 | 65.465 | 1.00 | 32.64 | 6 |
| | ATOM | 257 | N | ARG A | 35 | 20.364 | 51.311 | 62.823 | 1.00 | 27.32 | 7 |
| | ATOM | 258 | CA | ARG A | 35 | 19.081 | 51.557 | 62.189 | 1.00 | 29.35 | 6 |
| | ATOM | 259 | C | ARG A | 35 | 19.214 | 51.455 | 60.657 | 1.00 | 30.45 | 6 |
| 60 | ATOM | 260 | O | ARG A | 35 | 18.392 | 50.762 | 60.059 | 1.00 | 29.83 | 8 |
| | ATOM | 261 | CB | ARG A | 35 | 18.524 | 52.918 | 62.569 | 1.00 | 44.28 | 6 |
| | ATOM | 262 | CG | ARG A | 35 | 17.495 | 53.521 | 61.643 | 1.00 | 57.02 | 6 |
| | ATOM | 263 | CD | ARG A | 35 | 16.073 | 53.106 | 61.959 | 1.00 | 66.44 | 6 |
| | ATOM | 264 | NE | ARG A | 35 | 15.900 | 51.741 | 62.407 | 1.00 | 70.16 | 7 |
| 65 | ATOM | 265 | CZ | ARG A | 35 | 15.357 | 50.735 | 61.742 | 1.00 | 79.55 | 6 |

| ATOM | 266 | NH1 | ARG A | 35 | 14.861 | 50.835 | 60.517 | 1.00 | 84.75 | 7 |
|------|-----|-----|-------|----|--------|--------|--------|------|-------|---|
| ATOM | 267 | NH2 | ARG A | 35 | 15.301 | 49.545 | 62.326 | 1.00 | 84.97 | 7 |
| ATOM | 268 | N | ASN A | 36 | 20.248 | 52.071 | 60.108 | 1.00 | 30.64 | 7 |
| ATOM | 269 | CA | ASN A | 36 | 20.499 | 52.050 | 58.674 | 1.00 | 33.50 | 6 |
| ATOM | 270 | C | ASN A | 36 | 20.753 | 50.627 | 58.180 | 1.00 | 33.11 | 6 |
| ATOM | 271 | O | ASN A | 36 | 20.206 | 50.308 | 57.119 | 1.00 | 34.43 | 8 |
| ATOM | 272 | CB | ASN A | 36 | 21.733 | 52.898 | 58.251 | 1.00 | 33.25 | 6 |
| ATOM | 273 | CG | ASN A | 36 | 21.318 | 54.360 | 58.192 | 1.00 | 47.82 | 6 |
| ATOM | 274 | OD1 | ASN A | 36 | 20.207 | 54.652 | 57.727 | 1.00 | 57.93 | 8 |
| ATOM | 275 | ND2 | ASN A | 36 | 22.159 | 55.275 | 58.664 | 1.00 | 49.08 | 7 |
| ATOM | 276 | N | ARG A | 37 | 21.473 | 49.799 | 58.953 | 1.00 | 30.82 | 7 |
| ATOM | 277 | CA | ARG A | 37 | 21.675 | 48.412 | 58.544 | 1.00 | 28.45 | 6 |
| ATOM | 278 | C | ARG A | 37 | 20.462 | 47.517 | 58.755 | 1.00 | 27.29 | 6 |
| ATOM | 279 | O | ARG A | 37 | 20.537 | 46.312 | 58.476 | 1.00 | 28.02 | 8 |
| ATOM | 280 | CB | ARG A | 37 | 22.878 | 47.755 | 59.170 | 1.00 | 33.91 | 6 |
| ATOM | 281 | CG | ARG A | 37 | 24.277 | 48.255 | 58.983 | 1.00 | 48.35 | 6 |
| ATOM | 282 | CD | ARG A | 37 | 24.485 | 49.333 | 57.956 | 1.00 | 64.54 | 6 |
| ATOM | 283 | NE | ARG A | 37 | 25.152 | 48.953 | 56.738 | 1.00 | 78.70 | 7 |
| ATOM | 284 | CZ | ARG A | 37 | 24.836 | 48.073 | 55.801 | 1.00 | 90.48 | 6 |
| ATOM | 285 | NH1 | ARG A | 37 | 23.749 | 47.306 | 55.840 | 1.00 | 91.76 | 7 |
| ATOM | 286 | NH2 | ARG A | 37 | 25.672 | 47.941 | 54.763 | 1.00 | 96.24 | 7 |
| ATOM | 287 | N | GLY A | 38 | 19.312 | 47.981 | 59.205 | 1.00 | 26.89 | 7 |
| ATOM | 288 | CA | GLY A | 38 | 18.148 | 47.144 | 59.413 | 1.00 | 27.35 | 6 |
| ATOM | 289 | C | GLY A | 38 | 17.900 | 46.658 | 60.843 | 1.00 | 27.95 | 6 |
| ATOM | 290 | O | GLY A | 38 | 16.882 | 45.992 | 61.080 | 1.00 | 28.18 | 8 |
| ATOM | 291 | N | ILE A | 39 | 18.763 | 46.951 | 61.810 | 1.00 | 27.05 | 7 |
| ATOM | 292 | CA | ILE A | 39 | 18.517 | 46.493 | 63.191 | 1.00 | 24.22 | 6 |
| ATOM | 293 | C | ILE A | 39 | 17.353 | 47.254 | 63.782 | 1.00 | 22.57 | 6 |
| ATOM | 294 | O | ILE A | 39 | 17.452 | 48.494 | 63.788 | 1.00 | 22.56 | 8 |
| ATOM | 295 | CB | ILE A | 39 | 19.756 | 46.783 | 64.052 | 1.00 | 26.96 | 6 |
| ATOM | 296 | CG1 | ILE A | 39 | 21.004 | 46.133 | 63.441 | 1.00 | 16.93 | 6 |
| ATOM | 297 | CG2 | ILE A | 39 | 19.574 | 46.307 | 65.506 | 1.00 | 15.96 | 6 |
| ATOM | 298 | CD1 | ILE A | 39 | 20.880 | 44.660 | 63.164 | 1.00 | 17.43 | 6 |
| ATOM | 299 | N | THR A | 40 | 16.295 | 46.579 | 64.216 | 1.00 | 21.17 | 7 |
| ATOM | 300 | CA | THR A | 40 | 15.193 | 47.336 | 64.794 | 1.00 | 21.79 | 6 |
| ATOM | 301 | C | THR A | 40 | 15.082 | 47.205 | 66.334 | 1.00 | 22.68 | 6 |
| ATOM | 302 | O | THR A | 40 | 14.185 | 47.800 | 66.940 | 1.00 | 21.81 | 8 |
| ATOM | 303 | CB | THR A | 40 | 13.886 | 46.822 | 64.184 | 1.00 | 21.04 | 6 |
| ATOM | 304 | OG1 | THR A | 40 | 13.789 | 45.438 | 64.408 | 1.00 | 24.12 | 8 |
| ATOM | 305 | CG2 | THR A | 40 | 13.830 | 47.029 | 62.667 | 1.00 | 30.33 | 6 |
| ATOM | 306 | N | PRO A | 45 | 23.742 | 43.432 | 78.684 | 1.00 | 16.53 | 6 |
| ATOM | 343 | C | PRO A | 45 | 23.197 | 43.957 | 80.047 | 1.00 | 15.40 | 6 |
| ATOM | 344 | O | PRO A | 45 | 22.620 | 45.055 | 80.187 | 1.00 | 11.51 | 8 |
| ATOM | 345 | CB | PRO A | 45 | 25.283 | 43.566 | 78.614 | 1.00 | 15.61 | 6 |
| ATOM | 346 | CG | PRO A | 45 | 25.399 | 44.987 | 78.130 | 1.00 | 16.58 | 6 |
| ATOM | 347 | CD | PRO A | 45 | 24.258 | 45.220 | 77.138 | 1.00 | 17.71 | 6 |
| ATOM | 348 | N | PRO A | 46 | 23.250 | 43.079 | 81.026 | 1.00 | 15.72 | 7 |
| ATOM | 349 | CA | PRO A | 46 | 22.868 | 43.394 | 82.434 | 1.00 | 15.02 | 6 |
| ATOM | 350 | C | PRO A | 46 | 23.310 | 44.804 | 82.792 | 1.00 | 10.92 | 6 |
| ATOM | 351 | O | PRO A | 46 | 24.505 | 45.066 | 82.711 | 1.00 | 14.77 | 8 |
| ATOM | 352 | CB | PRO A | 46 | 23.553 | 42.319 | 83.299 | 1.00 | 15.77 | 6 |
| ATOM | 353 | CG | PRO A | 46 | 23.615 | 41.142 | 82.332 | 1.00 | 18.86 | 6 |
| ATOM | 354 | CD | PRO A | 46 | 23.898 | 41.758 | 80.967 | 1.00 | 15.86 | 6 |
| ATOM | 355 | N | ALA A | 47 | 22.400 | 45.735 | 83.008 | 1.00 | 8.30 | 7 |
| ATOM | 356 | CA | ALA A | 47 | 22.727 | 47.108 | 83.291 | 1.00 | 14.65 | 6 |
| ATOM | 357 | C | ALA A | 47 | 22.986 | 47.460 | 84.787 | 1.00 | 16.30 | 6 |
| ATOM | 358 | O | ALA A | 47 | 23.364 | 48.599 | 85.045 | 1.00 | 14.79 | 8 |
| ATOM | 359 | CB | ALA A | 47 | 21.507 | 47.957 | 82.916 | 1.00 | 11.00 | 6 |
| ATOM | 360 | N | TRP A | 48 | 22.763 | 46.486 | 85.681 | 1.00 | 18.56 | 7 |
| ATOM | 361 | CA | TRP A | 48 | 22.899 | 46.723 | 87.124 | 1.00 | 18.89 | 6 |
| ATOM | 362 | C | TRP A | 48 | 24.242 | 46.318 | 87.678 | 1.00 | 19.80 | 6 |
| ATOM | 363 | O | TRP A | 48 | 21.772 | 45.983 | 87.890 | 1.00 | 11.27 | 6 |
| ATOM | 365 | CG | TRP A | 48 | 21.837 | 44.535 | 87.479 | 1.00 | 14.85 | 6 |
| ATOM | 366 | CD1 | TRP A | 48 | 22.781 | 43.612 | 87.768 | 1.00 | 15.96 | 6 |
| ATOM | 367 | CD2 | TRP A | 48 | 20.934 | 43.899 | 86.561 | 1.00 | 12.45 | 6 |

| ATOM | 368 | NE1 | TRP A 48 | 22.512 | 42.415 | 87.101 | 1.00 | 17.91 | 7 |
| ATOM | 369 | CE2 | TRP A 48 | 21.398 | 42.608 | 86.343 | 1.00 | 19.48 | 6 |
| ATOM | 370 | CE3 | TRP A 48 | 19.826 | 44.347 | 85.840 | 1.00 | 20.02 | 6 |
| ATOM | 371 | CZ2 | TRP A 48 | 20.751 | 41.717 | 85.465 | 1.00 | 20.86 | 6 |
| ATOM | 372 | CZ3 | TRP A 48 | 19.175 | 43.484 | 84.997 | 1.00 | 16.49 | 6 |
| ATOM | 373 | CH2 | TRP A 48 | 19.632 | 42.176 | 84.845 | 1.00 | 16.15 | 6 |
| ATOM | 374 | N | LYS A 49 | 24.416 | 46.571 | 88.985 | 1.00 | 19.67 | 7 |
| ATOM | 375 | CA | LYS A 49 | 25.705 | 46.328 | 89.627 | 1.00 | 14.91 | 6 |
| ATOM | 376 | C | LYS A 49 | 25.911 | 44.879 | 89.895 | 1.00 | 14.00 | 6 |
| ATOM | 377 | O | LYS A 49 | 24.988 | 44.180 | 90.365 | 1.00 | 16.96 | 8 |
| ATOM | 378 | CB | LYS A 49 | 25.709 | 47.263 | 90.876 | 1.00 | 18.57 | 6 |
| ATOM | 379 | CG | LYS A 49 | 27.023 | 47.112 | 91.599 | 1.00 | 6.84 | 6 |
| ATOM | 380 | CD | LYS A 49 | 28.243 | 47.753 | 91.027 | 1.00 | 18.29 | 6 |
| ATOM | 381 | CE | LYS A 49 | 28.021 | 49.124 | 90.447 | 1.00 | 25.50 | 6 |
| ATOM | 382 | NZ | LYS A 49 | 27.754 | 50.191 | 91.434 | 1.00 | 23.70 | 7 |
| ATOM | 383 | N | GLY A 50 | 27.064 | 44.320 | 89.567 | 1.00 | 13.43 | 7 |
| ATOM | 384 | CA | GLY A 50 | 27.330 | 42.896 | 89.765 | 1.00 | 15.74 | 6 |
| ATOM | 385 | C | GLY A 50 | 28.336 | 42.721 | 90.912 | 1.00 | 19.14 | 6 |
| ATOM | 386 | O | GLY A 50 | 28.528 | 43.669 | 91.705 | 1.00 | 21.31 | 8 |
| ATOM | 387 | N | THR A 51 | 28.984 | 41.580 | 91.058 | 1.00 | 20.32 | 7 |
| ATOM | 388 | CA | THR A 51 | 29.835 | 41.344 | 92.215 | 1.00 | 23.25 | 6 |
| ATOM | 389 | C | THR A 51 | 31.107 | 42.157 | 92.218 | 1.00 | 25.68 | 6 |
| ATOM | 390 | O | THR A 51 | 31.775 | 42.183 | 93.232 | 1.00 | 24.47 | 8 |
| ATOM | 391 | CB | THR A 51 | 30.127 | 39.852 | 92.399 | 1.00 | 30.68 | 6 |
| ATOM | 392 | OG1 | THR A 51 | 30.831 | 39.427 | 91.237 | 1.00 | 28.77 | 8 |
| ATOM | 393 | CG2 | THR A 51 | 28.838 | 39.038 | 92.528 | 1.00 | 23.54 | 6 |
| ATOM | 394 | N | SER A 52 | 31.491 | 42.737 | 91.084 | 1.00 | 24.37 | 7 |
| ATOM | 395 | CA | SER A 52 | 32.625 | 43.577 | 90.915 | 1.00 | 24.00 | 6 |
| ATOM | 396 | C | SER A 52 | 32.414 | 44.439 | 89.656 | 1.00 | 25.53 | 6 |
| ATOM | 397 | O | SER A 52 | 31.411 | 44.331 | 88.931 | 1.00 | 24.62 | 8 |
| ATOM | 398 | CB | SER A 52 | 33.937 | 42.839 | 90.870 | 1.00 | 25.10 | 6 |
| ATOM | 399 | OG | SER A 52 | 34.166 | 42.313 | 89.577 | 1.00 | 36.64 | 8 |
| ATOM | 400 | N | GLN A 53 | 33.327 | 45.385 | 89.473 | 1.00 | 25.22 | 7 |
| ATOM | 401 | CA | GLN A 53 | 33.288 | 46.289 | 88.328 | 1.00 | 26.12 | 6 |
| ATOM | 402 | C | GLN A 53 | 33.403 | 45.510 | 87.001 | 1.00 | 24.89 | 6 |
| ATOM | 403 | O | GLN A 53 | 32.765 | 45.831 | 86.004 | 1.00 | 26.00 | 8 |
| ATOM | 404 | CB | GLN A 53 | 34.544 | 47.217 | 88.329 | 1.00 | 20.73 | 6 |
| ATOM | 405 | CG | GLN A 53 | 34.286 | 48.373 | 87.337 | 1.00 | 21.42 | 6 |
| ATOM | 406 | CD | GLN A 53 | 35.441 | 49.355 | 87.321 | 1.00 | 19.77 | 6 |
| ATOM | 407 | OE1 | GLN A 53 | 35.253 | 50.545 | 87.603 | 1.00 | 32.66 | 8 |
| ATOM | 408 | NE2 | GLN A 53 | 36.620 | 48.900 | 86.998 | 1.00 | 18.17 | 7 |
| ATOM | 409 | N | ASN A 54 | 34.237 | 44.495 | 86.953 | 1.00 | 23.60 | 7 |
| ATOM | 410 | CA | ASN A 54 | 34.407 | 43.693 | 85.769 | 1.00 | 24.91 | 6 |
| ATOM | 411 | C | ASN A 54 | 33.449 | 42.530 | 85.686 | 1.00 | 25.10 | 6 |
| ATOM | 412 | O | ASN A 54 | 33.632 | 41.635 | 84.847 | 1.00 | 27.57 | 8 |
| ATOM | 413 | CB | ASN A 54 | 35.849 | 43.247 | 85.543 | 1.00 | 35.23 | 6 |
| ATOM | 414 | CG | ASN A 54 | 36.394 | 42.608 | 86.793 | 1.00 | 50.63 | 6 |
| ATOM | 415 | OD1 | ASN A 54 | 36.661 | 43.330 | 87.761 | 1.00 | 67.24 | 8 |
| ATOM | 416 | ND2 | ASP A 55 | 30.145 | 42.704 | 84.859 | 1.00 | 23.09 | 8 |
| ATOM | 421 | CB | ASP A 55 | 30.385 | 41.381 | 87.478 | 1.00 | 23.10 | 6 |
| ATOM | 422 | CG | ASP A 55 | 29.678 | 40.060 | 87.574 | 1.00 | 23.18 | 6 |
| ATOM | 423 | OD1 | ASP A 55 | 30.133 | 39.153 | 88.301 | 1.00 | 45.89 | 8 |
| ATOM | 424 | OD2 | ASP A 55 | 28.671 | 39.779 | 86.928 | 1.00 | 23.98 | 8 |
| ATOM | 425 | N | VAL A 56 | 30.427 | 40.542 | 84.263 | 1.00 | 20.61 | 7 |
| ATOM | 426 | CA | VAL A 56 | 29.587 | 40.751 | 83.054 | 1.00 | 19.89 | 6 |
| ATOM | 427 | C | VAL A 56 | 28.230 | 41.223 | 83.474 | 1.00 | 17.10 | 6 |
| ATOM | 428 | O | VAL A 56 | 27.534 | 41.937 | 82.743 | 1.00 | 15.32 | 8 |
| ATOM | 429 | CB | VAL A 56 | 29.576 | 39.529 | 82.118 | 1.00 | 22.64 | 6 |
| ATOM | 430 | CG1 | VAL A 56 | 28.492 | 39.655 | 81.068 | 1.00 | 22.70 | 6 |
| ATOM | 431 | CG2 | VAL A 56 | 30.972 | 39.455 | 81.519 | 1.00 | 17.09 | 6 |
| ATOM | 432 | N | GLY A 57 | 27.754 | 40.807 | 84.660 | 1.00 | 16.15 | 7 |
| ATOM | 433 | CA | GLY A 57 | 26.548 | 41.378 | 85.247 | 1.00 | 12.79 | 6 |
| ATOM | 434 | C | GLY A 57 | 25.600 | 40.281 | 85.744 | 1.00 | 14.69 | 6 |
| ATOM | 435 | O | GLY A 57 | 24.595 | 40.638 | 86.356 | 1.00 | 13.97 | 8 |
| ATOM | 436 | N | TYR A 58 | 25.922 | 39.045 | 85.378 | 1.00 | 14.61 | 7 |

| ATOM | 437 | CA  | TYR A | 58 | 25.135 | 37.900 | 85.760 | 1.00 | 17.45 | 6 |
| ATOM | 438 | C   | TYR A | 58 | 25.379 | 37.525 | 87.257 | 1.00 | 19.31 | 6 |
| ATOM | 439 | O   | TYR A | 58 | 24.514 | 36.826 | 87.790 | 1.00 | 16.95 | 8 |
| ATOM | 440 | CB  | TYR A | 58 | 25.349 | 36.682 | 84.827 | 1.00 | 18.27 | 6 |
| ATOM | 441 | CG  | TYR A | 58 | 24.758 | 37.019 | 83.439 | 1.00 | 17.30 | 6 |
| ATOM | 442 | CD1 | TYR A | 58 | 23.415 | 37.075 | 83.197 | 1.00 | 12.56 | 6 |
| ATOM | 443 | CD2 | TYR A | 58 | 25.650 | 37.402 | 82.418 | 1.00 | 20.54 | 6 |
| ATOM | 444 | CE1 | TYR A | 58 | 22.896 | 37.482 | 81.965 | 1.00 | 16.37 | 6 |
| ATOM | 445 | CE2 | TYR A | 58 | 25.148 | 37.764 | 81.159 | 1.00 | 19.89 | 6 |
| ATOM | 446 | CZ  | TYR A | 58 | 23.788 | 37.799 | 80.934 | 1.00 | 19.27 | 6 |
| ATOM | 447 | OH  | TYR A | 58 | 23.319 | 38.198 | 79.690 | 1.00 | 18.17 | 8 |
| ATOM | 448 | N   | TYR A | 61 | 25.642 | 43.612 | 95.022 | 1.00 | 25.65 | 6 |
| ATOM | 463 | CD1 | TYR A | 61 | 25.542 | 42.911 | 96.225 | 1.00 | 24.25 | 6 |
| ATOM | 464 | CD2 | TYR A | 61 | 25.709 | 45.005 | 95.037 | 1.00 | 26.54 | 6 |
| ATOM | 465 | CE1 | TYR A | 61 | 25.515 | 43.611 | 97.434 | 1.00 | 27.00 | 6 |
| ATOM | 466 | CE2 | TYR A | 61 | 25.691 | 45.694 | 96.251 | 1.00 | 28.34 | 6 |
| ATOM | 467 | CZ  | TYR A | 61 | 25.593 | 44.987 | 97.445 | 1.00 | 27.80 | 6 |
| ATOM | 468 | OH  | TYR A | 61 | 25.575 | 45.686 | 98.624 | 1.00 | 28.01 | 8 |
| ATOM | 469 | N   | ASP A | 62 | 22.987 | 44.124 | 93.011 | 1.00 | 18.28 | 7 |
| ATOM | 470 | CA  | ASP A | 62 | 21.843 | 44.981 | 93.248 | 1.00 | 17.30 | 6 |
| ATOM | 471 | C   | ASP A | 62 | 21.159 | 45.440 | 91.967 | 1.00 | 17.70 | 6 |
| ATOM | 472 | O   | ASP A | 62 | 21.594 | 46.430 | 91.330 | 1.00 | 18.30 | 8 |
| ATOM | 473 | CB  | ASP A | 62 | 22.379 | 46.196 | 94.092 | 1.00 | 12.40 | 6 |
| ATOM | 474 | CG  | ASP A | 62 | 21.309 | 47.201 | 94.444 | 1.00 | 13.30 | 6 |
| ATOM | 475 | OD1 | ASP A | 62 | 20.080 | 46.972 | 94.340 | 1.00 | 13.11 | 8 |
| ATOM | 476 | OD2 | ASP A | 62 | 21.740 | 48.315 | 94.834 | 1.00 | 21.37 | 8 |
| ATOM | 477 | N   | LEU A | 63 | 19.951 | 44.961 | 91.758 | 1.00 | 17.70 | 7 |
| ATOM | 478 | CA  | LEU A | 63 | 19.104 | 45.322 | 90.647 | 1.00 | 20.95 | 6 |
| ATOM | 479 | C   | LEU A | 63 | 18.646 | 46.775 | 90.591 | 1.00 | 22.88 | 6 |
| ATOM | 480 | O   | LEU A | 63 | 18.114 | 47.141 | 89.515 | 1.00 | 22.24 | 8 |
| ATOM | 481 | CB  | LEU A | 63 | 17.862 | 44.436 | 90.567 | 1.00 | 16.46 | 6 |
| ATOM | 482 | CG  | LEU A | 63 | 18.088 | 42.925 | 90.539 | 1.00 | 20.24 | 6 |
| ATOM | 483 | CD1 | LEU A | 63 | 16.765 | 42.178 | 90.480 | 1.00 | 15.13 | 6 |
| ATOM | 484 | CD2 | LEU A | 63 | 18.994 | 42.499 | 89.388 | 1.00 | 16.31 | 6 |
| ATOM | 485 | N   | TYR A | 64 | 18.800 | 47.552 | 91.680 | 1.00 | 18.58 | 7 |
| ATOM | 486 | CA  | TYR A | 64 | 18.376 | 48.936 | 91.627 | 1.00 | 18.22 | 6 |
| ATOM | 487 | C   | TYR A | 64 | 19.576 | 49.858 | 91.469 | 1.00 | 19.00 | 6 |
| ATOM | 488 | O   | TYR A | 64 | 19.384 | 51.080 | 91.510 | 1.00 | 20.72 | 8 |
| ATOM | 489 | CB  | TYR A | 64 | 17.549 | 49.422 | 92.809 | 1.00 | 18.99 | 6 |
| ATOM | 490 | CG  | TYR A | 64 | 16.187 | 48.837 | 93.017 | 1.00 | 15.73 | 6 |
| ATOM | 491 | CD1 | TYR A | 64 | 15.059 | 49.473 | 92.530 | 1.00 | 15.90 | 6 |
| ATOM | 492 | CD2 | TYR A | 64 | 15.998 | 47.640 | 93.688 | 1.00 | 18.93 | 6 |
| ATOM | 493 | CE1 | TYR A | 64 | 13.794 | 48.935 | 92.725 | 1.00 | 16.95 | 6 |
| ATOM | 494 | CE2 | TYR A | 64 | 14.743 | 47.078 | 93.869 | 1.00 | 17.53 | 6 |
| ATOM | 495 | CZ  | TYR A | 64 | 13.644 | 47.753 | 93.407 | 1.00 | 17.22 | 6 |
| ATOM | 496 | OH  | TYR A | 64 | 12.375 | 47.252 | 93.591 | 1.00 | 20.36 | 8 |
| ATOM | 497 | N   | ASP A | 65 | 20.780 | 49.347 | 91.314 | 1.00 | 17.16 | 7 |
| ATOM | 498 | CA  | ASP A | 65 | 21.942 | 50.209 | 91.137 | 1.00 | 21.10 | 6 |
| ATOM | 499 | C   | ASP A | 65 | 22.397 | 50.041 | 89.650 | 1.00 | 24.74 | 6 |
| ATOM | 500 | O   | ASP A | 65 | 23.200 | 49.139 | 89.336 | 1.00 | 24.73 | 8 |
| ATOM | 501 | CB  | ASP A | 65 | 23.067 | 49.696 | 92.045 | 1.00 | 11.90 | 6 |
| ATOM | 502 | CG  | ASP A | 65 | 24.354 | 50.424 | 91.883 | 1.00 | 18.88 | 6 |
| ATOM | 503 | OD1 | ASP A | 65 | 23.634 | 51.622 | 87.115 | 1.00 | 27.24 | 8 |
| ATOM | 508 | O   | LEU A | 66 | 23.762 | 52.306 | 86.107 | 1.00 | 28.71 | 8 |
| ATOM | 509 | CB  | LEU A | 66 | 21.209 | 51.501 | 86.536 | 1.00 | 18.64 | 6 |
| ATOM | 510 | CG  | LEU A | 66 | 19.816 | 50.978 | 86.851 | 1.00 | 22.36 | 6 |
| ATOM | 511 | CD1 | LEU A | 66 | 18.686 | 51.757 | 86.184 | 1.00 | 20.71 | 6 |
| ATOM | 512 | CD2 | LEU A | 66 | 19.690 | 49.492 | 86.541 | 1.00 | 20.39 | 6 |
| ATOM | 513 | N   | GLY A | 67 | 24.664 | 51.443 | 87.921 | 1.00 | 27.26 | 7 |
| ATOM | 514 | CA  | GLY A | 67 | 25.895 | 52.188 | 87.804 | 1.00 | 29.41 | 6 |
| ATOM | 515 | C   | GLY A | 67 | 25.649 | 53.599 | 88.380 | 1.00 | 33.01 | 6 |
| ATOM | 516 | O   | GLY A | 67 | 26.134 | 54.570 | 87.772 | 1.00 | 31.97 | 8 |
| ATOM | 517 | N   | GLU A | 68 | 24.883 | 53.754 | 89.476 | 1.00 | 33.21 | 7 |
| ATOM | 518 | CA  | GLU A | 68 | 24.760 | 55.102 | 90.026 | 1.00 | 35.92 | 6 |
| ATOM | 519 | C   | GLU A | 68 | 25.245 | 55.205 | 91.479 | 1.00 | 37.18 | 6 |

| | ATOM | 520 | O   | GLU A | 68 | 25.462 | 56.313 | 91.959 | 1.00 | 37.26 | 8 |
|---|------|-----|-----|-------|----|--------|--------|--------|------|-------|---|
| | ATOM | 521 | CB  | GLU A | 68 | 23.441 | 55.828 | 89.892 | 1.00 | 38.75 | 6 |
| | ATOM | 522 | CG  | GLU A | 68 | 22.257 | 55.179 | 90.540 | 1.00 | 34.11 | 6 |
| | ATOM | 523 | CD  | GLU A | 68 | 21.000 | 56.008 | 90.475 | 1.00 | 35.08 | 6 |
| 5 | ATOM | 524 | OE1 | GLU A | 68 | 20.977 | 57.163 | 90.944 | 1.00 | 42.85 | 8 |
| | ATOM | 525 | OE2 | GLU A | 68 | 19.983 | 55.486 | 89.965 | 1.00 | 42.28 | 8 |
| | ATOM | 526 | N   | PHE A | 69 | 25.414 | 54.063 | 92.156 | 1.00 | 36.70 | 7 |
| | ATOM | 527 | CA  | PHE A | 69 | 25.849 | 54.029 | 93.531 | 1.00 | 34.43 | 6 |
| | ATOM | 528 | C   | PHE A | 69 | 27.229 | 53.434 | 93.693 | 1.00 | 33.96 | 6 |
| 10 | ATOM | 529 | O   | PHE A | 69 | 21.909 | 55.783 | 94.626 | 1.00 | 21.63 | 6 |
| | ATOM | 535 | CE2 | PHE A | 69 | 21.194 | 53.860 | 93.385 | 1.00 | 26.02 | 6 |
| | ATOM | 536 | CZ  | PHE A | 69 | 20.928 | 55.108 | 93.931 | 1.00 | 26.60 | 6 |
| | ATOM | 537 | N   | ASN A | 70 | 27.922 | 53.932 | 94.703 | 1.00 | 32.25 | 7 |
| | ATOM | 538 | CA  | ASN A | 70 | 29.264 | 53.496 | 95.050 | 1.00 | 30.57 | 6 |
| 15 | ATOM | 539 | C   | ASN A | 70 | 29.149 | 52.217 | 95.870 | 1.00 | 31.62 | 6 |
| | ATOM | 540 | O   | ASN A | 70 | 28.903 | 52.244 | 97.086 | 1.00 | 31.24 | 8 |
| | ATOM | 541 | CB  | ASN A | 70 | 29.904 | 54.618 | 95.879 | 1.00 | 35.22 | 6 |
| | ATOM | 542 | CG  | ASN A | 70 | 31.400 | 54.385 | 95.919 | 1.00 | 45.98 | 6 |
| | ATOM | 543 | OD1 | ASN A | 70 | 31.868 | 53.260 | 95.704 | 1.00 | 48.37 | 8 |
| 20 | ATOM | 544 | ND2 | ASN A | 70 | 32.112 | 55.478 | 96.171 | 1.00 | 59.74 | 7 |
| | ATOM | 545 | N   | GLN A | 71 | 29.137 | 51.063 | 95.221 | 1.00 | 29.14 | 7 |
| | ATOM | 546 | CA  | GLN A | 71 | 28.967 | 49.769 | 95.816 | 1.00 | 27.72 | 6 |
| | ATOM | 547 | C   | GLN A | 71 | 29.890 | 48.785 | 95.102 | 1.00 | 27.35 | 6 |
| | ATOM | 548 | O   | GLN A | 71 | 30.129 | 48.954 | 93.897 | 1.00 | 28.50 | 8 |
| 25 | ATOM | 549 | CB  | GLN A | 71 | 27.552 | 49.224 | 95.684 | 1.00 | 25.56 | 6 |
| | ATOM | 550 | CG  | GLN A | 71 | 26.447 | 50.165 | 95.980 | 1.00 | 28.71 | 6 |
| | ATOM | 551 | CD  | GLN A | 71 | 25.072 | 49.652 | 96.237 | 1.00 | 30.86 | 6 |
| | ATOM | 552 | OE1 | GLN A | 71 | 24.663 | 49.585 | 97.406 | 1.00 | 36.88 | 8 |
| | ATOM | 553 | NE2 | GLN A | 71 | 24.309 | 49.337 | 95.203 | 1.00 | 21.46 | 7 |
| 30 | ATOM | 554 | N   | LYS A | 72 | 30.339 | 47.777 | 95.805 | 1.00 | 24.50 | 7 |
| | ATOM | 555 | CA  | LYS A | 72 | 31.272 | 46.797 | 95.290 | 1.00 | 27.35 | 6 |
| | ATOM | 556 | C   | LYS A | 72 | 32.568 | 47.381 | 94.790 | 1.00 | 28.76 | 6 |
| | ATOM | 557 | O   | LYS A | 72 | 33.281 | 46.720 | 94.029 | 1.00 | 32.25 | 8 |
| | ATOM | 558 | CB  | LYS A | 72 | 30.608 | 45.899 | 94.225 | 1.00 | 23.29 | 6 |
| 35 | ATOM | 559 | CG  | LYS A | 72 | 29.407 | 45.149 | 94.803 | 1.00 | 28.84 | 6 |
| | ATOM | 560 | CD  | LYS A | 72 | 29.943 | 44.159 | 95.845 | 1.00 | 36.48 | 6 |
| | ATOM | 561 | CE  | LYS A | 72 | 28.888 | 43.822 | 96.892 | 1.00 | 35.12 | 6 |
| | ATOM | 562 | NZ  | LYS A | 72 | 29.356 | 42.633 | 97.676 | 1.00 | 38.56 | 7 |
| | ATOM | 563 | N   | GLY A | 73 | 33.040 | 48.526 | 95.263 | 1.00 | 28.49 | 7 |
| 40 | ATOM | 564 | CA  | GLY A | 73 | 34.313 | 49.069 | 94.825 | 1.00 | 27.50 | 6 |
| | ATOM | 565 | C   | GLY A | 73 | 34.177 | 49.967 | 93.592 | 1.00 | 28.94 | 6 |
| | ATOM | 566 | O   | GLY A | 73 | 35.241 | 50.214 | 93.014 | 1.00 | 30.09 | 8 |
| | ATOM | 567 | N   | THR A | 74 | 32.977 | 50.387 | 93.152 | 1.00 | 27.05 | 7 |
| | ATOM | 568 | CA  | THR A | 74 | 32.928 | 51.157 | 91.915 | 1.00 | 26.78 | 6 |
| 45 | ATOM | 569 | C   | THR A | 74 | 31.596 | 51.859 | 91.799 | 1.00 | 25.34 | 6 |
| | ATOM | 570 | O   | THR A | 74 | 30.631 | 51.367 | 92.386 | 1.00 | 24.37 | 8 |
| | ATOM | 571 | CB  | THR A | 74 | 33.103 | 50.222 | 90.664 | 1.00 | 31.26 | 6 |
| | ATOM | 572 | OG1 | THR A | 74 | 32.822 | 50.956 | 89.454 | 1.00 | 25.82 | 8 |
| | ATOM | 573 | CG2 | THR A | 74 | 32.107 | 49.060 | 90.679 | 1.00 | 26.69 | 6 |
| 50 | ATOM | 574 | N   | VAL A | 75 | 31.535 | 52.982 | 91.075 | 1.00 | 24.66 | 7 |
| | ATOM | 575 | CA  | VAL A | 75 | 30.194 | 53.577 | 90.919 | 1.00 | 25.58 | 6 |
| | ATOM | 576 | C   | VAL A | 75 | 29.585 | 52.986 | 89.631 | 1.00 | 26.93 | 6 |
| | ATOM | 577 | O   | VAL A | 75 | 28.472 | 52.460 | 89.626 | 1.00 | 24.90 | 8 |
| | ATOM | 578 | CB  | ARG A | 76 | 30.395 | 53.124 | 88.553 | 1.00 | 25.83 | 7 |
| 55 | ATOM | 582 | CA  | ARG A | 76 | 29.896 | 52.613 | 87.259 | 1.00 | 23.66 | 6 |
| | ATOM | 583 | C   | ARG A | 76 | 29.898 | 51.082 | 87.285 | 1.00 | 21.40 | 6 |
| | ATOM | 584 | O   | ARG A | 76 | 30.739 | 50.419 | 87.909 | 1.00 | 19.38 | 8 |
| | ATOM | 585 | CB  | ARG A | 76 | 30.853 | 53.148 | 86.159 | 1.00 | 13.83 | 6 |
| | ATOM | 586 | CG  | ARG A | 76 | 32.237 | 52.526 | 86.080 | 1.00 | 19.96 | 6 |
| 60 | ATOM | 587 | CD  | ARG A | 76 | 36.104 | 50.868 | 84.274 | 1.00 | 16.75 | 7 |
| | ATOM | 592 | N   | THR A | 77 | 29.024 | 50.487 | 86.445 | 1.00 | 21.32 | 7 |
| | ATOM | 593 | CA  | THR A | 77 | 29.166 | 49.057 | 86.135 | 1.00 | 20.79 | 6 |
| | ATOM | 594 | C   | THR A | 77 | 30.312 | 48.886 | 85.128 | 1.00 | 21.29 | 6 |
| | ATOM | 595 | O   | THR A | 77 | 31.057 | 49.798 | 84.761 | 1.00 | 19.53 | 8 |
| 65 | ATOM | 596 | CB  | THR A | 77 | 27.910 | 48.519 | 85.446 | 1.00 | 22.75 | 6 |

| | ATOM | 597 | OG1 | THR A | 77 | 27.781 | 49.215 | 84.171 | 1.00 | 22.39 | 8 |
|---|---|---|---|---|---|---|---|---|---|---|---|
| | ATOM | 598 | CG2 | THR A | 77 | 26.698 | 48.832 | 86.297 | 1.00 | 14.11 | 6 |
| | ATOM | 599 | N | LYS A | 78 | 30.454 | 47.669 | 84.584 | 1.00 | 22.44 | 7 |
| | ATOM | 600 | CA | LYS A | 78 | 31.439 | 47.367 | 83.545 | 1.00 | 21.30 | 6 |
| 5 | ATOM | 601 | C | LYS A | 78 | 31.304 | 48.242 | 82.284 | 1.00 | 19.80 | 6 |
| | ATOM | 602 | O | LYS A | 78 | 32.280 | 48.724 | 81.730 | 1.00 | 17.17 | 8 |
| | ATOM | 603 | CB | LYS A | 78 | 31.239 | 45.902 | 83.056 | 1.00 | 21.38 | 6 |
| | ATOM | 604 | CG | LYS A | 78 | 32.369 | 45.516 | 82.104 | 1.00 | 30.30 | 6 |
| | ATOM | 605 | CD | LYS A | 78 | 32.199 | 44.122 | 81.514 | 1.00 | 24.76 | 6 |
| 10 | ATOM | 606 | CE | LYS A | 78 | 33.277 | 43.942 | 80.452 | 1.00 | 18.99 | 6 |
| | ATOM | 607 | NZ | LYS A | 78 | 33.410 | 42.535 | 80.068 | 1.00 | 18.31 | 7 |
| | ATOM | 608 | N | TYR A | 79 | 30.097 | 48.505 | 81.886 | 1.00 | 20.90 | 7 |
| | ATOM | 609 | CA | TYR A | 79 | 29.630 | 49.216 | 80.722 | 1.00 | 23.91 | 6 |
| | ATOM | 610 | C | TYR A | 79 | 29.582 | 50.734 | 80.798 | 1.00 | 26.85 | 6 |
| 15 | ATOM | 611 | O | TYR A | 79 | 29.739 | 51.412 | 79.750 | 1.00 | 25.30 | 8 |
| | ATOM | 612 | CB | TYR A | 79 | 28.191 | 48.658 | 80.425 | 1.00 | 22.18 | 6 |
| | ATOM | 613 | CG | TYR A | 79 | 28.300 | 47.138 | 80.353 | 1.00 | 20.86 | 6 |
| | ATOM | 614 | CD1 | TYR A | 79 | 29.177 | 46.490 | 79.495 | 1.00 | 20.37 | 6 |
| | ATOM | 615 | CD2 | TYR A | 79 | 27.550 | 46.371 | 81.219 | 1.00 | 21.76 | 6 |
| 20 | ATOM | 616 | CE1 | TYR A | 79 | 29.277 | 45.109 | 79.469 | 1.00 | 19.56 | 6 |
| | ATOM | 617 | CE2 | TYR A | 79 | 27.623 | 44.977 | 81.218 | 1.00 | 19.94 | 6 |
| | ATOM | 618 | CZ | TYR A | 79 | 28.487 | 44.359 | 80.347 | 1.00 | 18.41 | 6 |
| | ATOM | 619 | OH | TYR A | 79 | 28.545 | 42.993 | 80.361 | 1.00 | 14.29 | 8 |
| | ATOM | 620 | N | GLY A | 80 | 29.444 | 51.307 | 82.010 | 1.00 | 25.28 | 7 |
| 25 | ATOM | 621 | CA | GLY A | 80 | 29.431 | 52.757 | 82.150 | 1.00 | 25.76 | 6 |
| | ATOM | 622 | C | GLY A | 80 | 28.537 | 53.169 | 83.321 | 1.00 | 26.75 | 6 |
| | ATOM | 623 | O | GLY A | 80 | 28.220 | 52.288 | 84.134 | 1.00 | 24.74 | 8 |
| | ATOM | 624 | N | THR A | 81 | 28.055 | 54.412 | 83.325 | 1.00 | 25.03 | 7 |
| | ATOM | 625 | CA | THR A | 81 | 27.175 | 54.853 | 84.404 | 1.00 | 26.29 | 6 |
| 30 | ATOM | 626 | C | THR A | 81 | 25.734 | 54.946 | 83.930 | 1.00 | 27.39 | 6 |
| | ATOM | 627 | O | THR A | 81 | 25.500 | 55.049 | 82.731 | 1.00 | 26.45 | 8 |
| | ATOM | 628 | CB | THR A | 81 | 27.482 | 56.330 | 84.815 | 1.00 | 29.85 | 6 |
| | ATOM | 629 | OG1 | THR A | 81 | 27.111 | 57.124 | 83.658 | 1.00 | 32.48 | 8 |
| | ATOM | 630 | CG2 | THR A | 81 | 28.951 | 56.536 | 85.109 | 1.00 | 28.09 | 6 |
| 35 | ATOM | 631 | N | ARG A | 82 | 24.808 | 55.096 | 84.880 | 1.00 | 26.31 | 7 |
| | ATOM | 632 | CA | ARG A | 82 | 23.417 | 55.253 | 84.557 | 1.00 | 27.17 | 6 |
| | ATOM | 633 | C | ARG A | 82 | 23.177 | 56.431 | 83.615 | 1.00 | 28.32 | 6 |
| | ATOM | 634 | O | ARG A | 82 | 22.235 | 56.296 | 82.817 | 1.00 | 30.27 | 8 |
| | ATOM | 635 | CB | ARG A | 82 | 22.522 | 55.403 | 85.777 | 1.00 | 18.09 | 6 |
| 40 | ATOM | 636 | CG | ARG A | 82 | 21.204 | 56.100 | 85.672 | 1.00 | 17.36 | 6 |
| | ATOM | 637 | CD | ARG A | 82 | 20.177 | 55.821 | 86.717 | 1.00 | 24.02 | 6 |
| | ATOM | 638 | NE | ARG A | 82 | 18.880 | 56.374 | 86.434 | 1.00 | 32.87 | 7 |
| | ATOM | 639 | CZ | ARG A | 82 | 17.812 | 56.490 | 87.206 | 1.00 | 37.23 | 6 |
| | ATOM | 640 | NH1 | ARG A | 82 | 17.809 | 56.078 | 88.472 | 1.00 | 40.74 | 7 |
| 45 | ATOM | 641 | NH2 | ARG A | 82 | 16.728 | 57.037 | 86.705 | 1.00 | 29.88 | 7 |
| | ATOM | 642 | N | SER A | 83 | 23.782 | 57.600 | 83.794 | 1.00 | 27.60 | 7 |
| | ATOM | 643 | CA | SER A | 83 | 23.411 | 58.673 | 82.846 | 1.00 | 29.66 | 6 |
| | ATOM | 644 | C | SER A | 83 | 23.908 | 58.301 | 81.423 | 1.00 | 27.02 | 6 |
| | ATOM | 645 | O | SER A | 83 | 23.185 | 58.587 | 80.470 | 1.00 | 27.16 | 8 |
| 50 | ATOM | 646 | CB | SER A | 83 | 23.920 | 60.039 | 83.273 | 1.00 | 24.26 | 6 |
| | ATOM | 647 | OG | SER A | 83 | 25.337 | 59.906 | 83.317 | 1.00 | 35.47 | 8 |
| | ATOM | 648 | N | GLN A | 84 | 25.089 | 57.704 | 81.332 | 1.00 | 25.08 | 7 |
| | ATOM | 649 | CA | GLN A | 84 | 25.598 | 57.208 | 80.066 | 1.00 | 27.26 | 6 |
| | ATOM | 650 | C | GLN A | 84 | 24.624 | 56.198 | 79.473 | 1.00 | 28.38 | 6 |
| 55 | ATOM | 651 | O | GLN A | 84 | 24.219 | 56.365 | 78.308 | 1.00 | 28.32 | 8 |
| | ATOM | 652 | CB | GLN A | 84 | 27.002 | 56.619 | 80.219 | 1.00 | 22.80 | 6 |
| | ATOM | 653 | CG | GLN A | 84 | 28.049 | 57.672 | 80.542 | 1.00 | 24.28 | 6 |
| | ATOM | 654 | CD | GLN A | 84 | 29.378 | 57.005 | 80.812 | 1.00 | 30.46 | 6 |
| | ATOM | 655 | OE1 | GLN A | 84 | 30.478 | 57.520 | 80.610 | 1.00 | 40.53 | 8 |
| 60 | ATOM | 656 | NE2 | GLN A | 84 | 29.368 | 55.759 | 81.267 | 1.00 | 25.18 | 7 |
| | ATOM | 657 | N | LEU A | 85 | 24.097 | 55.230 | 80.250 | 1.00 | 27.63 | 7 |
| | ATOM | 658 | CA | LEU A | 85 | 23.109 | 54.315 | 79.712 | 1.00 | 26.47 | 6 |
| | ATOM | 659 | C | LEU A | 85 | 21.867 | 55.033 | 79.204 | 1.00 | 28.93 | 6 |
| | ATOM | 660 | O | LEU A | 85 | 21.284 | 54.664 | 78.164 | 1.00 | 29.54 | 8 |
| 65 | ATOM | 661 | CB | LEU A | 85 | 22.654 | 53.270 | 80.708 | 1.00 | 22.28 | 6 |

| ATOM | 662 | CG | LEU A | 85 | 21.488 | 52.356 | 80.351 | 1.00 | 23.99 | 6 |
| --- | --- | --- | --- | --- | --- | --- | --- | --- | --- | --- |
| ATOM | 663 | CD1 | LEU A | 85 | 21.726 | 51.532 | 79.093 | 1.00 | 20.87 | 6 |
| ATOM | 664 | CD2 | LEU A | 85 | 21.261 | 51.347 | 81.489 | 1.00 | 28.27 | 6 |
| ATOM | 665 | N | GLU A | 86 | 21.329 | 55.957 | 79.988 | 1.00 | 27.07 | 7 |
| ATOM | 666 | CA | GLU A | 86 | 20.123 | 56.671 | 79.575 | 1.00 | 27.80 | 6 |
| ATOM | 667 | C | GLU A | 86 | 20.374 | 57.493 | 78.302 | 1.00 | 27.01 | 6 |
| ATOM | 668 | O | GLU A | 86 | 19.458 | 57.657 | 77.464 | 1.00 | 26.06 | 8 |
| ATOM | 669 | CB | GLU A | 86 | 19.696 | 57.582 | 80.748 | 1.00 | 40.30 | 6 |
| ATOM | 670 | CG | GLU A | 86 | 19.235 | 56.861 | 81.995 | 1.00 | 48.52 | 6 |
| ATOM | 671 | CD | GLU A | 86 | 18.760 | 57.679 | 83.176 | 1.00 | 52.20 | 6 |
| ATOM | 672 | OE1 | GLU A | 86 | 19.624 | 58.224 | 83.903 | 1.00 | 61.23 | 8 |
| ATOM | 673 | OE2 | GLU A | 86 | 17.545 | 57.797 | 83.458 | 1.00 | 49.66 | 8 |
| ATOM | 674 | N | SER A | 87 | 21.530 | 58.085 | 78.056 | 1.00 | 26.53 | 7 |
| ATOM | 675 | CA | SER A | 87 | 21.645 | 58.870 | 76.809 | 1.00 | 29.75 | 6 |
| ATOM | 676 | C | SER A | 87 | 21.731 | 57.901 | 75.618 | 1.00 | 30.32 | 6 |
| ATOM | 677 | O | SER A | 87 | 21.116 | 58.150 | 74.583 | 1.00 | 30.73 | 8 |
| ATOM | 678 | CB | SER A | 87 | 22.681 | 59.961 | 76.772 | 1.00 | 32.20 | 6 |
| ATOM | 679 | OG | SER A | 87 | 23.973 | 59.484 | 77.049 | 1.00 | 42.05 | 8 |
| ATOM | 680 | N | ALA A | 88 | 22.378 | 56.752 | 75.818 | 1.00 | 29.76 | 7 |
| ATOM | 681 | CA | ALA A | 88 | 22.413 | 55.724 | 74.788 | 1.00 | 27.74 | 6 |
| ATOM | 682 | C | ALA A | 88 | 20.985 | 55.297 | 74.496 | 1.00 | 26.48 | 6 |
| ATOM | 683 | O | ALA A | 88 | 20.561 | 55.293 | 73.334 | 1.00 | 26.88 | 8 |
| ATOM | 684 | CB | ALA A | 88 | 23.281 | 54.524 | 75.077 | 1.00 | 25.94 | 6 |
| ATOM | 685 | N | ILE A | 89 | 20.148 | 55.072 | 75.490 | 1.00 | 24.88 | 7 |
| ATOM | 686 | CA | ILE A | 89 | 18.768 | 54.692 | 75.217 | 1.00 | 23.52 | 6 |
| ATOM | 687 | C | ILE A | 89 | 18.053 | 55.828 | 74.481 | 1.00 | 25.44 | 6 |
| ATOM | 688 | O | ILE A | 89 | 17.120 | 55.529 | 73.701 | 1.00 | 24.83 | 8 |
| ATOM | 689 | CB | ILE A | 89 | 18.002 | 54.210 | 76.457 | 1.00 | 21.65 | 6 |
| ATOM | 690 | CG1 | ILE A | 89 | 18.574 | 52.875 | 77.001 | 1.00 | 28.88 | 6 |
| ATOM | 691 | CG2 | ILE A | 89 | 16.526 | 54.039 | 76.223 | 1.00 | 13.66 | 6 |
| ATOM | 692 | CD1 | ILE A | 89 | 17.955 | 52.441 | 78.324 | 1.00 | 30.45 | 6 |
| ATOM | 693 | N | HIS A | 90 | 18.392 | 57.088 | 74.779 | 1.00 | 24.28 | 7 |
| ATOM | 694 | CA | HIS A | 90 | 17.727 | 58.199 | 74.112 | 1.00 | 28.25 | 6 |
| ATOM | 695 | C | HIS A | 90 | 18.037 | 58.199 | 72.591 | 1.00 | 26.88 | 6 |
| ATOM | 696 | O | HIS A | 90 | 17.173 | 58.406 | 71.747 | 1.00 | 25.73 | 8 |
| ATOM | 697 | CB | HIS A | 90 | 18.236 | 59.573 | 74.618 | 1.00 | 41.06 | 6 |
| ATOM | 698 | CG | HIS A | 90 | 17.378 | 60.661 | 74.031 | 1.00 | 59.86 | 6 |
| ATOM | 699 | ND1 | HIS A | 90 | 16.033 | 60.458 | 73.761 | 1.00 | 65.74 | 7 |
| ATOM | 700 | CD2 | HIS A | 90 | 17.648 | 61.935 | 73.657 | 1.00 | 65.92 | 6 |
| ATOM | 701 | CE1 | HIS A | 90 | 15.520 | 61.574 | 73.267 | 1.00 | 67.17 | 6 |
| ATOM | 702 | NE2 | HIS A | 90 | 16.477 | 62.487 | 73.190 | 1.00 | 67.40 | 7 |
| ATOM | 703 | N | ALA A | 91 | 19.333 | 58.038 | 72.335 | 1.00 | 27.28 | 7 |
| ATOM | 704 | CA | ALA A | 91 | 19.768 | 57.944 | 70.934 | 1.00 | 30.32 | 6 |
| ATOM | 705 | C | ALA A | 91 | 19.032 | 56.824 | 70.210 | 1.00 | 31.56 | 6 |
| ATOM | 706 | O | ALA A | 91 | 18.437 | 57.058 | 69.144 | 1.00 | 32.93 | 8 |
| ATOM | 707 | CB | ALA A | 91 | 21.267 | 57.723 | 70.921 | 1.00 | 33.17 | 6 |
| ATOM | 708 | N | LEU A | 92 | 18.930 | 55.617 | 70.792 | 1.00 | 30.95 | 7 |
| ATOM | 709 | CA | LEU A | 92 | 18.225 | 54.502 | 70.166 | 1.00 | 28.50 | 6 |
| ATOM | 710 | C | LEU A | 92 | 16.790 | 54.823 | 69.856 | 1.00 | 26.16 | 6 |
| ATOM | 711 | O | LEU A | 92 | 16.249 | 54.541 | 68.798 | 1.00 | 26.07 | 8 |
| ATOM | 712 | CB | LEU A | 92 | 18.264 | 53.207 | 71.008 | 1.00 | 26.14 | 6 |
| ATOM | 713 | CG | LEU A | 92 | 19.652 | 52.613 | 71.189 | 1.00 | 27.87 | 6 |
| ATOM | 714 | CD1 | LEU A | 92 | 19.575 | 51.308 | 71.985 | 1.00 | 30.16 | 6 |
| ATOM | 715 | CD2 | LEU A | 92 | 20.401 | 52.325 | 69.902 | 1.00 | 19.42 | 6 |
| ATOM | 716 | N | LYS A | 93 | 16.120 | 55.418 | 70.826 | 1.00 | 26.45 | 7 |
| ATOM | 717 | CA | LYS A | 93 | 14.704 | 55.754 | 70.718 | 1.00 | 26.60 | 6 |
| ATOM | 718 | C | LYS A | 93 | 14.539 | 56.842 | 69.633 | 1.00 | 27.98 | 6 |
| ATOM | 719 | O | LYS A | 93 | 13.541 | 56.873 | 68.916 | 1.00 | 25.59 | 8 |
| ATOM | 720 | CB | LYS A | 93 | 14.224 | 56.224 | 72.079 | 1.00 | 37.62 | 6 |
| ATOM | 721 | CG | LYS A | 93 | 13.149 | 55.529 | 72.860 | 1.00 | 39.22 | 6 |
| ATOM | 722 | CD | LYS A | 93 | 13.436 | 54.121 | 73.320 | 1.00 | 34.53 | 6 |
| ATOM | 723 | CE | LYS A | 93 | 12.624 | 53.763 | 74.546 | 1.00 | 36.60 | 6 |
| ATOM | 724 | NZ | LYS A | 93 | 11.468 | 52.873 | 74.376 | 1.00 | 34.30 | 7 |
| ATOM | 725 | N | ASN A | 94 | 15.511 | 57.730 | 69.524 | 1.00 | 30.08 | 7 |
| ATOM | 726 | CA | ASN A | 94 | 15.447 | 58.800 | 68.525 | 1.00 | 35.42 | 6 |

| ATOM | 727 | C   | ASN A 94  | 15.613 | 58.239 | 67.124 | 1.00 | 37.33 | 6 |
| ATOM | 728 | O   | ASN A 94  | 14.991 | 58.775 | 66.201 | 1.00 | 39.60 | 8 |
| ATOM | 729 | CB  | ASN A 94  | 16.419 | 59.943 | 68.838 | 1.00 | 44.84 | 6 |
| ATOM | 730 | CG  | ASN A 94  | 15.585 | 61.034 | 69.505 | 1.00 | 55.65 | 6 |
| ATOM | 731 | OD1 | ASN A 94  | 15.624 | 62.186 | 69.098 | 1.00 | 73.22 | 8 |
| ATOM | 732 | ND2 | ASN A 94  | 14.764 | 60.682 | 70.487 | 1.00 | 56.79 | 7 |
| ATOM | 733 | N   | ASN A 95  | 16.314 | 57.113 | 66.981 | 1.00 | 35.93 | 7 |
| ATOM | 734 | CA  | ASN A 95  | 16.458 | 56.453 | 65.701 | 1.00 | 33.37 | 6 |
| ATOM | 735 | C   | ASN A 95  | 15.482 | 55.332 | 65.486 | 1.00 | 32.25 | 6 |
| ATOM | 736 | O   | ASN A 95  | 15.761 | 54.421 | 64.693 | 1.00 | 34.32 | 8 |
| ATOM | 737 | CB  | ASN A 95  | 17.887 | 55.932 | 65.573 | 1.00 | 34.99 | 6 |
| ATOM | 738 | CG  | ASN A 95  | 18.799 | 57.098 | 65.245 | 1.00 | 45.21 | 6 |
| ATOM | 739 | OD1 | ASN A 95  | 19.110 | 57.368 | 64.085 | 1.00 | 46.20 | 8 |
| ATOM | 740 | ND2 | ASN A 95  | 19.235 | 57.795 | 66.278 | 1.00 | 40.71 | 7 |
| ATOM | 741 | N   | GLY A 96  | 14.357 | 55.277 | 66.188 | 1.00 | 31.16 | 7 |
| ATOM | 742 | CA  | GLY A 96  | 13.369 | 54.240 | 66.044 | 1.00 | 28.59 | 6 |
| ATOM | 743 | C   | GLY A 96  | 13.766 | 52.828 | 66.455 | 1.00 | 28.70 | 6 |
| ATOM | 744 | O   | GLY A 96  | 13.023 | 51.874 | 66.136 | 1.00 | 29.32 | 8 |
| ATOM | 745 | N   | VAL A 97  | 14.880 | 52.615 | 67.134 | 1.00 | 26.43 | 7 |
| ATOM | 746 | CA  | VAL A 97  | 15.260 | 51.274 | 67.575 | 1.00 | 26.61 | 6 |
| ATOM | 747 | C   | VAL A 97  | 14.691 | 50.959 | 68.959 | 1.00 | 27.97 | 6 |
| ATOM | 748 | O   | VAL A 97  | 14.850 | 51.807 | 69.853 | 1.00 | 27.20 | 8 |
| ATOM | 749 | CB  | VAL A 97  | 16.792 | 51.169 | 67.662 | 1.00 | 26.27 | 6 |
| ATOM | 750 | CG1 | VAL A 97  | 17.244 | 49.754 | 67.987 | 1.00 | 14.11 | 6 |
| ATOM | 751 | CG2 | VAL A 97  | 17.425 | 51.629 | 66.342 | 1.00 | 31.58 | 6 |
| ATOM | 752 | N   | GLN A 98  | 14.104 | 49.795 | 69.159 | 1.00 | 27.95 | 7 |
| ATOM | 753 | CA  | GLN A 98  | 13.575 | 49.334 | 70.448 | 1.00 | 25.14 | 6 |
| ATOM | 754 | C   | GLN A 98  | 14.625 | 48.760 | 71.397 | 1.00 | 25.16 | 6 |
| ATOM | 755 | O   | GLN A 98  | 15.696 | 48.353 | 70.944 | 1.00 | 22.76 | 8 |
| ATOM | 756 | CB  | GLN A 98  | 12.539 | 48.251 | 70.157 | 1.00 | 17.49 | 6 |
| ATOM | 757 | CG  | GLN A 98  | 11.170 | 48.854 | 69.932 | 1.00 | 29.35 | 6 |
| ATOM | 758 | CD  | GLN A 98  | 10.184 | 47.795 | 69.503 | 1.00 | 42.26 | 6 |
| ATOM | 759 | OE1 | GLN A 98  | 10.540 | 46.655 | 69.269 | 1.00 | 45.15 | 8 |
| ATOM | 760 | NE2 | GLN A 98  |  8.924 | 48.192 | 69.376 | 1.00 | 56.07 | 7 |
| ATOM | 761 | N   | VAL A 99  | 14.402 | 48.902 | 72.739 | 1.00 | 23.46 | 7 |
| ATOM | 762 | CA  | VAL A 99  | 15.424 | 48.448 | 73.692 | 1.00 | 21.32 | 6 |
| ATOM | 763 | C   | VAL A 99  | 14.917 | 47.330 | 74.598 | 1.00 | 19.22 | 6 |
| ATOM | 764 | O   | VAL A 99  | 13.817 | 47.437 | 75.184 | 1.00 | 19.88 | 8 |
| ATOM | 765 | CB  | VAL A 99  | 15.895 | 49.580 | 74.623 | 1.00 | 28.07 | 6 |
| ATOM | 766 | CG1 | VAL A 99  | 17.158 | 49.135 | 75.360 | 1.00 | 27.17 | 6 |
| ATOM | 767 | CG2 | VAL A 99  | 16.243 | 50.827 | 73.822 | 1.00 | 40.90 | 6 |
| ATOM | 768 | N   | TYR A 100 | 15.590 | 46.194 | 74.586 | 1.00 | 17.68 | 7 |
| ATOM | 769 | CA  | TYR A 100 | 15.261 | 45.045 | 75.395 | 1.00 | 17.15 | 6 |
| ATOM | 770 | C   | TYR A 100 | 16.291 | 44.869 | 76.527 | 1.00 | 17.39 | 6 |
| ATOM | 771 | O   | TYR A 100 | 17.483 | 44.789 | 76.233 | 1.00 | 15.80 | 8 |
| ATOM | 772 | CB  | TYR A 100 | 15.270 | 43.716 | 74.633 | 1.00 | 20.33 | 6 |
| ATOM | 773 | CG  | TYR A 100 | 14.287 | 43.618 | 73.496 | 1.00 | 23.97 | 6 |
| ATOM | 774 | CD1 | TYR A 100 | 13.133 | 44.397 | 73.447 | 1.00 | 23.67 | 6 |
| ATOM | 775 | CD2 | TYR A 100 | 14.564 | 42.732 | 72.441 | 1.00 | 24.39 | 6 |
| ATOM | 776 | CE1 | TYR A 100 | 12.275 | 44.292 | 72.366 | 1.00 | 25.53 | 6 |
| ATOM | 777 | CE2 | TYR A 100 | 13.704 | 42.635 | 71.358 | 1.00 | 23.58 | 6 |
| ATOM | 778 | CZ  | TYR A 100 | 12.585 | 43.417 | 71.313 | 1.00 | 23.55 | 6 |
| ATOM | 779 | OH  | TYR A 100 | 11.716 | 43.320 | 70.278 | 1.00 | 22.25 | 8 |
| ATOM | 780 | N   | GLY A 101 | 15.790 | 44.787 | 77.780 | 1.00 | 17.34 | 7 |
| ATOM | 781 | CA  | GLY A 101 | 16.727 | 44.623 | 78.906 | 1.00 | 14.59 | 6 |
| ATOM | 782 | C   | GLY A 101 | 16.908 | 43.192 | 79.386 | 1.00 | 11.65 | 6 |
| ATOM | 783 | O   | GLY A 101 | 15.973 | 42.408 | 79.355 | 1.00 | 12.65 | 8 |
| ATOM | 784 | N   | ASP A 102 | 18.121 | 42.759 | 79.744 | 1.00 | 13.34 | 7 |
| ATOM | 785 | CA  | ASP A 102 | 18.304 | 41.431 | 80.353 | 1.00 | 13.47 | 6 |
| ATOM | 786 | C   | ASP A 102 | 17.648 | 41.507 | 81.777 | 1.00 | 15.09 | 6 |
| ATOM | 787 | O   | ASP A 102 | 17.463 | 42.598 | 82.341 | 1.00 | 14.56 | 8 |
| ATOM | 788 | CB  | ASP A 102 | 19.795 | 41.183 | 80.569 | 1.00 | 11.48 | 6 |
| ATOM | 789 | CG  | ASP A 102 | 20.159 | 39.752 | 80.306 | 1.00 | 12.52 | 6 |
| ATOM | 790 | OD1 | ASP A 102 | 19.384 | 38.867 | 80.788 | 1.00 | 15.17 | 8 |
| ATOM | 791 | OD2 | ASP A 102 | 21.185 | 39.489 | 79.599 | 1.00 | 17.64 | 8 |

| ATOM | 792 | N | VAL A 103 | 17.229 | 40.390 | 82.280 | 1.00 | 14.82 | 7 |
|------|-----|-----|-----------|--------|--------|--------|------|-------|-----|
| ATOM | 793 | CA | VAL A 103 | 16.493 | 40.167 | 83.502 | 1.00 | 14.92 | 6 |
| ATOM | 794 | C | VAL A 103 | 17.058 | 38.928 | 84.207 | 1.00 | 14.68 | 6 |
| ATOM | 795 | O | VAL A 103 | 16.849 | 37.788 | 83.790 | 1.00 | 13.55 | 8 |
| ATOM | 796 | CB | VAL A 103 | 15.005 | 39.890 | 83.261 | 1.00 | 18.86 | 6 |
| ATOM | 797 | CG1 | VAL A 103 | 14.282 | 39.583 | 84.577 | 1.00 | 24.13 | 6 |
| ATOM | 798 | CG2 | VAL A 103 | 14.338 | 41.114 | 82.610 | 1.00 | 23.58 | 6 |
| ATOM | 799 | N | VAL A 104 | 17.756 | 39.187 | 85.343 | 1.00 | 13.33 | 7 |
| ATOM | 800 | CA | VAL A 104 | 18.345 | 38.106 | 86.118 | 1.00 | 11.70 | 6 |
| ATOM | 801 | C | VAL A 104 | 17.667 | 38.025 | 87.518 | 1.00 | 14.62 | 6 |
| ATOM | 802 | O | VAL A 104 | 17.907 | 38.921 | 88.344 | 1.00 | 11.28 | 8 |
| ATOM | 803 | CB | VAL A 104 | 19.843 | 38.363 | 86.246 | 1.00 | 12.15 | 6 |
| ATOM | 804 | CG1 | VAL A 104 | 20.493 | 37.200 | 87.026 | 1.00 | 15.28 | 6 |
| ATOM | 805 | CG2 | VAL A 104 | 20.516 | 38.434 | 84.866 | 1.00 | 24.46 | 6 |
| ATOM | 806 | N | MET A 105 | 16.738 | 37.112 | 87.714 | 1.00 | 13.63 | 7 |
| ATOM | 807 | CA | MET A 105 | 15.988 | 36.987 | 88.961 | 1.00 | 15.45 | 6 |
| ATOM | 808 | C | MET A 105 | 16.313 | 35.668 | 89.656 | 1.00 | 15.72 | 6 |
| ATOM | 809 | O | MET A 105 | 15.681 | 35.344 | 90.656 | 1.00 | 16.37 | 8 |
| ATOM | 810 | CB | MET A 105 | 14.464 | 36.975 | 88.608 | 1.00 | 5.32 | 6 |
| ATOM | 811 | CG | MET A 105 | 14.085 | 38.454 | 88.115 | 1.00 | 9.60 | 6 |
| ATOM | 812 | SD | MET A 105 | 12.331 | 38.446 | 87.765 | 1.00 | 24.51 | 16 |
| ATOM | 813 | CE | MET A 105 | 11.881 | 39.900 | 88.682 | 1.00 | 45.97 | 6 |
| ATOM | 814 | N | ASN A 106 | 17.102 | 34.751 | 89.065 | 1.00 | 13.34 | 7 |
| ATOM | 815 | CA | ASN A 106 | 17.261 | 33.440 | 89.636 | 1.00 | 13.70 | 6 |
| ATOM | 816 | C | ASN A 106 | 18.025 | 33.465 | 91.013 | 1.00 | 14.43 | 6 |
| ATOM | 817 | O | ASN A 106 | 17.708 | 32.625 | 91.845 | 1.00 | 13.26 | 8 |
| ATOM | 818 | CB | ASN A 106 | 18.066 | 32.548 | 88.719 | 1.00 | 6.27 | 6 |
| ATOM | 819 | CG | ASN A 106 | 18.651 | 31.318 | 89.258 | 1.00 | 8.00 | 6 |
| ATOM | 820 | OD1 | ASN A 106 | 19.688 | 30.774 | 89.540 | 1.00 | 11.69 | 8 |
| ATOM | 821 | ND2 | ASN A 106 | 17.629 | 30.519 | 89.481 | 1.00 | 2.77 | 7 |
| ATOM | 822 | N | HIS A 107 | 19.030 | 34.285 | 91.095 | 1.00 | 11.91 | 7 |
| ATOM | 823 | CA | HIS A 107 | 19.986 | 34.236 | 92.154 | 1.00 | 10.48 | 6 |
| ATOM | 824 | C | HIS A 107 | 20.535 | 35.624 | 92.397 | 1.00 | 12.08 | 6 |
| ATOM | 825 | O | HIS A 107 | 20.227 | 36.573 | 91.672 | 1.00 | 11.45 | 8 |
| ATOM | 826 | CB | HIS A 107 | 21.191 | 33.361 | 91.805 | 1.00 | 16.81 | 6 |
| ATOM | 827 | CG | HIS A 107 | 21.832 | 33.780 | 90.505 | 1.00 | 26.29 | 6 |
| ATOM | 828 | ND1 | HIS A 107 | 21.509 | 33.126 | 89.312 | 1.00 | 25.26 | 7 |
| ATOM | 829 | CD2 | HIS A 107 | 22.724 | 34.735 | 90.199 | 1.00 | 25.06 | 6 |
| ATOM | 830 | CE1 | HIS A 107 | 22.215 | 33.687 | 88.353 | 1.00 | 22.21 | 6 |
| ATOM | 831 | NE2 | HIS A 107 | 22.945 | 34.679 | 88.842 | 1.00 | 20.55 | 7 |
| ATOM | 832 | N | LEU A 108 | 21.234 | 35.733 | 93.529 | 1.00 | 12.42 | 7 |
| ATOM | 833 | CA | LEU A 108 | 21.821 | 36.997 | 93.952 | 1.00 | 11.65 | 6 |
| ATOM | 834 | C | LEU A 108 | 23.215 | 36.660 | 94.443 | 1.00 | 12.15 | 6 |
| ATOM | 835 | O | LEU A 108 | 23.406 | 35.699 | 95.209 | 1.00 | 14.67 | 8 |
| ATOM | 836 | CB | LEU A 108 | 21.042 | 37.746 | 95.003 | 1.00 | 21.94 | 6 |
| ATOM | 837 | CG | LEU A 108 | 19.744 | 38.457 | 94.808 | 1.00 | 21.68 | 6 |
| ATOM | 838 | CD1 | LEU A 108 | 18.553 | 37.510 | 94.757 | 1.00 | 39.57 | 6 |
| ATOM | 839 | CD2 | LEU A 108 | 19.311 | 39.330 | 95.982 | 1.00 | 22.08 | 6 |
| ATOM | 840 | N | GLY A 109 | 24.199 | 37.441 | 94.005 | 1.00 | 12.09 | 7 |
| ATOM | 841 | CA | GLY A 109 | 25.565 | 37.136 | 94.430 | 1.00 | 11.56 | 6 |
| ATOM | 842 | C | GLY A 109 | 26.202 | 38.357 | 95.083 | 1.00 | 12.72 | 6 |
| ATOM | 843 | O | GLY A 109 | 25.681 | 39.484 | 95.013 | 1.00 | 13.88 | 8 |
| ATOM | 844 | N | GLY A 110 | 27.383 | 38.153 | 95.652 | 1.00 | 13.11 | 7 |
| ATOM | 845 | CA | GLY A 110 | 28.067 | 39.328 | 96.240 | 1.00 | 15.14 | 6 |
| ATOM | 846 | C | GLY A 110 | 27.439 | 39.811 | 97.559 | 1.00 | 14.99 | 6 |
| ATOM | 847 | O | GLY A 110 | 27.472 | 41.015 | 97.810 | 1.00 | 13.87 | 8 |
| ATOM | 848 | N | ALA A 111 | 26.791 | 38.972 | 98.352 | 1.00 | 14.85 | 7 |
| ATOM | 849 | CA | ALA A 111 | 26.179 | 39.445 | 99.591 | 1.00 | 18.80 | 6 |
| ATOM | 850 | C | ALA A 111 | 27.108 | 40.326 | 100.430 | 1.00 | 18.06 | 6 |
| ATOM | 851 | O | ALA A 111 | 28.296 | 40.106 | 100.516 | 1.00 | 18.52 | 8 |
| ATOM | 852 | CB | ALA A 111 | 25.772 | 38.304 | 100.518 | 1.00 | 14.03 | 6 |
| ATOM | 853 | N | ASP A 112 | 26.529 | 41.293 | 101.126 | 1.00 | 21.22 | 7 |
| ATOM | 854 | CA | ASP A 112 | 27.346 | 42.122 | 102.035 | 1.00 | 23.75 | 6 |
| ATOM | 855 | C | ASP A 112 | 27.869 | 41.314 | 103.234 | 1.00 | 23.71 | 6 |
| ATOM | 856 | O | ASP A 112 | 28.969 | 41.671 | 103.682 | 1.00 | 23.18 | 8 |

| ATOM | 857 | CB | ASP A 112 | 26.496 | 43.284 | 102.503 | 1.00 | 22.42 | 6 |
|---|---|---|---|---|---|---|---|---|---|
| ATOM | 858 | CG | ASP A 112 | 26.071 | 44.169 | 101.348 | 1.00 | 20.14 | 6 |
| ATOM | 859 | OD1 | ASP A 112 | 26.995 | 44.523 | 100.598 | 1.00 | 27.30 | 8 |
| ATOM | 860 | OD2 | ASP A 112 | 24.879 | 44.509 | 101.271 | 1.00 | 20.89 | 8 |
| ATOM | 861 | N | ALA A 113 | 27.194 | 40.251 | 103.702 | 1.00 | 24.00 | 7 |
| ATOM | 862 | CA | ALA A 113 | 27.759 | 39.527 | 104.868 | 1.00 | 24.01 | 6 |
| ATOM | 863 | C | ALA A 113 | 27.179 | 38.131 | 105.013 | 1.00 | 23.94 | 6 |
| ATOM | 864 | O | ALA A 113 | 26.110 | 37.890 | 104.451 | 1.00 | 22.13 | 8 |
| ATOM | 865 | CB | ALA A 113 | 27.342 | 40.331 | 106.122 | 1.00 | 26.22 | 6 |
| ATOM | 866 | N | THR A 114 | 27.826 | 37.278 | 105.810 | 1.00 | 22.06 | 7 |
| ATOM | 867 | CA | THR A 114 | 27.281 | 35.943 | 106.016 | 1.00 | 21.69 | 6 |
| ATOM | 868 | C | THR A 114 | 26.312 | 35.843 | 107.186 | 1.00 | 22.01 | 6 |
| ATOM | 869 | O | THR A 114 | 26.155 | 36.802 | 107.929 | 1.00 | 20.55 | 8 |
| ATOM | 870 | CB | THR A 114 | 28.387 | 34.909 | 106.254 | 1.00 | 27.87 | 6 |
| ATOM | 871 | OG1 | THR A 114 | 28.996 | 35.251 | 107.512 | 1.00 | 29.11 | 8 |
| ATOM | 872 | CG2 | VAL A 117 | 21.913 | 29.028 | 108.776 | 1.00 | 20.64 | 6 |
| ATOM | 892 | C | VAL A 117 | 21.937 | 27.532 | 108.893 | 1.00 | 17.39 | 6 |
| ATOM | 893 | O | VAL A 117 | 22.915 | 26.888 | 108.527 | 1.00 | 19.05 | 8 |
| ATOM | 894 | CB | VAL A 117 | 21.661 | 29.432 | 107.278 | 1.00 | 19.42 | 6 |
| ATOM | 895 | CG1 | VAL A 117 | 20.322 | 28.897 | 106.753 | 1.00 | 17.44 | 6 |
| ATOM | 896 | CG2 | VAL A 117 | 21.569 | 30.946 | 107.143 | 1.00 | 18.54 | 6 |
| ATOM | 897 | N | THR A 118 | 20.829 | 27.010 | 109.358 | 1.00 | 17.83 | 7 |
| ATOM | 898 | CA | THR A 118 | 20.756 | 25.536 | 109.467 | 1.00 | 19.80 | 6 |
| ATOM | 899 | C | THR A 118 | 20.402 | 25.048 | 108.042 | 1.00 | 18.35 | 6 |
| ATOM | 900 | O | THR A 118 | 19.399 | 25.534 | 107.507 | 1.00 | 16.70 | 8 |
| ATOM | 901 | CB | THR A 118 | 19.548 | 25.042 | 110.320 | 1.00 | 17.44 | 6 |
| ATOM | 902 | OG1 | THR A 118 | 19.233 | 26.096 | 111.204 | 1.00 | 44.59 | 8 |
| ATOM | 903 | CG2 | THR A 118 | 19.779 | 23.693 | 110.989 | 1.00 | 22.04 | 6 |
| ATOM | 904 | N | ALA A 119 | 21.103 | 24.023 | 107.604 | 1.00 | 19.84 | 7 |
| ATOM | 905 | CA | ALA A 119 | 20.887 | 23.578 | 106.200 | 1.00 | 19.90 | 6 |
| ATOM | 906 | C | ALA A 119 | 21.136 | 22.103 | 106.100 | 1.00 | 21.67 | 6 |
| ATOM | 907 | O | ALA A 119 | 21.679 | 21.551 | 107.079 | 1.00 | 22.42 | 8 |
| ATOM | 908 | CB | ALA A 119 | 22.069 | 24.322 | 105.517 | 1.00 | 19.05 | 6 |
| ATOM | 909 | N | VAL A 120 | 20.764 | 21.406 | 105.044 | 1.00 | 20.76 | 7 |
| ATOM | 910 | CA | VAL A 120 | 21.100 | 19.986 | 104.883 | 1.00 | 19.40 | 6 |
| ATOM | 911 | C | VAL A 120 | 21.803 | 19.899 | 103.514 | 1.00 | 21.46 | 6 |
| ATOM | 912 | O | VAL A 120 | 21.498 | 20.756 | 102.676 | 1.00 | 21.10 | 8 |
| ATOM | 913 | CB | VAL A 120 | 19.868 | 19.080 | 104.936 | 1.00 | 12.56 | 6 |
| ATOM | 914 | CG1 | VAL A 120 | 18.742 | 19.485 | 104.021 | 1.00 | 15.21 | 6 |
| ATOM | 915 | CG2 | VAL A 120 | 20.238 | 17.612 | 104.692 | 1.00 | 13.03 | 6 |
| ATOM | 916 | N | GLU A 121 | 22.737 | 19.042 | 103.259 | 1.00 | 20.32 | 7 |
| ATOM | 917 | CA | GLU A 121 | 23.390 | 18.922 | 101.980 | 1.00 | 22.51 | 6 |
| ATOM | 918 | C | GLU A 121 | 22.518 | 18.029 | 101.072 | 1.00 | 23.97 | 6 |
| ATOM | 919 | O | GLU A 121 | 21.864 | 17.068 | 101.531 | 1.00 | 23.54 | 8 |
| ATOM | 920 | CB | GLU A 121 | 24.754 | 18.289 | 102.125 | 1.00 | 22.70 | 6 |
| ATOM | 921 | CG | GLU A 121 | 25.819 | 19.157 | 102.767 | 1.00 | 26.10 | 6 |
| ATOM | 922 | CD | GLU A 121 | 27.114 | 18.370 | 102.881 | 1.00 | 33.79 | 6 |
| ATOM | 923 | OE1 | GLU A 121 | 27.363 | 17.496 | 102.035 | 1.00 | 31.76 | 8 |
| ATOM | 924 | OE2 | GLU A 121 | 27.912 | 18.621 | 103.804 | 1.00 | 33.28 | 8 |
| ATOM | 925 | N | VAL A 122 | 22.516 | 18.382 | 99.779 | 1.00 | 22.10 | 7 |
| ATOM | 926 | CA | VAL A 122 | 21.801 | 17.498 | 98.828 | 1.00 | 21.06 | 6 |
| ATOM | 927 | C | VAL A 122 | 22.809 | 16.962 | 97.815 | 1.00 | 20.23 | 6 |
| ATOM | 928 | O | VAL A 122 | 23.896 | 17.513 | 97.598 | 1.00 | 17.86 | 8 |
| ATOM | 929 | CB | VAL A 122 | 20.624 | 18.196 | 98.134 | 1.00 | 21.72 | 6 |
| ATOM | 930 | CG1 | VAL A 122 | 19.599 | 18.610 | 99.182 | 1.00 | 12.05 | 6 |
| ATOM | 931 | CG2 | VAL A 122 | 21.116 | 19.434 | 97.365 | 1.00 | 8.76 | 6 |
| ATOM | 932 | N | ASN A 123 | 22.387 | 15.895 | 97.128 | 1.00 | 20.00 | 7 |
| ATOM | 933 | CA | ASN A 123 | 23.253 | 15.301 | 96.107 | 1.00 | 20.45 | 6 |
| ATOM | 934 | C | ASN A 123 | 23.269 | 16.215 | 94.888 | 1.00 | 19.88 | 6 |
| ATOM | 935 | O | ASN A 123 | 22.211 | 16.559 | 94.335 | 1.00 | 19.99 | 8 |
| ATOM | 936 | CB | ASN A 123 | 22.661 | 13.917 | 95.794 | 1.00 | 17.50 | 6 |
| ATOM | 937 | CG | ASN A 123 | 23.481 | 13.213 | 94.706 | 1.00 | 32.28 | 6 |
| ATOM | 938 | OD1 | ASN A 123 | 24.360 | 13.796 | 94.071 | 1.00 | 25.05 | 8 |
| ATOM | 939 | ND2 | ASN A 123 | 23.208 | 11.935 | 94.490 | 1.00 | 31.02 | 7 |
| ATOM | 940 | N | PRO A 124 | 24.406 | 16.647 | 94.423 | 1.00 | 20.38 | 7 |

| | ATOM | 941 | CA | PRO A 124 | 24.556 | 17.529 | 93.260 | 1.00 | 21.02 | 6 |
|---|---|---|---|---|---|---|---|---|---|---|
| | ATOM | 942 | C | PRO A 124 | 23.926 | 16.947 | 92.001 | 1.00 | 20.97 | 6 |
| | ATOM | 943 | O | PRO A 124 | 23.353 | 17.709 | 91.218 | 1.00 | 22.17 | 8 |
| | ATOM | 944 | CB | PRO A 124 | 26.045 | 17.813 | 93.054 | 1.00 | 20.22 | 6 |
| 5 | ATOM | 945 | CG | PRO A 124 | 26.565 | 17.458 | 94.441 | 1.00 | 21.81 | 6 |
| | ATOM | 946 | CD | PRO A 124 | 25.725 | 16.290 | 94.956 | 1.00 | 21.61 | 6 |
| | ATOM | 947 | N | ASN A 125 | 23.881 | 15.634 | 91.873 | 1.00 | 20.24 | 7 |
| | ATOM | 948 | CA | ASN A 125 | 23.325 | 14.948 | 90.722 | 1.00 | 22.34 | 6 |
| | ATOM | 949 | C | ASN A 125 | 21.864 | 14.604 | 90.954 | 1.00 | 21.73 | 6 |
| 10 | ATOM | 950 | O | ASN A 125 | 21.226 | 14.008 | 90.082 | 1.00 | 21.29 | 8 |
| | ATOM | 951 | CB | ASN A 125 | 24.077 | 13.632 | 90.428 | 1.00 | 22.86 | 6 |
| | ATOM | 952 | CG | ASN A 125 | 25.505 | 13.887 | 89.964 | 1.00 | 30.09 | 6 |
| | ATOM | 953 | OD1 | ASN A 125 | 25.803 | 14.951 | 89.436 | 1.00 | 35.43 | 8 |
| | ATOM | 954 | ND2 | ASN A 125 | 26.467 | 12.978 | 90.138 | 1.00 | 38.09 | 7 |
| 15 | ATOM | 955 | N | ASN A 126 | 21.387 | 14.845 | 92.169 | 1.00 | 20.38 | 7 |
| | ATOM | 956 | CA | ASN A 126 | 19.977 | 14.571 | 92.459 | 1.00 | 19.66 | 6 |
| | ATOM | 957 | C | ASN A 126 | 19.575 | 15.450 | 93.620 | 1.00 | 21.05 | 6 |
| | ATOM | 958 | O | ASN A 126 | 19.660 | 15.015 | 94.775 | 1.00 | 21.00 | 8 |
| | ATOM | 959 | CB | ASN A 126 | 19.775 | 13.075 | 92.788 | 1.00 | 15.30 | 6 |
| 20 | ATOM | 960 | CG | ASN A 126 | 18.274 | 12.880 | 93.006 | 1.00 | 23.22 | 6 |
| | ATOM | 961 | OD1 | ASN A 126 | 17.452 | 13.810 | 93.032 | 1.00 | 26.30 | 8 |
| | ATOM | 962 | ND2 | ASN A 126 | 17.922 | 11.613 | 93.138 | 1.00 | 28.44 | 7 |
| | ATOM | 963 | N | ARG A 127 | 19.221 | 16.720 | 93.401 | 1.00 | 19.57 | 7 |
| | ATOM | 964 | CA | ARG A 127 | 18.962 | 17.676 | 94.443 | 1.00 | 17.56 | 6 |
| 25 | ATOM | 965 | C | ARG A 127 | 17.752 | 17.288 | 95.308 | 1.00 | 18.63 | 6 |
| | ATOM | 966 | O | ARG A 127 | 17.461 | 18.065 | 96.243 | 1.00 | 16.95 | 8 |
| | ATOM | 967 | CB | ARG A 127 | 18.856 | 19.092 | 93.904 | 1.00 | 12.51 | 6 |
| | ATOM | 968 | CG | ARG A 127 | 20.138 | 19.752 | 93.386 | 1.00 | 14.72 | 6 |
| | ATOM | 969 | CD | ARG A 127 | 20.547 | 19.160 | 92.023 | 1.00 | 14.85 | 6 |
| 30 | ATOM | 970 | NE | ARG A 127 | 21.631 | 19.938 | 91.401 | 1.00 | 14.09 | 7 |
| | ATOM | 971 | CZ | ARG A 127 | 21.533 | 21.187 | 90.999 | 1.00 | 15.80 | 6 |
| | ATOM | 972 | NH1 | ARG A 127 | 20.374 | 21.834 | 91.097 | 1.00 | 16.14 | 7 |
| | ATOM | 973 | NH2 | ARG A 127 | 22.546 | 21.860 | 90.471 | 1.00 | 17.52 | 7 |
| | ATOM | 974 | N | ASN A 128 | 17.002 | 16.258 | 94.938 | 1.00 | 17.64 | 7 |
| 35 | ATOM | 975 | CA | ASN A 128 | 15.857 | 15.806 | 95.706 | 1.00 | 20.96 | 6 |
| | ATOM | 976 | C | ASN A 128 | 16.316 | 14.849 | 96.834 | 1.00 | 21.64 | 6 |
| | ATOM | 977 | O | ASN A 128 | 15.520 | 14.474 | 97.658 | 1.00 | 21.03 | 8 |
| | ATOM | 978 | CB | ASN A 128 | 14.855 | 14.998 | 94.847 | 1.00 | 20.92 | 6 |
| | ATOM | 979 | CG | ASN A 128 | 13.982 | 15.912 | 94.008 | 1.00 | 25.08 | 6 |
| 40 | ATOM | 980 | OD1 | ASN A 128 | 13.652 | 17.021 | 94.421 | 1.00 | 27.32 | 8 |
| | ATOM | 981 | ND2 | ASN A 128 | 13.692 | 15.454 | 92.798 | 1.00 | 25.22 | 7 |
| | ATOM | 982 | N | GLN A 129 | 17.568 | 14.425 | 96.839 | 1.00 | 23.60 | 7 |
| | ATOM | 983 | CA | GLN A 129 | 18.149 | 13.518 | 97.822 | 1.00 | 25.40 | 6 |
| | ATOM | 984 | C | GLN A 129 | 19.039 | 14.238 | 98.841 | 1.00 | 25.85 | 6 |
| 45 | ATOM | 985 | O | GLN A 129 | 20.053 | 14.857 | 98.528 | 1.00 | 25.31 | 8 |
| | ATOM | 986 | CB | GLN A 129 | 18.969 | 12.476 | 97.065 | 1.00 | 30.26 | 6 |
| | ATOM | 987 | CG | GLN A 129 | 19.650 | 11.443 | 97.896 | 1.00 | 36.65 | 6 |
| | ATOM | 988 | CD | GLN A 129 | 20.688 | 10.589 | 97.220 | 1.00 | 50.60 | 6 |
| | ATOM | 989 | OE1 | GLN A 129 | 21.389 | 10.920 | 96.262 | 1.00 | 50.90 | 8 |
| 50 | ATOM | 990 | NE2 | GLN A 129 | 20.789 | 9.382 | 97.783 | 1.00 | 59.68 | 7 |
| | ATOM | 991 | N | GLU A 130 | 18.617 | 14.169 | 100.106 | 1.00 | 26.25 | 7 |
| | ATOM | 992 | CA | GLU A 130 | 19.380 | 14.786 | 101.215 | 1.00 | 25.65 | 6 |
| | ATOM | 993 | C | GLU A 130 | 20.520 | 13.881 | 101.601 | 1.00 | 24.59 | 6 |
| | ATOM | 994 | O | GLU A 130 | 20.267 | 12.674 | 101.678 | 1.00 | 26.10 | 8 |
| 55 | ATOM | 995 | CB | GLU A 130 | 18.439 | 15.032 | 102.378 | 1.00 | 24.08 | 6 |
| | ATOM | 996 | CG | GLU A 130 | 17.425 | 16.128 | 102.051 | 1.00 | 24.36 | 6 |
| | ATOM | 997 | CD | GLU A 130 | 16.469 | 16.440 | 103.190 | 1.00 | 29.99 | 6 |
| | ATOM | 998 | OE1 | GLU A 130 | 16.642 | 15.811 | 104.263 | 1.00 | 27.95 | 8 |
| | ATOM | 999 | OE2 | GLU A 130 | 15.583 | 17.309 | 103.034 | 1.00 | 26.77 | 8 |
| 60 | ATOM | 1000 | N | ILE A 131 | 21.765 | 14.341 | 101.646 | 1.00 | 25.24 | 7 |
| | ATOM | 1001 | CA | ILE A 131 | 22.833 | 13.388 | 101.907 | 1.00 | 28.06 | 6 |
| | ATOM | 1002 | C | ILE A 131 | 23.624 | 13.682 | 103.171 | 1.00 | 29.97 | 6 |
| | ATOM | 1003 | O | ILE A 131 | 24.751 | 13.220 | 103.380 | 1.00 | 31.06 | 8 |
| | ATOM | 1004 | CB | ILE A 131 | 23.693 | 13.048 | 100.699 | 1.00 | 26.19 | 6 |
| 65 | ATOM | 1005 | CG1 | ILE A 131 | 24.647 | 14.095 | 100.166 | 1.00 | 28.34 | 6 |

| ATOM | 1006 | CG2 | ILE | A | 131 | 22.896 | 12.567 | 99.475 | 1.00 | 33.58 | 6 |
|---|---|---|---|---|---|---|---|---|---|---|---|
| ATOM | 1007 | CD1 | ILE | A | 131 | 24.858 | 15.364 | 100.874 | 1.00 | 35.74 | 6 |
| ATOM | 1008 | N | SER | A | 132 | 23.082 | 14.483 | 104.080 | 1.00 | 30.13 | 7 |
| ATOM | 1009 | CA | SER | A | 132 | 23.789 | 14.743 | 105.351 | 1.00 | 30.02 | 6 |
| ATOM | 1010 | C | SER | A | 132 | 22.716 | 14.997 | 106.410 | 1.00 | 29.25 | 6 |
| ATOM | 1011 | O | SER | A | 132 | 21.514 | 14.973 | 106.087 | 1.00 | 28.53 | 8 |
| ATOM | 1012 | CB | SER | A | 132 | 24.781 | 15.922 | 105.207 | 1.00 | 19.90 | 6 |
| ATOM | 1013 | OG | SER | A | 132 | 24.034 | 17.111 | 105.470 | 1.00 | 23.39 | 8 |
| ATOM | 1014 | N | GLY | A | 133 | 23.137 | 15.175 | 107.666 | 1.00 | 29.91 | 7 |
| ATOM | 1015 | CA | GLY | A | 133 | 22.164 | 15.515 | 108.732 | 1.00 | 27.01 | 6 |
| ATOM | 1016 | C | GLY | A | 133 | 22.126 | 17.045 | 108.731 | 1.00 | 27.96 | 6 |
| ATOM | 1017 | O | GLY | A | 133 | 22.988 | 17.643 | 108.055 | 1.00 | 28.15 | 8 |
| ATOM | 1018 | N | ASP | A | 134 | 21.170 | 17.687 | 109.401 | 1.00 | 26.57 | 7 |
| ATOM | 1019 | CA | ASP | A | 134 | 21.163 | 19.127 | 109.408 | 1.00 | 26.44 | 6 |
| ATOM | 1020 | C | ASP | A | 134 | 22.423 | 19.663 | 110.046 | 1.00 | 28.36 | 6 |
| ATOM | 1021 | O | ASP | A | 134 | 22.940 | 19.010 | 110.945 | 1.00 | 29.89 | 8 |
| ATOM | 1022 | CB | ASP | A | 134 | 19.960 | 19.692 | 110.178 | 1.00 | 25.17 | 6 |
| ATOM | 1023 | CG | ASP | A | 134 | 18.672 | 19.184 | 109.560 | 1.00 | 31.21 | 6 |
| ATOM | 1024 | OD1 | ASP | A | 134 | 18.758 | 18.348 | 108.637 | 1.00 | 33.74 | 8 |
| ATOM | 1025 | OD2 | ASP | A | 134 | 17.599 | 19.645 | 110.004 | 1.00 | 36.81 | 8 |
| ATOM | 1026 | N | TYR | A | 135 | 22.883 | 20.858 | 109.733 | 1.00 | 27.86 | 7 |
| ATOM | 1027 | CA | TYR | A | 135 | 24.017 | 21.450 | 110.430 | 1.00 | 27.39 | 6 |
| ATOM | 1028 | C | TYR | A | 135 | 24.095 | 22.913 | 110.033 | 1.00 | 28.21 | 6 |
| ATOM | 1029 | O | TYR | A | 135 | 23.466 | 23.263 | 109.032 | 1.00 | 27.76 | 8 |
| ATOM | 1030 | CB | TYR | A | 135 | 25.310 | 20.707 | 110.279 | 1.00 | 28.84 | 6 |
| ATOM | 1031 | CG | TYR | A | 135 | 26.031 | 20.662 | 108.957 | 1.00 | 24.62 | 6 |
| ATOM | 1032 | CD1 | TYR | A | 135 | 26.991 | 21.596 | 108.643 | 1.00 | 24.15 | 6 |
| ATOM | 1033 | CD2 | TYR | A | 135 | 25.761 | 19.660 | 108.042 | 1.00 | 25.71 | 6 |
| ATOM | 1034 | CE1 | TYR | A | 135 | 27.689 | 21.546 | 107.443 | 1.00 | 24.99 | 6 |
| ATOM | 1035 | CE2 | TYR | A | 135 | 26.442 | 19.601 | 106.829 | 1.00 | 24.95 | 6 |
| ATOM | 1036 | CZ | TYR | A | 135 | 27.401 | 20.542 | 106.540 | 1.00 | 25.76 | 6 |
| ATOM | 1037 | OH | TYR | A | 135 | 28.087 | 20.465 | 105.350 | 1.00 | 27.67 | 8 |
| ATOM | 1038 | N | THR | A | 136 | 24.829 | 23.709 | 110.794 | 1.00 | 26.69 | 7 |
| ATOM | 1039 | CA | THR | A | 136 | 24.874 | 25.132 | 110.547 | 1.00 | 25.35 | 6 |
| ATOM | 1040 | C | THR | A | 136 | 26.030 | 25.509 | 109.642 | 1.00 | 24.11 | 6 |
| ATOM | 1041 | O | THR | A | 136 | 27.142 | 25.073 | 109.831 | 1.00 | 21.73 | 8 |
| ATOM | 1042 | CB | THR | A | 136 | 25.003 | 25.938 | 111.855 | 1.00 | 26.43 | 6 |
| ATOM | 1043 | OG1 | THR | A | 136 | 23.789 | 25.695 | 112.576 | 1.00 | 37.87 | 8 |
| ATOM | 1044 | CG2 | THR | A | 136 | 25.020 | 27.430 | 111.593 | 1.00 | 32.50 | 6 |
| ATOM | 1045 | N | ILE | A | 137 | 25.684 | 26.380 | 108.659 | 1.00 | 23.93 | 7 |
| ATOM | 1046 | CA | ILE | A | 137 | 26.723 | 26.842 | 107.737 | 1.00 | 21.01 | 6 |
| ATOM | 1047 | C | ILE | A | 137 | 26.748 | 28.359 | 107.805 | 1.00 | 20.59 | 6 |
| ATOM | 1048 | O | ILE | A | 137 | 25.781 | 28.967 | 108.272 | 1.00 | 22.54 | 8 |
| ATOM | 1049 | CB | ILE | A | 137 | 26.471 | 26.381 | 106.280 | 1.00 | 20.65 | 6 |
| ATOM | 1050 | CG1 | ILE | A | 137 | 25.177 | 26.998 | 105.733 | 1.00 | 16.56 | 6 |
| ATOM | 1051 | CG2 | ILE | A | 137 | 26.437 | 24.861 | 106.202 | 1.00 | 17.98 | 6 |
| ATOM | 1052 | CD1 | ILE | A | 137 | 24.964 | 26.666 | 104.249 | 1.00 | 24.92 | 6 |
| ATOM | 1053 | N | GLU | A | 138 | 27.858 | 28.918 | 107.332 | 1.00 | 20.50 | 7 |
| ATOM | 1054 | CA | GLU | A | 138 | 27.921 | 30.389 | 107.257 | 1.00 | 21.16 | 6 |
| ATOM | 1055 | C | GLU | A | 138 | 27.650 | 30.730 | 105.769 | 1.00 | 20.45 | 6 |
| ATOM | 1056 | O | GLU | A | 138 | 28.464 | 30.333 | 104.916 | 1.00 | 21.84 | 8 |
| ATOM | 1057 | CB | GLU | A | 138 | 29.342 | 30.790 | 107.636 | 1.00 | 17.31 | 6 |
| ATOM | 1058 | CG | GLU | A | 138 | 29.425 | 32.264 | 108.031 | 1.00 | 35.20 | 6 |
| ATOM | 1059 | CD | GLU | A | 138 | 30.871 | 32.570 | 108.420 | 1.00 | 47.73 | 6 |
| ATOM | 1060 | OE1 | GLU | A | 138 | 31.483 | 31.664 | 109.037 | 1.00 | 46.82 | 8 |
| ATOM | 1061 | OE2 | GLU | A | 138 | 31.367 | 33.676 | 108.096 | 1.00 | 52.74 | 8 |
| ATOM | 1062 | N | ALA | A | 139 | 26.496 | 31.293 | 105.485 | 1.00 | 19.42 | 7 |
| ATOM | 1063 | CA | ALA | A | 139 | 26.047 | 31.439 | 104.093 | 1.00 | 18.49 | 6 |
| ATOM | 1064 | C | ALA | A | 139 | 26.084 | 32.876 | 103.660 | 1.00 | 18.67 | 6 |
| ATOM | 1065 | O | ALA | A | 139 | 25.783 | 33.763 | 104.485 | 1.00 | 15.46 | 8 |
| ATOM | 1066 | CB | ALA | A | 139 | 24.628 | 30.904 | 103.958 | 1.00 | 13.24 | 6 |
| ATOM | 1067 | N | TRP | A | 140 | 26.400 | 33.140 | 102.371 | 1.00 | 17.04 | 7 |
| ATOM | 1068 | CA | TRP | A | 140 | 26.363 | 34.570 | 101.978 | 1.00 | 15.11 | 6 |
| ATOM | 1069 | C | TRP | A | 140 | 24.968 | 34.964 | 101.565 | 1.00 | 17.06 | 6 |
| ATOM | 1070 | O | TRP | A | 140 | 24.558 | 34.917 | 100.370 | 1.00 | 15.64 | 8 |

| ATOM | 1071 | CB  | TRP A 140 | 27.419 | 34.845 | 100.924 | 1.00 | 19.76 | 6 |
| ATOM | 1072 | CG  | TRP A 140 | 28.834 | 34.726 | 101.357 | 1.00 | 14.16 | 6 |
| ATOM | 1073 | CD1 | TRP A 140 | 29.615 | 33.616 | 101.329 | 1.00 | 20.68 | 6 |
| ATOM | 1074 | CD2 | TRP A 140 | 29.646 | 35.779 | 101.900 | 1.00 | 15.22 | 6 |
| ATOM | 1075 | NE1 | TRP A 140 | 30.859 | 33.908 | 101.820 | 1.00 | 22.96 | 7 |
| ATOM | 1076 | CE2 | TRP A 140 | 30.922 | 35.232 | 102.155 | 1.00 | 19.66 | 6 |
| ATOM | 1077 | CE3 | TRP A 140 | 29.419 | 37.116 | 102.209 | 1.00 | 17.43 | 6 |
| ATOM | 1078 | CZ2 | TRP A 140 | 31.966 | 35.972 | 102.715 | 1.00 | 19.26 | 6 |
| ATOM | 1079 | CZ3 | TRP A 140 | 30.454 | 37.880 | 102.709 | 1.00 | 17.26 | 6 |
| ATOM | 1080 | CH2 | TRP A 140 | 31.698 | 37.287 | 102.977 | 1.00 | 19.26 | 6 |
| ATOM | 1081 | N   | THR A 141 | 24.123 | 35.431 | 102.510 | 1.00 | 13.71 | 7 |
| ATOM | 1082 | CA  | THR A 141 | 22.735 | 35.685 | 102.263 | 1.00 | 12.75 | 6 |
| ATOM | 1083 | C   | THR A 141 | 22.279 | 37.074 | 102.694 | 1.00 | 13.45 | 6 |
| ATOM | 1084 | O   | THR A 141 | 21.144 | 37.474 | 102.421 | 1.00 | 11.95 | 8 |
| ATOM | 1085 | CB  | THR A 141 | 21.832 | 34.675 | 103.023 | 1.00 | 19.93 | 6 |
| ATOM | 1086 | OG1 | THR A 141 | 22.368 | 34.660 | 104.351 | 1.00 | 20.34 | 8 |
| ATOM | 1087 | CG2 | THR A 141 | 21.940 | 33.269 | 102.445 | 1.00 | 18.23 | 6 |
| ATOM | 1088 | N   | LYS A 142 | 23.237 | 37.833 | 103.243 | 1.00 | 14.14 | 7 |
| ATOM | 1089 | CA  | LYS A 142 | 22.803 | 39.127 | 103.724 | 1.00 | 13.25 | 6 |
| ATOM | 1090 | C   | LYS A 142 | 23.119 | 40.343 | 102.875 | 1.00 | 12.07 | 6 |
| ATOM | 1091 | O   | LYS A 142 | 24.272 | 40.602 | 102.715 | 1.00 | 12.38 | 8 |
| ATOM | 1092 | CB  | LYS A 142 | 23.366 | 39.384 | 105.167 | 1.00 | 22.24 | 6 |
| ATOM | 1093 | CG  | LYS A 142 | 22.617 | 40.641 | 105.665 | 1.00 | 24.68 | 6 |
| ATOM | 1094 | CD  | LYS A 142 | 23.632 | 41.559 | 106.331 | 1.00 | 47.57 | 6 |
| ATOM | 1095 | CE  | LYS A 142 | 23.167 | 41.885 | 107.765 | 1.00 | 41.52 | 6 |
| ATOM | 1096 | NZ  | LYS A 142 | 22.754 | 40.564 | 108.327 | 1.00 | 49.23 | 7 |
| ATOM | 1097 | N   | PHE A 143 | 22.058 | 41.048 | 102.474 | 1.00 | 12.20 | 7 |
| ATOM | 1098 | CA  | PHE A 143 | 22.273 | 42.185 | 101.586 | 1.00 | 15.87 | 6 |
| ATOM | 1099 | C   | PHE A 143 | 21.631 | 43.432 | 102.175 | 1.00 | 15.91 | 6 |
| ATOM | 1100 | O   | PHE A 143 | 20.429 | 43.476 | 102.346 | 1.00 | 17.13 | 8 |
| ATOM | 1101 | CB  | PHE A 143 | 21.581 | 41.919 | 100.181 | 1.00 | 17.78 | 6 |
| ATOM | 1102 | CG  | PHE A 143 | 22.117 | 40.744 | 99.384  | 1.00 | 15.53 | 6 |
| ATOM | 1103 | CD1 | PHE A 143 | 21.833 | 39.445 | 99.678  | 1.00 | 15.38 | 6 |
| ATOM | 1104 | CD2 | PHE A 143 | 22.904 | 40.993 | 98.248  | 1.00 | 21.45 | 6 |
| ATOM | 1105 | CE1 | PHE A 143 | 22.333 | 38.370 | 98.939  | 1.00 | 20.18 | 6 |
| ATOM | 1106 | CE2 | PHE A 143 | 23.401 | 39.957 | 97.489  | 1.00 | 13.29 | 6 |
| ATOM | 1107 | CZ  | PHE A 143 | 23.143 | 38.640 | 97.839  | 1.00 | 16.41 | 6 |
| ATOM | 1108 | N   | ASP A 144 | 22.452 | 44.460 | 102.391 | 1.00 | 18.78 | 7 |
| ATOM | 1109 | CA  | ASP A 144 | 21.878 | 45.710 | 102.908 | 1.00 | 23.30 | 6 |
| ATOM | 1110 | C   | ASP A 144 | 21.469 | 47.888 | 102.095 | 1.00 | 23.01 | 8 |
| ATOM | 1112 | CB  | ASP A 144 | 22.387 | 46.060 | 104.309 | 1.00 | 23.28 | 6 |
| ATOM | 1113 | CG  | ASP A 144 | 22.039 | 45.013 | 105.363 | 1.00 | 27.65 | 6 |
| ATOM | 1114 | OD1 | ASP A 144 | 20.865 | 44.750 | 105.635 | 1.00 | 25.54 | 8 |
| ATOM | 1115 | OD2 | ASP A 144 | 22.996 | 44.435 | 105.907 | 1.00 | 38.42 | 8 |
| ATOM | 1116 | N   | PHE A 145 | 23.045 | 46.682 | 100.963 | 1.00 | 25.63 | 7 |
| ATOM | 1117 | CA  | PHE A 145 | 23.195 | 47.725 | 99.925  | 1.00 | 24.68 | 6 |
| ATOM | 1118 | C   | PHE A 145 | 23.555 | 49.047 | 100.600 | 1.00 | 25.85 | 6 |
| ATOM | 1119 | O   | PHE A 145 | 22.898 | 50.077 | 100.518 | 1.00 | 25.95 | 8 |
| ATOM | 1120 | CB  | PHE A 145 | 21.868 | 47.911 | 99.141  | 1.00 | 12.40 | 6 |
| ATOM | 1121 | CG  | PHE A 145 | 21.212 | 46.667 | 98.629  | 1.00 | 17.44 | 6 |
| ATOM | 1122 | CD1 | PHE A 145 | 21.859 | 45.822 | 97.722  | 1.00 | 22.23 | 6 |
| ATOM | 1123 | CD2 | PHE A 145 | 19.941 | 46.319 | 99.032  | 1.00 | 21.70 | 6 |
| ATOM | 1124 | CE1 | PHE A 145 | 21.265 | 44.662 | 97.257  | 1.00 | 15.92 | 6 |
| ATOM | 1125 | CE2 | PHE A 145 | 19.311 | 45.171 | 98.552  | 1.00 | 26.05 | 6 |
| ATOM | 1126 | CZ  | PHE A 145 | 19.976 | 44.330 | 97.661  | 1.00 | 17.21 | 6 |
| ATOM | 1127 | N   | PRO A 146 | 24.698 | 49.038 | 101.255 | 1.00 | 27.30 | 7 |
| ATOM | 1128 | CA  | PRO A 146 | 25.269 | 50.166 | 101.962 | 1.00 | 29.33 | 6 |
| ATOM | 1129 | C   | PRO A 146 | 25.443 | 51.408 | 101.107 | 1.00 | 30.70 | 6 |
| ATOM | 1130 | O   | PRO A 146 | 25.143 | 52.508 | 101.576 | 1.00 | 29.79 | 8 |
| ATOM | 1131 | CB  | PRO A 146 | 26.732 | 49.809 | 102.381 | 1.00 | 28.88 | 6 |
| ATOM | 1132 | CG  | PRO A 146 | 26.943 | 48.518 | 101.641 | 1.00 | 30.07 | 6 |
| ATOM | 1133 | CD  | PRO A 146 | 25.592 | 47.888 | 101.328 | 1.00 | 27.29 | 6 |
| ATOM | 1134 | N   | GLY A 147 | 25.957 | 51.200 | 99.866  | 1.00 | 29.98 | 7 |
| ATOM | 1135 | CA  | GLY A 147 | 26.215 | 52.382 | 99.045  | 1.00 | 29.30 | 6 |
| ATOM | 1136 | C   | GLY A 147 | 24.928 | 53.057 | 98.626  | 1.00 | 29.97 | 6 |

| | ATOM | 1137 | O   | GLY A 147 | 24.919 | 54.261 | 98.349  | 1.00 32.02 | 8 |
|---|------|------|-----|-----------|--------|--------|---------|------------|---|
|   | ATOM | 1138 | N   | ARG A 148 | 23.821 | 52.346 | 98.518  | 1.00 29.43 | 7 |
|   | ATOM | 1139 | CA  | ARG A 148 | 22.601 | 52.956 | 98.020  | 1.00 29.69 | 6 |
|   | ATOM | 1140 | C   | ARG A 148 | 21.630 | 53.394 | 99.118  | 1.00 31.82 | 6 |
| 5 | ATOM | 1141 | O   | ARG A 148 | 20.685 | 54.157 | 98.885  | 1.00 29.76 | 8 |
|   | ATOM | 1142 | CB  | ARG A 148 | 21.917 | 51.843 | 97.180  | 1.00 19.70 | 6 |
|   | ATOM | 1143 | CG  | ARG A 148 | 20.541 | 52.278 | 96.709  | 1.00 20.29 | 6 |
|   | ATOM | 1144 | CD  | ARG A 148 | 19.906 | 51.409 | 95.676  | 1.00 24.90 | 6 |
|   | ATOM | 1145 | NE  | ARG A 148 | 19.796 | 49.964 | 95.964  | 1.00 21.80 | 7 |
| 10| ATOM | 1146 | CZ  | ARG A 148 | 18.704 | 49.454 | 96.514  | 1.00 12.63 | 6 |
|   | ATOM | 1147 | NH1 | ARG A 148 | 17.762 | 50.295 | 96.916  | 1.00 14.67 | 7 |
|   | ATOM | 1148 | NH2 | ARG A 148 | 18.590 | 48.144 | 96.715  | 1.00 17.35 | 7 |
|   | ATOM | 1149 | N   | GLY A 149 | 21.715 | 52.710 | 100.267 | 1.00 33.44 | 7 |
|   | ATOM | 1150 | CA  | GLY A 149 | 20.777 | 52.979 | 101.365 | 1.00 33.67 | 6 |
| 15| ATOM | 1151 | C   | GLY A 149 | 19.397 | 52.506 | 100.928 | 1.00 33.52 | 6 |
|   | ATOM | 1152 | O   | GLY A 149 | 19.309 | 51.396 | 100.384 | 1.00 34.95 | 8 |
|   | ATOM | 1153 | N   | ASN A 150 | 18.362 | 53.307 | 101.158 | 1.00 31.50 | 7 |
|   | ATOM | 1154 | CA  | ASN A 150 | 17.027 | 52.915 | 100.732 | 1.00 29.53 | 6 |
|   | ATOM | 1155 | C   | ASN A 150 | 16.504 | 53.699 | 99.520  | 1.00 27.75 | 6 |
| 20| ATOM | 1156 | O   | ASN A 150 | 15.287 | 53.760 | 99.281  | 1.00 25.07 | 8 |
|   | ATOM | 1157 | CB  | ASN A 150 | 16.070 | 53.058 | 101.922 | 1.00 40.30 | 6 |
|   | ATOM | 1158 | CG  | ASN A 150 | 16.456 | 52.237 | 103.138 | 1.00 55.09 | 6 |
|   | ATOM | 1159 | OD1 | ASN A 150 | 16.260 | 52.655 | 104.285 | 1.00 63.25 | 8 |
|   | ATOM | 1160 | ND2 | ASN A 150 | 17.016 | 51.048 | 102.957 | 1.00 53.95 | 7 |
| 25| ATOM | 1161 | N   | THR A 151 | 17.389 | 54.302 | 98.720  | 1.00 28.99 | 7 |
|   | ATOM | 1162 | CA  | THR A 151 | 16.858 | 55.022 | 97.512  | 1.00 28.81 | 6 |
|   | ATOM | 1163 | C   | THR A 151 | 16.178 | 54.052 | 96.570  | 1.00 27.33 | 6 |
|   | ATOM | 1164 | O   | THR A 151 | 16.637 | 52.926 | 96.314  | 1.00 28.63 | 8 |
|   | ATOM | 1165 | CB  | THR A 151 | 18.044 | 55.679 | 96.808  | 1.00 36.51 | 6 |
| 30| ATOM | 1166 | OG1 | THR A 151 | 18.794 | 56.322 | 97.830  | 1.00 35.60 | 8 |
|   | ATOM | 1167 | CG2 | THR A 151 | 17.618 | 56.610 | 95.680  | 1.00 30.56 | 6 |
|   | ATOM | 1168 | N   | TYR A 152 | 14.983 | 54.307 | 96.080  | 1.00 27.71 | 7 |
|   | ATOM | 1169 | CA  | TYR A 152 | 14.180 | 53.485 | 95.184  | 1.00 28.08 | 6 |
|   | ATOM | 1170 | C   | TYR A 152 | 13.577 | 52.275 | 95.869  | 1.00 27.94 | 6 |
| 35| ATOM | 1171 | O   | TYR A 152 | 12.467 | 51.879 | 95.493  | 1.00 29.37 | 8 |
|   | ATOM | 1172 | CB  | TYR A 152 | 14.906 | 53.008 | 93.906  | 1.00 27.24 | 6 |
|   | ATOM | 1173 | CG  | TYR A 152 | 15.743 | 54.043 | 93.196  | 1.00 27.33 | 6 |
|   | ATOM | 1174 | CD1 | TYR A 152 | 15.198 | 55.276 | 92.854  | 1.00 29.84 | 6 |
|   | ATOM | 1175 | CD2 | TYR A 152 | 17.075 | 53.839 | 92.891  | 1.00 27.70 | 6 |
| 40| ATOM | 1176 | CE1 | TYR A 152 | 15.959 | 56.239 | 92.210  | 1.00 30.71 | 6 |
|   | ATOM | 1177 | CE2 | TYR A 152 | 17.850 | 54.777 | 92.235  | 1.00 28.02 | 6 |
|   | ATOM | 1178 | CZ  | TYR A 152 | 17.275 | 55.985 | 91.899  | 1.00 30.18 | 6 |
|   | ATOM | 1179 | OH  | TYR A 152 | 18.007 | 56.985 | 91.276  | 1.00 31.59 | 8 |
|   | ATOM | 1180 | N   | SER A 153 | 14.308 | 51.601 | 96.769  | 1.00 26.11 | 7 |
| 45| ATOM | 1181 | CA  | SER A 153 | 13.693 | 50.434 | 97.420  | 1.00 25.69 | 6 |
|   | ATOM | 1182 | C   | SER A 153 | 14.190 | 50.276 | 98.884  | 1.00 25.09 | 6 |
|   | ATOM | 1183 | O   | SER A 153 | 15.393 | 50.338 | 99.160  | 1.00 22.81 | 8 |
|   | ATOM | 1184 | CB  | SER A 153 | 14.088 | 49.186 | 96.606  | 1.00 24.66 | 6 |
|   | ATOM | 1185 | OG  | SER A 153 | 13.415 | 48.028 | 97.114  | 1.00 29.86 | 8 |
| 50| ATOM | 1186 | N   | ASP A 154 | 13.273 | 49.927 | 99.793  | 1.00 24.96 | 7 |
|   | ATOM | 1187 | CA  | ASP A 154 | 13.817 | 49.687 | 101.156 | 1.00 28.71 | 6 |
|   | ATOM | 1188 | C   | ASP A 154 | 13.944 | 48.191 | 101.429 | 1.00 27.53 | 6 |
|   | ATOM | 1189 | O   | ASP A 154 | 14.252 | 47.821 | 102.561 | 1.00 26.49 | 8 |
|   | ATOM | 1190 | CB  | ASP A 154 | 12.991 | 50.404 | 102.222 | 1.00 34.87 | 6 |
| 55| ATOM | 1191 | CG  | ASP A 154 | 11.563 | 49.912 | 102.224 | 1.00 39.14 | 6 |
|   | ATOM | 1192 | OD1 | ASP A 154 | 11.289 | 48.783 | 101.767 | 1.00 50.57 | 8 |
|   | ATOM | 1193 | OD2 | ASP A 154 | 10.674 | 50.664 | 102.696 | 1.00 55.34 | 8 |
|   | ATOM | 1194 | N   | PHE A 155 | 13.724 | 47.310 | 100.445 | 1.00 25.05 | 7 |
|   | ATOM | 1195 | CA  | PHE A 155 | 13.850 | 45.877 | 100.719 | 1.00 22.73 | 6 |
| 60| ATOM | 1196 | C   | PHE A 155 | 15.243 | 45.408 | 101.069 | 1.00 20.67 | 6 |
|   | ATOM | 1197 | O   | PHE A 155 | 16.211 | 45.747 | 100.396 | 1.00 21.78 | 8 |
|   | ATOM | 1198 | CB  | PHE A 155 | 13.280 | 45.099 | 99.567  | 1.00 17.71 | 6 |
|   | ATOM | 1199 | CG  | PHE A 155 | 12.927 | 43.663 | 99.752  | 1.00 22.13 | 6 |
|   | ATOM | 1200 | CD1 | PHE A 155 | 11.632 | 43.319 | 100.096 | 1.00 20.02 | 6 |
| 65| ATOM | 1201 | CD2 | PHE A 155 | 13.861 | 42.663 | 99.531  | 1.00 19.53 | 6 |

| | ATOM | 1202 | CE1 | PHE | A | 155 | 11.252 | 41.995 | 100.217 | 1.00 | 24.70 | 6 |
|---|---|---|---|---|---|---|---|---|---|---|---|---|
| | ATOM | 1203 | CE2 | PHE | A | 155 | 13.475 | 41.332 | 99.676 | 1.00 | 23.28 | 6 |
| | ATOM | 1204 | CZ | PHE | A | 155 | 12.174 | 40.989 | 100.006 | 1.00 | 20.40 | 6 |
| | ATOM | 1205 | N | LYS | A | 156 | 15.386 | 44.484 | 102.046 | 1.00 | 17.13 | 7 |
| 5 | ATOM | 1206 | CA | LYS | A | 156 | 16.718 | 43.965 | 102.361 | 1.00 | 14.59 | 6 |
| | ATOM | 1207 | C | LYS | A | 156 | 16.629 | 42.469 | 102.207 | 1.00 | 12.80 | 6 |
| | ATOM | 1208 | O | LYS | A | 156 | 15.512 | 41.997 | 102.422 | 1.00 | 15.89 | 8 |
| | ATOM | 1209 | CB | LYS | A | 156 | 17.168 | 44.274 | 103.807 | 1.00 | 20.78 | 6 |
| | ATOM | 1210 | CG | LYS | A | 156 | 17.086 | 45.757 | 104.093 | 1.00 | 21.02 | 6 |
| 10 | ATOM | 1211 | CD | LYS | A | 156 | 18.251 | 46.516 | 103.515 | 1.00 | 23.93 | 6 |
| | ATOM | 1212 | CE | LYS | A | 156 | 17.953 | 48.016 | 103.618 | 1.00 | 30.28 | 6 |
| | ATOM | 1213 | NZ | LYS | A | 156 | 19.072 | 48.837 | 103.037 | 1.00 | 32.80 | 7 |
| | ATOM | 1214 | N | TRP | A | 157 | 17.695 | 41.778 | 101.877 | 1.00 | 11.89 | 7 |
| | ATOM | 1215 | CA | TRP | A | 157 | 17.454 | 40.339 | 101.625 | 1.00 | 13.27 | 6 |
| 15 | ATOM | 1216 | C | TRP | A | 157 | 18.109 | 39.600 | 102.809 | 1.00 | 9.91 | 6 |
| | ATOM | 1217 | O | TRP | A | 157 | 19.144 | 40.070 | 103.255 | 1.00 | 10.57 | 8 |
| | ATOM | 1218 | CB | TRP | A | 157 | 18.172 | 39.893 | 100.292 | 1.00 | 12.07 | 6 |
| | ATOM | 1219 | CG | TRP | A | 157 | 17.439 | 40.438 | 99.052 | 1.00 | 20.71 | 6 |
| | ATOM | 1220 | CD1 | TRP | A | 157 | 17.449 | 41.728 | 98.608 | 1.00 | 18.19 | 6 |
| 20 | ATOM | 1221 | CD2 | TRP | A | 157 | 16.566 | 39.735 | 98.161 | 1.00 | 15.04 | 6 |
| | ATOM | 1222 | NE1 | TRP | A | 157 | 16.611 | 41.881 | 97.510 | 1.00 | 17.50 | 7 |
| | ATOM | 1223 | CE2 | TRP | A | 157 | 16.083 | 40.660 | 97.218 | 1.00 | 18.56 | 6 |
| | ATOM | 1224 | CE3 | TRP | A | 157 | 16.189 | 38.392 | 98.039 | 1.00 | 12.01 | 6 |
| | ATOM | 1225 | CZ2 | TRP | A | 157 | 15.259 | 40.295 | 96.158 | 1.00 | 17.59 | 6 |
| 25 | ATOM | 1226 | CZ3 | TRP | A | 157 | 15.333 | 38.040 | 97.023 | 1.00 | 20.95 | 6 |
| | ATOM | 1227 | CH2 | TRP | A | 157 | 14.871 | 38.981 | 96.079 | 1.00 | 22.76 | 6 |
| | ATOM | 1228 | N | ARG | A | 158 | 17.550 | 38.478 | 103.162 | 1.00 | 10.27 | 7 |
| | ATOM | 1229 | CA | ARG | A | 158 | 18.164 | 37.704 | 104.259 | 1.00 | 15.83 | 6 |
| | ATOM | 1230 | C | ARG | A | 158 | 18.104 | 36.234 | 103.874 | 1.00 | 15.51 | 6 |
| 30 | ATOM | 1231 | O | ARG | A | 158 | 17.369 | 35.938 | 102.912 | 1.00 | 15.73 | 8 |
| | ATOM | 1232 | CB | ARG | A | 158 | 17.324 | 37.927 | 105.580 | 1.00 | 12.73 | 6 |
| | ATOM | 1233 | CG | ARG | A | 158 | 17.354 | 39.383 | 106.074 | 1.00 | 12.20 | 6 |
| | ATOM | 1234 | CD | ARG | A | 158 | 18.729 | 39.676 | 106.661 | 1.00 | 19.33 | 6 |
| | ATOM | 1235 | NE | ARG | A | 158 | 18.853 | 41.071 | 107.038 | 1.00 | 24.10 | 7 |
| 35 | ATOM | 1236 | CZ | ARG | A | 158 | 19.328 | 42.154 | 106.473 | 1.00 | 32.65 | 6 |
| | ATOM | 1237 | NH1 | ARG | A | 158 | 19.889 | 42.211 | 105.253 | 1.00 | 17.30 | 7 |
| | ATOM | 1238 | NH2 | ARG | A | 158 | 19.249 | 43.300 | 107.168 | 1.00 | 28.36 | 7 |
| | ATOM | 1239 | N | TRP | A | 159 | 18.709 | 35.335 | 104.665 | 1.00 | 13.20 | 7 |
| | ATOM | 1240 | CA | TRP | A | 159 | 18.673 | 33.945 | 104.395 | 1.00 | 12.34 | 6 |
| 40 | ATOM | 1241 | C | TRP | A | 159 | 17.282 | 33.431 | 104.062 | 1.00 | 15.51 | 6 |
| | ATOM | 1242 | O | TRP | A | 159 | 17.193 | 32.484 | 103.236 | 1.00 | 14.77 | 8 |
| | ATOM | 1243 | CB | TRP | A | 159 | 19.345 | 33.054 | 105.463 | 1.00 | 18.26 | 6 |
| | ATOM | 1244 | CG | TRP | A | 159 | 18.445 | 33.005 | 106.687 | 1.00 | 14.02 | 6 |
| | ATOM | 1245 | CD1 | TRP | A | 159 | 18.397 | 33.991 | 107.651 | 1.00 | 16.36 | 6 |
| 45 | ATOM | 1246 | CD2 | TRP | A | 159 | 17.427 | 32.062 | 106.958 | 1.00 | 13.35 | 6 |
| | ATOM | 1247 | NE1 | TRP | A | 159 | 17.416 | 33.645 | 108.558 | 1.00 | 23.93 | 7 |
| | ATOM | 1248 | CE2 | TRP | A | 159 | 16.827 | 32.473 | 108.185 | 1.00 | 23.09 | 6 |
| | ATOM | 1249 | CE3 | TRP | A | 159 | 16.985 | 30.884 | 106.376 | 1.00 | 12.10 | 6 |
| | ATOM | 1250 | CZ2 | TRP | A | 159 | 15.771 | 31.777 | 108.765 | 1.00 | 24.07 | 6 |
| 50 | ATOM | 1251 | CZ3 | TRP | A | 159 | 15.964 | 30.168 | 106.964 | 1.00 | 22.85 | 6 |
| | ATOM | 1252 | CH2 | TRP | A | 159 | 15.355 | 30.607 | 108.161 | 1.00 | 26.32 | 6 |
| | ATOM | 1253 | N | TYR | A | 160 | 16.211 | 33.902 | 104.731 | 1.00 | 15.24 | 7 |
| | ATOM | 1254 | CA | TYR | A | 160 | 14.917 | 33.287 | 104.520 | 1.00 | 15.26 | 6 |
| | ATOM | 1255 | C | TYR | A | 160 | 14.279 | 33.656 | 103.174 | 1.00 | 14.17 | 6 |
| 55 | ATOM | 1256 | O | TYR | A | 160 | 13.291 | 33.045 | 102.816 | 1.00 | 12.44 | 8 |
| | ATOM | 1257 | CB | TYR | A | 160 | 13.917 | 33.558 | 105.687 | 1.00 | 14.38 | 6 |
| | ATOM | 1258 | CG | TYR | A | 160 | 13.860 | 34.993 | 106.096 | 1.00 | 15.35 | 6 |
| | ATOM | 1259 | CD1 | TYR | A | 160 | 12.954 | 35.892 | 105.531 | 1.00 | 19.38 | 6 |
| | ATOM | 1260 | CD2 | TYR | A | 160 | 14.712 | 35.464 | 107.096 | 1.00 | 16.13 | 6 |
| 60 | ATOM | 1261 | CE1 | TYR | A | 160 | 12.935 | 37.246 | 105.893 | 1.00 | 21.09 | 6 |
| | ATOM | 1262 | CE2 | TYR | A | 160 | 14.711 | 36.795 | 107.507 | 1.00 | 15.66 | 6 |
| | ATOM | 1263 | CZ | TYR | A | 160 | 13.821 | 37.660 | 106.908 | 1.00 | 21.37 | 6 |
| | ATOM | 1264 | OH | TYR | A | 160 | 13.802 | 38.972 | 107.303 | 1.00 | 20.64 | 8 |
| | ATOM | 1265 | N | HIS | A | 161 | 14.814 | 34.621 | 102.434 | 1.00 | 16.14 | 7 |
| 65 | ATOM | 1266 | CA | HIS | A | 161 | 14.328 | 34.887 | 101.056 | 1.00 | 16.93 | 6 |

| | ATOM | 1267 | C   | HIS A 161 | 14.971 | 33.936 | 100.019 | 1.00 | 17.46 | 6 |
|---|------|------|-----|-----------|--------|--------|---------|------|-------|---|
| | ATOM | 1268 | O   | HIS A 161 | 14.654 | 33.984 | 98.823  | 1.00 | 15.86 | 8 |
| | ATOM | 1269 | CB  | HIS A 161 | 14.750 | 36.316 | 100.683 | 1.00 | 10.99 | 6 |
| | ATOM | 1270 | CG  | HIS A 161 | 14.061 | 37.316 | 101.550 | 1.00 | 16.42 | 6 |
| 5 | ATOM | 1271 | ND1 | HIS A 161 | 14.740 | 38.364 | 102.160 | 1.00 | 24.17 | 7 |
| | ATOM | 1272 | CD2 | HIS A 161 | 12.765 | 37.417 | 101.916 | 1.00 | 15.95 | 6 |
| | ATOM | 1273 | CE1 | HIS A 161 | 13.853 | 39.120 | 102.804 | 1.00 | 15.69 | 6 |
| | ATOM | 1274 | NE2 | HIS A 161 | 12.666 | 38.565 | 102.667 | 1.00 | 16.91 | 7 |
| | ATOM | 1275 | N   | PHE A 162 | 15.871 | 33.044 | 100.404 | 1.00 | 14.97 | 7 |
| 10 | ATOM | 1276 | CA  | PHE A 162 | 16.594 | 32.118 | 99.627  | 1.00 | 12.83 | 6 |
| | ATOM | 1277 | C   | PHE A 162 | 16.376 | 30.671 | 99.966  | 1.00 | 14.26 | 6 |
| | ATOM | 1278 | O   | PHE A 162 | 15.853 | 30.313 | 101.031 | 1.00 | 14.52 | 8 |
| | ATOM | 1279 | CB  | PHE A 162 | 18.103 | 32.347 | 99.720  | 1.00 | 9.13  | 6 |
| | ATOM | 1280 | CG  | PHE A 162 | 18.490 | 33.738 | 99.311  | 1.00 | 18.06 | 6 |
| 15 | ATOM | 1281 | CD1 | PHE A 162 | 18.476 | 34.088 | 97.949  | 1.00 | 21.87 | 6 |
| | ATOM | 1282 | CD2 | PHE A 162 | 18.892 | 34.689 | 100.208 | 1.00 | 13.90 | 6 |
| | ATOM | 1283 | CE1 | PHE A 162 | 18.826 | 35.366 | 97.541  | 1.00 | 13.60 | 6 |
| | ATOM | 1284 | CE2 | PHE A 162 | 19.271 | 35.961 | 99.824  | 1.00 | 15.51 | 6 |
| | ATOM | 1285 | CZ  | PHE A 162 | 19.241 | 36.321 | 98.470  | 1.00 | 23.43 | 6 |
| 20 | ATOM | 1286 | N   | ASP A 163 | 16.546 | 29.790 | 98.981  | 1.00 | 10.90 | 7 |
| | ATOM | 1287 | CA  | ASP A 163 | 16.403 | 28.392 | 99.176  | 1.00 | 10.39 | 6 |
| | ATOM | 1288 | C   | ASP A 163 | 17.693 | 27.700 | 99.562  | 1.00 | 11.49 | 6 |
| | ATOM | 1289 | O   | ASP A 163 | 17.556 | 26.593 | 100.122 | 1.00 | 11.71 | 8 |
| | ATOM | 1290 | CB  | ASP A 163 | 15.857 | 27.587 | 97.983  | 1.00 | 12.96 | 6 |
| 25 | ATOM | 1291 | CG  | ASP A 163 | 14.402 | 27.850 | 97.958  | 1.00 | 26.57 | 6 |
| | ATOM | 1292 | OD1 | ASP A 163 | 13.659 | 27.893 | 98.995  | 1.00 | 16.13 | 8 |
| | ATOM | 1293 | OD2 | ASP A 163 | 13.857 | 27.981 | 96.835  | 1.00 | 12.30 | 8 |
| | ATOM | 1294 | N   | GLY A 164 | 18.804 | 28.196 | 99.030  | 1.00 | 12.90 | 7 |
| | ATOM | 1295 | CA  | GLY A 164 | 20.030 | 27.375 | 99.336  | 1.00 | 12.98 | 6 |
| 30 | ATOM | 1296 | C   | GLY A 164 | 21.179 | 28.077 | 98.628  | 1.00 | 13.37 | 6 |
| | ATOM | 1297 | O   | GLY A 164 | 20.969 | 29.133 | 97.996  | 1.00 | 12.18 | 8 |
| | ATOM | 1298 | N   | VAL A 165 | 22.384 | 27.600 | 98.870  | 1.00 | 12.35 | 7 |
| | ATOM | 1299 | CA  | VAL A 165 | 23.607 | 28.204 | 98.394  | 1.00 | 13.69 | 6 |
| | ATOM | 1300 | C   | VAL A 165 | 24.550 | 27.046 | 98.062  | 1.00 | 12.21 | 6 |
| 35 | ATOM | 1301 | O   | VAL A 165 | 24.229 | 25.901 | 98.384  | 1.00 | 12.79 | 8 |
| | ATOM | 1302 | CB  | VAL A 165 | 24.355 | 29.033 | 99.478  | 1.00 | 14.33 | 6 |
| | ATOM | 1303 | CG1 | VAL A 165 | 23.590 | 30.310 | 99.744  | 1.00 | 12.75 | 6 |
| | ATOM | 1304 | CG2 | VAL A 165 | 24.616 | 28.170 | 100.718 | 1.00 | 15.74 | 6 |
| | ATOM | 1305 | N   | ASP A 166 | 25.713 | 27.351 | 97.518  | 1.00 | 12.34 | 7 |
| 40 | ATOM | 1306 | CA  | ASP A 166 | 26.606 | 26.208 | 97.282  | 1.00 | 15.26 | 6 |
| | ATOM | 1307 | C   | ASP A 166 | 27.935 | 26.463 | 98.013  | 1.00 | 17.23 | 6 |
| | ATOM | 1308 | O   | ASP A 166 | 28.984 | 25.926 | 97.629  | 1.00 | 18.39 | 8 |
| | ATOM | 1309 | CB  | ASP A 166 | 26.875 | 26.081 | 95.788  | 1.00 | 18.07 | 6 |
| | ATOM | 1310 | CG  | ASP A 166 | 27.487 | 27.319 | 95.177  | 1.00 | 19.91 | 6 |
| 45 | ATOM | 1311 | OD1 | ASP A 166 | 27.650 | 28.427 | 95.717  | 1.00 | 16.51 | 8 |
| | ATOM | 1312 | OD2 | ASP A 166 | 27.864 | 27.223 | 93.968  | 1.00 | 28.31 | 8 |
| | ATOM | 1313 | N   | TRP A 167 | 27.990 | 27.429 | 98.897  | 1.00 | 14.83 | 7 |
| | ATOM | 1314 | CA  | TRP A 167 | 29.294 | 27.690 | 99.508  | 1.00 | 17.67 | 6 |
| | ATOM | 1315 | C   | TRP A 167 | 29.108 | 27.944 | 101.013 | 1.00 | 18.96 | 6 |
| 50 | ATOM | 1316 | O   | TRP A 167 | 28.289 | 28.817 | 101.338 | 1.00 | 17.91 | 8 |
| | ATOM | 1317 | CB  | TRP A 167 | 29.814 | 28.982 | 98.886  | 1.00 | 14.01 | 6 |
| | ATOM | 1318 | CG  | TRP A 167 | 31.187 | 29.314 | 99.401  | 1.00 | 19.38 | 6 |
| | ATOM | 1319 | CD1 | TRP A 167 | 31.570 | 30.362 | 100.163 | 1.00 | 18.10 | 6 |
| | ATOM | 1320 | CD2 | TRP A 167 | 32.367 | 28.539 | 99.143  | 1.00 | 25.35 | 6 |
| 55 | ATOM | 1321 | NE1 | TRP A 167 | 32.927 | 30.286 | 100.393 | 1.00 | 27.77 | 7 |
| | ATOM | 1322 | CE2 | TRP A 167 | 33.437 | 29.185 | 99.790  | 1.00 | 24.31 | 6 |
| | ATOM | 1323 | CE3 | TRP A 167 | 32.622 | 27.366 | 98.417  | 1.00 | 27.58 | 6 |
| | ATOM | 1324 | CZ2 | TRP A 167 | 34.742 | 28.702 | 99.720  | 1.00 | 30.95 | 6 |
| | ATOM | 1325 | CZ3 | TRP A 167 | 33.909 | 26.871 | 98.349  | 1.00 | 28.47 | 6 |
| 60 | ATOM | 1326 | CH2 | TRP A 167 | 34.956 | 27.554 | 98.988  | 1.00 | 28.98 | 6 |
| | ATOM | 1327 | N   | ASP A 168 | 29.877 | 27.216 | 101.797 | 1.00 | 20.19 | 7 |
| | ATOM | 1328 | CA  | ASP A 168 | 29.804 | 27.341 | 103.274 | 1.00 | 20.28 | 6 |
| | ATOM | 1329 | C   | ASP A 168 | 31.066 | 28.117 | 103.686 | 1.00 | 20.80 | 6 |
| | ATOM | 1330 | O   | ASP A 168 | 32.128 | 27.479 | 103.710 | 1.00 | 19.17 | 8 |
| 65 | ATOM | 1331 | CB  | ASP A 168 | 29.928 | 25.971 | 103.959 | 1.00 | 24.57 | 6 |

| | ATOM | 1332 | CG  | ASP A 168 | 29.951 | 26.015 | 105.493 | 1.00 | 21.84 | 6 |
|---|------|------|-----|-----------|--------|--------|---------|------|-------|---|
| | ATOM | 1333 | OD1 | ASP A 168 | 30.118 | 27.080 | 106.121 | 1.00 | 16.16 | 8 |
| | ATOM | 1334 | OD2 | ASP A 168 | 29.787 | 24.907 | 106.047 | 1.00 | 26.17 | 8 |
| | ATOM | 1335 | N   | GLN A 169 | 30.951 | 29.384 | 104.022 | 1.00 | 21.96 | 7 |
| 5 | ATOM | 1336 | CA | GLN A 169 | 32.157 | 30.143 | 104.321 | 1.00 | 25.62 | 6 |
| | ATOM | 1337 | C   | GLN A 169 | 33.047 | 29.549 | 105.412 | 1.00 | 28.23 | 6 |
| | ATOM | 1338 | O   | GLN A 169 | 34.271 | 29.681 | 105.365 | 1.00 | 27.18 | 8 |
| | ATOM | 1339 | CB  | GLN A 169 | 31.826 | 31.590 | 104.639 | 1.00 | 14.99 | 6 |
| | ATOM | 1340 | CG  | GLN A 169 | 33.097 | 32.409 | 104.761 | 1.00 | 25.50 | 6 |
| 10 | ATOM | 1341 | CD | GLN A 169 | 33.840 | 32.535 | 103.439 | 1.00 | 40.11 | 6 |
| | ATOM | 1342 | OE1 | GLN A 169 | 33.261 | 32.400 | 102.343 | 1.00 | 34.31 | 8 |
| | ATOM | 1343 | NE2 | GLN A 169 | 35.138 | 32.821 | 103.531 | 1.00 | 36.92 | 7 |
| | ATOM | 1344 | N   | SER A 170 | 32.454 | 28.854 | 106.387 | 1.00 | 30.01 | 7 |
| | ATOM | 1345 | CA  | SER A 170 | 33.267 | 28.219 | 107.409 | 1.00 | 30.93 | 6 |
| 15 | ATOM | 1346 | C  | SER A 170 | 33.959 | 26.959 | 106.983 | 1.00 | 34.16 | 6 |
| | ATOM | 1347 | O   | SER A 170 | 34.930 | 26.640 | 107.695 | 1.00 | 36.58 | 8 |
| | ATOM | 1348 | CB  | SER A 170 | 32.410 | 28.039 | 108.667 | 1.00 | 20.08 | 6 |
| | ATOM | 1349 | OG  | SER A 170 | 31.551 | 26.927 | 108.481 | 1.00 | 22.36 | 8 |
| | ATOM | 1350 | N   | ARG A 171 | 33.630 | 26.158 | 105.981 | 1.00 | 33.63 | 7 |
| 20 | ATOM | 1351 | CA | ARG A 171 | 34.350 | 24.913 | 105.705 | 1.00 | 33.38 | 6 |
| | ATOM | 1352 | C   | ARG A 171 | 34.951 | 24.875 | 104.302 | 1.00 | 34.23 | 6 |
| | ATOM | 1353 | O   | ARG A 171 | 35.944 | 24.213 | 103.981 | 1.00 | 32.41 | 8 |
| | ATOM | 1354 | CB  | ARG A 171 | 33.468 | 23.695 | 105.939 | 1.00 | 27.27 | 6 |
| | ATOM | 1355 | CG  | ARG A 171 | 33.012 | 23.494 | 107.353 | 1.00 | 33.00 | 6 |
| 25 | ATOM | 1356 | CD | ARG A 171 | 31.872 | 22.500 | 107.407 | 1.00 | 39.19 | 6 |
| | ATOM | 1357 | NE  | ARG A 171 | 31.388 | 22.325 | 108.770 | 1.00 | 39.85 | 7 |
| | ATOM | 1358 | CZ  | ARG A 171 | 30.408 | 23.012 | 109.340 | 1.00 | 43.41 | 6 |
| | ATOM | 1359 | NH1 | ARG A 171 | 29.725 | 23.983 | 108.734 | 1.00 | 29.35 | 7 |
| | ATOM | 1360 | NH2 | ARG A 171 | 30.110 | 22.693 | 110.606 | 1.00 | 44.37 | 7 |
| 30 | ATOM | 1361 | N  | GLN A 172 | 34.304 | 25.642 | 103.410 | 1.00 | 33.77 | 7 |
| | ATOM | 1362 | CA  | GLN A 172 | 34.824 | 25.847 | 102.066 | 1.00 | 33.35 | 6 |
| | ATOM | 1363 | C   | GLN A 172 | 35.157 | 24.625 | 101.241 | 1.00 | 31.96 | 6 |
| | ATOM | 1364 | O   | GLN A 172 | 36.210 | 24.583 | 100.568 | 1.00 | 33.96 | 8 |
| | ATOM | 1365 | CB  | GLN A 172 | 36.076 | 26.747 | 102.222 | 1.00 | 42.50 | 6 |
| 35 | ATOM | 1366 | CG | GLN A 172 | 35.640 | 28.090 | 102.820 | 1.00 | 49.13 | 6 |
| | ATOM | 1367 | CD  | GLN A 172 | 36.811 | 28.995 | 103.127 | 1.00 | 58.31 | 6 |
| | ATOM | 1368 | OE1 | GLN A 172 | 36.603 | 30.173 | 103.425 | 1.00 | 58.18 | 8 |
| | ATOM | 1369 | NE2 | GLN A 172 | 38.009 | 28.427 | 103.051 | 1.00 | 62.72 | 7 |
| | ATOM | 1370 | N   | PHE A 173 | 34.269 | 23.659 | 101.211 | 1.00 | 30.25 | 7 |
| 40 | ATOM | 1371 | CA | PHE A 173 | 34.431 | 22.480 | 100.363 | 1.00 | 29.08 | 6 |
| | ATOM | 1372 | C   | PHE A 173 | 33.761 | 22.758 | 99.013  | 1.00 | 28.52 | 6 |
| | ATOM | 1373 | O   | PHE A 173 | 32.782 | 23.518 | 99.080  | 1.00 | 26.08 | 8 |
| | ATOM | 1374 | CB  | PHE A 173 | 33.523 | 21.401 | 100.979 | 1.00 | 34.67 | 6 |
| | ATOM | 1375 | CG  | PHE A 173 | 33.945 | 20.938 | 102.338 | 1.00 | 35.82 | 6 |
| 45 | ATOM | 1376 | CD1 | PHE A 173 | 35.268 | 20.654 | 102.612 | 1.00 | 36.63 | 6 |
| | ATOM | 1377 | CD2 | PHE A 173 | 33.012 | 20.769 | 103.335 | 1.00 | 33.85 | 6 |
| | ATOM | 1378 | CE1 | PHE A 173 | 35.662 | 20.221 | 103.872 | 1.00 | 45.83 | 6 |
| | ATOM | 1379 | CE2 | PHE A 173 | 33.378 | 20.336 | 104.594 | 1.00 | 39.40 | 6 |
| | ATOM | 1380 | CZ  | PHE A 173 | 34.709 | 20.058 | 104.868 | 1.00 | 38.34 | 6 |
| 50 | ATOM | 1381 | N  | GLN A 174 | 34.128 | 22.107 | 97.888  | 1.00 | 28.71 | 7 |
| | ATOM | 1382 | CA  | GLN A 174 | 33.196 | 22.333 | 96.794  | 1.00 | 29.82 | 6 |
| | ATOM | 1383 | C   | GLN A 174 | 32.546 | 21.071 | 96.280  | 1.00 | 29.35 | 6 |
| | ATOM | 1384 | O   | GLN A 174 | 32.603 | 20.035 | 96.933  | 1.00 | 30.96 | 8 |
| | ATOM | 1385 | CB  | GLN A 174 | 33.216 | 23.494 | 95.843  | 1.00 | 53.27 | 6 |
| 55 | ATOM | 1386 | CG | GLN A 174 | 31.939 | 24.362 | 95.817  | 1.00 | 60.86 | 6 |
| | ATOM | 1387 | CD  | GLN A 174 | 30.996 | 24.108 | 96.976  | 1.00 | 55.96 | 6 |
| | ATOM | 1388 | OE1 | GLN A 174 | 30.235 | 23.170 | 97.136  | 1.00 | 47.07 | 8 |
| | ATOM | 1389 | NE2 | GLN A 174 | 31.083 | 25.001 | 97.961  | 1.00 | 62.44 | 7 |
| | ATOM | 1390 | N   | ASN A 175 | 31.699 | 21.302 | 95.282  | 1.00 | 27.07 | 7 |
| 60 | ATOM | 1391 | CA | ASN A 175 | 30.822 | 20.245 | 94.812  | 1.00 | 26.14 | 6 |
| | ATOM | 1392 | C   | ASN A 175 | 29.838 | 19.874 | 95.936  | 1.00 | 23.99 | 6 |
| | ATOM | 1393 | O   | ASN A 175 | 29.386 | 18.733 | 96.097  | 1.00 | 23.58 | 8 |
| | ATOM | 1394 | CB  | ASN A 175 | 31.616 | 19.093 | 94.213  | 1.00 | 29.32 | 6 |
| | ATOM | 1395 | CG  | ASN A 175 | 30.663 | 18.073 | 93.581  | 1.00 | 36.03 | 6 |
| 65 | ATOM | 1396 | OD1 | ASN A 175 | 29.890 | 18.446 | 92.704  | 1.00 | 43.41 | 8 |

| ATOM | 1397 | ND2 | ASN A 175 | 30.695 | 16.832 | 94.049 | 1.00 | 40.76 | 7 |
|------|------|-----|-----------|--------|--------|--------|------|-------|---|
| ATOM | 1398 | N | ARG A 176 | 29.402 | 20.871 | 96.719 | 1.00 | 20.65 | 7 |
| ATOM | 1399 | CA | ARG A 176 | 28.335 | 20.697 | 97.680 | 1.00 | 20.93 | 6 |
| ATOM | 1400 | C | ARG A 176 | 27.188 | 21.654 | 97.362 | 1.00 | 18.46 | 6 |
| ATOM | 1401 | O | ARG A 176 | 27.458 | 22.800 | 96.980 | 1.00 | 18.62 | 8 |
| ATOM | 1402 | CB | ARG A 176 | 28.690 | 21.084 | 99.142 | 1.00 | 31.62 | 6 |
| ATOM | 1403 | CG | ARG A 176 | 30.003 | 20.520 | 99.625 | 1.00 | 34.75 | 6 |
| ATOM | 1404 | CD | ARG A 176 | 29.901 | 19.018 | 99.769 | 1.00 | 36.13 | 6 |
| ATOM | 1405 | NE | ARG A 176 | 31.137 | 18.503 | 100.325 | 1.00 | 47.87 | 7 |
| ATOM | 1406 | CZ | ARG A 176 | 31.416 | 18.089 | 101.543 | 1.00 | 49.61 | 6 |
| ATOM | 1407 | NH1 | ARG A 176 | 30.563 | 18.063 | 102.550 | 1.00 | 46.30 | 7 |
| ATOM | 1408 | NH2 | ARG A 176 | 32.658 | 17.662 | 101.749 | 1.00 | 55.95 | 7 |
| ATOM | 1409 | N | ILE A 177 | 25.981 | 21.182 | 97.672 | 1.00 | 16.68 | 7 |
| ATOM | 1410 | CA | ILE A 177 | 24.860 | 22.144 | 97.505 | 1.00 | 16.11 | 6 |
| ATOM | 1411 | C | ILE A 177 | 24.091 | 22.054 | 98.836 | 1.00 | 15.68 | 6 |
| ATOM | 1412 | O | ILE A 177 | 23.828 | 20.927 | 99.235 | 1.00 | 16.63 | 8 |
| ATOM | 1413 | CB | ILE A 177 | 23.940 | 21.719 | 96.337 | 1.00 | 13.12 | 6 |
| ATOM | 1414 | CG1 | ILE A 177 | 24.667 | 22.007 | 94.985 | 1.00 | 23.05 | 6 |
| ATOM | 1415 | CG2 | ILE A 177 | 22.629 | 22.507 | 96.345 | 1.00 | 10.60 | 6 |
| ATOM | 1416 | CD1 | ILE A 177 | 23.895 | 21.379 | 93.831 | 1.00 | 18.83 | 6 |
| ATOM | 1417 | N | TYR A 178 | 23.727 | 23.189 | 99.412 | 1.00 | 16.89 | 7 |
| ATOM | 1418 | CA | TYR A 178 | 23.017 | 23.203 | 100.683 | 1.00 | 16.31 | 6 |
| ATOM | 1419 | C | TYR A 178 | 21.599 | 23.740 | 100.577 | 1.00 | 15.83 | 6 |
| ATOM | 1420 | O | TYR A 178 | 21.432 | 24.909 | 100.222 | 1.00 | 18.10 | 8 |
| ATOM | 1421 | CB | TYR A 178 | 23.741 | 24.169 | 101.700 | 1.00 | 14.58 | 6 |
| ATOM | 1422 | CG | TYR A 178 | 25.224 | 23.899 | 101.776 | 1.00 | 18.47 | 6 |
| ATOM | 1423 | CD1 | TYR A 178 | 25.713 | 22.976 | 102.686 | 1.00 | 19.67 | 6 |
| ATOM | 1424 | CD2 | TYR A 178 | 26.159 | 24.534 | 100.966 | 1.00 | 21.12 | 6 |
| ATOM | 1425 | CE1 | TYR A 178 | 27.055 | 22.694 | 102.824 | 1.00 | 19.76 | 6 |
| ATOM | 1426 | CE2 | TYR A 178 | 27.519 | 24.286 | 101.077 | 1.00 | 22.80 | 6 |
| ATOM | 1427 | CZ | TYR A 178 | 27.959 | 23.343 | 102.006 | 1.00 | 23.23 | 6 |
| ATOM | 1428 | OH | TYR A 178 | 29.301 | 23.045 | 102.135 | 1.00 | 22.73 | 8 |
| ATOM | 1429 | N | LYS A 179 | 20.602 | 22.972 | 100.926 | 1.00 | 13.95 | 7 |
| ATOM | 1430 | CA | LYS A 179 | 19.229 | 23.456 | 101.016 | 1.00 | 15.91 | 6 |
| ATOM | 1431 | C | LYS A 179 | 18.979 | 23.979 | 102.441 | 1.00 | 18.32 | 6 |
| ATOM | 1432 | O | LYS A 179 | 19.390 | 23.307 | 103.414 | 1.00 | 18.01 | 8 |
| ATOM | 1433 | CB | LYS A 179 | 18.376 | 22.221 | 100.747 | 1.00 | 13.64 | 6 |
| ATOM | 1434 | CG | LYS A 179 | 16.890 | 22.544 | 100.722 | 1.00 | 14.01 | 6 |
| ATOM | 1435 | CD | LYS A 179 | 16.131 | 21.266 | 100.433 | 1.00 | 19.62 | 6 |
| ATOM | 1436 | CE | LYS A 179 | 16.270 | 20.192 | 101.483 | 1.00 | 16.36 | 6 |
| ATOM | 1437 | NZ | LYS A 179 | 15.227 | 19.138 | 101.260 | 1.00 | 18.20 | 7 |
| ATOM | 1438 | N | PHE A 180 | 18.404 | 25.143 | 102.594 | 1.00 | 17.85 | 7 |
| ATOM | 1439 | CA | PHE A 180 | 18.139 | 25.718 | 103.920 | 1.00 | 20.43 | 6 |
| ATOM | 1440 | C | PHE A 180 | 16.959 | 25.011 | 104.598 | 1.00 | 21.42 | 6 |
| ATOM | 1441 | O | PHE A 180 | 15.986 | 24.567 | 103.955 | 1.00 | 21.98 | 8 |
| ATOM | 1442 | CB | PHE A 180 | 17.857 | 27.203 | 103.751 | 1.00 | 10.99 | 6 |
| ATOM | 1443 | CG | PHE A 180 | 19.005 | 28.092 | 103.351 | 1.00 | 11.27 | 6 |
| ATOM | 1444 | CD1 | PHE A 180 | 20.321 | 27.717 | 103.401 | 1.00 | 14.93 | 6 |
| ATOM | 1445 | CD2 | PHE A 180 | 18.756 | 29.383 | 102.939 | 1.00 | 10.08 | 6 |
| ATOM | 1446 | CE1 | PHE A 180 | 21.351 | 28.581 | 103.081 | 1.00 | 14.29 | 6 |
| ATOM | 1447 | CE2 | PHE A 180 | 19.747 | 30.272 | 102.622 | 1.00 | 15.90 | 6 |
| ATOM | 1448 | CZ | PHE A 180 | 21.064 | 29.862 | 102.681 | 1.00 | 17.25 | 6 |
| ATOM | 1449 | N | ARG A 181 | 17.043 | 24.843 | 105.932 | 1.00 | 22.19 | 7 |
| ATOM | 1450 | CA | ARG A 181 | 15.904 | 24.275 | 106.697 | 1.00 | 20.04 | 6 |
| ATOM | 1451 | C | ARG A 181 | 14.961 | 25.397 | 107.043 | 1.00 | 18.91 | 6 |
| ATOM | 1452 | O | ARG A 181 | 15.339 | 26.564 | 107.084 | 1.00 | 20.54 | 8 |
| ATOM | 1453 | CB | ARG A 181 | 16.414 | 23.589 | 107.966 | 1.00 | 20.73 | 6 |
| ATOM | 1454 | CG | ARG A 181 | 17.128 | 22.268 | 107.640 | 1.00 | 15.66 | 6 |
| ATOM | 1455 | CD | ARG A 181 | 16.076 | 21.326 | 107.101 | 1.00 | 19.94 | 6 |
| ATOM | 1456 | NE | ARG A 181 | 16.565 | 19.949 | 107.059 | 1.00 | 22.50 | 7 |
| ATOM | 1457 | CZ | ARG A 181 | 16.137 | 19.042 | 106.182 | 1.00 | 31.69 | 6 |
| ATOM | 1458 | NH1 | ARG A 181 | 15.269 | 19.370 | 105.222 | 1.00 | 29.02 | 7 |
| ATOM | 1459 | NH2 | ARG A 181 | 16.662 | 17.820 | 106.294 | 1.00 | 31.49 | 7 |
| ATOM | 1460 | N | GLY A 182 | 13.697 | 25.174 | 107.337 | 1.00 | 20.46 | 7 |
| ATOM | 1461 | CA | GLY A 182 | 12.859 | 26.345 | 107.675 | 1.00 | 21.18 | 6 |

| ATOM | 1462 | C | GLY | A | 182 | 11.452 | 25.903 | 107.256 | 1.00 | 24.79 | 6 |
|------|------|-----|-----|---|-----|--------|--------|---------|------|-------|---|
| ATOM | 1463 | O | GLY | A | 182 | 11.256 | 24.957 | 106.480 | 1.00 | 24.88 | 8 |
| ATOM | 1464 | N | ASP | A | 183 | 10.517 | 26.696 | 107.733 | 1.00 | 24.99 | 7 |
| ATOM | 1465 | CA | ASP | A | 183 | 9.120 | 26.406 | 107.485 | 1.00 | 28.22 | 6 |
| ATOM | 1466 | C | ASP | A | 183 | 8.757 | 26.520 | 106.019 | 1.00 | 26.65 | 6 |
| ATOM | 1467 | O | ASP | A | 183 | 8.862 | 27.603 | 105.453 | 1.00 | 27.60 | 8 |
| ATOM | 1468 | CB | ASP | A | 183 | 8.295 | 27.420 | 108.313 | 1.00 | 56.42 | 6 |
| ATOM | 1469 | CG | ASP | A | 183 | 7.075 | 26.720 | 108.892 | 1.00 | 70.56 | 6 |
| ATOM | 1470 | OD1 | ASP | A | 183 | 7.167 | 25.516 | 109.215 | 1.00 | 75.66 | 8 |
| ATOM | 1471 | OD2 | ASP | A | 183 | 6.041 | 27.413 | 109.000 | 1.00 | 82.78 | 8 |
| ATOM | 1472 | N | GLY | A | 184 | 8.311 | 25.397 | 105.455 | 1.00 | 26.42 | 7 |
| ATOM | 1473 | CA | GLY | A | 184 | 7.963 | 25.502 | 104.021 | 1.00 | 25.46 | 6 |
| ATOM | 1474 | C | GLY | A | 184 | 9.233 | 25.707 | 103.182 | 1.00 | 23.60 | 6 |
| ATOM | 1475 | O | GLY | A | 184 | 9.093 | 26.357 | 102.155 | 1.00 | 22.86 | 8 |
| ATOM | 1476 | N | LYS | A | 185 | 10.408 | 25.261 | 103.568 | 1.00 | 21.74 | 7 |
| ATOM | 1477 | CA | LYS | A | 185 | 11.597 | 25.434 | 102.800 | 1.00 | 20.76 | 6 |
| ATOM | 1478 | C | LYS | A | 185 | 11.734 | 24.222 | 101.877 | 1.00 | 20.17 | 6 |
| ATOM | 1479 | O | LYS | A | 185 | 11.787 | 23.114 | 102.397 | 1.00 | 18.16 | 8 |
| ATOM | 1480 | CB | LYS | A | 185 | 12.914 | 25.617 | 103.556 | 1.00 | 18.80 | 6 |
| ATOM | 1481 | CG | LYS | A | 185 | 13.105 | 27.046 | 103.982 | 1.00 | 18.48 | 6 |
| ATOM | 1482 | CD | LYS | A | 185 | 13.381 | 27.981 | 102.791 | 1.00 | 17.41 | 6 |
| ATOM | 1483 | CE | LYS | A | 185 | 13.007 | 29.383 | 103.057 | 1.00 | 14.81 | 6 |
| ATOM | 1484 | NZ | LYS | A | 185 | 13.385 | 30.535 | 102.205 | 1.00 | 19.47 | 7 |
| ATOM | 1485 | N | ALA | A | 186 | 11.700 | 24.509 | 100.556 | 1.00 | 17.48 | 7 |
| ATOM | 1486 | CA | ALA | A | 186 | 11.900 | 23.396 | 99.598 | 1.00 | 15.05 | 6 |
| ATOM | 1487 | C | ALA | A | 186 | 12.364 | 23.870 | 98.205 | 1.00 | 14.06 | 6 |
| ATOM | 1488 | O | ALA | A | 186 | 12.093 | 25.012 | 97.975 | 1.00 | 10.55 | 8 |
| ATOM | 1489 | CB | ALA | A | 186 | 10.652 | 22.577 | 99.407 | 1.00 | 16.40 | 6 |
| ATOM | 1490 | N | TRP | A | 187 | 12.960 | 23.127 | 97.305 | 1.00 | 12.54 | 7 |
| ATOM | 1491 | CA | TRP | A | 187 | 13.290 | 23.693 | 95.969 | 1.00 | 13.33 | 6 |
| ATOM | 1492 | C | TRP | A | 187 | 11.974 | 24.064 | 95.287 | 1.00 | 9.00 | 6 |
| ATOM | 1493 | O | TRP | A | 187 | 10.955 | 23.363 | 95.437 | 1.00 | 8.49 | 8 |
| ATOM | 1494 | CB | TRP | A | 187 | 13.985 | 22.535 | 95.204 | 1.00 | 8.05 | 6 |
| ATOM | 1495 | CG | TRP | A | 187 | 15.346 | 22.215 | 95.750 | 1.00 | 5.34 | 6 |
| ATOM | 1496 | CD1 | TRP | A | 187 | 15.790 | 20.949 | 96.045 | 1.00 | 8.08 | 6 |
| ATOM | 1497 | CD2 | TRP | A | 187 | 16.448 | 23.098 | 96.034 | 1.00 | 2.71 | 6 |
| ATOM | 1498 | NE1 | TRP | A | 187 | 17.107 | 20.983 | 96.478 | 1.00 | 6.12 | 7 |
| ATOM | 1499 | CE2 | TRP | A | 187 | 17.495 | 22.305 | 96.483 | 1.00 | 6.57 | 6 |
| ATOM | 1500 | CE3 | TRP | A | 187 | 16.632 | 24.476 | 95.993 | 1.00 | 4.12 | 6 |
| ATOM | 1501 | CZ2 | TRP | A | 187 | 18.734 | 22.815 | 96.917 | 1.00 | 13.17 | 6 |
| ATOM | 1502 | CZ3 | TRP | A | 187 | 17.858 | 24.993 | 96.414 | 1.00 | 4.12 | 6 |
| ATOM | 1503 | CH2 | TRP | A | 187 | 18.895 | 24.160 | 96.868 | 1.00 | 5.94 | 6 |
| ATOM | 1504 | N | ASP | A | 188 | 11.914 | 25.155 | 94.566 | 1.00 | 9.68 | 7 |
| ATOM | 1505 | CA | ASP | A | 188 | 10.697 | 25.489 | 93.799 | 1.00 | 11.71 | 6 |
| ATOM | 1506 | C | ASP | A | 188 | 10.263 | 24.423 | 92.812 | 1.00 | 10.59 | 6 |
| ATOM | 1507 | O | ASP | A | 188 | 11.039 | 23.569 | 92.427 | 1.00 | 11.68 | 8 |
| ATOM | 1508 | CB | ASP | A | 188 | 10.994 | 26.753 | 93.006 | 1.00 | 11.90 | 6 |
| ATOM | 1509 | CG | ASP | A | 188 | 11.305 | 27.859 | 93.976 | 1.00 | 17.27 | 6 |
| ATOM | 1510 | OD1 | ASP | A | 188 | 10.635 | 27.762 | 95.013 | 1.00 | 16.53 | 8 |
| ATOM | 1511 | OD2 | ASP | A | 188 | 11.952 | 28.884 | 93.890 | 1.00 | 11.59 | 8 |
| ATOM | 1512 | N | TRP | A | 189 | 9.004 | 24.449 | 92.380 | 1.00 | 11.75 | 7 |
| ATOM | 1513 | CA | TRP | A | 189 | 8.438 | 23.580 | 91.387 | 1.00 | 12.99 | 6 |
| ATOM | 1514 | C | TRP | A | 189 | 7.283 | 24.372 | 90.753 | 1.00 | 16.78 | 6 |
| ATOM | 1515 | O | TRP | A | 189 | 6.721 | 25.203 | 91.463 | 1.00 | 16.54 | 8 |
| ATOM | 1516 | CB | TRP | A | 189 | 7.896 | 22.310 | 91.974 | 1.00 | 10.02 | 6 |
| ATOM | 1517 | CG | TRP | A | 189 | 7.311 | 21.334 | 90.992 | 1.00 | 17.66 | 6 |
| ATOM | 1518 | CD1 | TRP | A | 189 | 5.989 | 21.060 | 90.752 | 1.00 | 13.06 | 6 |
| ATOM | 1519 | CD2 | TRP | A | 189 | 8.081 | 20.530 | 90.096 | 1.00 | 15.06 | 6 |
| ATOM | 1520 | NE1 | TRP | A | 189 | 5.911 | 20.076 | 89.785 | 1.00 | 14.69 | 7 |
| ATOM | 1521 | CE2 | TRP | A | 189 | 7.178 | 19.753 | 89.365 | 1.00 | 14.15 | 6 |
| ATOM | 1522 | CE3 | TRP | A | 189 | 9.445 | 20.394 | 89.843 | 1.00 | 20.41 | 6 |
| ATOM | 1523 | CZ2 | TRP | A | 189 | 7.606 | 18.856 | 88.380 | 1.00 | 18.86 | 6 |
| ATOM | 1524 | CZ3 | TRP | A | 189 | 9.857 | 19.518 | 88.861 | 1.00 | 15.20 | 6 |
| ATOM | 1525 | CH2 | TRP | A | 189 | 8.945 | 18.745 | 88.151 | 1.00 | 12.94 | 6 |
| ATOM | 1526 | N | GLU | A | 190 | 7.110 | 24.333 | 89.431 | 1.00 | 16.45 | 7 |

| ATOM | 1527 | CA  | GLU A 190 | 7.843  | 23.484 | 88.501 | 1.00 | 14.15 | 6 |
| ATOM | 1528 | C   | GLU A 190 | 9.100  | 24.138 | 87.965 | 1.00 | 11.80 | 6 |
| ATOM | 1529 | O   | GLU A 190 | 9.100  | 25.327 | 87.614 | 1.00 | 13.59 | 8 |
| ATOM | 1530 | CB  | GLU A 190 | 6.913  | 23.273 | 87.234 | 1.00 | 18.03 | 6 |
| ATOM | 1531 | CG  | GLU A 190 | 7.561  | 22.319 | 86.234 | 1.00 | 15.34 | 6 |
| ATOM | 1532 | CD  | GLU A 190 | 6.635  | 21.758 | 85.154 | 1.00 | 18.34 | 6 |
| ATOM | 1533 | OE1 | GLU A 190 | 5.430  | 22.032 | 85.206 | 1.00 | 11.63 | 8 |
| ATOM | 1534 | OE2 | GLU A 190 | 7.130  | 21.043 | 84.278 | 1.00 | 18.43 | 8 |
| ATOM | 1535 | N   | VAL A 191 | 10.153 | 23.337 | 87.867 | 1.00 | 13.43 | 7 |
| ATOM | 1536 | CA  | VAL A 191 | 11.424 | 23.766 | 87.270 | 1.00 | 13.29 | 6 |
| ATOM | 1537 | C   | VAL A 191 | 11.901 | 22.612 | 86.373 | 1.00 | 12.80 | 6 |
| ATOM | 1538 | O   | VAL A 191 | 11.352 | 21.515 | 86.481 | 1.00 | 11.36 | 8 |
| ATOM | 1539 | CB  | VAL A 191 | 12.556 | 24.142 | 88.261 | 1.00 | 15.48 | 6 |
| ATOM | 1540 | CG1 | VAL A 191 | 12.244 | 25.469 | 88.971 | 1.00 | 7.91  | 6 |
| ATOM | 1541 | CG2 | VAL A 191 | 12.830 | 23.000 | 89.226 | 1.00 | 9.01  | 6 |
| ATOM | 1542 | N   | ASP A 192 | 12.973 | 22.785 | 85.599 | 1.00 | 13.22 | 7 |
| ATOM | 1543 | CA  | ASP A 192 | 13.508 | 21.670 | 84.807 | 1.00 | 12.54 | 6 |
| ATOM | 1544 | C   | ASP A 192 | 13.923 | 20.545 | 85.728 | 1.00 | 14.99 | 6 |
| ATOM | 1545 | O   | ASP A 192 | 14.443 | 20.794 | 86.838 | 1.00 | 16.15 | 8 |
| ATOM | 1546 | CB  | ASP A 192 | 14.729 | 22.142 | 83.981 | 1.00 | 14.61 | 6 |
| ATOM | 1547 | CG  | ASP A 192 | 15.256 | 21.039 | 83.073 | 1.00 | 12.27 | 6 |
| ATOM | 1548 | OD1 | ASP A 192 | 14.462 | 20.560 | 82.244 | 1.00 | 18.65 | 8 |
| ATOM | 1549 | OD2 | ASP A 192 | 16.369 | 20.590 | 83.300 | 1.00 | 16.21 | 8 |
| ATOM | 1550 | N   | SER A 193 | 13.822 | 19.303 | 85.306 | 1.00 | 13.14 | 7 |
| ATOM | 1551 | CA  | SER A 193 | 14.074 | 18.138 | 86.116 | 1.00 | 14.27 | 6 |
| ATOM | 1552 | C   | SER A 193 | 15.416 | 17.506 | 85.990 | 1.00 | 17.10 | 6 |
| ATOM | 1553 | O   | SER A 193 | 15.652 | 16.494 | 86.634 | 1.00 | 18.48 | 8 |
| ATOM | 1554 | CB  | SER A 193 | 12.952 | 17.115 | 85.914 | 1.00 | 26.77 | 6 |
| ATOM | 1555 | OG  | SER A 193 | 12.955 | 16.710 | 84.539 | 1.00 | 29.00 | 8 |
| ATOM | 1556 | N   | GLU A 194 | 16.299 | 18.056 | 85.164 | 1.00 | 18.40 | 7 |
| ATOM | 1557 | CA  | GLU A 194 | 17.659 | 17.525 | 85.057 | 1.00 | 19.32 | 6 |
| ATOM | 1558 | C   | GLU A 194 | 18.328 | 17.724 | 86.447 | 1.00 | 19.49 | 6 |
| ATOM | 1559 | O   | GLU A 194 | 18.132 | 18.756 | 87.087 | 1.00 | 17.74 | 8 |
| ATOM | 1560 | CB  | GLU A 194 | 18.473 | 18.378 | 84.026 | 1.00 | 14.77 | 6 |
| ATOM | 1561 | CG  | GLU A 194 | 19.922 | 17.922 | 84.051 | 1.00 | 16.84 | 6 |
| ATOM | 1562 | CD  | GLU A 194 | 20.843 | 18.632 | 83.071 | 1.00 | 36.83 | 6 |
| ATOM | 1563 | OE1 | GLU A 194 | 20.344 | 19.311 | 82.168 | 1.00 | 24.18 | 8 |
| ATOM | 1564 | OE2 | GLU A 194 | 22.098 | 18.522 | 83.150 | 1.00 | 39.46 | 8 |
| ATOM | 1565 | N   | ASN A 195 | 19.075 | 16.714 | 86.868 | 1.00 | 18.99 | 7 |
| ATOM | 1566 | CA  | ASN A 195 | 19.645 | 16.590 | 88.199 | 1.00 | 20.82 | 6 |
| ATOM | 1567 | C   | ASN A 195 | 18.522 | 16.398 | 89.230 | 1.00 | 20.55 | 6 |
| ATOM | 1568 | O   | ASN A 195 | 18.638 | 16.891 | 90.350 | 1.00 | 23.35 | 8 |
| ATOM | 1569 | CB  | ASN A 195 | 20.448 | 17.811 | 88.628 | 1.00 | 13.63 | 6 |
| ATOM | 1570 | CG  | ASN A 195 | 21.625 | 18.101 | 87.712 | 1.00 | 25.71 | 6 |
| ATOM | 1571 | OD1 | ASN A 195 | 21.858 | 19.253 | 87.318 | 1.00 | 28.78 | 8 |
| ATOM | 1572 | ND2 | ASN A 195 | 22.329 | 17.039 | 87.388 | 1.00 | 19.03 | 7 |
| ATOM | 1573 | N   | GLY A 196 | 17.370 | 15.874 | 88.887 | 1.00 | 18.63 | 7 |
| ATOM | 1574 | CA  | GLY A 196 | 16.252 | 15.689 | 89.806 | 1.00 | 15.28 | 6 |
| ATOM | 1575 | C   | GLY A 196 | 15.410 | 16.927 | 89.909 | 1.00 | 13.09 | 6 |
| ATOM | 1576 | O   | GLY A 196 | 14.229 | 16.925 | 89.587 | 1.00 | 15.77 | 8 |
| ATOM | 1577 | N   | ASN A 197 | 15.969 | 18.061 | 90.274 | 1.00 | 13.90 | 7 |
| ATOM | 1578 | CA  | ASN A 197 | 15.287 | 19.333 | 90.380 | 1.00 | 14.20 | 6 |
| ATOM | 1579 | C   | ASN A 197 | 16.363 | 20.345 | 90.053 | 1.00 | 13.47 | 6 |
| ATOM | 1580 | O   | ASN A 197 | 17.331 | 20.320 | 90.804 | 1.00 | 14.96 | 8 |
| ATOM | 1581 | CB  | ASN A 197 | 14.726 | 19.574 | 91.793 | 1.00 | 11.86 | 6 |
| ATOM | 1582 | CG  | ASN A 197 | 14.107 | 20.947 | 91.973 | 1.00 | 9.73  | 6 |
| ATOM | 1583 | OD1 | ASN A 197 | 14.848 | 21.955 | 91.990 | 1.00 | 9.97  | 8 |
| ATOM | 1584 | ND2 | ASN A 197 | 12.788 | 21.059 | 92.111 | 1.00 | 7.43  | 7 |
| ATOM | 1585 | N   | TYR A 198 | 16.193 | 21.192 | 89.041 | 1.00 | 11.73 | 7 |
| ATOM | 1586 | CA  | TYR A 198 | 17.310 | 22.082 | 88.700 | 1.00 | 13.36 | 6 |
| ATOM | 1587 | C   | TYR A 198 | 17.075 | 23.499 | 89.136 | 1.00 | 10.84 | 6 |
| ATOM | 1588 | O   | TYR A 198 | 17.564 | 24.522 | 88.641 | 1.00 | 10.06 | 8 |
| ATOM | 1589 | CB  | TYR A 198 | 17.596 | 22.046 | 87.168 | 1.00 | 13.55 | 6 |
| ATOM | 1590 | CG  | TYR A 198 | 19.009 | 22.282 | 86.714 | 1.00 | 14.34 | 6 |
| ATOM | 1591 | CD1 | TYR A 198 | 20.016 | 22.855 | 87.492 | 1.00 | 13.73 | 6 |

| ATOM | 1592 | CD2 | TYR A 198 | 19.362 | 21.779 | 85.436 | 1.00 | 11.59 | 6 |
| --- | --- | --- | --- | --- | --- | --- | --- | --- | --- |
| ATOM | 1593 | CE1 | TYR A 198 | 21.321 | 23.013 | 87.038 | 1.00 | 13.97 | 6 |
| ATOM | 1594 | CE2 | TYR A 198 | 20.642 | 21.931 | 84.962 | 1.00 | 11.79 | 6 |
| ATOM | 1595 | CZ | TYR A 198 | 21.597 | 22.557 | 85.726 | 1.00 | 12.84 | 6 |
| ATOM | 1596 | OH | TYR A 198 | 22.864 | 22.651 | 85.193 | 1.00 | 13.95 | 8 |
| ATOM | 1597 | N | ASP A 199 | 16.285 | 23.625 | 90.222 | 1.00 | 11.61 | 7 |
| ATOM | 1598 | CA | ASP A 199 | 16.082 | 25.006 | 90.757 | 1.00 | 6.05 | 6 |
| ATOM | 1599 | C | ASP A 199 | 17.423 | 25.461 | 91.157 | 1.00 | 4.34 | 6 |
| ATOM | 1600 | O | ASP A 199 | 17.699 | 26.673 | 90.916 | 1.00 | 8.06 | 8 |
| ATOM | 1601 | CB | ASP A 199 | 15.078 | 24.839 | 91.949 | 1.00 | 11.81 | 6 |
| ATOM | 1602 | CG | ASP A 199 | 14.739 | 26.085 | 92.655 | 1.00 | 21.25 | 6 |
| ATOM | 1603 | OD1 | ASP A 199 | 14.885 | 27.212 | 92.094 | 1.00 | 5.27 | 8 |
| ATOM | 1604 | OD2 | ASP A 199 | 14.254 | 26.128 | 93.823 | 1.00 | 17.12 | 8 |
| ATOM | 1605 | N | TYR A 200 | 18.435 | 24.875 | 91.732 | 1.00 | 7.57 | 7 |
| ATOM | 1606 | CA | TYR A 200 | 19.631 | 25.578 | 92.190 | 1.00 | 7.08 | 6 |
| ATOM | 1607 | C | TYR A 200 | 20.625 | 25.573 | 90.999 | 1.00 | 9.10 | 6 |
| ATOM | 1608 | O | TYR A 200 | 20.853 | 24.522 | 90.402 | 1.00 | 10.97 | 8 |
| ATOM | 1609 | CB | TYR A 200 | 20.304 | 24.756 | 93.389 | 1.00 | 8.94 | 6 |
| ATOM | 1610 | CG | TYR A 200 | 21.515 | 25.582 | 93.795 | 1.00 | 10.82 | 6 |
| ATOM | 1611 | CD1 | TYR A 200 | 21.350 | 26.662 | 94.650 | 1.00 | 8.86 | 6 |
| ATOM | 1612 | CD2 | TYR A 200 | 22.779 | 25.369 | 93.222 | 1.00 | 10.54 | 6 |
| ATOM | 1613 | CE1 | TYR A 200 | 22.420 | 27.501 | 94.957 | 1.00 | 9.83 | 6 |
| ATOM | 1614 | CE2 | TYR A 200 | 23.827 | 26.217 | 93.513 | 1.00 | 10.73 | 6 |
| ATOM | 1615 | CZ | TYR A 200 | 23.645 | 27.284 | 94.377 | 1.00 | 11.56 | 6 |
| ATOM | 1616 | OH | TYR A 200 | 24.685 | 28.169 | 94.657 | 1.00 | 8.88 | 8 |
| ATOM | 1617 | N | LEU A 201 | 21.244 | 26.706 | 90.779 | 1.00 | 10.58 | 7 |
| ATOM | 1618 | CA | LEU A 201 | 22.265 | 26.813 | 89.730 | 1.00 | 9.44 | 6 |
| ATOM | 1619 | C | LEU A 201 | 23.521 | 27.412 | 90.320 | 1.00 | 6.35 | 6 |
| ATOM | 1620 | O | LEU A 201 | 24.590 | 26.823 | 90.208 | 1.00 | 9.88 | 8 |
| ATOM | 1621 | CB | LEU A 201 | 21.772 | 27.860 | 88.683 | 1.00 | 10.07 | 6 |
| ATOM | 1622 | CG | LEU A 201 | 22.848 | 28.119 | 87.567 | 1.00 | 8.98 | 6 |
| ATOM | 1623 | CD1 | LEU A 201 | 23.129 | 26.765 | 86.878 | 1.00 | 11.75 | 6 |
| ATOM | 1624 | CD2 | LEU A 201 | 22.175 | 29.082 | 86.583 | 1.00 | 11.24 | 6 |
| ATOM | 1625 | N | MET A 202 | 23.451 | 28.635 | 90.847 | 1.00 | 8.21 | 7 |
| ATOM | 1626 | CA | MET A 202 | 24.653 | 29.206 | 91.458 | 1.00 | 9.75 | 6 |
| ATOM | 1627 | C | MET A 202 | 24.369 | 30.318 | 92.473 | 1.00 | 7.69 | 6 |
| ATOM | 1628 | O | MET A 202 | 23.255 | 30.785 | 92.622 | 1.00 | 9.81 | 8 |
| ATOM | 1629 | CB | MET A 202 | 25.514 | 29.878 | 90.308 | 1.00 | 12.10 | 6 |
| ATOM | 1630 | CG | MET A 202 | 24.611 | 30.882 | 89.567 | 1.00 | 10.97 | 6 |
| ATOM | 1631 | SD | MET A 202 | 25.654 | 31.671 | 88.182 | 1.00 | 21.46 | 16 |
| ATOM | 1632 | CE | MET A 202 | 26.028 | 30.134 | 87.333 | 1.00 | 16.25 | 6 |
| ATOM | 1633 | N | TYR A 203 | 25.406 | 30.811 | 93.167 | 1.00 | 11.04 | 7 |
| ATOM | 1634 | CA | TYR A 203 | 25.192 | 31.876 | 94.200 | 1.00 | 11.53 | 6 |
| ATOM | 1635 | C | TYR A 203 | 24.131 | 31.534 | 95.262 | 1.00 | 10.29 | 6 |
| ATOM | 1636 | O | TYR A 203 | 23.917 | 30.362 | 95.584 | 1.00 | 11.59 | 8 |
| ATOM | 1637 | CB | TYR A 203 | 24.766 | 33.119 | 93.372 | 1.00 | 13.34 | 6 |
| ATOM | 1638 | CG | TYR A 203 | 26.015 | 33.736 | 92.767 | 1.00 | 19.37 | 6 |
| ATOM | 1639 | CD1 | TYR A 203 | 27.047 | 34.149 | 93.618 | 1.00 | 20.46 | 6 |
| ATOM | 1640 | CD2 | TYR A 203 | 26.203 | 33.879 | 91.379 | 1.00 | 17.82 | 6 |
| ATOM | 1641 | CE1 | TYR A 203 | 28.208 | 34.722 | 93.123 | 1.00 | 22.58 | 6 |
| ATOM | 1642 | CE2 | TYR A 203 | 27.365 | 34.450 | 90.885 | 1.00 | 19.42 | 6 |
| ATOM | 1643 | CZ | TYR A 203 | 28.366 | 34.856 | 91.734 | 1.00 | 24.00 | 6 |
| ATOM | 1644 | OH | TYR A 203 | 29.553 | 35.431 | 91.281 | 1.00 | 23.69 | 8 |
| ATOM | 1645 | N | ALA A 204 | 23.329 | 32.520 | 95.669 | 1.00 | 11.94 | 7 |
| ATOM | 1646 | CA | ALA A 204 | 22.206 | 32.292 | 96.570 | 1.00 | 10.93 | 6 |
| ATOM | 1647 | C | ALA A 204 | 20.929 | 32.206 | 95.736 | 1.00 | 10.49 | 6 |
| ATOM | 1648 | O | ALA A 204 | 20.477 | 33.172 | 95.131 | 1.00 | 9.71 | 8 |
| ATOM | 1649 | CB | ALA A 204 | 22.068 | 33.473 | 97.589 | 1.00 | 9.30 | 6 |
| ATOM | 1650 | N | ASP A 205 | 20.254 | 31.078 | 95.797 | 1.00 | 9.32 | 7 |
| ATOM | 1651 | CA | ASP A 205 | 19.056 | 30.845 | 95.020 | 1.00 | 9.79 | 6 |
| ATOM | 1652 | C | ASP A 205 | 17.797 | 31.470 | 95.540 | 1.00 | 14.23 | 6 |
| ATOM | 1653 | O | ASP A 205 | 17.369 | 31.145 | 96.701 | 1.00 | 13.37 | 8 |
| ATOM | 1654 | CB | ASP A 205 | 18.907 | 29.308 | 95.034 | 1.00 | 11.48 | 6 |
| ATOM | 1655 | CG | ASP A 205 | 17.997 | 29.001 | 93.864 | 1.00 | 17.50 | 6 |
| ATOM | 1656 | OD1 | ASP A 205 | 18.477 | 29.186 | 92.710 | 1.00 | 14.51 | 8 |

| | ATOM | 1657 | OD2 | ASP | A | 205 | 16.831 | 28.644 | 94.068 | 1.00 | 7.75 | 8 |
|---|---|---|---|---|---|---|---|---|---|---|---|---|
| | ATOM | 1658 | N | VAL | A | 206 | 17.146 | 32.307 | 94.734 | 1.00 | 11.30 | 7 |
| | ATOM | 1659 | CA | VAL | A | 206 | 15.945 | 32.995 | 95.132 | 1.00 | 9.20 | 6 |
| | ATOM | 1660 | C | VAL | A | 206 | 14.815 | 32.084 | 95.466 | 1.00 | 12.62 | 6 |
| 5 | ATOM | 1661 | O | VAL | A | 206 | 14.566 | 31.138 | 94.683 | 1.00 | 11.57 | 8 |
| | ATOM | 1662 | CB | VAL | A | 206 | 15.540 | 34.120 | 94.202 | 1.00 | 13.76 | 6 |
| | ATOM | 1663 | CG1 | VAL | A | 206 | 14.245 | 34.804 | 94.653 | 1.00 | 13.90 | 6 |
| | ATOM | 1664 | CG2 | VAL | A | 206 | 16.684 | 35.101 | 94.179 | 1.00 | 11.36 | 6 |
| | ATOM | 1665 | N | ASP | A | 207 | 14.092 | 32.323 | 96.581 | 1.00 | 10.69 | 7 |
| 10 | ATOM | 1666 | CA | ASP | A | 207 | 12.992 | 31.406 | 96.913 | 1.00 | 11.90 | 6 |
| | ATOM | 1667 | C | ASP | A | 207 | 11.718 | 31.981 | 96.310 | 1.00 | 13.90 | 6 |
| | ATOM | 1668 | O | ASP | A | 207 | 11.131 | 32.928 | 96.871 | 1.00 | 12.71 | 8 |
| | ATOM | 1669 | CB | ASP | A | 207 | 12.836 | 31.346 | 98.443 | 1.00 | 15.17 | 6 |
| | ATOM | 1670 | CG | ASP | A | 207 | 11.726 | 30.503 | 98.952 | 1.00 | 22.74 | 6 |
| 15 | ATOM | 1671 | OD1 | ASP | A | 207 | 10.964 | 29.956 | 98.108 | 1.00 | 19.17 | 8 |
| | ATOM | 1672 | OD2 | ASP | A | 207 | 11.521 | 30.286 | 100.169 | 1.00 | 20.54 | 8 |
| | ATOM | 1673 | N | MET | A | 208 | 11.225 | 31.367 | 95.216 | 1.00 | 13.35 | 7 |
| | ATOM | 1674 | CA | MET | A | 208 | 10.079 | 31.963 | 94.507 | 1.00 | 15.70 | 6 |
| | ATOM | 1675 | C | MET | A | 208 | 8.768 | 31.646 | 95.201 | 1.00 | 17.50 | 6 |
| 20 | ATOM | 1676 | O | MET | A | 208 | 7.700 | 32.148 | 94.848 | 1.00 | 18.55 | 8 |
| | ATOM | 1677 | CB | MET | A | 208 | 9.976 | 31.477 | 93.030 | 1.00 | 17.03 | 6 |
| | ATOM | 1678 | CG | MET | A | 208 | 11.197 | 31.966 | 92.202 | 1.00 | 12.28 | 6 |
| | ATOM | 1679 | SD | MET | A | 208 | 11.381 | 33.711 | 92.110 | 1.00 | 23.21 | 16 |
| | ATOM | 1680 | CE | MET | A | 208 | 12.944 | 34.091 | 91.430 | 1.00 | 20.00 | 6 |
| 25 | ATOM | 1681 | N | ASP | A | 209 | 8.827 | 30.719 | 96.163 | 1.00 | 16.74 | 7 |
| | ATOM | 1682 | CA | ASP | A | 209 | 7.640 | 30.466 | 96.979 | 1.00 | 20.55 | 6 |
| | ATOM | 1683 | C | ASP | A | 209 | 7.425 | 31.556 | 98.040 | 1.00 | 19.95 | 6 |
| | ATOM | 1684 | O | ASP | A | 209 | 6.318 | 31.628 | 98.566 | 1.00 | 21.59 | 8 |
| | ATOM | 1685 | CB | ASP | A | 209 | 7.690 | 29.136 | 97.686 | 1.00 | 17.97 | 6 |
| 30 | ATOM | 1686 | CG | ASP | A | 209 | 7.557 | 27.883 | 96.835 | 1.00 | 31.63 | 6 |
| | ATOM | 1687 | OD1 | ASP | A | 209 | 6.800 | 28.001 | 95.847 | 1.00 | 31.19 | 8 |
| | ATOM | 1688 | OD2 | ASP | A | 209 | 8.251 | 26.896 | 97.233 | 1.00 | 32.40 | 8 |
| | ATOM | 1689 | N | HIS | A | 210 | 8.380 | 32.411 | 98.375 | 1.00 | 20.52 | 7 |
| | ATOM | 1690 | CA | HIS | A | 210 | 8.186 | 33.429 | 99.385 | 1.00 | 18.61 | 6 |
| 35 | ATOM | 1691 | C | HIS | A | 210 | 7.420 | 34.626 | 98.888 | 1.00 | 19.89 | 6 |
| | ATOM | 1692 | O | HIS | A | 210 | 7.830 | 35.435 | 98.052 | 1.00 | 19.58 | 8 |
| | ATOM | 1693 | CB | HIS | A | 210 | 9.561 | 33.808 | 99.938 | 1.00 | 19.59 | 6 |
| | ATOM | 1694 | CG | HIS | A | 210 | 9.481 | 34.653 | 101.178 | 1.00 | 27.83 | 6 |
| | ATOM | 1695 | ND1 | HIS | A | 210 | 9.945 | 34.202 | 102.414 | 1.00 | 32.20 | 7 |
| 40 | ATOM | 1696 | CD2 | HIS | A | 210 | 8.970 | 35.884 | 101.394 | 1.00 | 20.96 | 6 |
| | ATOM | 1697 | CE1 | HIS | A | 210 | 9.736 | 35.153 | 103.327 | 1.00 | 23.85 | 6 |
| | ATOM | 1698 | NE2 | HIS | A | 210 | 9.169 | 36.180 | 102.716 | 1.00 | 34.38 | 7 |
| | ATOM | 1699 | N | PRO | A | 211 | 6.289 | 34.918 | 99.532 | 1.00 | 22.38 | 7 |
| | ATOM | 1700 | CA | PRO | A | 211 | 5.376 | 35.976 | 99.137 | 1.00 | 21.41 | 6 |
| 45 | ATOM | 1701 | C | PRO | A | 211 | 6.026 | 37.320 | 99.125 | 1.00 | 22.35 | 6 |
| | ATOM | 1702 | O | PRO | A | 211 | 5.636 | 38.134 | 98.241 | 1.00 | 24.85 | 8 |
| | ATOM | 1703 | CB | PRO | A | 211 | 4.089 | 35.908 | 99.974 | 1.00 | 22.59 | 6 |
| | ATOM | 1704 | CG | PRO | A | 211 | 4.546 | 34.989 | 101.059 | 1.00 | 22.80 | 6 |
| | ATOM | 1705 | CD | PRO | A | 211 | 5.670 | 34.076 | 100.574 | 1.00 | 21.75 | 6 |
| 50 | ATOM | 1706 | N | GLU | A | 212 | 7.058 | 37.600 | 99.904 | 1.00 | 19.19 | 7 |
| | ATOM | 1707 | CA | GLU | A | 212 | 7.541 | 38.984 | 99.779 | 1.00 | 20.41 | 6 |
| | ATOM | 1708 | C | GLU | A | 212 | 8.578 | 39.110 | 98.673 | 1.00 | 19.26 | 6 |
| | ATOM | 1709 | O | GLU | A | 212 | 8.905 | 40.204 | 98.189 | 1.00 | 17.10 | 8 |
| | ATOM | 1710 | CB | GLU | A | 212 | 7.888 | 39.558 | 101.141 | 1.00 | 29.62 | 6 |
| 55 | ATOM | 1711 | CG | GLU | A | 212 | 9.158 | 39.175 | 101.818 | 1.00 | 44.14 | 6 |
| | ATOM | 1712 | CD | GLU | A | 212 | 9.381 | 39.713 | 103.232 | 1.00 | 53.86 | 6 |
| | ATOM | 1713 | OE1 | GLU | A | 212 | 8.401 | 40.209 | 103.827 | 1.00 | 61.45 | 8 |
| | ATOM | 1714 | OE2 | GLU | A | 212 | 10.514 | 39.666 | 103.781 | 1.00 | 32.90 | 8 |
| | ATOM | 1715 | N | VAL | A | 213 | 9.160 | 37.972 | 98.313 | 1.00 | 19.73 | 7 |
| 60 | ATOM | 1716 | CA | VAL | A | 213 | 10.109 | 37.977 | 97.173 | 1.00 | 20.44 | 6 |
| | ATOM | 1717 | C | VAL | A | 213 | 9.278 | 38.201 | 95.886 | 1.00 | 18.35 | 6 |
| | ATOM | 1718 | O | VAL | A | 213 | 9.541 | 39.130 | 95.138 | 1.00 | 18.56 | 8 |
| | ATOM | 1719 | CB | VAL | A | 213 | 10.799 | 36.605 | 97.149 | 1.00 | 21.92 | 6 |
| | ATOM | 1720 | CG1 | VAL | A | 213 | 11.469 | 36.366 | 95.797 | 1.00 | 22.74 | 6 |
| 65 | ATOM | 1721 | CG2 | VAL | A | 213 | 11.799 | 36.623 | 98.297 | 1.00 | 25.64 | 6 |

| ATOM | 1722 | N | VAL | A | 214 | 8.200 | 37.480 | 95.732 | 1.00 | 18.19 | 7 |
|---|---|---|---|---|---|---|---|---|---|---|---|
| ATOM | 1723 | CA | VAL | A | 214 | 7.316 | 37.633 | 94.592 | 1.00 | 20.51 | 6 |
| ATOM | 1724 | C | VAL | A | 214 | 6.928 | 39.081 | 94.441 | 1.00 | 23.51 | 6 |
| ATOM | 1725 | O | VAL | A | 214 | 7.049 | 39.704 | 93.356 | 1.00 | 24.81 | 8 |
| ATOM | 1726 | CB | VAL | A | 214 | 6.053 | 36.773 | 94.667 | 1.00 | 22.40 | 6 |
| ATOM | 1727 | CG1 | VAL | A | 214 | 5.078 | 37.088 | 93.544 | 1.00 | 32.00 | 6 |
| ATOM | 1728 | CG2 | VAL | A | 214 | 6.399 | 35.293 | 94.639 | 1.00 | 21.53 | 6 |
| ATOM | 1729 | N | ASN | A | 215 | 6.490 | 39.701 | 95.540 | 1.00 | 22.11 | 7 |
| ATOM | 1730 | CA | ASN | A | 215 | 6.067 | 41.089 | 95.499 | 1.00 | 20.65 | 6 |
| ATOM | 1731 | C | ASN | A | 215 | 7.195 | 42.036 | 95.194 | 1.00 | 19.24 | 6 |
| ATOM | 1732 | O | ASN | A | 215 | 7.027 | 43.008 | 94.446 | 1.00 | 19.17 | 8 |
| ATOM | 1733 | CB | ASN | A | 215 | 5.269 | 41.478 | 96.761 | 1.00 | 35.08 | 6 |
| ATOM | 1734 | CG | ASN | A | 215 | 3.881 | 40.869 | 96.604 | 1.00 | 35.00 | 6 |
| ATOM | 1735 | OD1 | ASN | A | 215 | 3.164 | 41.271 | 95.689 | 1.00 | 58.96 | 8 |
| ATOM | 1736 | ND2 | ASN | A | 215 | 3.472 | 39.903 | 97.402 | 1.00 | 52.78 | 7 |
| ATOM | 1737 | N | GLU | A | 216 | 8.377 | 41.768 | 95.716 | 1.00 | 17.10 | 7 |
| ATOM | 1738 | CA | GLU | A | 216 | 9.466 | 42.704 | 95.478 | 1.00 | 17.74 | 6 |
| ATOM | 1739 | C | GLU | A | 216 | 9.882 | 42.652 | 93.964 | 1.00 | 17.58 | 6 |
| ATOM | 1740 | O | GLU | A | 216 | 10.301 | 43.672 | 93.415 | 1.00 | 13.53 | 8 |
| ATOM | 1741 | CB | GLU | A | 216 | 10.640 | 42.358 | 96.358 | 1.00 | 17.67 | 6 |
| ATOM | 1742 | CG | GLU | A | 216 | 11.948 | 43.068 | 96.105 | 1.00 | 28.42 | 6 |
| ATOM | 1743 | CD | GLU | A | 216 | 11.838 | 44.580 | 96.017 | 1.00 | 23.80 | 6 |
| ATOM | 1744 | OE1 | GLU | A | 216 | 10.776 | 45.098 | 96.371 | 1.00 | 30.40 | 8 |
| ATOM | 1745 | OE2 | GLU | A | 216 | 12.804 | 45.270 | 95.617 | 1.00 | 31.36 | 8 |
| ATOM | 1746 | N | LEU | A | 217 | 9.935 | 41.444 | 93.443 | 1.00 | 17.03 | 7 |
| ATOM | 1747 | CA | LEU | A | 217 | 10.411 | 41.180 | 92.084 | 1.00 | 19.84 | 6 |
| ATOM | 1748 | C | LEU | A | 217 | 9.412 | 41.774 | 91.079 | 1.00 | 20.75 | 6 |
| ATOM | 1749 | O | LEU | A | 217 | 9.832 | 42.493 | 90.189 | 1.00 | 21.48 | 8 |
| ATOM | 1750 | CB | LEU | A | 217 | 10.653 | 39.700 | 91.932 | 1.00 | 11.86 | 6 |
| ATOM | 1751 | CG | LEU | A | 217 | 12.078 | 39.172 | 91.888 | 1.00 | 19.48 | 6 |
| ATOM | 1752 | CD1 | LEU | A | 217 | 13.209 | 39.933 | 92.505 | 1.00 | 16.47 | 6 |
| ATOM | 1753 | CD2 | LEU | A | 217 | 12.099 | 37.703 | 92.249 | 1.00 | 12.39 | 6 |
| ATOM | 1754 | N | ARG | A | 218 | 8.112 | 41.741 | 91.333 | 1.00 | 21.19 | 7 |
| ATOM | 1755 | CA | ARG | A | 218 | 7.147 | 42.417 | 90.508 | 1.00 | 22.98 | 6 |
| ATOM | 1756 | C | ARG | A | 218 | 7.344 | 43.914 | 90.478 | 1.00 | 25.87 | 6 |
| ATOM | 1757 | O | ARG | A | 218 | 7.189 | 44.576 | 89.450 | 1.00 | 25.87 | 8 |
| ATOM | 1758 | CB | ARG | A | 218 | 5.699 | 42.152 | 90.944 | 1.00 | 18.95 | 6 |
| ATOM | 1759 | CG | ARG | A | 218 | 5.394 | 40.694 | 90.636 | 1.00 | 10.41 | 6 |
| ATOM | 1760 | CD | ARG | A | 218 | 3.962 | 40.385 | 91.065 | 1.00 | 12.60 | 6 |
| ATOM | 1761 | NE | ARG | A | 218 | 3.837 | 38.941 | 90.836 | 1.00 | 23.07 | 7 |
| ATOM | 1762 | CZ | ARG | A | 218 | 2.659 | 38.338 | 90.698 | 1.00 | 30.77 | 6 |
| ATOM | 1763 | NH1 | ARG | A | 218 | 1.556 | 39.063 | 90.731 | 1.00 | 41.73 | 7 |
| ATOM | 1764 | NH2 | ARG | A | 218 | 2.630 | 37.025 | 90.508 | 1.00 | 34.53 | 7 |
| ATOM | 1765 | N | ARG | A | 219 | 7.633 | 44.448 | 91.669 | 1.00 | 26.91 | 7 |
| ATOM | 1766 | CA | ARG | A | 219 | 7.809 | 45.891 | 91.779 | 1.00 | 25.88 | 6 |
| ATOM | 1767 | C | ARG | A | 219 | 9.097 | 46.275 | 91.108 | 1.00 | 23.84 | 6 |
| ATOM | 1768 | O | ARG | A | 219 | 9.172 | 47.352 | 90.497 | 1.00 | 23.41 | 8 |
| ATOM | 1769 | CB | ARG | A | 219 | 7.666 | 46.341 | 93.233 | 1.00 | 37.02 | 6 |
| ATOM | 1770 | CG | ARG | A | 219 | 8.704 | 47.268 | 93.798 | 1.00 | 55.61 | 6 |
| ATOM | 1771 | CD | ARG | A | 219 | 8.297 | 48.719 | 93.748 | 1.00 | 79.18 | 6 |
| ATOM | 1772 | NE | ARG | A | 219 | 9.295 | 49.624 | 93.196 | 1.00 | 96.62 | 7 |
| ATOM | 1773 | CZ | ARG | A | 219 | 9.203 | 50.951 | 93.059 | 1.00 | 104.91 | 6 |
| ATOM | 1774 | NH1 | ARG | A | 219 | 8.132 | 51.621 | 93.451 | 1.00 | 111.12 | 7 |
| ATOM | 1775 | NH2 | ARG | A | 219 | 10.236 | 51.611 | 92.543 | 1.00 | 106.48 | 7 |
| ATOM | 1776 | N | TRP | A | 220 | 10.149 | 45.464 | 91.279 | 1.00 | 21.44 | 7 |
| ATOM | 1777 | CA | TRP | A | 220 | 11.404 | 45.840 | 90.635 | 1.00 | 21.83 | 6 |
| ATOM | 1778 | C | TRP | A | 220 | 11.138 | 45.866 | 89.093 | 1.00 | 21.82 | 6 |
| ATOM | 1779 | O | TRP | A | 220 | 11.533 | 46.795 | 88.420 | 1.00 | 21.38 | 8 |
| ATOM | 1780 | CB | TRP | A | 220 | 12.599 | 44.973 | 91.041 | 1.00 | 13.52 | 6 |
| ATOM | 1781 | CG | TRP | A | 220 | 13.727 | 45.208 | 90.059 | 1.00 | 21.56 | 6 |
| ATOM | 1782 | CD1 | TRP | A | 220 | 14.642 | 46.203 | 90.022 | 1.00 | 22.24 | 6 |
| ATOM | 1783 | CD2 | TRP | A | 220 | 13.998 | 44.369 | 88.926 | 1.00 | 14.67 | 6 |
| ATOM | 1784 | NE1 | TRP | A | 220 | 15.508 | 46.024 | 88.940 | 1.00 | 16.13 | 7 |
| ATOM | 1785 | CE2 | TRP | A | 220 | 15.125 | 44.887 | 88.286 | 1.00 | 21.21 | 6 |
| ATOM | 1786 | CE3 | TRP | A | 220 | 13.387 | 43.195 | 88.444 | 1.00 | 25.00 | 6 |

| ATOM | 1787 | CZ2 | TRP A 220 | 15.653 | 44.325 | 87.109 | 1.00 17.63 | 6 |
|------|------|-----|-----------|--------|--------|--------|------------|---|
| ATOM | 1788 | CZ3 | TRP A 220 | 13.914 | 42.622 | 87.289 | 1.00 23.47 | 6 |
| ATOM | 1789 | CH2 | TRP A 220 | 15.016 | 43.208 | 86.660 | 1.00 20.65 | 6 |
| ATOM | 1790 | N | GLY A 221 | 10.446 | 44.915 | 88.545 | 1.00 20.99 | 7 |
| ATOM | 1791 | CA | GLY A 221 | 9.967 | 44.762 | 87.199 | 1.00 24.79 | 6 |
| ATOM | 1792 | C | GLY A 221 | 9.384 | 46.035 | 86.595 | 1.00 24.57 | 6 |
| ATOM | 1793 | O | GLY A 221 | 9.942 | 46.595 | 85.643 | 1.00 22.41 | 8 |
| ATOM | 1794 | N | GLU A 222 | 8.413 | 46.611 | 87.304 | 1.00 25.64 | 7 |
| ATOM | 1795 | CA | GLU A 222 | 7.801 | 47.881 | 86.928 | 1.00 23.20 | 6 |
| ATOM | 1796 | C | GLU A 222 | 8.796 | 49.012 | 86.978 | 1.00 24.03 | 6 |
| ATOM | 1797 | O | GLU A 222 | 8.879 | 49.889 | 86.109 | 1.00 24.03 | 8 |
| ATOM | 1798 | CB | GLU A 222 | 6.774 | 48.279 | 87.985 | 1.00 22.11 | 6 |
| ATOM | 1799 | CG | GLU A 222 | 5.405 | 47.683 | 87.787 | 1.00 40.46 | 6 |
| ATOM | 1800 | CD | GLU A 222 | 4.516 | 48.274 | 88.906 | 1.00 50.60 | 6 |
| ATOM | 1801 | OE1 | GLU A 222 | 4.478 | 49.528 | 88.896 | 1.00 48.94 | 8 |
| ATOM | 1802 | OE2 | GLU A 222 | 3.974 | 47.454 | 89.687 | 1.00 46.61 | 8 |
| ATOM | 1803 | N | TRP A 223 | 9.563 | 49.070 | 88.069 | 1.00 22.02 | 7 |
| ATOM | 1804 | CA | TRP A 223 | 10.507 | 50.196 | 88.175 | 1.00 22.34 | 6 |
| ATOM | 1805 | C | TRP A 223 | 11.543 | 50.187 | 87.046 | 1.00 24.50 | 6 |
| ATOM | 1806 | O | TRP A 223 | 11.997 | 51.232 | 86.571 | 1.00 24.43 | 8 |
| ATOM | 1807 | CB | TRP A 223 | 11.280 | 49.965 | 89.495 | 1.00 23.32 | 6 |
| ATOM | 1808 | CG | TRP A 223 | 12.332 | 50.997 | 89.722 | 1.00 12.36 | 6 |
| ATOM | 1809 | CD1 | TRP A 223 | 12.096 | 52.257 | 90.194 | 1.00 12.65 | 6 |
| ATOM | 1810 | CD2 | TRP A 223 | 13.730 | 50.898 | 89.482 | 1.00 14.74 | 6 |
| ATOM | 1811 | NE1 | TRP A 223 | 13.307 | 52.928 | 90.308 | 1.00 14.71 | 7 |
| ATOM | 1812 | CE2 | TRP A 223 | 14.307 | 52.121 | 89.855 | 1.00 13.39 | 6 |
| ATOM | 1813 | CE3 | TRP A 223 | 14.567 | 49.910 | 88.959 | 1.00 17.71 | 6 |
| ATOM | 1814 | CZ2 | TRP A 223 | 15.675 | 52.408 | 89.749 | 1.00 18.37 | 6 |
| ATOM | 1815 | CZ3 | TRP A 223 | 15.913 | 50.186 | 88.851 | 1.00 17.26 | 6 |
| ATOM | 1816 | CH2 | TRP A 223 | 16.469 | 51.401 | 89.250 | 1.00 21.97 | 6 |
| ATOM | 1817 | N | TYR A 224 | 12.142 | 49.020 | 86.780 | 1.00 22.93 | 7 |
| ATOM | 1818 | CA | TYR A 224 | 13.196 | 48.885 | 85.759 | 1.00 22.60 | 6 |
| ATOM | 1819 | C | TYR A 224 | 12.620 | 49.271 | 84.357 | 1.00 20.78 | 6 |
| ATOM | 1820 | O | TYR A 224 | 13.238 | 50.024 | 83.644 | 1.00 20.47 | 8 |
| ATOM | 1821 | CB | TYR A 224 | 13.618 | 47.428 | 85.695 | 1.00 23.16 | 6 |
| ATOM | 1822 | CG | TYR A 224 | 14.692 | 46.916 | 84.770 | 1.00 21.12 | 6 |
| ATOM | 1823 | CD1 | TYR A 224 | 15.898 | 47.567 | 84.607 | 1.00 20.00 | 6 |
| ATOM | 1824 | CD2 | TYR A 224 | 14.491 | 45.716 | 84.087 | 1.00 20.21 | 6 |
| ATOM | 1825 | CE1 | TYR A 224 | 16.909 | 47.056 | 83.812 | 1.00 19.68 | 6 |
| ATOM | 1826 | CE2 | TYR A 224 | 15.489 | 45.203 | 83.293 | 1.00 19.23 | 6 |
| ATOM | 1827 | CZ | TYR A 224 | 16.668 | 45.880 | 83.143 | 1.00 19.19 | 6 |
| ATOM | 1828 | OH | TYR A 224 | 17.629 | 45.330 | 82.336 | 1.00 20.77 | 8 |
| ATOM | 1829 | N | THR A 225 | 11.445 | 48.786 | 84.040 | 1.00 21.36 | 7 |
| ATOM | 1830 | CA | THR A 225 | 10.767 | 49.090 | 82.822 | 1.00 26.04 | 6 |
| ATOM | 1831 | C | THR A 225 | 10.585 | 50.602 | 82.698 | 1.00 30.55 | 6 |
| ATOM | 1832 | O | THR A 225 | 11.111 | 51.175 | 81.742 | 1.00 30.61 | 8 |
| ATOM | 1833 | CB | THR A 225 | 9.427 | 48.372 | 82.725 | 1.00 23.52 | 6 |
| ATOM | 1834 | OG1 | THR A 225 | 9.726 | 46.984 | 82.687 | 1.00 26.82 | 8 |
| ATOM | 1835 | CG2 | THR A 225 | 8.707 | 48.745 | 81.418 | 1.00 31.34 | 6 |
| ATOM | 1836 | N | ASN A 226 | 9.974 | 51.244 | 83.704 | 1.00 31.50 | 7 |
| ATOM | 1837 | CA | ASN A 226 | 9.766 | 52.676 | 83.718 | 1.00 31.16 | 6 |
| ATOM | 1838 | C | ASN A 226 | 11.026 | 53.473 | 83.808 | 1.00 32.12 | 6 |
| ATOM | 1839 | O | ASN A 226 | 11.188 | 54.509 | 83.143 | 1.00 33.63 | 8 |
| ATOM | 1840 | CB | ASN A 226 | 8.840 | 53.077 | 84.891 | 1.00 29.40 | 6 |
| ATOM | 1841 | CG | ASN A 226 | 7.454 | 52.571 | 84.563 | 1.00 30.15 | 6 |
| ATOM | 1842 | OD1 | ASN A 226 | 7.237 | 52.230 | 83.399 | 1.00 39.98 | 8 |
| ATOM | 1843 | ND2 | ASN A 226 | 6.524 | 52.463 | 85.483 | 1.00 41.24 | 7 |
| ATOM | 1844 | N | THR A 227 | 11.990 | 53.011 | 84.593 | 1.00 33.58 | 7 |
| ATOM | 1845 | CA | THR A 227 | 13.179 | 53.871 | 84.732 | 1.00 34.37 | 6 |
| ATOM | 1846 | C | THR A 227 | 13.950 | 54.002 | 83.429 | 1.00 34.33 | 6 |
| ATOM | 1847 | O | THR A 227 | 14.624 | 55.022 | 83.187 | 1.00 33.24 | 8 |
| ATOM | 1848 | CB | THR A 227 | 13.993 | 53.466 | 85.970 | 1.00 33.49 | 6 |
| ATOM | 1849 | OG1 | THR A 227 | 15.097 | 54.351 | 86.173 | 1.00 47.56 | 8 |
| ATOM | 1850 | CG2 | THR A 227 | 14.627 | 52.095 | 85.722 | 1.00 53.36 | 6 |
| ATOM | 1851 | N | LEU A 228 | 13.989 | 52.951 | 82.599 | 1.00 34.32 | 7 |

| ATOM | 1852 | CA  | LEU A 228 | 14.809 | 52.959 | 81.387 | 1.00 | 31.35 | 6 |
| ATOM | 1853 | C   | LEU A 228 | 13.954 | 52.937 | 80.121 | 1.00 | 32.12 | 6 |
| ATOM | 1854 | O   | LEU A 228 | 14.487 | 52.726 | 79.028 | 1.00 | 33.07 | 8 |
| ATOM | 1855 | CB  | LEU A 228 | 15.697 | 51.732 | 81.399 | 1.00 | 19.92 | 6 |
| ATOM | 1856 | CG  | LEU A 228 | 16.872 | 51.635 | 82.343 | 1.00 | 28.23 | 6 |
| ATOM | 1857 | CD1 | LEU A 228 | 17.626 | 50.347 | 82.084 | 1.00 | 22.94 | 6 |
| ATOM | 1858 | CD2 | LEU A 228 | 17.793 | 52.837 | 82.321 | 1.00 | 28.36 | 6 |
| ATOM | 1859 | N   | ASN A 229 | 12.652 | 53.106 | 80.259 | 1.00 | 30.09 | 7 |
| ATOM | 1860 | CA  | ASN A 229 | 11.717 | 53.072 | 79.147 | 1.00 | 31.01 | 6 |
| ATOM | 1861 | C   | ASN A 229 | 11.965 | 51.870 | 78.238 | 1.00 | 29.35 | 6 |
| ATOM | 1862 | O   | ASN A 229 | 12.074 | 52.027 | 77.024 | 1.00 | 29.88 | 8 |
| ATOM | 1863 | CB  | ASN A 229 | 11.753 | 54.401 | 78.392 | 1.00 | 35.74 | 6 |
| ATOM | 1864 | CG  | ASN A 229 | 10.564 | 54.629 | 77.480 | 1.00 | 44.56 | 6 |
| ATOM | 1865 | OD1 | ASN A 229 | 9.494  | 54.024 | 77.526 | 1.00 | 48.29 | 8 |
| ATOM | 1866 | ND2 | ASN A 229 | 10.739 | 55.572 | 76.547 | 1.00 | 47.22 | 7 |
| ATOM | 1867 | N   | LEU A 230 | 11.969 | 50.651 | 78.747 | 1.00 | 26.34 | 7 |
| ATOM | 1868 | CA  | LEU A 230 | 12.151 | 49.434 | 77.963 | 1.00 | 24.98 | 6 |
| ATOM | 1869 | C   | LEU A 230 | 10.985 | 49.012 | 77.078 | 1.00 | 23.59 | 6 |
| ATOM | 1870 | O   | LEU A 230 | 9.815  | 49.179 | 77.394 | 1.00 | 24.27 | 8 |
| ATOM | 1871 | CB  | LEU A 230 | 12.478 | 48.268 | 78.919 | 1.00 | 25.61 | 6 |
| ATOM | 1872 | CG  | LEU A 230 | 13.741 | 48.428 | 79.759 | 1.00 | 18.62 | 6 |
| ATOM | 1873 | CD1 | LEU A 230 | 14.014 | 47.133 | 80.513 | 1.00 | 27.61 | 6 |
| ATOM | 1874 | CD2 | LEU A 230 | 14.967 | 48.696 | 78.877 | 1.00 | 28.13 | 6 |
| ATOM | 1875 | N   | ASP A 231 | 11.278 | 48.365 | 75.924 | 1.00 | 21.79 | 7 |
| ATOM | 1876 | CA  | ASP A 231 | 10.246 | 47.835 | 75.043 | 1.00 | 20.65 | 6 |
| ATOM | 1877 | C   | ASP A 231 | 10.110 | 46.339 | 75.292 | 1.00 | 20.30 | 6 |
| ATOM | 1878 | O   | ASP A 231 | 9.103  | 45.756 | 74.891 | 1.00 | 20.54 | 8 |
| ATOM | 1879 | CB  | ASP A 231 | 10.618 | 48.043 | 73.528 | 1.00 | 21.94 | 6 |
| ATOM | 1880 | CG  | ASP A 231 | 10.901 | 49.525 | 73.367 | 1.00 | 13.94 | 6 |
| ATOM | 1881 | OD1 | ASP A 231 | 9.942  | 50.286 | 73.503 | 1.00 | 24.69 | 8 |
| ATOM | 1882 | OD2 | ASP A 231 | 12.054 | 49.949 | 73.183 | 1.00 | 20.63 | 8 |
| ATOM | 1883 | N   | GLY A 232 | 11.122 | 45.727 | 75.946 | 1.00 | 18.68 | 7 |
| ATOM | 1884 | CA  | GLY A 232 | 10.932 | 44.300 | 76.199 | 1.00 | 16.67 | 6 |
| ATOM | 1885 | C   | GLY A 232 | 12.089 | 43.727 | 76.991 | 1.00 | 15.71 | 6 |
| ATOM | 1886 | O   | GLY A 232 | 12.953 | 44.439 | 77.478 | 1.00 | 16.01 | 8 |
| ATOM | 1887 | N   | PHE A 233 | 12.086 | 42.394 | 77.129 | 1.00 | 14.55 | 7 |
| ATOM | 1888 | CA  | PHE A 233 | 13.180 | 41.803 | 77.919 | 1.00 | 13.86 | 6 |
| ATOM | 1889 | C   | PHE A 233 | 13.750 | 40.550 | 77.278 | 1.00 | 12.54 | 6 |
| ATOM | 1890 | O   | PHE A 233 | 13.006 | 39.820 | 76.615 | 1.00 | 12.13 | 8 |
| ATOM | 1891 | CB  | PHE A 233 | 12.440 | 41.134 | 79.160 | 1.00 | 12.94 | 6 |
| ATOM | 1892 | CG  | PHE A 233 | 11.624 | 42.107 | 79.987 | 1.00 | 4.98  | 6 |
| ATOM | 1893 | CD1 | PHE A 233 | 12.212 | 43.177 | 80.588 | 1.00 | 6.42  | 6 |
| ATOM | 1894 | CD2 | PHE A 233 | 10.279 | 41.877 | 80.166 | 1.00 | 15.69 | 6 |
| ATOM | 1895 | CE1 | PHE A 233 | 11.475 | 44.065 | 81.375 | 1.00 | 15.76 | 6 |
| ATOM | 1896 | CE2 | PHE A 233 | 9.528  | 42.742 | 80.945 | 1.00 | 25.06 | 6 |
| ATOM | 1897 | CZ  | PHE A 233 | 10.115 | 43.834 | 81.532 | 1.00 | 14.14 | 6 |
| ATOM | 1898 | N   | ARG A 234 | 14.941 | 40.227 | 77.730 | 1.00 | 12.74 | 7 |
| ATOM | 1899 | CA  | ARG A 234 | 15.505 | 38.901 | 77.488 | 1.00 | 12.43 | 6 |
| ATOM | 1900 | C   | ARG A 234 | 15.587 | 38.314 | 78.928 | 1.00 | 14.55 | 6 |
| ATOM | 1901 | O   | ARG A 234 | 16.230 | 38.935 | 79.814 | 1.00 | 14.89 | 8 |
| ATOM | 1902 | CB  | ARG A 234 | 16.899 | 39.022 | 76.882 | 1.00 | 5.93  | 6 |
| ATOM | 1903 | CG  | ARG A 234 | 17.586 | 37.656 | 76.732 | 1.00 | 10.20 | 6 |
| ATOM | 1904 | CD  | ARG A 234 | 18.540 | 37.408 | 77.899 | 1.00 | 15.00 | 6 |
| ATOM | 1905 | NE  | ARG A 234 | 19.404 | 36.232 | 77.692 | 1.00 | 14.34 | 7 |
| ATOM | 1906 | CZ  | ARG A 234 | 20.182 | 35.688 | 78.615 | 1.00 | 24.46 | 6 |
| ATOM | 1907 | NH1 | ARG A 234 | 20.160 | 36.173 | 79.871 | 1.00 | 13.27 | 7 |
| ATOM | 1908 | NH2 | ARG A 234 | 20.930 | 34.647 | 78.289 | 1.00 | 12.67 | 7 |
| ATOM | 1909 | N   | ILE A 235 | 14.928 | 37.217 | 79.185 | 1.00 | 14.15 | 7 |
| ATOM | 1910 | CA  | ILE A 235 | 14.874 | 36.653 | 80.533 | 1.00 | 12.69 | 6 |
| ATOM | 1911 | C   | ILE A 235 | 15.873 | 35.548 | 80.793 | 1.00 | 12.06 | 6 |
| ATOM | 1912 | O   | ILE A 235 | 15.773 | 34.464 | 80.203 | 1.00 | 12.54 | 8 |
| ATOM | 1913 | CB  | ILE A 235 | 13.446 | 36.187 | 80.820 | 1.00 | 10.54 | 6 |
| ATOM | 1914 | CG1 | ILE A 235 | 12.504 | 37.385 | 80.567 | 1.00 | 9.10  | 6 |
| ATOM | 1915 | CG2 | ILE A 235 | 13.310 | 35.831 | 82.331 | 1.00 | 16.58 | 6 |
| ATOM | 1916 | CD1 | ILE A 235 | 11.115 | 36.763 | 80.407 | 1.00 | 15.58 | 6 |

| ATOM | 1917 | N   | ASP | A | 236 | 16.776 | 35.785 | 81.749 | 1.00 | 9.36  | 7 |
| ATOM | 1918 | CA  | ASP | A | 236 | 17.781 | 34.796 | 82.093 | 1.00 | 10.49 | 6 |
| ATOM | 1919 | C   | ASP | A | 236 | 17.441 | 33.558 | 82.860 | 1.00 | 12.64 | 6 |
| ATOM | 1920 | O   | ASP | A | 236 | 16.607 | 33.534 | 83.759 | 1.00 | 15.01 | 8 |
| ATOM | 1921 | CB  | ASP | A | 236 | 18.886 | 35.533 | 82.806 | 1.00 | 10.07 | 6 |
| ATOM | 1922 | CG  | ASP | A | 236 | 20.154 | 34.798 | 83.084 | 1.00 | 20.01 | 6 |
| ATOM | 1923 | OD1 | ASP | A | 236 | 20.882 | 34.542 | 82.112 | 1.00 | 14.97 | 8 |
| ATOM | 1924 | OD2 | ASP | A | 236 | 20.455 | 34.555 | 84.310 | 1.00 | 22.16 | 8 |
| ATOM | 1925 | N   | ALA | A | 237 | 18.050 | 32.429 | 82.484 | 1.00 | 11.95 | 7 |
| ATOM | 1926 | CA  | ALA | A | 237 | 18.011 | 31.158 | 83.169 | 1.00 | 12.87 | 6 |
| ATOM | 1927 | C   | ALA | A | 237 | 16.653 | 30.687 | 83.598 | 1.00 | 16.11 | 6 |
| ATOM | 1928 | O   | ALA | A | 237 | 16.440 | 30.225 | 84.762 | 1.00 | 15.77 | 8 |
| ATOM | 1929 | CB  | ALA | A | 237 | 18.924 | 31.424 | 84.407 | 1.00 | 13.46 | 6 |
| ATOM | 1930 | N   | VAL | A | 238 | 15.677 | 30.602 | 82.687 | 1.00 | 9.31  | 7 |
| ATOM | 1931 | CA  | VAL | A | 238 | 14.320 | 30.328 | 83.035 | 1.00 | 7.91  | 6 |
| ATOM | 1932 | C   | VAL | A | 238 | 14.133 | 28.877 | 83.391 | 1.00 | 9.01  | 6 |
| ATOM | 1933 | O   | VAL | A | 238 | 13.113 | 28.602 | 84.037 | 1.00 | 10.54 | 8 |
| ATOM | 1934 | CB  | VAL | A | 238 | 13.212 | 30.742 | 82.045 | 1.00 | 14.17 | 6 |
| ATOM | 1935 | CG1 | VAL | A | 238 | 13.273 | 32.240 | 81.788 | 1.00 | 13.29 | 6 |
| ATOM | 1936 | CG2 | VAL | A | 238 | 13.486 | 29.997 | 80.712 | 1.00 | 15.01 | 6 |
| ATOM | 1937 | N   | LYS | A | 239 | 15.066 | 27.991 | 83.077 | 1.00 | 5.59  | 7 |
| ATOM | 1938 | CA  | LYS | A | 239 | 14.711 | 26.629 | 83.448 | 1.00 | 10.08 | 6 |
| ATOM | 1939 | C   | LYS | A | 239 | 14.865 | 26.363 | 85.008 | 1.00 | 7.29  | 6 |
| ATOM | 1940 | O   | LYS | A | 239 | 14.529 | 25.276 | 85.419 | 1.00 | 7.91  | 8 |
| ATOM | 1941 | CB  | LYS | A | 239 | 15.636 | 25.685 | 82.762 | 1.00 | 12.33 | 6 |
| ATOM | 1942 | CG  | LYS | A | 239 | 17.092 | 25.584 | 82.801 | 1.00 | 25.74 | 6 |
| ATOM | 1943 | CD  | LYS | A | 239 | 17.278 | 24.453 | 81.732 | 1.00 | 25.18 | 6 |
| ATOM | 1944 | CE  | LYS | A | 239 | 18.708 | 24.141 | 81.578 | 1.00 | 26.14 | 6 |
| ATOM | 1945 | NZ  | LYS | A | 239 | 19.049 | 22.792 | 81.090 | 1.00 | 29.06 | 7 |
| ATOM | 1946 | N   | HIS | A | 240 | 15.615 | 27.232 | 85.621 | 1.00 | 8.92  | 7 |
| ATOM | 1947 | CA  | HIS | A | 240 | 15.904 | 27.175 | 87.047 | 1.00 | 14.13 | 6 |
| ATOM | 1948 | C   | HIS | A | 240 | 14.880 | 28.058 | 87.743 | 1.00 | 15.09 | 6 |
| ATOM | 1949 | O   | HIS | A | 240 | 15.029 | 28.277 | 88.936 | 1.00 | 10.80 | 8 |
| ATOM | 1950 | CB  | HIS | A | 240 | 17.327 | 27.746 | 87.264 | 1.00 | 10.84 | 6 |
| ATOM | 1951 | CG  | HIS | A | 240 | 18.312 | 27.095 | 86.328 | 1.00 | 7.11  | 6 |
| ATOM | 1952 | ND1 | HIS | A | 240 | 18.625 | 25.766 | 86.369 | 1.00 | 6.30  | 7 |
| ATOM | 1953 | CD2 | HIS | A | 240 | 18.997 | 27.608 | 85.226 | 1.00 | 9.29  | 6 |
| ATOM | 1954 | CE1 | HIS | A | 240 | 19.524 | 25.452 | 85.416 | 1.00 | 10.25 | 6 |
| ATOM | 1955 | NE2 | HIS | A | 240 | 19.767 | 26.568 | 84.761 | 1.00 | 6.19  | 7 |
| ATOM | 1956 | N   | ILE | A | 241 | 13.855 | 28.688 | 87.174 | 1.00 | 11.07 | 7 |
| ATOM | 1957 | CA  | ILE | A | 241 | 12.949 | 29.591 | 87.887 | 1.00 | 9.64  | 6 |
| ATOM | 1958 | C   | ILE | A | 241 | 11.555 | 29.021 | 87.800 | 1.00 | 14.21 | 6 |
| ATOM | 1959 | O   | ILE | A | 241 | 11.114 | 28.540 | 86.713 | 1.00 | 9.89  | 8 |
| ATOM | 1960 | CB  | ILE | A | 241 | 13.014 | 30.983 | 87.274 | 1.00 | 10.12 | 6 |
| ATOM | 1961 | CG1 | ILE | A | 241 | 14.389 | 31.615 | 87.488 | 1.00 | 7.20  | 6 |
| ATOM | 1962 | CG2 | ILE | A | 241 | 11.921 | 31.942 | 87.733 | 1.00 | 13.70 | 6 |
| ATOM | 1963 | CD1 | ILE | A | 241 | 14.592 | 32.912 | 86.714 | 1.00 | 8.67  | 6 |
| ATOM | 1964 | N   | LYS | A | 242 | 10.790 | 29.009 | 88.919 | 1.00 | 11.24 | 7 |
| ATOM | 1965 | CA  | LYS | A | 242 | 9.482  | 28.353 | 88.886 | 1.00 | 11.43 | 6 |
| ATOM | 1966 | C   | LYS | A | 242 | 8.667  | 28.791 | 87.642 | 1.00 | 11.92 | 6 |
| ATOM | 1967 | O   | LYS | A | 242 | 8.506  | 29.992 | 87.454 | 1.00 | 12.59 | 8 |
| ATOM | 1968 | CB  | LYS | A | 242 | 8.805  | 28.706 | 90.226 | 1.00 | 9.80  | 6 |
| ATOM | 1969 | CG  | LYS | A | 242 | 7.375  | 28.212 | 90.391 | 1.00 | 14.60 | 6 |
| ATOM | 1970 | CD  | LYS | A | 242 | 6.822  | 28.881 | 91.688 | 1.00 | 23.88 | 6 |
| ATOM | 1971 | CE  | LYS | A | 242 | 5.656  | 28.032 | 92.185 | 1.00 | 30.29 | 6 |
| ATOM | 1972 | NZ  | LYS | A | 242 | 5.228  | 28.446 | 93.546 | 1.00 | 51.79 | 7 |
| ATOM | 1973 | N   | TYR | A | 243 | 8.207  | 27.886 | 86.794 | 1.00 | 12.14 | 7 |
| ATOM | 1974 | CA  | TYR | A | 243 | 7.591  | 28.335 | 85.513 | 1.00 | 12.18 | 6 |
| ATOM | 1975 | C   | TYR | A | 243 | 6.430  | 29.283 | 85.699 | 1.00 | 13.50 | 6 |
| ATOM | 1976 | O   | TYR | A | 243 | 6.349  | 30.392 | 85.138 | 1.00 | 10.33 | 8 |
| ATOM | 1977 | CB  | TYR | A | 243 | 7.177  | 27.155 | 84.639 | 1.00 | 11.39 | 6 |
| ATOM | 1978 | CG  | TYR | A | 243 | 8.272  | 26.205 | 84.196 | 1.00 | 8.33  | 6 |
| ATOM | 1979 | CD1 | TYR | A | 243 | 9.605  | 26.506 | 84.310 | 1.00 | 9.57  | 6 |
| ATOM | 1980 | CD2 | TYR | A | 243 | 7.937  | 24.971 | 83.661 | 1.00 | 6.42  | 6 |
| ATOM | 1981 | CE1 | TYR | A | 243 | 10.610 | 25.624 | 83.980 | 1.00 | 7.83  | 6 |

| ATOM | 1982 | CE2 | TYR A 243 | 8.937 | 24.099 | 83.234 | 1.00 | 6.98 | 6 |
| ATOM | 1983 | CZ | TYR A 243 | 10.260 | 24.446 | 83.402 | 1.00 | 7.87 | 6 |
| ATOM | 1984 | OH | TYR A 243 | 11.213 | 23.503 | 83.006 | 1.00 | 8.46 | 8 |
| ATOM | 1985 | N | SER A 244 | 5.514 | 28.975 | 86.659 | 1.00 | 12.18 | 7 |
| ATOM | 1986 | CA | SER A 244 | 4.381 | 29.873 | 86.861 | 1.00 | 11.90 | 6 |
| ATOM | 1987 | C | SER A 244 | 4.708 | 31.236 | 87.348 | 1.00 | 12.87 | 6 |
| ATOM | 1988 | O | SER A 244 | 4.008 | 32.267 | 87.088 | 1.00 | 15.15 | 8 |
| ATOM | 1989 | CB | SER A 244 | 3.275 | 29.152 | 87.666 | 1.00 | 25.44 | 6 |
| ATOM | 1990 | OG | SER A 244 | 3.751 | 28.984 | 88.988 | 1.00 | 28.03 | 8 |
| ATOM | 1991 | N | PHE A 245 | 5.861 | 31.370 | 88.033 | 1.00 | 11.37 | 7 |
| ATOM | 1992 | CA | PHE A 245 | 6.246 | 32.688 | 88.460 | 1.00 | 11.43 | 6 |
| ATOM | 1993 | C | PHE A 245 | 6.616 | 33.538 | 87.223 | 1.00 | 13.09 | 6 |
| ATOM | 1994 | O | PHE A 245 | 6.337 | 34.745 | 87.182 | 1.00 | 13.56 | 8 |
| ATOM | 1995 | CB | PHE A 245 | 7.424 | 32.575 | 89.450 | 1.00 | 3.88 | 6 |
| ATOM | 1996 | CG | PHE A 245 | 8.040 | 33.938 | 89.664 | 1.00 | 9.47 | 6 |
| ATOM | 1997 | CD1 | PHE A 245 | 7.518 | 34.846 | 90.543 | 1.00 | 15.08 | 6 |
| ATOM | 1998 | CD2 | PHE A 245 | 9.205 | 34.267 | 89.009 | 1.00 | 10.42 | 6 |
| ATOM | 1999 | CE1 | PHE A 245 | 8.111 | 36.094 | 90.721 | 1.00 | 18.19 | 6 |
| ATOM | 2000 | CE2 | PHE A 245 | 9.788 | 35.507 | 89.127 | 1.00 | 19.59 | 6 |
| ATOM | 2001 | CZ | PHE A 245 | 9.257 | 36.439 | 90.015 | 1.00 | 20.86 | 6 |
| ATOM | 2002 | N | THR A 246 | 7.457 | 32.964 | 86.332 | 1.00 | 13.88 | 7 |
| ATOM | 2003 | CA | THR A 246 | 7.914 | 33.765 | 85.147 | 1.00 | 12.92 | 6 |
| ATOM | 2004 | C | THR A 246 | 6.725 | 34.265 | 84.322 | 1.00 | 9.66 | 6 |
| ATOM | 2005 | O | THR A 246 | 6.471 | 35.411 | 84.043 | 1.00 | 11.86 | 8 |
| ATOM | 2006 | CB | THR A 246 | 8.840 | 32.888 | 84.303 | 1.00 | 18.73 | 6 |
| ATOM | 2007 | OG1 | THR A 246 | 10.005 | 32.537 | 85.091 | 1.00 | 14.92 | 8 |
| ATOM | 2008 | CG2 | THR A 246 | 9.307 | 33.704 | 83.074 | 1.00 | 18.81 | 6 |
| ATOM | 2009 | N | ARG A 247 | 5.796 | 33.383 | 84.079 | 1.00 | 12.73 | 7 |
| ATOM | 2010 | CA | ARG A 247 | 4.532 | 33.626 | 83.444 | 1.00 | 17.39 | 6 |
| ATOM | 2011 | C | ARG A 247 | 3.756 | 34.764 | 84.072 | 1.00 | 19.55 | 6 |
| ATOM | 2012 | O | ARG A 247 | 3.361 | 35.700 | 83.384 | 1.00 | 17.62 | 8 |
| ATOM | 2013 | CB | ARG A 247 | 3.709 | 32.309 | 83.590 | 1.00 | 15.50 | 6 |
| ATOM | 2014 | CG | ARG A 247 | 2.457 | 32.504 | 82.725 | 1.00 | 22.20 | 6 |
| ATOM | 2015 | CD | ARG A 247 | 1.449 | 31.398 | 82.962 | 1.00 | 25.17 | 6 |
| ATOM | 2016 | NE | ARG A 247 | 0.951 | 31.529 | 84.344 | 1.00 | 24.49 | 7 |
| ATOM | 2017 | CZ | ARG A 247 | 0.495 | 30.539 | 85.084 | 1.00 | 29.19 | 6 |
| ATOM | 2018 | NH1 | ARG A 247 | 0.442 | 29.281 | 84.679 | 1.00 | 27.83 | 7 |
| ATOM | 2019 | NH2 | ARG A 247 | 0.116 | 30.825 | 86.338 | 1.00 | 43.27 | 7 |
| ATOM | 2020 | N | ASP A 248 | 3.532 | 34.712 | 85.422 | 1.00 | 19.59 | 7 |
| ATOM | 2021 | CA | ASP A 248 | 2.722 | 35.793 | 86.019 | 1.00 | 17.00 | 6 |
| ATOM | 2022 | C | ASP A 248 | 3.558 | 36.996 | 86.271 | 1.00 | 15.85 | 6 |
| ATOM | 2023 | O | ASP A 248 | 3.007 | 38.103 | 86.247 | 1.00 | 19.31 | 8 |
| ATOM | 2024 | CB | ASP A 248 | 2.006 | 35.325 | 87.287 | 1.00 | 22.99 | 6 |
| ATOM | 2025 | CG | ASP A 248 | 1.126 | 34.143 | 86.996 | 1.00 | 24.92 | 6 |
| ATOM | 2026 | OD1 | ASP A 248 | 0.595 | 33.975 | 85.867 | 1.00 | 34.48 | 8 |
| ATOM | 2027 | OD2 | ASP A 248 | 0.997 | 33.283 | 87.871 | 1.00 | 26.88 | 8 |
| ATOM | 2028 | N | TRP A 249 | 4.881 | 36.900 | 86.402 | 1.00 | 14.97 | 7 |
| ATOM | 2029 | CA | TRP A 249 | 5.636 | 38.154 | 86.525 | 1.00 | 15.57 | 6 |
| ATOM | 2030 | C | TRP A 249 | 5.437 | 39.001 | 85.260 | 1.00 | 17.82 | 6 |
| ATOM | 2031 | O | TRP A 249 | 5.272 | 40.222 | 85.230 | 1.00 | 17.70 | 8 |
| ATOM | 2032 | CB | TRP A 249 | 7.110 | 37.767 | 86.721 | 1.00 | 15.81 | 6 |
| ATOM | 2033 | CG | TRP A 249 | 8.030 | 38.925 | 86.795 | 1.00 | 12.74 | 6 |
| ATOM | 2034 | CD1 | TRP A 249 | 8.260 | 39.669 | 87.926 | 1.00 | 21.36 | 6 |
| ATOM | 2035 | CD2 | TRP A 249 | 8.874 | 39.499 | 85.786 | 1.00 | 23.21 | 6 |
| ATOM | 2036 | NE1 | TRP A 249 | 9.177 | 40.677 | 87.677 | 1.00 | 19.21 | 7 |
| ATOM | 2037 | CE2 | TRP A 249 | 9.555 | 40.598 | 86.353 | 1.00 | 19.38 | 6 |
| ATOM | 2038 | CE3 | TRP A 249 | 9.075 | 39.225 | 84.427 | 1.00 | 21.80 | 6 |
| ATOM | 2039 | CZ2 | TRP A 249 | 10.457 | 41.403 | 85.647 | 1.00 | 18.58 | 6 |
| ATOM | 2040 | CZ3 | TRP A 249 | 9.946 | 40.033 | 83.699 | 1.00 | 21.96 | 6 |
| ATOM | 2041 | CH2 | TRP A 249 | 10.635 | 41.099 | 84.319 | 1.00 | 25.93 | 6 |
| ATOM | 2042 | N | LEU A 250 | 5.564 | 38.362 | 84.084 | 1.00 | 19.80 | 7 |
| ATOM | 2043 | CA | LEU A 250 | 5.504 | 39.085 | 82.783 | 1.00 | 18.64 | 6 |
| ATOM | 2044 | C | LEU A 250 | 4.123 | 39.711 | 82.615 | 1.00 | 16.90 | 6 |
| ATOM | 2045 | O | LEU A 250 | 4.040 | 40.899 | 82.268 | 1.00 | 21.03 | 8 |
| ATOM | 2046 | CB | LEU A 250 | 5.720 | 38.052 | 81.682 | 1.00 | 20.74 | 6 |

| | ATOM | 2047 | CG | LEU A 250 | 6.535 | 38.290 | 80.438 | 1.00 | 36.99 | 6 |
|---|---|---|---|---|---|---|---|---|---|---|
| | ATOM | 2048 | CD1 | LEU A 250 | 7.712 | 39.215 | 80.654 | 1.00 | 30.25 | 6 |
| | ATOM | 2049 | CD2 | LEU A 250 | 6.983 | 36.903 | 79.940 | 1.00 | 36.20 | 6 |
| | ATOM | 2050 | N | THR A 251 | 3.090 | 38.984 | 82.947 | 1.00 | 16.98 | 7 |
| 5 | ATOM | 2051 | CA | THR A 251 | 1.733 | 39.547 | 82.859 | 1.00 | 21.47 | 6 |
| | ATOM | 2052 | C | THR A 251 | 1.536 | 40.765 | 83.748 | 1.00 | 25.19 | 6 |
| | ATOM | 2053 | O | THR A 251 | 1.017 | 41.836 | 83.338 | 1.00 | 24.99 | 8 |
| | ATOM | 2054 | CB | THR A 251 | 0.710 | 38.482 | 83.236 | 1.00 | 25.31 | 6 |
| | ATOM | 2055 | OG1 | THR A 251 | 0.819 | 37.400 | 82.317 | 1.00 | 19.58 | 8 |
| 10 | ATOM | 2056 | CG2 | THR A 251 | -0.704 | 39.048 | 83.064 | 1.00 | 35.15 | 6 |
| | ATOM | 2057 | N | HIS A 252 | 2.109 | 40.616 | 84.975 | 1.00 | 25.52 | 7 |
| | ATOM | 2058 | CA | HIS A 252 | 2.076 | 41.706 | 85.938 | 1.00 | 26.37 | 6 |
| | ATOM | 2059 | C | HIS A 252 | 2.714 | 42.971 | 85.388 | 1.00 | 24.27 | 6 |
| | ATOM | 2060 | O | HIS A 252 | 2.183 | 44.083 | 85.511 | 1.00 | 22.81 | 8 |
| 15 | ATOM | 2061 | CB | HIS A 252 | 2.821 | 41.311 | 87.262 | 1.00 | 30.15 | 6 |
| | ATOM | 2062 | CG | HIS A 252 | 2.744 | 42.478 | 88.218 | 1.00 | 26.03 | 6 |
| | ATOM | 2063 | ND1 | HIS A 252 | 3.699 | 43.461 | 88.309 | 1.00 | 23.15 | 7 |
| | ATOM | 2064 | CD2 | HIS A 252 | 1.767 | 42.804 | 89.089 | 1.00 | 25.20 | 6 |
| | ATOM | 2065 | CE1 | HIS A 252 | 3.343 | 44.369 | 89.189 | 1.00 | 23.46 | 6 |
| 20 | ATOM | 2066 | NE2 | HIS A 252 | 2.176 | 43.970 | 89.685 | 1.00 | 31.78 | 7 |
| | ATOM | 2067 | N | VAL A 253 | 3.935 | 42.813 | 84.862 | 1.00 | 22.82 | 7 |
| | ATOM | 2068 | CA | VAL A 253 | 4.628 | 43.984 | 84.345 | 1.00 | 23.83 | 6 |
| | ATOM | 2069 | C | VAL A 253 | 3.928 | 44.549 | 83.089 | 1.00 | 25.77 | 6 |
| | ATOM | 2070 | O | VAL A 253 | 3.866 | 45.775 | 82.954 | 1.00 | 24.97 | 8 |
| 25 | ATOM | 2071 | CB | VAL A 253 | 6.097 | 43.672 | 84.050 | 1.00 | 24.83 | 6 |
| | ATOM | 2072 | CG1 | VAL A 253 | 6.804 | 44.884 | 83.495 | 1.00 | 20.28 | 6 |
| | ATOM | 2073 | CG2 | VAL A 253 | 6.788 | 43.156 | 85.302 | 1.00 | 31.84 | 6 |
| | ATOM | 2074 | N | ARG A 254 | 3.387 | 43.673 | 82.241 | 1.00 | 26.27 | 7 |
| | ATOM | 2075 | CA | ARG A 254 | 2.661 | 44.167 | 81.068 | 1.00 | 29.21 | 6 |
| 30 | ATOM | 2076 | C | ARG A 254 | 1.428 | 44.949 | 81.521 | 1.00 | 30.40 | 6 |
| | ATOM | 2077 | O | ARG A 254 | 1.295 | 46.102 | 81.106 | 1.00 | 31.03 | 8 |
| | ATOM | 2078 | CB | ARG A 254 | 2.312 | 43.037 | 80.111 | 1.00 | 30.34 | 6 |
| | ATOM | 2079 | CG | ARG A 254 | 3.530 | 42.557 | 79.251 | 1.00 | 20.49 | 6 |
| | ATOM | 2080 | CD | ARG A 254 | 3.130 | 41.213 | 78.623 | 1.00 | 18.72 | 6 |
| 35 | ATOM | 2081 | NE | ARG A 254 | 4.228 | 40.726 | 77.790 | 1.00 | 21.16 | 7 |
| | ATOM | 2082 | CZ | ARG A 254 | 4.369 | 39.491 | 77.347 | 1.00 | 21.93 | 6 |
| | ATOM | 2083 | NH1 | ARG A 254 | 3.498 | 38.564 | 77.689 | 1.00 | 19.85 | 7 |
| | ATOM | 2084 | NH2 | ARG A 254 | 5.415 | 39.197 | 76.567 | 1.00 | 24.23 | 7 |
| | ATOM | 2085 | N | ASN A 255 | 0.576 | 44.394 | 82.369 | 1.00 | 31.01 | 7 |
| 40 | ATOM | 2086 | CA | ASN A 255 | -0.566 | 45.115 | 82.915 | 1.00 | 31.98 | 6 |
| | ATOM | 2087 | C | ASN A 255 | -0.178 | 46.372 | 83.672 | 1.00 | 33.52 | 6 |
| | ATOM | 2088 | O | ASN A 255 | -0.792 | 47.422 | 83.476 | 1.00 | 33.39 | 8 |
| | ATOM | 2089 | CB | ASN A 255 | -1.418 | 44.249 | 83.838 | 1.00 | 35.19 | 6 |
| | ATOM | 2090 | CG | ASN A 255 | -1.980 | 43.048 | 83.118 | 1.00 | 43.21 | 6 |
| 45 | ATOM | 2091 | OD1 | ASN A 255 | -1.921 | 42.986 | 81.887 | 1.00 | 59.02 | 8 |
| | ATOM | 2092 | ND2 | ASN A 255 | -2.520 | 42.052 | 83.792 | 1.00 | 50.05 | 7 |
| | ATOM | 2093 | N | ALA A 256 | 0.861 | 46.351 | 84.513 | 1.00 | 34.99 | 7 |
| | ATOM | 2094 | CA | ALA A 256 | 1.219 | 47.546 | 85.250 | 1.00 | 36.39 | 6 |
| | ATOM | 2095 | C | ALA A 256 | 1.742 | 48.650 | 84.363 | 1.00 | 39.16 | 6 |
| 50 | ATOM | 2096 | O | ALA A 256 | 1.546 | 49.803 | 84.753 | 1.00 | 39.92 | 8 |
| | ATOM | 2097 | CB | ALA A 256 | 2.275 | 47.346 | 86.325 | 1.00 | 36.68 | 6 |
| | ATOM | 2098 | N | THR A 257 | 2.486 | 48.360 | 83.303 | 1.00 | 39.44 | 7 |
| | ATOM | 2099 | CA | THR A 257 | 3.051 | 49.482 | 82.545 | 1.00 | 40.36 | 6 |
| | ATOM | 2100 | C | THR A 257 | 2.098 | 49.887 | 81.428 | 1.00 | 40.85 | 6 |
| 55 | ATOM | 2101 | O | THR A 257 | 2.331 | 50.920 | 80.803 | 1.00 | 42.44 | 8 |
| | ATOM | 2102 | CB | THR A 257 | 4.397 | 49.077 | 81.893 | 1.00 | 39.97 | 6 |
| | ATOM | 2103 | OG1 | THR A 257 | 4.124 | 47.852 | 81.178 | 1.00 | 37.26 | 8 |
| | ATOM | 2104 | CG2 | THR A 257 | 5.472 | 48.822 | 82.927 | 1.00 | 34.15 | 6 |
| | ATOM | 2105 | N | GLY A 258 | 1.130 | 49.050 | 81.085 | 1.00 | 40.80 | 7 |
| 60 | ATOM | 2106 | CA | GLY A 258 | 0.263 | 49.337 | 79.965 | 1.00 | 41.62 | 6 |
| | ATOM | 2107 | C | GLY A 258 | 0.931 | 49.107 | 78.618 | 1.00 | 43.26 | 6 |
| | ATOM | 2108 | O | GLY A 258 | 0.382 | 49.531 | 77.591 | 1.00 | 44.58 | 8 |
| | ATOM | 2109 | N | LYS A 259 | 2.064 | 48.436 | 78.539 | 1.00 | 43.07 | 7 |
| | ATOM | 2110 | CA | LYS A 259 | 2.812 | 48.174 | 77.323 | 1.00 | 42.68 | 6 |
| 65 | ATOM | 2111 | C | LYS A 259 | 2.834 | 46.694 | 76.956 | 1.00 | 41.44 | 6 |

| ATOM | 2112 | O   | LYS A 259 | 2.890  | 45.847 | 77.845 | 1.00 | 41.40 | 8  |
| ATOM | 2113 | CB  | LYS A 259 | 4.276  | 48.563 | 77.540 | 1.00 | 48.99 | 6  |
| ATOM | 2114 | CG  | LYS A 259 | 4.585  | 50.028 | 77.728 | 1.00 | 52.01 | 6  |
| ATOM | 2115 | CD  | LYS A 259 | 5.936  | 50.184 | 78.421 | 1.00 | 53.13 | 6  |
| ATOM | 2116 | CE  | LYS A 259 | 7.023  | 50.603 | 77.455 | 1.00 | 53.64 | 6  |
| ATOM | 2117 | NZ  | LYS A 259 | 8.088  | 51.407 | 78.132 | 1.00 | 54.27 | 7  |
| ATOM | 2118 | N   | GLU A 260 | 2.914  | 46.352 | 75.682 | 1.00 | 41.04 | 7  |
| ATOM | 2119 | CA  | GLU A 260 | 2.959  | 44.974 | 75.194 | 1.00 | 39.46 | 6  |
| ATOM | 2120 | C   | GLU A 260 | 4.157  | 44.136 | 75.641 | 1.00 | 35.90 | 6  |
| ATOM | 2121 | O   | GLU A 260 | 4.059  | 42.918 | 75.735 | 1.00 | 36.93 | 8  |
| ATOM | 2122 | CB  | GLU A 260 | 2.927  | 45.027 | 73.650 | 1.00 | 62.65 | 6  |
| ATOM | 2123 | CG  | GLU A 260 | 3.452  | 43.824 | 72.907 | 1.00 | 77.65 | 6  |
| ATOM | 2124 | CD  | GLU A 260 | 4.228  | 44.064 | 71.627 | 1.00 | 84.79 | 6  |
| ATOM | 2125 | OE1 | GLU A 260 | 4.274  | 45.218 | 71.142 | 1.00 | 87.14 | 8  |
| ATOM | 2126 | OE2 | GLU A 260 | 4.814  | 43.082 | 71.092 | 1.00 | 81.45 | 8  |
| ATOM | 2127 | N   | MET A 261 | 5.306  | 44.722 | 75.855 | 1.00 | 32.24 | 7  |
| ATOM | 2128 | CA  | MET A 261 | 6.527  | 44.101 | 76.247 | 1.00 | 29.42 | 6  |
| ATOM | 2129 | C   | MET A 261 | 6.721  | 42.716 | 75.616 | 1.00 | 27.28 | 6  |
| ATOM | 2130 | O   | MET A 261 | 6.291  | 41.663 | 76.054 | 1.00 | 28.96 | 8  |
| ATOM | 2131 | CB  | MET A 261 | 6.747  | 44.016 | 77.743 | 1.00 | 27.19 | 6  |
| ATOM | 2132 | CG  | MET A 261 | 6.436  | 45.227 | 78.605 | 1.00 | 31.84 | 6  |
| ATOM | 2133 | SD  | MET A 261 | 7.576  | 46.582 | 78.418 | 1.00 | 42.23 | 16 |
| ATOM | 2134 | CE  | MET A 261 | 9.138  | 45.895 | 78.957 | 1.00 | 31.14 | 6  |
| ATOM | 2135 | N   | PHE A 262 | 7.510  | 42.703 | 74.566 | 1.00 | 24.48 | 7  |
| ATOM | 2136 | CA  | PHE A 262 | 7.943  | 41.467 | 73.921 | 1.00 | 22.71 | 6  |
| ATOM | 2137 | C   | PHE A 262 | 8.924  | 40.804 | 74.917 | 1.00 | 19.54 | 6  |
| ATOM | 2138 | O   | PHE A 262 | 9.719  | 41.573 | 75.440 | 1.00 | 21.34 | 8  |
| ATOM | 2139 | CB  | PHE A 262 | 8.837  | 41.850 | 72.694 | 1.00 | 12.70 | 6  |
| ATOM | 2140 | CG  | PHE A 262 | 9.496  | 40.626 | 72.136 | 1.00 | 12.10 | 6  |
| ATOM | 2141 | CD1 | PHE A 262 | 8.740  | 39.641 | 71.535 | 1.00 | 18.73 | 6  |
| ATOM | 2142 | CD2 | PHE A 262 | 10.846 | 40.436 | 72.243 | 1.00 | 10.21 | 6  |
| ATOM | 2143 | CE1 | PHE A 262 | 9.330  | 38.481 | 71.012 | 1.00 | 15.61 | 6  |
| ATOM | 2144 | CE2 | PHE A 262 | 11.454 | 39.326 | 71.738 | 1.00 | 12.87 | 6  |
| ATOM | 2145 | CZ  | PHE A 262 | 10.691 | 38.352 | 71.125 | 1.00 | 11.25 | 6  |
| ATOM | 2146 | N   | ALA A 263 | 8.997  | 39.482 | 74.973 | 1.00 | 19.06 | 7  |
| ATOM | 2147 | CA  | ALA A 263 | 10.069 | 38.925 | 75.791 | 1.00 | 18.90 | 6  |
| ATOM | 2148 | C   | ALA A 263 | 10.522 | 37.600 | 75.167 | 1.00 | 14.30 | 6  |
| ATOM | 2149 | O   | ALA A 263 | 9.720  | 36.809 | 74.716 | 1.00 | 16.72 | 8  |
| ATOM | 2150 | CB  | ALA A 263 | 9.538  | 38.600 | 77.231 | 1.00 | 16.61 | 6  |
| ATOM | 2151 | N   | VAL A 264 | 11.809 | 37.352 | 75.318 | 1.00 | 14.17 | 7  |
| ATOM | 2152 | CA  | VAL A 264 | 12.291 | 36.027 | 74.899 | 1.00 | 13.57 | 6  |
| ATOM | 2153 | C   | VAL A 264 | 13.018 | 35.448 | 76.120 | 1.00 | 12.86 | 6  |
| ATOM | 2154 | O   | VAL A 264 | 13.840 | 36.092 | 76.773 | 1.00 | 12.22 | 8  |
| ATOM | 2155 | CB  | VAL A 264 | 13.259 | 36.200 | 73.695 | 1.00 | 7.10  | 6  |
| ATOM | 2156 | CG1 | VAL A 264 | 14.352 | 37.209 | 73.955 | 1.00 | 4.19  | 6  |
| ATOM | 2157 | CG2 | VAL A 264 | 13.796 | 34.868 | 73.266 | 1.00 | 4.85  | 6  |
| ATOM | 2158 | N   | ALA A 265 | 12.840 | 34.168 | 76.346 | 1.00 | 12.26 | 7  |
| ATOM | 2159 | CA  | ALA A 265 | 13.451 | 33.519 | 77.500 | 1.00 | 13.87 | 6  |
| ATOM | 2160 | C   | ALA A 265 | 14.544 | 32.577 | 77.071 | 1.00 | 13.85 | 6  |
| ATOM | 2161 | O   | ALA A 265 | 14.370 | 31.837 | 76.071 | 1.00 | 14.15 | 8  |
| ATOM | 2162 | CB  | ALA A 265 | 12.349 | 32.652 | 78.180 | 1.00 | 9.68  | 6  |
| ATOM | 2163 | N   | GLU A 266 | 15.639 | 32.607 | 77.821 | 1.00 | 10.52 | 7  |
| ATOM | 2164 | CA  | GLU A 266 | 16.711 | 31.664 | 77.669 | 1.00 | 6.70  | 6  |
| ATOM | 2165 | C   | GLU A 266 | 16.463 | 30.382 | 78.430 | 1.00 | 14.18 | 6  |
| ATOM | 2166 | O   | GLU A 266 | 16.733 | 30.218 | 79.665 | 1.00 | 12.91 | 8  |
| ATOM | 2167 | CB  | GLU A 266 | 18.058 | 32.279 | 78.038 | 1.00 | 6.87  | 6  |
| ATOM | 2168 | CG  | GLU A 266 | 19.243 | 31.294 | 77.841 | 1.00 | 10.70 | 6  |
| ATOM | 2169 | CD  | GLU A 266 | 20.193 | 31.084 | 79.001 | 1.00 | 28.43 | 6  |
| ATOM | 2170 | OE1 | GLU A 266 | 19.858 | 31.387 | 80.192 | 1.00 | 24.40 | 8  |
| ATOM | 2171 | OE2 | GLU A 266 | 21.365 | 30.604 | 78.811 | 1.00 | 16.24 | 8  |
| ATOM | 2172 | N   | PHE A 267 | 15.916 | 29.380 | 77.736 | 1.00 | 13.24 | 7  |
| ATOM | 2173 | CA  | PHE A 267 | 15.792 | 28.055 | 78.292 | 1.00 | 11.67 | 6  |
| ATOM | 2174 | C   | PHE A 267 | 16.843 | 27.158 | 77.636 | 1.00 | 14.76 | 6  |
| ATOM | 2175 | O   | PHE A 267 | 16.573 | 26.528 | 76.597 | 1.00 | 15.16 | 8  |
| ATOM | 2176 | CB  | PHE A 267 | 14.383 | 27.547 | 78.026 | 1.00 | 13.42 | 6  |

| ATOM | 2177 | CG | PHE | A | 267 | 14.035 | 26.272 | 78.734 | 1.00 | 13.78 | 6 |
|------|------|------|------|---|-----|--------|--------|--------|------|-------|---|
| ATOM | 2178 | CD1 | PHE | A | 267 | 14.609 | 25.058 | 78.433 | 1.00 | 9.97 | 6 |
| ATOM | 2179 | CD2 | PHE | A | 267 | 13.051 | 26.337 | 79.737 | 1.00 | 8.86 | 6 |
| ATOM | 2180 | CE1 | PHE | A | 267 | 14.232 | 23.901 | 79.124 | 1.00 | 21.47 | 6 |
| ATOM | 2181 | CE2 | PHE | A | 267 | 12.702 | 25.188 | 80.435 | 1.00 | 10.17 | 6 |
| ATOM | 2182 | CZ | PHE | A | 267 | 13.271 | 23.954 | 80.167 | 1.00 | 7.77 | 6 |
| ATOM | 2183 | N | TRP | A | 268 | 18.024 | 27.031 | 78.178 | 1.00 | 11.88 | 7 |
| ATOM | 2184 | CA | TRP | A | 268 | 19.092 | 26.287 | 77.557 | 1.00 | 13.36 | 6 |
| ATOM | 2185 | C | TRP | A | 268 | 19.051 | 24.789 | 77.661 | 1.00 | 16.10 | 6 |
| ATOM | 2186 | O | TRP | A | 268 | 19.582 | 24.124 | 78.545 | 1.00 | 18.52 | 8 |
| ATOM | 2187 | CB | TRP | A | 268 | 20.484 | 26.773 | 77.869 | 1.00 | 7.98 | 6 |
| ATOM | 2188 | CG | TRP | A | 268 | 21.559 | 26.333 | 76.900 | 1.00 | 11.23 | 6 |
| ATOM | 2189 | CD1 | TRP | A | 268 | 22.226 | 25.165 | 76.785 | 1.00 | 14.63 | 6 |
| ATOM | 2190 | CD2 | TRP | A | 268 | 22.016 | 27.154 | 75.816 | 1.00 | 13.22 | 6 |
| ATOM | 2191 | NE1 | TRP | A | 268 | 23.116 | 25.210 | 75.736 | 1.00 | 12.62 | 7 |
| ATOM | 2192 | CE2 | TRP | A | 268 | 22.988 | 26.427 | 75.134 | 1.00 | 14.70 | 6 |
| ATOM | 2193 | CE3 | TRP | A | 268 | 21.658 | 28.452 | 75.390 | 1.00 | 17.12 | 6 |
| ATOM | 2194 | CZ2 | TRP | A | 268 | 23.644 | 26.942 | 74.005 | 1.00 | 18.35 | 6 |
| ATOM | 2195 | CZ3 | TRP | A | 268 | 22.311 | 28.963 | 74.259 | 1.00 | 19.48 | 6 |
| ATOM | 2196 | CH2 | TRP | A | 268 | 23.317 | 28.208 | 73.619 | 1.00 | 8.78 | 6 |
| ATOM | 2197 | N | LYS | A | 269 | 18.447 | 24.173 | 76.643 | 1.00 | 16.93 | 7 |
| ATOM | 2198 | CA | LYS | A | 269 | 18.410 | 22.732 | 76.582 | 1.00 | 15.46 | 6 |
| ATOM | 2199 | C | LYS | A | 269 | 18.213 | 22.360 | 75.088 | 1.00 | 15.49 | 6 |
| ATOM | 2200 | O | LYS | A | 269 | 17.316 | 22.923 | 74.471 | 1.00 | 12.29 | 8 |
| ATOM | 2201 | CB | LYS | A | 269 | 17.182 | 22.267 | 77.362 | 1.00 | 14.40 | 6 |
| ATOM | 2202 | CG | LYS | A | 269 | 17.499 | 20.809 | 77.692 | 1.00 | 18.39 | 6 |
| ATOM | 2203 | CD | LYS | A | 269 | 16.292 | 20.205 | 78.426 | 1.00 | 27.57 | 6 |
| ATOM | 2204 | CE | LYS | A | 269 | 17.007 | 19.267 | 79.381 | 1.00 | 35.05 | 6 |
| ATOM | 2205 | NZ | LYS | A | 269 | 17.031 | 17.880 | 78.885 | 1.00 | 41.79 | 7 |
| ATOM | 2206 | N | ASN | A | 270 | 18.983 | 21.413 | 74.623 | 1.00 | 15.03 | 7 |
| ATOM | 2207 | CA | ASN | A | 270 | 18.845 | 20.988 | 73.226 | 1.00 | 15.62 | 6 |
| ATOM | 2208 | C | ASN | A | 270 | 17.758 | 19.943 | 73.144 | 1.00 | 14.07 | 6 |
| ATOM | 2209 | O | ASN | A | 270 | 18.024 | 18.769 | 72.933 | 1.00 | 13.60 | 8 |
| ATOM | 2210 | CB | ASN | A | 270 | 20.181 | 20.434 | 72.746 | 1.00 | 14.33 | 6 |
| ATOM | 2211 | CG | ASN | A | 270 | 20.143 | 20.084 | 71.245 | 1.00 | 23.70 | 6 |
| ATOM | 2212 | OD1 | ASN | A | 270 | 19.220 | 20.565 | 70.577 | 1.00 | 17.65 | 8 |
| ATOM | 2213 | ND2 | ASN | A | 270 | 21.079 | 19.263 | 70.787 | 1.00 | 10.70 | 7 |
| ATOM | 2214 | N | ASP | A | 271 | 16.511 | 20.338 | 73.307 | 1.00 | 16.99 | 7 |
| ATOM | 2215 | CA | ASP | A | 271 | 15.453 | 19.319 | 73.432 | 1.00 | 18.25 | 6 |
| ATOM | 2216 | C | ASP | A | 271 | 14.144 | 20.076 | 73.255 | 1.00 | 19.23 | 6 |
| ATOM | 2217 | O | ASP | A | 271 | 13.662 | 20.828 | 74.109 | 1.00 | 18.38 | 8 |
| ATOM | 2218 | CB | ASP | A | 271 | 15.525 | 18.727 | 74.853 | 1.00 | 26.80 | 6 |
| ATOM | 2219 | CG | ASP | A | 271 | 14.461 | 17.665 | 75.102 | 1.00 | 39.25 | 6 |
| ATOM | 2220 | OD1 | ASP | A | 271 | 13.251 | 17.922 | 75.022 | 1.00 | 39.03 | 8 |
| ATOM | 2221 | OD2 | ASP | A | 271 | 14.814 | 16.512 | 75.402 | 1.00 | 53.52 | 8 |
| ATOM | 2222 | N | LEU | A | 272 | 13.528 | 19.745 | 72.113 | 1.00 | 16.74 | 7 |
| ATOM | 2223 | CA | LEU | A | 272 | 12.307 | 20.447 | 71.735 | 1.00 | 17.19 | 6 |
| ATOM | 2224 | C | LEU | A | 272 | 11.143 | 20.097 | 72.672 | 1.00 | 13.55 | 6 |
| ATOM | 2225 | O | LEU | A | 272 | 10.339 | 20.973 | 72.944 | 1.00 | 12.34 | 8 |
| ATOM | 2226 | CB | LEU | A | 272 | 12.023 | 20.131 | 70.241 | 1.00 | 14.98 | 6 |
| ATOM | 2227 | CG | LEU | A | 272 | 10.672 | 20.700 | 69.831 | 1.00 | 13.62 | 6 |
| ATOM | 2228 | CD1 | LEU | A | 272 | 10.649 | 22.196 | 69.942 | 1.00 | 16.93 | 6 |
| ATOM | 2229 | CD2 | LEU | A | 272 | 10.343 | 20.272 | 68.393 | 1.00 | 27.80 | 6 |
| ATOM | 2230 | N | GLY | A | 273 | 11.102 | 18.845 | 73.111 | 1.00 | 13.14 | 7 |
| ATOM | 2231 | CA | GLY | A | 273 | 10.087 | 18.437 | 74.095 | 1.00 | 17.42 | 6 |
| ATOM | 2232 | C | GLY | A | 273 | 10.111 | 19.307 | 75.393 | 1.00 | 16.23 | 6 |
| ATOM | 2233 | O | GLY | A | 273 | 9.098 | 19.859 | 75.857 | 1.00 | 13.91 | 8 |
| ATOM | 2234 | N | ALA | A | 274 | 11.308 | 19.525 | 75.958 | 1.00 | 15.44 | 7 |
| ATOM | 2235 | CA | ALA | A | 274 | 11.404 | 20.360 | 77.165 | 1.00 | 14.48 | 6 |
| ATOM | 2236 | C | ALA | A | 274 | 10.928 | 21.766 | 76.900 | 1.00 | 16.65 | 6 |
| ATOM | 2237 | O | ALA | A | 274 | 10.285 | 22.449 | 77.719 | 1.00 | 13.98 | 8 |
| ATOM | 2238 | CB | ALA | A | 274 | 12.880 | 20.359 | 77.568 | 1.00 | 10.97 | 6 |
| ATOM | 2239 | N | LEU | A | 275 | 11.280 | 22.296 | 75.666 | 1.00 | 14.39 | 7 |
| ATOM | 2240 | CA | LEU | A | 275 | 10.893 | 23.652 | 75.329 | 1.00 | 10.53 | 6 |
| ATOM | 2241 | C | LEU | A | 275 | 9.398 | 23.814 | 75.156 | 1.00 | 11.28 | 6 |

| ATOM | 2242 | O | LEU | A | 275 | 8.797 | 24.824 | 75.571 | 1.00 | 11.68 | 8 |
|------|------|-----|-----|---|-----|-------|--------|--------|------|-------|---|
| ATOM | 2243 | CB | LEU | A | 275 | 11.657 | 24.168 | 74.087 | 1.00 | 15.03 | 6 |
| ATOM | 2244 | CG | LEU | A | 275 | 13.161 | 24.299 | 74.333 | 1.00 | 21.33 | 6 |
| ATOM | 2245 | CD1 | LEU | A | 275 | 14.000 | 24.218 | 73.048 | 1.00 | 20.57 | 6 |
| ATOM | 2246 | CD2 | LEU | A | 275 | 13.353 | 25.663 | 74.996 | 1.00 | 13.26 | 6 |
| ATOM | 2247 | N | GLU | A | 276 | 8.752 | 22.794 | 74.582 | 1.00 | 10.24 | 7 |
| ATOM | 2248 | CA | GLU | A | 276 | 7.289 | 22.892 | 74.457 | 1.00 | 12.93 | 6 |
| ATOM | 2249 | C | GLU | A | 276 | 6.595 | 22.784 | 75.843 | 1.00 | 14.28 | 6 |
| ATOM | 2250 | O | GLU | A | 276 | 5.521 | 23.356 | 76.036 | 1.00 | 15.27 | 8 |
| ATOM | 2251 | CB | GLU | A | 276 | 6.761 | 21.730 | 73.572 | 1.00 | 13.24 | 6 |
| ATOM | 2252 | CG | GLU | A | 276 | 7.260 | 21.889 | 72.130 | 1.00 | 34.25 | 6 |
| ATOM | 2253 | CD | GLU | A | 276 | 6.825 | 20.834 | 71.145 | 1.00 | 39.49 | 6 |
| ATOM | 2254 | OE1 | GLU | A | 276 | 6.737 | 19.619 | 71.394 | 1.00 | 36.50 | 8 |
| ATOM | 2255 | OE2 | GLU | A | 276 | 6.546 | 21.221 | 69.992 | 1.00 | 45.71 | 8 |
| ATOM | 2256 | N | ASN | A | 277 | 7.169 | 21.984 | 76.749 | 1.00 | 14.65 | 7 |
| ATOM | 2257 | CA | ASN | A | 277 | 6.571 | 21.916 | 78.128 | 1.00 | 12.73 | 6 |
| ATOM | 2258 | C | ASN | A | 277 | 6.602 | 23.281 | 78.737 | 1.00 | 10.71 | 6 |
| ATOM | 2259 | O | ASN | A | 277 | 5.607 | 23.931 | 79.099 | 1.00 | 13.72 | 8 |
| ATOM | 2260 | CB | ASN | A | 277 | 7.313 | 20.778 | 78.849 | 1.00 | 15.75 | 6 |
| ATOM | 2261 | CG | ASN | A | 277 | 6.865 | 20.857 | 80.335 | 1.00 | 26.77 | 6 |
| ATOM | 2262 | OD1 | ASN | A | 277 | 5.702 | 20.667 | 80.586 | 1.00 | 15.27 | 8 |
| ATOM | 2263 | ND2 | ASN | A | 277 | 7.699 | 21.168 | 81.300 | 1.00 | 10.18 | 7 |
| ATOM | 2264 | N | TYR | A | 278 | 7.743 | 23.963 | 78.681 | 1.00 | 11.83 | 7 |
| ATOM | 2265 | CA | TYR | A | 278 | 7.915 | 25.320 | 79.150 | 1.00 | 12.29 | 6 |
| ATOM | 2266 | C | TYR | A | 278 | 6.889 | 26.262 | 78.575 | 1.00 | 14.54 | 6 |
| ATOM | 2267 | O | TYR | A | 278 | 6.217 | 27.109 | 79.227 | 1.00 | 13.66 | 8 |
| ATOM | 2268 | CB | TYR | A | 278 | 9.369 | 25.831 | 78.890 | 1.00 | 9.85 | 6 |
| ATOM | 2269 | CG | TYR | A | 278 | 9.561 | 27.264 | 79.336 | 1.00 | 11.93 | 6 |
| ATOM | 2270 | CD1 | TYR | A | 278 | 9.700 | 27.581 | 80.725 | 1.00 | 12.91 | 6 |
| ATOM | 2271 | CD2 | TYR | A | 278 | 9.590 | 28.306 | 78.440 | 1.00 | 10.42 | 6 |
| ATOM | 2272 | CE1 | TYR | A | 278 | 9.854 | 28.897 | 81.123 | 1.00 | 11.06 | 6 |
| ATOM | 2273 | CE2 | TYR | A | 278 | 9.690 | 29.636 | 78.833 | 1.00 | 10.81 | 6 |
| ATOM | 2274 | CZ | TYR | A | 278 | 9.864 | 29.912 | 80.198 | 1.00 | 13.63 | 6 |
| ATOM | 2275 | OH | TYR | A | 278 | 9.989 | 31.239 | 80.563 | 1.00 | 13.37 | 8 |
| ATOM | 2276 | N | LEU | A | 279 | 6.749 | 26.175 | 77.201 | 1.00 | 15.84 | 7 |
| ATOM | 2277 | CA | LEU | A | 279 | 5.837 | 27.144 | 76.541 | 1.00 | 12.10 | 6 |
| ATOM | 2278 | C | LEU | A | 279 | 4.398 | 26.841 | 76.957 | 1.00 | 10.12 | 6 |
| ATOM | 2279 | O | LEU | A | 279 | 3.590 | 27.755 | 77.102 | 1.00 | 13.43 | 8 |
| ATOM | 2280 | CB | LEU | A | 279 | 5.957 | 26.966 | 75.033 | 1.00 | 27.35 | 6 |
| ATOM | 2281 | CG | LEU | A | 279 | 6.798 | 27.756 | 74.077 | 1.00 | 19.86 | 6 |
| ATOM | 2282 | CD1 | LEU | A | 279 | 7.360 | 29.080 | 74.426 | 1.00 | 14.50 | 6 |
| ATOM | 2283 | CD2 | LEU | A | 279 | 7.884 | 26.930 | 73.416 | 1.00 | 19.52 | 6 |
| ATOM | 2284 | N | ASN | A | 280 | 4.056 | 25.581 | 77.114 | 1.00 | 12.52 | 7 |
| ATOM | 2285 | CA | ASN | A | 280 | 2.674 | 25.297 | 77.551 | 1.00 | 16.58 | 6 |
| ATOM | 2286 | C | ASN | A | 280 | 2.448 | 25.814 | 78.985 | 1.00 | 18.62 | 6 |
| ATOM | 2287 | O | ASN | A | 280 | 1.569 | 26.632 | 79.240 | 1.00 | 19.40 | 8 |
| ATOM | 2288 | CB | ASN | A | 280 | 2.527 | 23.766 | 77.511 | 1.00 | 17.54 | 6 |
| ATOM | 2289 | CG | ASN | A | 280 | 2.154 | 23.278 | 76.119 | 1.00 | 30.66 | 6 |
| ATOM | 2290 | OD1 | ASN | A | 280 | 2.550 | 22.183 | 75.708 | 1.00 | 34.93 | 8 |
| ATOM | 2291 | ND2 | ASN | A | 280 | 1.390 | 24.095 | 75.409 | 1.00 | 33.44 | 7 |
| ATOM | 2292 | N | LYS | A | 281 | 3.394 | 25.467 | 79.887 | 1.00 | 18.75 | 7 |
| ATOM | 2293 | CA | LYS | A | 281 | 3.305 | 25.918 | 81.293 | 1.00 | 17.49 | 6 |
| ATOM | 2294 | C | LYS | A | 281 | 3.343 | 27.395 | 81.418 | 1.00 | 16.48 | 6 |
| ATOM | 2295 | O | LYS | A | 281 | 2.771 | 27.964 | 82.380 | 1.00 | 20.69 | 8 |
| ATOM | 2296 | CB | LYS | A | 281 | 4.433 | 25.289 | 82.127 | 1.00 | 13.25 | 6 |
| ATOM | 2297 | CG | LYS | A | 281 | 4.497 | 23.774 | 82.206 | 1.00 | 13.95 | 6 |
| ATOM | 2298 | CD | LYS | A | 281 | 3.243 | 23.306 | 82.907 | 1.00 | 17.14 | 6 |
| ATOM | 2299 | CE | LYS | A | 281 | 2.970 | 21.830 | 82.684 | 1.00 | 7.97 | 6 |
| ATOM | 2300 | NZ | LYS | A | 281 | 4.215 | 21.104 | 83.039 | 1.00 | 13.19 | 7 |
| ATOM | 2301 | N | THR | A | 282 | 3.902 | 28.186 | 80.512 | 1.00 | 16.82 | 7 |
| ATOM | 2302 | CA | THR | A | 282 | 3.872 | 29.638 | 80.592 | 1.00 | 13.27 | 6 |
| ATOM | 2303 | C | THR | A | 282 | 2.761 | 30.179 | 79.680 | 1.00 | 13.92 | 6 |
| ATOM | 2304 | O | THR | A | 282 | 2.734 | 31.369 | 79.367 | 1.00 | 13.05 | 8 |
| ATOM | 2305 | CB | THR | A | 282 | 5.199 | 30.321 | 80.271 | 1.00 | 25.12 | 6 |
| ATOM | 2306 | OG1 | THR | A | 282 | 5.667 | 29.872 | 78.968 | 1.00 | 20.09 | 8 |

| ATOM | 2307 | CG2 | THR A 282 | 6.215 | 29.936 | 81.369 | 1.00 | 17.02 | 6 |
|------|------|-----|-----------|-------|--------|--------|------|-------|---|
| ATOM | 2308 | N   | ASN A 283 | 1.899 | 29.294 | 79.218 | 1.00 | 14.25 | 7 |
| ATOM | 2309 | CA  | ASN A 283 | 0.798 | 29.771 | 78.374 | 1.00 | 19.43 | 6 |
| ATOM | 2310 | C   | ASN A 283 | 1.131 | 30.541 | 77.089 | 1.00 | 20.89 | 6 |
| ATOM | 2311 | O   | ASN A 283 | 0.380 | 31.442 | 76.680 | 1.00 | 19.32 | 8 |
| ATOM | 2312 | CB  | ASN A 283 | -0.077 | 30.671 | 79.255 | 1.00 | 29.96 | 6 |
| ATOM | 2313 | CG  | ASN A 283 | -0.989 | 29.957 | 80.214 | 1.00 | 49.27 | 6 |
| ATOM | 2314 | OD1 | ASN A 283 | -2.037 | 30.523 | 80.557 | 1.00 | 63.24 | 8 |
| ATOM | 2315 | ND2 | ASN A 283 | -0.657 | 28.762 | 80.704 | 1.00 | 57.30 | 7 |
| ATOM | 2316 | N   | TRP A 284 | 2.209 | 30.262 | 76.387 | 1.00 | 19.27 | 7 |
| ATOM | 2317 | CA  | TRP A 284 | 2.582 | 30.844 | 75.117 | 1.00 | 21.66 | 6 |
| ATOM | 2318 | C   | TRP A 284 | 2.641 | 32.329 | 75.187 | 1.00 | 21.59 | 6 |
| ATOM | 2319 | O   | TRP A 284 | 2.435 | 32.954 | 74.157 | 1.00 | 23.14 | 8 |
| ATOM | 2320 | CB  | TRP A 284 | 1.556 | 30.421 | 73.978 | 1.00 | 15.89 | 6 |
| ATOM | 2321 | CG  | TRP A 284 | 1.629 | 28.927 | 73.876 | 1.00 | 17.98 | 6 |
| ATOM | 2322 | CD1 | TRP A 284 | 0.841 | 28.047 | 74.594 | 1.00 | 32.38 | 6 |
| ATOM | 2323 | CD2 | TRP A 284 | 2.516 | 28.115 | 73.125 | 1.00 | 21.72 | 6 |
| ATOM | 2324 | NE1 | TRP A 284 | 1.202 | 26.742 | 74.328 | 1.00 | 22.08 | 7 |
| ATOM | 2325 | CE2 | TRP A 284 | 2.216 | 26.766 | 73.416 | 1.00 | 17.99 | 6 |
| ATOM | 2326 | CE3 | TRP A 284 | 3.547 | 28.397 | 72.221 | 1.00 | 23.27 | 6 |
| ATOM | 2327 | CZ2 | TRP A 284 | 2.905 | 25.687 | 72.839 | 1.00 | 21.96 | 6 |
| ATOM | 2328 | CZ3 | TRP A 284 | 4.225 | 27.313 | 71.658 | 1.00 | 27.52 | 6 |
| ATOM | 2329 | CH2 | TRP A 284 | 3.917 | 25.987 | 71.965 | 1.00 | 25.63 | 6 |
| ATOM | 2330 | N   | ASN A 285 | 2.958 | 32.939 | 76.338 | 1.00 | 20.45 | 7 |
| ATOM | 2331 | CA  | ASN A 285 | 2.889 | 34.381 | 76.427 | 1.00 | 14.22 | 6 |
| ATOM | 2332 | C   | ASN A 285 | 4.222 | 35.004 | 76.135 | 1.00 | 13.71 | 6 |
| ATOM | 2333 | O   | ASN A 285 | 4.360 | 36.215 | 76.292 | 1.00 | 16.62 | 8 |
| ATOM | 2334 | CB  | ASN A 285 | 2.266 | 34.837 | 77.754 | 1.00 | 23.77 | 6 |
| ATOM | 2335 | CG  | ASN A 285 | 3.180 | 34.903 | 78.970 | 1.00 | 27.16 | 6 |
| ATOM | 2336 | OD1 | ASN A 285 | 4.369 | 34.524 | 78.933 | 1.00 | 16.54 | 8 |
| ATOM | 2337 | ND2 | ASN A 285 | 2.672 | 35.424 | 80.111 | 1.00 | 21.01 | 7 |
| ATOM | 2338 | N   | HIS A 286 | 5.253 | 34.220 | 75.778 | 1.00 | 15.57 | 7 |
| ATOM | 2339 | CA  | HIS A 286 | 6.501 | 34.895 | 75.381 | 1.00 | 12.65 | 6 |
| ATOM | 2340 | C   | HIS A 286 | 7.300 | 33.916 | 74.506 | 1.00 | 11.98 | 6 |
| ATOM | 2341 | O   | HIS A 286 | 6.854 | 32.804 | 74.345 | 1.00 | 14.13 | 8 |
| ATOM | 2342 | CB  | HIS A 286 | 7.264 | 35.443 | 76.587 | 1.00 | 19.68 | 6 |
| ATOM | 2343 | CG  | HIS A 286 | 7.742 | 34.382 | 77.537 | 1.00 | 17.05 | 6 |
| ATOM | 2344 | ND1 | HIS A 286 | 6.887 | 33.754 | 78.456 | 1.00 | 16.46 | 7 |
| ATOM | 2345 | CD2 | HIS A 286 | 8.948 | 33.817 | 77.703 | 1.00 | 18.10 | 6 |
| ATOM | 2346 | CE1 | HIS A 286 | 7.630 | 32.868 | 79.117 | 1.00 | 17.83 | 6 |
| ATOM | 2347 | NE2 | HIS A 286 | 8.870 | 32.870 | 78.693 | 1.00 | 17.71 | 7 |
| ATOM | 2348 | N   | SER A 287 | 8.426 | 34.322 | 73.915 | 1.00 | 12.20 | 7 |
| ATOM | 2349 | CA  | SER A 287 | 9.164 | 33.385 | 73.059 | 1.00 | 14.12 | 6 |
| ATOM | 2350 | C   | SER A 287 | 10.374 | 32.782 | 73.741 | 1.00 | 14.82 | 6 |
| ATOM | 2351 | O   | SER A 287 | 10.774 | 33.248 | 74.825 | 1.00 | 17.15 | 8 |
| ATOM | 2352 | CB  | SER A 287 | 9.754 | 34.254 | 71.893 | 1.00 | 16.58 | 6 |
| ATOM | 2353 | OG  | SER A 287 | 8.684 | 34.771 | 71.102 | 1.00 | 17.00 | 8 |
| ATOM | 2354 | N   | VAL A 288 | 11.054 | 31.840 | 73.121 | 1.00 | 12.79 | 7 |
| ATOM | 2355 | CA  | VAL A 288 | 12.250 | 31.203 | 73.563 | 1.00 | 14.52 | 6 |
| ATOM | 2356 | C   | VAL A 288 | 13.371 | 31.262 | 72.497 | 1.00 | 16.11 | 6 |
| ATOM | 2357 | O   | VAL A 288 | 13.084 | 31.296 | 71.293 | 1.00 | 14.78 | 8 |
| ATOM | 2358 | CB  | VAL A 288 | 12.044 | 29.731 | 73.950 | 1.00 | 13.45 | 6 |
| ATOM | 2359 | CG1 | VAL A 288 | 11.129 | 29.540 | 75.214 | 1.00 | 8.20  | 6 |
| ATOM | 2360 | CG2 | VAL A 288 | 11.456 | 28.913 | 72.829 | 1.00 | 13.24 | 6 |
| ATOM | 2361 | N   | PHE A 289 | 14.620 | 31.197 | 72.912 | 1.00 | 11.88 | 7 |
| ATOM | 2362 | CA  | PHE A 289 | 15.732 | 31.147 | 71.988 | 1.00 | 14.18 | 6 |
| ATOM | 2363 | C   | PHE A 289 | 15.709 | 29.767 | 71.359 | 1.00 | 13.88 | 6 |
| ATOM | 2364 | O   | PHE A 289 | 15.346 | 28.776 | 72.043 | 1.00 | 9.88  | 6 |
| ATOM | 2365 | CB  | PHE A 289 | 17.087 | 31.415 | 72.599 | 1.00 | 9.88  | 6 |
| ATOM | 2366 | CG  | PHE A 289 | 17.309 | 32.868 | 72.865 | 1.00 | 13.13 | 6 |
| ATOM | 2367 | CD1 | PHE A 289 | 17.630 | 33.713 | 71.811 | 1.00 | 10.95 | 6 |
| ATOM | 2368 | CD2 | PHE A 289 | 17.268 | 33.384 | 74.167 | 1.00 | 18.20 | 6 |
| ATOM | 2369 | CE1 | PHE A 289 | 17.900 | 35.050 | 72.049 | 1.00 | 17.86 | 6 |
| ATOM | 2370 | CE2 | PHE A 289 | 17.561 | 34.726 | 74.383 | 1.00 | 16.59 | 6 |
| ATOM | 2371 | CZ  | PHE A 289 | 17.877 | 35.587 | 73.336 | 1.00 | 16.81 | 6 |

| ATOM | 2372 | N | ASP | A | 290 | 16.003 | 29.722 | 70.036 | 1.00 | 11.93 | 7 |
| ATOM | 2373 | CA | ASP | A | 290 | 15.918 | 28.405 | 69.381 | 1.00 | 10.84 | 6 |
| ATOM | 2374 | C | ASP | A | 290 | 17.241 | 27.703 | 69.580 | 1.00 | 13.22 | 6 |
| ATOM | 2375 | O | ASP | A | 290 | 18.127 | 27.521 | 68.720 | 1.00 | 11.57 | 8 |
| ATOM | 2376 | CB | ASP | A | 290 | 15.592 | 28.596 | 67.882 | 1.00 | 17.74 | 6 |
| ATOM | 2377 | CG | ASP | A | 290 | 15.165 | 27.305 | 67.203 | 1.00 | 8.50 | 6 |
| ATOM | 2378 | OD1 | ASP | A | 290 | 15.413 | 26.178 | 67.665 | 1.00 | 10.35 | 8 |
| ATOM | 2379 | OD2 | ASP | A | 290 | 14.479 | 27.377 | 66.115 | 1.00 | 14.66 | 8 |
| ATOM | 2380 | N | VAL | A | 291 | 17.338 | 26.969 | 70.722 | 1.00 | 11.25 | 7 |
| ATOM | 2381 | CA | VAL | A | 291 | 18.561 | 26.296 | 71.086 | 1.00 | 5.98 | 6 |
| ATOM | 2382 | C | VAL | A | 291 | 18.871 | 25.107 | 70.214 | 1.00 | 6.18 | 6 |
| ATOM | 2383 | O | VAL | A | 291 | 20.044 | 24.846 | 69.880 | 1.00 | 7.63 | 8 |
| ATOM | 2384 | CB | VAL | A | 291 | 18.627 | 26.021 | 72.658 | 1.00 | 11.65 | 6 |
| ATOM | 2385 | CG1 | VAL | A | 291 | 19.839 | 25.216 | 72.998 | 1.00 | 9.12 | 6 |
| ATOM | 2386 | CG2 | VAL | A | 291 | 18.797 | 27.390 | 73.361 | 1.00 | 5.15 | 6 |
| ATOM | 2387 | N | PRO | A | 292 | 17.960 | 24.206 | 69.956 | 1.00 | 6.90 | 7 |
| ATOM | 2388 | CA | PRO | A | 292 | 18.131 | 23.122 | 68.992 | 1.00 | 8.93 | 6 |
| ATOM | 2389 | C | PRO | A | 292 | 18.692 | 23.624 | 67.645 | 1.00 | 7.94 | 6 |
| ATOM | 2390 | O | PRO | A | 292 | 19.613 | 22.995 | 67.165 | 1.00 | 11.81 | 8 |
| ATOM | 2391 | CB | PRO | A | 292 | 16.749 | 22.501 | 68.809 | 1.00 | 9.92 | 6 |
| ATOM | 2392 | CG | PRO | A | 292 | 16.058 | 22.934 | 70.114 | 1.00 | 8.69 | 6 |
| ATOM | 2393 | CD | PRO | A | 292 | 16.537 | 24.373 | 70.327 | 1.00 | 7.60 | 6 |
| ATOM | 2394 | N | LEU | A | 293 | 18.247 | 24.714 | 67.062 | 1.00 | 10.68 | 7 |
| ATOM | 2395 | CA | LEU | A | 293 | 18.737 | 25.213 | 65.763 | 1.00 | 11.10 | 6 |
| ATOM | 2396 | C | LEU | A | 293 | 20.192 | 25.650 | 65.885 | 1.00 | 12.31 | 6 |
| ATOM | 2397 | O | LEU | A | 293 | 21.080 | 25.293 | 65.104 | 1.00 | 13.69 | 8 |
| ATOM | 2398 | CB | LEU | A | 293 | 17.883 | 26.394 | 65.252 | 1.00 | 8.55 | 6 |
| ATOM | 2399 | CG | LEU | A | 293 | 18.529 | 27.085 | 64.005 | 1.00 | 8.91 | 6 |
| ATOM | 2400 | CD1 | LEU | A | 293 | 18.547 | 26.028 | 62.889 | 1.00 | 14.47 | 6 |
| ATOM | 2401 | CD2 | LEU | A | 293 | 17.697 | 28.283 | 63.570 | 1.00 | 6.40 | 6 |
| ATOM | 2402 | N | HIS | A | 294 | 20.584 | 26.306 | 66.998 | 1.00 | 10.78 | 7 |
| ATOM | 2403 | CA | HIS | A | 294 | 21.999 | 26.615 | 67.259 | 1.00 | 8.98 | 6 |
| ATOM | 2404 | C | HIS | A | 294 | 22.834 | 25.349 | 67.238 | 1.00 | 8.37 | 6 |
| ATOM | 2405 | O | HIS | A | 294 | 23.918 | 25.401 | 66.617 | 1.00 | 10.24 | 8 |
| ATOM | 2406 | CB | HIS | A | 294 | 22.216 | 27.414 | 68.575 | 1.00 | 14.04 | 6 |
| ATOM | 2407 | CG | HIS | A | 294 | 23.648 | 27.309 | 69.026 | 1.00 | 9.37 | 6 |
| ATOM | 2408 | ND1 | HIS | A | 294 | 24.571 | 28.222 | 68.589 | 1.00 | 10.24 | 7 |
| ATOM | 2409 | CD2 | HIS | A | 294 | 24.315 | 26.446 | 69.840 | 1.00 | 10.07 | 6 |
| ATOM | 2410 | CE1 | HIS | A | 294 | 25.764 | 27.943 | 69.105 | 1.00 | 11.91 | 6 |
| ATOM | 2411 | NE2 | HIS | A | 294 | 25.671 | 26.832 | 69.818 | 1.00 | 8.31 | 7 |
| ATOM | 2412 | N | TYR | A | 295 | 22.438 | 24.229 | 67.818 | 1.00 | 7.59 | 7 |
| ATOM | 2413 | CA | TYR | A | 295 | 23.272 | 23.041 | 67.767 | 1.00 | 10.71 | 6 |
| ATOM | 2414 | C | TYR | A | 295 | 23.301 | 22.399 | 66.331 | 1.00 | 12.73 | 6 |
| ATOM | 2415 | O | TYR | A | 295 | 24.343 | 21.839 | 65.992 | 1.00 | 11.33 | 8 |
| ATOM | 2416 | CB | TYR | A | 295 | 22.815 | 21.988 | 68.830 | 1.00 | 12.97 | 6 |
| ATOM | 2417 | CG | TYR | A | 295 | 23.371 | 22.374 | 70.208 | 1.00 | 16.51 | 6 |
| ATOM | 2418 | CD1 | TYR | A | 295 | 24.687 | 22.187 | 70.543 | 1.00 | 15.81 | 6 |
| ATOM | 2419 | CD2 | TYR | A | 295 | 22.540 | 22.989 | 71.154 | 1.00 | 18.65 | 6 |
| ATOM | 2420 | CE1 | TYR | A | 295 | 25.220 | 22.604 | 71.752 | 1.00 | 17.42 | 6 |
| ATOM | 2421 | CE2 | TYR | A | 295 | 23.019 | 23.388 | 72.373 | 1.00 | 19.62 | 6 |
| ATOM | 2422 | CZ | TYR | A | 295 | 24.355 | 23.197 | 72.675 | 1.00 | 22.11 | 6 |
| ATOM | 2423 | OH | TYR | A | 295 | 24.804 | 23.591 | 73.924 | 1.00 | 21.14 | 8 |
| ATOM | 2424 | N | ASN | A | 296 | 22.173 | 22.434 | 65.605 | 1.00 | 8.29 | 7 |
| ATOM | 2425 | CA | ASN | A | 296 | 22.141 | 21.907 | 64.219 | 1.00 | 10.41 | 6 |
| ATOM | 2426 | C | ASN | A | 296 | 23.189 | 22.685 | 63.414 | 1.00 | 6.38 | 6 |
| ATOM | 2427 | O | ASN | A | 296 | 24.030 | 22.072 | 62.803 | 1.00 | 7.68 | 8 |
| ATOM | 2428 | CB | ASN | A | 296 | 20.748 | 22.243 | 63.617 | 1.00 | 7.49 | 6 |
| ATOM | 2429 | CG | ASN | A | 296 | 19.773 | 21.165 | 63.988 | 1.00 | 9.99 | 6 |
| ATOM | 2430 | OD1 | ASN | A | 296 | 20.061 | 20.282 | 64.830 | 1.00 | 12.42 | 8 |
| ATOM | 2431 | ND2 | ASN | A | 296 | 18.578 | 21.090 | 63.424 | 1.00 | 13.13 | 7 |
| ATOM | 2432 | N | LEU | A | 297 | 23.235 | 23.991 | 63.539 | 1.00 | 6.28 | 7 |
| ATOM | 2433 | CA | LEU | A | 297 | 24.228 | 24.816 | 62.913 | 1.00 | 7.26 | 6 |
| ATOM | 2434 | C | LEU | A | 297 | 25.651 | 24.549 | 63.305 | 1.00 | 12.65 | 6 |
| ATOM | 2435 | O | LEU | A | 297 | 26.574 | 24.474 | 62.450 | 1.00 | 11.73 | 8 |
| ATOM | 2436 | CB | LEU | A | 297 | 23.906 | 26.290 | 63.098 | 1.00 | 3.62 | 6 |

| ATOM | 2437 | CG | LEU A 297 | 22.496 | 26.762 | 62.637 | 1.00 | 13.98 | 6 |
| --- | --- | --- | --- | --- | --- | --- | --- | --- | --- |
| ATOM | 2438 | CD1 | LEU A 297 | 22.357 | 28.272 | 62.977 | 1.00 | 5.32 | 6 |
| ATOM | 2439 | CD2 | LEU A 297 | 22.424 | 26.576 | 61.117 | 1.00 | 10.90 | 6 |
| ATOM | 2440 | N | TYR A 298 | 25.892 | 24.420 | 64.642 | 1.00 | 9.91 | 7 |
| ATOM | 2441 | CA | TYR A 298 | 27.252 | 24.121 | 65.117 | 1.00 | 8.20 | 6 |
| ATOM | 2442 | C | TYR A 298 | 27.660 | 22.763 | 64.599 | 1.00 | 6.55 | 6 |
| ATOM | 2443 | O | TYR A 298 | 28.803 | 22.585 | 64.123 | 1.00 | 9.41 | 8 |
| ATOM | 2444 | CB | TYR A 298 | 27.099 | 24.033 | 66.689 | 1.00 | 9.28 | 6 |
| ATOM | 2445 | CG | TYR A 298 | 28.271 | 23.362 | 67.349 | 1.00 | 8.40 | 6 |
| ATOM | 2446 | CD1 | TYR A 298 | 29.502 | 23.971 | 67.360 | 1.00 | 8.56 | 6 |
| ATOM | 2447 | CD2 | TYR A 298 | 28.121 | 22.138 | 67.959 | 1.00 | 12.60 | 6 |
| ATOM | 2448 | CE1 | TYR A 298 | 30.595 | 23.359 | 68.011 | 1.00 | 11.66 | 6 |
| ATOM | 2449 | CE2 | TYR A 298 | 29.186 | 21.534 | 68.612 | 1.00 | 12.63 | 6 |
| ATOM | 2450 | CZ | TYR A 298 | 30.390 | 22.159 | 68.624 | 1.00 | 12.14 | 6 |
| ATOM | 2451 | OH | TYR A 298 | 31.461 | 21.534 | 69.222 | 1.00 | 18.26 | 8 |
| ATOM | 2452 | N | ASN A 299 | 26.803 | 21.744 | 64.652 | 1.00 | 6.95 | 7 |
| ATOM | 2453 | CA | ASN A 299 | 27.263 | 20.456 | 64.134 | 1.00 | 9.55 | 6 |
| ATOM | 2454 | C | ASN A 299 | 27.468 | 20.453 | 62.571 | 1.00 | 13.82 | 6 |
| ATOM | 2455 | O | ASN A 299 | 28.443 | 19.870 | 62.073 | 1.00 | 11.91 | 8 |
| ATOM | 2456 | CB | ASN A 299 | 26.080 | 19.553 | 64.517 | 1.00 | 12.01 | 6 |
| ATOM | 2457 | CG | ASN A 299 | 26.192 | 19.058 | 65.973 | 1.00 | 18.94 | 6 |
| ATOM | 2458 | OD1 | ASN A 299 | 27.318 | 18.757 | 66.382 | 1.00 | 13.12 | 8 |
| ATOM | 2459 | ND2 | ASN A 299 | 25.118 | 18.927 | 66.739 | 1.00 | 11.91 | 7 |
| ATOM | 2460 | N | ALA A 300 | 26.608 | 21.178 | 61.829 | 1.00 | 10.90 | 7 |
| ATOM | 2461 | CA | ALA A 300 | 26.728 | 21.193 | 60.341 | 1.00 | 13.38 | 6 |
| ATOM | 2462 | C | ALA A 300 | 28.063 | 21.837 | 60.015 | 1.00 | 11.55 | 6 |
| ATOM | 2463 | O | ALA A 300 | 28.877 | 21.283 | 59.284 | 1.00 | 9.92 | 8 |
| ATOM | 2464 | CB | ALA A 300 | 25.627 | 22.057 | 59.713 | 1.00 | 5.87 | 6 |
| ATOM | 2465 | N | SER A 301 | 28.416 | 22.908 | 60.779 | 1.00 | 10.29 | 7 |
| ATOM | 2466 | CA | SER A 301 | 29.669 | 23.576 | 60.587 | 1.00 | 8.35 | 6 |
| ATOM | 2467 | C | SER A 301 | 30.917 | 22.770 | 60.935 | 1.00 | 11.77 | 6 |
| ATOM | 2468 | O | SER A 301 | 31.982 | 23.182 | 60.431 | 1.00 | 9.86 | 8 |
| ATOM | 2469 | CB | SER A 301 | 29.730 | 24.937 | 61.305 | 1.00 | 16.73 | 6 |
| ATOM | 2470 | OG | SER A 301 | 30.179 | 24.745 | 62.651 | 1.00 | 16.74 | 8 |
| ATOM | 2471 | N | ASN A 302 | 30.797 | 21.642 | 61.635 | 1.00 | 9.53 | 7 |
| ATOM | 2472 | CA | ASN A 302 | 31.979 | 20.871 | 61.987 | 1.00 | 12.86 | 6 |
| ATOM | 2473 | C | ASN A 302 | 31.981 | 19.582 | 61.175 | 1.00 | 12.44 | 6 |
| ATOM | 2474 | O | ASN A 302 | 32.842 | 18.715 | 61.393 | 1.00 | 12.66 | 8 |
| ATOM | 2475 | CB | ASN A 302 | 31.833 | 20.448 | 63.536 | 1.00 | 10.96 | 6 |
| ATOM | 2476 | CG | ASN A 302 | 32.455 | 21.559 | 64.362 | 1.00 | 12.81 | 6 |
| ATOM | 2477 | OD1 | ASN A 302 | 33.671 | 21.716 | 64.316 | 1.00 | 10.84 | 8 |
| ATOM | 2478 | ND2 | ASN A 302 | 31.695 | 22.416 | 65.059 | 1.00 | 11.91 | 7 |
| ATOM | 2479 | N | SER A 303 | 30.990 | 19.419 | 60.303 | 1.00 | 9.65 | 7 |
| ATOM | 2480 | CA | SER A 303 | 30.905 | 18.161 | 59.584 | 1.00 | 11.59 | 6 |
| ATOM | 2481 | C | SER A 303 | 31.581 | 18.096 | 58.201 | 1.00 | 11.60 | 6 |
| ATOM | 2482 | O | SER A 303 | 31.515 | 17.032 | 57.607 | 1.00 | 11.47 | 8 |
| ATOM | 2483 | CB | SER A 303 | 29.469 | 17.674 | 59.486 | 1.00 | 21.93 | 6 |
| ATOM | 2484 | OG | SER A 303 | 28.928 | 17.533 | 60.790 | 1.00 | 20.56 | 8 |
| ATOM | 2485 | N | GLY A 304 | 32.374 | 19.057 | 57.832 | 1.00 | 14.77 | 7 |
| ATOM | 2486 | CA | GLY A 304 | 33.210 | 19.066 | 56.618 | 1.00 | 17.32 | 6 |
| ATOM | 2487 | C | GLY A 304 | 32.397 | 18.788 | 55.312 | 1.00 | 17.00 | 6 |
| ATOM | 2488 | O | GLY A 304 | 32.911 | 18.072 | 54.447 | 1.00 | 17.50 | 8 |
| ATOM | 2489 | N | GLY A 305 | 31.166 | 19.213 | 55.226 | 1.00 | 14.82 | 7 |
| ATOM | 2490 | CA | GLY A 305 | 30.290 | 18.985 | 54.094 | 1.00 | 15.48 | 6 |
| ATOM | 2491 | C | GLY A 305 | 29.588 | 17.703 | 54.314 | 1.00 | 16.63 | 6 |
| ATOM | 2492 | O | GLY A 305 | 28.693 | 17.463 | 53.504 | 1.00 | 16.11 | 8 |
| ATOM | 2493 | N | ASN A 306 | 29.788 | 16.819 | 55.278 | 1.00 | 15.13 | 7 |
| ATOM | 2494 | CA | ASN A 306 | 28.948 | 15.624 | 55.355 | 1.00 | 15.73 | 6 |
| ATOM | 2495 | C | ASN A 306 | 27.640 | 15.815 | 56.075 | 1.00 | 14.60 | 6 |
| ATOM | 2496 | O | ASN A 306 | 26.890 | 14.812 | 56.192 | 1.00 | 16.40 | 8 |
| ATOM | 2497 | CB | ASN A 306 | 29.730 | 14.515 | 56.100 | 1.00 | 27.81 | 6 |
| ATOM | 2498 | CG | ASN A 306 | 30.761 | 13.901 | 55.189 | 1.00 | 33.85 | 6 |
| ATOM | 2499 | OD1 | ASN A 306 | 30.662 | 14.051 | 53.980 | 1.00 | 27.05 | 8 |
| ATOM | 2500 | ND2 | ASN A 306 | 31.756 | 13.197 | 55.701 | 1.00 | 27.79 | 7 |
| ATOM | 2501 | N | TYR A 307 | 27.215 | 16.978 | 56.472 | 1.00 | 12.08 | 7 |

| ATOM | 2502 | CA | TYR A 307 | 25.952 | 17.035 | 57.241 | 1.00 | 14.18 | 6 |
|---|---|---|---|---|---|---|---|---|---|
| ATOM | 2503 | C | TYR A 307 | 24.781 | 16.883 | 56.264 | 1.00 | 16.05 | 6 |
| ATOM | 2504 | O | TYR A 307 | 24.907 | 17.587 | 55.299 | 1.00 | 12.72 | 8 |
| ATOM | 2505 | CB | TYR A 307 | 25.858 | 18.413 | 57.926 | 1.00 | 11.27 | 6 |
| ATOM | 2506 | CG | TYR A 307 | 24.701 | 18.546 | 58.899 | 1.00 | 15.63 | 6 |
| ATOM | 2507 | CD1 | TYR A 307 | 24.883 | 18.120 | 60.218 | 1.00 | 17.92 | 6 |
| ATOM | 2508 | CD2 | TYR A 307 | 23.486 | 19.084 | 58.561 | 1.00 | 16.39 | 6 |
| ATOM | 2509 | CE1 | TYR A 307 | 23.853 | 18.253 | 61.133 | 1.00 | 22.23 | 6 |
| ATOM | 2510 | CE2 | TYR A 307 | 22.444 | 19.219 | 59.444 | 1.00 | 19.66 | 6 |
| ATOM | 2511 | CZ | TYR A 307 | 22.642 | 18.802 | 60.759 | 1.00 | 23.46 | 6 |
| ATOM | 2512 | OH | TYR A 307 | 21.642 | 18.869 | 61.695 | 1.00 | 25.41 | 8 |
| ATOM | 2513 | N | ASP A 308 | 23.591 | 16.418 | 56.401 | 1.00 | 13.94 | 7 |
| ATOM | 2514 | CA | ASP A 308 | 22.531 | 16.460 | 55.437 | 1.00 | 13.17 | 6 |
| ATOM | 2515 | C | ASP A 308 | 21.776 | 17.751 | 55.543 | 1.00 | 14.66 | 6 |
| ATOM | 2516 | O | ASP A 308 | 20.839 | 17.941 | 56.332 | 1.00 | 15.00 | 8 |
| ATOM | 2517 | CB | ASP A 308 | 21.684 | 15.233 | 55.628 | 1.00 | 9.65 | 6 |
| ATOM | 2518 | CG | ASP A 308 | 20.585 | 15.152 | 54.567 | 1.00 | 16.73 | 6 |
| ATOM | 2519 | OD1 | ASP A 308 | 20.400 | 16.065 | 53.758 | 1.00 | 16.88 | 8 |
| ATOM | 2520 | OD2 | ASP A 308 | 19.891 | 14.137 | 54.693 | 1.00 | 14.99 | 8 |
| ATOM | 2521 | N | MET A 309 | 22.105 | 18.682 | 54.620 | 1.00 | 12.06 | 7 |
| ATOM | 2522 | CA | MET A 309 | 21.479 | 19.984 | 54.669 | 1.00 | 10.03 | 6 |
| ATOM | 2523 | C | MET A 309 | 19.995 | 19.925 | 54.496 | 1.00 | 11.61 | 6 |
| ATOM | 2524 | O | MET A 309 | 19.380 | 20.906 | 54.955 | 1.00 | 12.12 | 8 |
| ATOM | 2525 | CB | MET A 309 | 22.080 | 20.994 | 53.681 | 1.00 | 20.14 | 6 |
| ATOM | 2526 | CG | MET A 309 | 23.601 | 21.176 | 53.875 | 1.00 | 17.95 | 6 |
| ATOM | 2527 | SD | MET A 309 | 23.869 | 22.451 | 55.168 | 1.00 | 17.26 | 16 |
| ATOM | 2528 | CE | MET A 309 | 23.532 | 23.967 | 54.322 | 1.00 | 10.92 | 6 |
| ATOM | 2529 | N | ALA A 310 | 19.391 | 18.896 | 53.908 | 1.00 | 10.05 | 7 |
| ATOM | 2530 | CA | ALA A 310 | 17.926 | 18.938 | 53.854 | 1.00 | 14.66 | 6 |
| ATOM | 2531 | C | ALA A 310 | 17.317 | 18.815 | 55.281 | 1.00 | 17.97 | 6 |
| ATOM | 2532 | O | ALA A 310 | 16.133 | 19.091 | 55.442 | 1.00 | 15.37 | 8 |
| ATOM | 2533 | CB | ALA A 310 | 17.404 | 17.690 | 53.130 | 1.00 | 7.97 | 6 |
| ATOM | 2534 | N | LYS A 311 | 18.097 | 18.340 | 56.246 | 1.00 | 18.30 | 7 |
| ATOM | 2535 | CA | LYS A 311 | 17.577 | 18.186 | 57.613 | 1.00 | 21.21 | 6 |
| ATOM | 2536 | C | LYS A 311 | 17.995 | 19.322 | 58.542 | 1.00 | 20.93 | 6 |
| ATOM | 2537 | O | LYS A 311 | 17.689 | 19.170 | 59.721 | 1.00 | 22.60 | 8 |
| ATOM | 2538 | CB | LYS A 311 | 18.134 | 16.857 | 58.122 | 1.00 | 17.90 | 6 |
| ATOM | 2539 | CG | LYS A 311 | 17.596 | 15.669 | 57.320 | 1.00 | 27.66 | 6 |
| ATOM | 2540 | CD | LYS A 311 | 17.919 | 14.390 | 58.048 | 1.00 | 40.46 | 6 |
| ATOM | 2541 | CE | LYS A 311 | 18.018 | 13.147 | 57.187 | 1.00 | 53.31 | 6 |
| ATOM | 2542 | NZ | LYS A 311 | 19.293 | 12.385 | 57.486 | 1.00 | 60.95 | 7 |
| ATOM | 2543 | N | LEU A 312 | 18.546 | 20.444 | 58.086 | 1.00 | 18.62 | 7 |
| ATOM | 2544 | CA | LEU A 312 | 18.952 | 21.512 | 58.957 | 1.00 | 16.83 | 6 |
| ATOM | 2545 | C | LEU A 312 | 17.889 | 22.045 | 59.932 | 1.00 | 16.10 | 6 |
| ATOM | 2546 | O | LEU A 312 | 18.314 | 22.536 | 61.000 | 1.00 | 16.57 | 8 |
| ATOM | 2547 | CB | LEU A 312 | 19.465 | 22.772 | 58.296 | 1.00 | 14.38 | 6 |
| ATOM | 2548 | CG | LEU A 312 | 20.877 | 23.279 | 58.342 | 1.00 | 20.88 | 6 |
| ATOM | 2549 | CD1 | LEU A 312 | 20.864 | 24.762 | 58.061 | 1.00 | 20.98 | 6 |
| ATOM | 2550 | CD2 | LEU A 312 | 21.681 | 22.941 | 59.568 | 1.00 | 25.82 | 6 |
| ATOM | 2551 | N | LEU A 313 | 16.642 | 22.116 | 59.613 | 1.00 | 13.56 | 7 |
| ATOM | 2552 | CA | LEU A 313 | 15.615 | 22.672 | 60.475 | 1.00 | 14.51 | 6 |
| ATOM | 2553 | C | LEU A 313 | 14.935 | 21.585 | 61.308 | 1.00 | 15.32 | 6 |
| ATOM | 2554 | O | LEU A 313 | 14.075 | 21.927 | 62.129 | 1.00 | 14.10 | 8 |
| ATOM | 2555 | CB | LEU A 313 | 14.525 | 23.397 | 59.644 | 1.00 | 12.48 | 6 |
| ATOM | 2556 | CG | LEU A 313 | 15.077 | 24.595 | 58.877 | 1.00 | 21.20 | 6 |
| ATOM | 2557 | CD1 | LEU A 313 | 13.988 | 25.262 | 58.044 | 1.00 | 17.97 | 6 |
| ATOM | 2558 | CD2 | LEU A 313 | 15.715 | 25.619 | 59.844 | 1.00 | 16.09 | 6 |
| ATOM | 2559 | N | ASN A 314 | 15.293 | 20.315 | 61.111 | 1.00 | 14.54 | 7 |
| ATOM | 2560 | CA | ASN A 314 | 14.549 | 19.306 | 61.859 | 1.00 | 18.06 | 6 |
| ATOM | 2561 | C | ASN A 314 | 14.791 | 19.401 | 63.387 | 1.00 | 18.92 | 6 |
| ATOM | 2562 | O | ASN A 314 | 15.930 | 19.568 | 63.824 | 1.00 | 15.49 | 8 |
| ATOM | 2563 | CB | ASN A 314 | 14.974 | 17.893 | 61.401 | 1.00 | 23.05 | 6 |
| ATOM | 2564 | CG | ASN A 314 | 14.330 | 17.460 | 60.071 | 1.00 | 29.52 | 6 |
| ATOM | 2565 | OD1 | ASN A 314 | 13.468 | 18.106 | 59.463 | 1.00 | 23.14 | 8 |
| ATOM | 2566 | ND2 | ASN A 314 | 14.787 | 16.326 | 59.564 | 1.00 | 22.18 | 7 |

| ATOM | 2567 | N   | GLY A 315 | 13.721 | 19.262 | 64.155 | 1.00 | 19.24 | 7 |
| ATOM | 2568 | CA  | GLY A 315 | 13.833 | 19.187 | 65.610 | 1.00 | 17.88 | 6 |
| ATOM | 2569 | C   | GLY A 315 | 14.003 | 20.576 | 66.173 | 1.00 | 16.97 | 6 |
| ATOM | 2570 | O   | GLY A 315 | 14.437 | 20.709 | 67.319 | 1.00 | 20.46 | 8 |
| ATOM | 2571 | N   | THR A 316 | 13.686 | 21.634 | 65.428 | 1.00 | 13.17 | 7 |
| ATOM | 2572 | CA  | THR A 316 | 13.939 | 22.972 | 65.936 | 1.00 | 10.52 | 6 |
| ATOM | 2573 | C   | THR A 316 | 12.657 | 23.638 | 66.379 | 1.00 | 11.28 | 6 |
| ATOM | 2574 | O   | THR A 316 | 11.548 | 23.166 | 66.032 | 1.00 | 13.19 | 8 |
| ATOM | 2575 | CB  | THR A 316 | 14.583 | 23.888 | 64.845 | 1.00 | 16.57 | 6 |
| ATOM | 2576 | OG1 | THR A 316 | 13.639 | 23.868 | 63.748 | 1.00 | 13.69 | 8 |
| ATOM | 2577 | CG2 | THR A 316 | 15.886 | 23.264 | 64.400 | 1.00 | 11.29 | 6 |
| ATOM | 2578 | N   | VAL A 317 | 12.808 | 24.754 | 67.083 | 1.00 | 9.48  | 7 |
| ATOM | 2579 | CA  | VAL A 317 | 11.615 | 25.465 | 67.500 | 1.00 | 10.33 | 6 |
| ATOM | 2580 | C   | VAL A 317 | 11.073 | 26.218 | 66.265 | 1.00 | 11.64 | 6 |
| ATOM | 2581 | O   | VAL A 317 | 9.860  | 26.352 | 66.100 | 1.00 | 12.12 | 8 |
| ATOM | 2582 | CB  | VAL A 317 | 11.883 | 26.544 | 68.593 | 1.00 | 10.20 | 6 |
| ATOM | 2583 | CG1 | VAL A 317 | 10.551 | 27.181 | 69.018 | 1.00 | 10.92 | 6 |
| ATOM | 2584 | CG2 | VAL A 317 | 12.568 | 25.916 | 69.807 | 1.00 | 10.14 | 6 |
| ATOM | 2585 | N   | VAL A 318 | 11.985 | 26.824 | 65.488 | 1.00 | 10.03 | 7 |
| ATOM | 2586 | CA  | VAL A 318 | 11.498 | 27.594 | 64.324 | 1.00 | 12.79 | 6 |
| ATOM | 2587 | C   | VAL A 318 | 10.720 | 26.750 | 63.334 | 1.00 | 12.26 | 6 |
| ATOM | 2588 | O   | VAL A 318 | 9.691  | 27.169 | 62.821 | 1.00 | 14.96 | 8 |
| ATOM | 2589 | CB  | VAL A 318 | 12.579 | 28.500 | 63.750 | 1.00 | 10.04 | 6 |
| ATOM | 2590 | CG1 | VAL A 318 | 13.618 | 27.626 | 63.021 | 1.00 | 3.78  | 6 |
| ATOM | 2591 | CG2 | VAL A 318 | 11.948 | 29.590 | 62.919 | 1.00 | 17.99 | 6 |
| ATOM | 2592 | N   | GLN A 319 | 10.935 | 25.467 | 63.190 | 1.00 | 14.71 | 7 |
| ATOM | 2593 | CA  | GLN A 319 | 10.195 | 24.610 | 62.319 | 1.00 | 17.78 | 6 |
| ATOM | 2594 | C   | GLN A 319 | 8.783  | 24.386 | 62.812 | 1.00 | 22.17 | 6 |
| ATOM | 2595 | O   | GLN A 319 | 7.802  | 24.453 | 62.056 | 1.00 | 19.34 | 8 |
| ATOM | 2596 | CB  | GLN A 319 | 10.980 | 23.316 | 62.105 | 1.00 | 12.50 | 6 |
| ATOM | 2597 | CG  | GLN A 319 | 10.253 | 22.339 | 61.198 | 1.00 | 13.69 | 6 |
| ATOM | 2598 | CD  | GLN A 319 | 10.889 | 20.989 | 61.098 | 1.00 | 22.01 | 6 |
| ATOM | 2599 | OE1 | GLN A 319 | 11.040 | 20.278 | 62.086 | 1.00 | 27.91 | 8 |
| ATOM | 2600 | NE2 | GLN A 319 | 11.344 | 20.567 | 59.900 | 1.00 | 26.90 | 7 |
| ATOM | 2601 | N   | LYS A 320 | 8.644  | 24.072 | 64.113 | 1.00 | 22.53 | 7 |
| ATOM | 2602 | CA  | LYS A 320 | 7.369  | 23.743 | 64.731 | 1.00 | 20.27 | 6 |
| ATOM | 2603 | C   | LYS A 320 | 6.600  | 24.914 | 65.270 | 1.00 | 20.25 | 6 |
| ATOM | 2604 | O   | LYS A 320 | 5.387  | 24.879 | 65.097 | 1.00 | 22.65 | 8 |
| ATOM | 2605 | CB  | LYS A 320 | 7.557  | 22.758 | 65.878 | 1.00 | 28.06 | 6 |
| ATOM | 2606 | CG  | LYS A 320 | 6.854  | 21.444 | 65.592 | 1.00 | 41.77 | 6 |
| ATOM | 2607 | CD  | LYS A 320 | 5.644  | 21.334 | 66.488 | 1.00 | 50.06 | 6 |
| ATOM | 2608 | CE  | LYS A 320 | 5.485  | 19.947 | 67.110 | 1.00 | 53.75 | 6 |
| ATOM | 2609 | NZ  | LYS A 320 | 4.273  | 19.915 | 67.987 | 1.00 | 53.30 | 7 |
| ATOM | 2610 | N   | HIS A 321 | 7.185  | 25.939 | 65.872 | 1.00 | 17.78 | 7 |
| ATOM | 2611 | CA  | HIS A 321 | 6.451  | 27.070 | 66.406 | 1.00 | 17.78 | 6 |
| ATOM | 2612 | C   | HIS A 321 | 7.193  | 28.343 | 66.059 | 1.00 | 19.94 | 6 |
| ATOM | 2613 | O   | HIS A 321 | 7.826  | 29.049 | 66.885 | 1.00 | 20.97 | 8 |
| ATOM | 2614 | CB  | HIS A 321 | 6.440  | 27.016 | 67.996 | 1.00 | 17.17 | 6 |
| ATOM | 2615 | CG  | HIS A 321 | 5.844  | 25.741 | 68.489 | 1.00 | 7.99  | 6 |
| ATOM | 2616 | ND1 | HIS A 321 | 6.584  | 24.678 | 68.967 | 1.00 | 21.64 | 7 |
| ATOM | 2617 | CD2 | HIS A 321 | 4.569  | 25.292 | 68.428 | 1.00 | 12.69 | 6 |
| ATOM | 2618 | CE1 | HIS A 321 | 5.763  | 23.670 | 69.234 | 1.00 | 18.85 | 6 |
| ATOM | 2619 | NE2 | HIS A 321 | 4.530  | 24.013 | 68.913 | 1.00 | 20.43 | 7 |
| ATOM | 2620 | N   | PRO A 322 | 7.113  | 28.801 | 64.817 | 1.00 | 18.84 | 7 |
| ATOM | 2621 | CA  | PRO A 322 | 7.857  | 29.919 | 64.297 | 1.00 | 16.35 | 6 |
| ATOM | 2622 | C   | PRO A 322 | 7.495  | 31.214 | 64.937 | 1.00 | 15.92 | 6 |
| ATOM | 2623 | O   | PRO A 322 | 8.327  | 32.103 | 65.048 | 1.00 | 17.57 | 8 |
| ATOM | 2624 | CB  | PRO A 322 | 7.551  | 30.051 | 62.767 | 1.00 | 18.11 | 6 |
| ATOM | 2625 | CG  | PRO A 322 | 6.291  | 29.215 | 62.690 | 1.00 | 19.63 | 6 |
| ATOM | 2626 | CD  | PRO A 322 | 6.391  | 28.081 | 63.734 | 1.00 | 19.70 | 6 |
| ATOM | 2627 | N   | MET A 323 | 6.270  | 31.375 | 65.380 | 1.00 | 15.79 | 7 |
| ATOM | 2628 | CA  | MET A 323 | 5.946  | 32.674 | 65.999 | 1.00 | 18.66 | 6 |
| ATOM | 2629 | C   | MET A 323 | 6.503  | 32.728 | 67.439 | 1.00 | 19.54 | 6 |
| ATOM | 2630 | O   | MET A 323 | 6.450  | 33.810 | 68.009 | 1.00 | 18.49 | 8 |
| ATOM | 2631 | CB  | MET A 323 | 4.417  | 32.838 | 65.991 | 1.00 | 24.07 | 6 |

| ATOM | 2632 | CG | MET | A | 323 | 3.940 | 33.170 | 64.565 | 1.00 | 52.61 | 6 |
| ATOM | 2633 | SD | MET | A | 323 | 2.249 | 33.780 | 64.474 | 1.00 | 69.72 | 16 |
| ATOM | 2634 | CE | MET | A | 323 | 1.332 | 32.252 | 64.705 | 1.00 | 60.17 | 6 |
| ATOM | 2635 | N | HIS | A | 324 | 7.050 | 31.633 | 67.964 | 1.00 | 18.53 | 7 |
| ATOM | 2636 | CA | HIS | A | 324 | 7.611 | 31.719 | 69.331 | 1.00 | 17.80 | 6 |
| ATOM | 2637 | C | HIS | A | 324 | 9.089 | 31.424 | 69.336 | 1.00 | 19.06 | 6 |
| ATOM | 2638 | O | HIS | A | 324 | 9.603 | 31.068 | 70.408 | 1.00 | 18.98 | 8 |
| ATOM | 2639 | CB | HIS | A | 324 | 6.895 | 30.630 | 70.147 | 1.00 | 19.82 | 6 |
| ATOM | 2640 | CG | HIS | A | 324 | 5.495 | 31.084 | 70.453 | 1.00 | 24.52 | 6 |
| ATOM | 2641 | ND1 | HIS | A | 324 | 4.404 | 30.648 | 69.731 | 1.00 | 29.89 | 7 |
| ATOM | 2642 | CD2 | HIS | A | 324 | 5.038 | 31.953 | 71.384 | 1.00 | 30.43 | 6 |
| ATOM | 2643 | CE1 | HIS | A | 324 | 3.321 | 31.243 | 70.218 | 1.00 | 34.69 | 6 |
| ATOM | 2644 | NE2 | HIS | A | 324 | 3.667 | 32.032 | 71.226 | 1.00 | 30.63 | 7 |
| ATOM | 2645 | N | ALA | A | 325 | 9.753 | 31.465 | 68.169 | 1.00 | 17.22 | 7 |
| ATOM | 2646 | CA | ALA | A | 325 | 11.175 | 31.186 | 68.083 | 1.00 | 15.46 | 6 |
| ATOM | 2647 | C | ALA | A | 325 | 11.989 | 32.439 | 67.872 | 1.00 | 16.14 | 6 |
| ATOM | 2648 | O | ALA | A | 325 | 11.688 | 33.248 | 66.983 | 1.00 | 15.68 | 8 |
| ATOM | 2649 | CB | ALA | A | 325 | 11.517 | 30.230 | 66.918 | 1.00 | 13.81 | 6 |
| ATOM | 2650 | N | VAL | A | 326 | 13.053 | 32.650 | 68.662 | 1.00 | 14.07 | 7 |
| ATOM | 2651 | CA | VAL | A | 326 | 14.017 | 33.699 | 68.433 | 1.00 | 11.09 | 6 |
| ATOM | 2652 | C | VAL | A | 326 | 15.268 | 32.951 | 67.941 | 1.00 | 12.79 | 6 |
| ATOM | 2653 | O | VAL | A | 326 | 15.707 | 32.027 | 68.603 | 1.00 | 13.69 | 8 |
| ATOM | 2654 | CB | VAL | A | 326 | 14.411 | 34.668 | 69.512 | 1.00 | 10.21 | 6 |
| ATOM | 2655 | CG1 | VAL | A | 326 | 15.622 | 35.512 | 69.255 | 1.00 | 5.75 | 6 |
| ATOM | 2656 | CG2 | VAL | A | 326 | 13.181 | 35.529 | 69.857 | 1.00 | 15.88 | 6 |
| ATOM | 2657 | N | THR | A | 327 | 15.643 | 33.230 | 66.653 | 1.00 | 10.18 | 7 |
| ATOM | 2658 | CA | THR | A | 327 | 16.738 | 32.402 | 66.088 | 1.00 | 5.75 | 6 |
| ATOM | 2659 | C | THR | A | 327 | 18.036 | 33.115 | 66.280 | 1.00 | 2.58 | 6 |
| ATOM | 2660 | O | THR | A | 327 | 18.105 | 34.346 | 66.171 | 1.00 | 7.39 | 8 |
| ATOM | 2661 | CB | THR | A | 327 | 16.477 | 32.120 | 64.556 | 1.00 | 11.93 | 6 |
| ATOM | 2662 | OG1 | THR | A | 327 | 16.120 | 33.376 | 63.955 | 1.00 | 8.64 | 8 |
| ATOM | 2663 | CG2 | THR | A | 327 | 15.247 | 31.232 | 64.436 | 1.00 | 6.52 | 6 |
| ATOM | 2664 | N | PHE | A | 328 | 19.092 | 32.256 | 66.427 | 1.00 | 4.68 | 7 |
| ATOM | 2665 | CA | PHE | A | 328 | 20.356 | 33.009 | 66.544 | 1.00 | 5.31 | 6 |
| ATOM | 2666 | C | PHE | A | 328 | 21.426 | 32.064 | 66.018 | 1.00 | 4.46 | 6 |
| ATOM | 2667 | O | PHE | A | 328 | 21.174 | 30.887 | 66.007 | 1.00 | 7.88 | 8 |
| ATOM | 2668 | CB | PHE | A | 328 | 20.729 | 33.361 | 68.040 | 1.00 | 10.06 | 6 |
| ATOM | 2669 | CG | PHE | A | 328 | 20.892 | 32.177 | 68.973 | 1.00 | 8.83 | 6 |
| ATOM | 2670 | CD1 | PHE | A | 328 | 19.810 | 31.411 | 69.353 | 1.00 | 7.17 | 6 |
| ATOM | 2671 | CD2 | PHE | A | 328 | 22.110 | 31.846 | 69.500 | 1.00 | 11.93 | 6 |
| ATOM | 2672 | CE1 | PHE | A | 328 | 19.952 | 30.319 | 70.200 | 1.00 | 12.02 | 6 |
| ATOM | 2673 | CE2 | PHE | A | 328 | 22.292 | 30.785 | 70.376 | 1.00 | 6.08 | 6 |
| ATOM | 2674 | CZ | PHE | A | 328 | 21.166 | 30.014 | 70.717 | 1.00 | 4.49 | 6 |
| ATOM | 2675 | N | VAL | A | 329 | 22.618 | 32.516 | 65.776 | 1.00 | 3.61 | 7 |
| ATOM | 2676 | CA | VAL | A | 329 | 23.689 | 31.561 | 65.419 | 1.00 | 6.19 | 6 |
| ATOM | 2677 | C | VAL | A | 329 | 24.612 | 31.281 | 66.621 | 1.00 | 8.45 | 6 |
| ATOM | 2678 | O | VAL | A | 329 | 25.080 | 30.150 | 66.823 | 1.00 | 5.56 | 8 |
| ATOM | 2679 | CB | VAL | A | 329 | 24.559 | 32.288 | 64.293 | 1.00 | 9.54 | 6 |
| ATOM | 2680 | CG1 | VAL | A | 329 | 25.572 | 31.346 | 63.707 | 1.00 | 3.85 | 6 |
| ATOM | 2681 | CG2 | VAL | A | 329 | 23.621 | 32.666 | 63.148 | 1.00 | 8.28 | 6 |
| ATOM | 2682 | N | ASP | A | 330 | 25.071 | 32.366 | 67.289 | 1.00 | 9.42 | 7 |
| ATOM | 2683 | CA | ASP | A | 330 | 25.997 | 32.213 | 68.400 | 1.00 | 11.97 | 6 |
| ATOM | 2684 | C | ASP | A | 330 | 25.663 | 33.266 | 69.475 | 1.00 | 11.48 | 6 |
| ATOM | 2685 | O | ASP | A | 330 | 24.962 | 34.225 | 69.185 | 1.00 | 9.81 | 8 |
| ATOM | 2686 | CB | ASP | A | 330 | 27.485 | 32.325 | 68.053 | 1.00 | 9.87 | 6 |
| ATOM | 2687 | CG | ASP | A | 330 | 28.078 | 31.041 | 67.577 | 1.00 | 21.67 | 6 |
| ATOM | 2688 | OD1 | ASP | A | 330 | 27.916 | 30.053 | 68.325 | 1.00 | 12.86 | 8 |
| ATOM | 2689 | OD2 | ASP | A | 330 | 28.713 | 30.985 | 66.479 | 1.00 | 13.95 | 8 |
| ATOM | 2690 | N | ASN | A | 331 | 26.186 | 33.083 | 70.706 | 1.00 | 13.63 | 7 |
| ATOM | 2691 | CA | ASN | A | 331 | 25.883 | 34.116 | 71.729 | 1.00 | 12.71 | 6 |
| ATOM | 2692 | C | ASN | A | 331 | 27.005 | 34.153 | 72.747 | 1.00 | 13.53 | 6 |
| ATOM | 2693 | O | ASN | A | 331 | 28.031 | 33.495 | 72.513 | 1.00 | 13.75 | 8 |
| ATOM | 2694 | CB | ASN | A | 331 | 24.491 | 33.935 | 72.300 | 1.00 | 7.36 | 6 |
| ATOM | 2695 | CG | ASN | A | 331 | 24.423 | 32.664 | 73.177 | 1.00 | 16.83 | 6 |
| ATOM | 2696 | OD1 | ASN | A | 331 | 25.399 | 32.003 | 73.561 | 1.00 | 15.71 | 8 |

| | ATOM | 2697 | ND2 | ASN A 331 | 23.214 | 32.296 | 73.527 | 1.00 | 14.16 | 7 |
|---|---|---|---|---|---|---|---|---|---|---|
| | ATOM | 2698 | N | HIS A 332 | 26.851 | 34.918 | 73.819 | 1.00 | 14.73 | 7 |
| | ATOM | 2699 | CA | HIS A 332 | 27.992 | 35.058 | 74.772 | 1.00 | 16.51 | 6 |
| | ATOM | 2700 | C | HIS A 332 | 28.287 | 33.755 | 75.481 | 1.00 | 15.53 | 6 |
| | ATOM | 2701 | O | HIS A 332 | 29.413 | 33.627 | 75.940 | 1.00 | 23.15 | 8 |
| | ATOM | 2702 | CB | HIS A 332 | 27.751 | 36.178 | 75.772 | 1.00 | 15.38 | 6 |
| | ATOM | 2703 | CG | HIS A 332 | 26.554 | 35.863 | 76.594 | 1.00 | 18.78 | 6 |
| | ATOM | 2704 | ND1 | HIS A 332 | 25.280 | 35.846 | 76.055 | 1.00 | 26.51 | 7 |
| | ATOM | 2705 | CD2 | HIS A 332 | 26.427 | 35.519 | 77.907 | 1.00 | 16.53 | 6 |
| | ATOM | 2706 | CE1 | HIS A 332 | 24.394 | 35.521 | 77.003 | 1.00 | 21.51 | 6 |
| | ATOM | 2707 | NE2 | HIS A 332 | 25.084 | 35.316 | 78.122 | 1.00 | 18.42 | 7 |
| | ATOM | 2708 | N | ASP A 333 | 27.425 | 32.794 | 75.583 | 1.00 | 13.82 | 7 |
| | ATOM | 2709 | CA | ASP A 333 | 27.648 | 31.483 | 76.118 | 1.00 | 14.31 | 6 |
| | ATOM | 2710 | C | ASP A 333 | 28.355 | 30.563 | 75.119 | 1.00 | 15.52 | 6 |
| | ATOM | 2711 | O | ASP A 333 | 29.083 | 29.676 | 75.561 | 1.00 | 13.90 | 8 |
| | ATOM | 2712 | CB | ASP A 333 | 26.325 | 30.770 | 76.388 | 1.00 | 13.27 | 6 |
| | ATOM | 2713 | CG | ASP A 333 | 25.254 | 31.297 | 77.309 | 1.00 | 44.51 | 6 |
| | ATOM | 2714 | OD1 | ASP A 333 | 25.641 | 31.795 | 78.383 | 1.00 | 22.07 | 8 |
| | ATOM | 2715 | OD2 | ASP A 333 | 24.000 | 31.244 | 77.004 | 1.00 | 51.59 | 8 |
| | ATOM | 2716 | N | SER A 334 | 28.022 | 30.614 | 73.775 | 1.00 | 15.01 | 7 |
| | ATOM | 2717 | CA | SER A 334 | 28.678 | 29.600 | 72.897 | 1.00 | 12.67 | 6 |
| | ATOM | 2718 | C | SER A 334 | 29.996 | 30.054 | 72.336 | 1.00 | 13.90 | 6 |
| | ATOM | 2719 | O | SER A 334 | 30.756 | 29.295 | 71.664 | 1.00 | 15.43 | 8 |
| | ATOM | 2720 | CB | SER A 334 | 27.670 | 29.290 | 71.743 | 1.00 | 13.31 | 6 |
| | ATOM | 2721 | OG | SER A 334 | 27.467 | 30.528 | 71.037 | 1.00 | 7.52 | 8 |
| | ATOM | 2722 | N | GLN A 335 | 30.391 | 31.294 | 72.559 | 1.00 | 15.37 | 7 |
| | ATOM | 2723 | CA | GLN A 335 | 31.655 | 31.863 | 72.059 | 1.00 | 15.42 | 6 |
| | ATOM | 2724 | C | GLN A 335 | 32.828 | 31.146 | 72.696 | 1.00 | 19.12 | 6 |
| | ATOM | 2725 | O | GLN A 335 | 32.726 | 30.487 | 73.733 | 1.00 | 18.06 | 8 |
| | ATOM | 2726 | CB | GLN A 335 | 31.759 | 33.374 | 72.246 | 1.00 | 15.85 | 6 |
| | ATOM | 2727 | CG | GLN A 335 | 31.874 | 33.849 | 73.727 | 1.00 | 21.14 | 6 |
| | ATOM | 2728 | CD | GLN A 335 | 31.977 | 35.359 | 73.825 | 1.00 | 14.14 | 6 |
| | ATOM | 2729 | OE1 | GLN A 335 | 30.999 | 36.082 | 73.978 | 1.00 | 15.97 | 8 |
| | ATOM | 2730 | NE2 | GLN A 335 | 33.183 | 35.919 | 73.666 | 1.00 | 20.22 | 7 |
| | ATOM | 2731 | N | PRO A 336 | 33.988 | 31.195 | 72.045 | 1.00 | 18.66 | 7 |
| | ATOM | 2732 | CA | PRO A 336 | 35.141 | 30.422 | 72.427 | 1.00 | 21.11 | 6 |
| | ATOM | 2733 | C | PRO A 336 | 35.535 | 30.541 | 73.910 | 1.00 | 21.47 | 6 |
| | ATOM | 2734 | O | PRO A 336 | 35.630 | 31.632 | 74.463 | 1.00 | 20.06 | 8 |
| | ATOM | 2735 | CB | PRO A 336 | 36.315 | 30.898 | 71.533 | 1.00 | 21.26 | 6 |
| | ATOM | 2736 | CG | PRO A 336 | 35.498 | 31.327 | 70.307 | 1.00 | 22.42 | 6 |
| | ATOM | 2737 | CD | PRO A 336 | 34.207 | 31.946 | 70.824 | 1.00 | 21.11 | 6 |
| | ATOM | 2738 | N | GLY A 337 | 35.756 | 29.389 | 74.519 | 1.00 | 23.46 | 7 |
| | ATOM | 2739 | CA | GLY A 337 | 36.227 | 29.335 | 75.895 | 1.00 | 25.50 | 6 |
| | ATOM | 2740 | C | GLY A 337 | 35.071 | 29.447 | 76.884 | 1.00 | 25.73 | 6 |
| | ATOM | 2741 | O | GLY A 337 | 35.352 | 29.084 | 78.031 | 1.00 | 27.95 | 8 |
| | ATOM | 2742 | N | GLU A 338 | 33.917 | 29.999 | 76.559 | 1.00 | 22.43 | 7 |
| | ATOM | 2743 | CA | GLU A 338 | 32.827 | 30.090 | 77.484 | 1.00 | 22.33 | 6 |
| | ATOM | 2744 | C | GLU A 338 | 32.125 | 28.786 | 77.828 | 1.00 | 22.91 | 6 |
| | ATOM | 2745 | O | GLU A 338 | 32.358 | 27.685 | 77.351 | 1.00 | 22.68 | 8 |
| | ATOM | 2746 | CB | GLU A 338 | 31.812 | 31.168 | 77.168 | 1.00 | 17.78 | 6 |
| | ATOM | 2747 | CG | GLU A 338 | 32.440 | 32.564 | 77.270 | 1.00 | 22.34 | 6 |
| | ATOM | 2748 | CD | GLU A 338 | 32.952 | 32.755 | 78.715 | 1.00 | 29.04 | 6 |
| | ATOM | 2749 | OE1 | GLU A 338 | 32.114 | 32.805 | 79.623 | 1.00 | 27.92 | 8 |
| | ATOM | 2750 | OE2 | GLU A 338 | 34.187 | 32.810 | 78.861 | 1.00 | 19.42 | 8 |
| | ATOM | 2751 | N | SER A 339 | 31.197 | 28.939 | 78.777 | 1.00 | 24.21 | 7 |
| | ATOM | 2752 | CA | SER A 339 | 30.450 | 27.883 | 79.434 | 1.00 | 24.36 | 6 |
| | ATOM | 2753 | C | SER A 339 | 29.691 | 26.926 | 78.538 | 1.00 | 21.82 | 6 |
| | ATOM | 2754 | O | SER A 339 | 29.675 | 25.711 | 78.789 | 1.00 | 24.25 | 8 |
| | ATOM | 2755 | CB | SER A 339 | 29.444 | 28.501 | 80.457 | 1.00 | 32.53 | 6 |
| | ATOM | 2756 | OG | SER A 339 | 30.214 | 29.253 | 81.421 | 1.00 | 35.18 | 8 |
| | ATOM | 2757 | N | LEU A 340 | 29.040 | 27.416 | 77.495 | 1.00 | 20.02 | 7 |
| | ATOM | 2758 | CA | LEU A 340 | 28.344 | 26.458 | 76.592 | 1.00 | 18.17 | 6 |
| | ATOM | 2759 | C | LEU A 340 | 29.104 | 26.412 | 75.236 | 1.00 | 19.43 | 6 |
| | ATOM | 2760 | O | LEU A 340 | 28.447 | 26.384 | 74.171 | 1.00 | 15.42 | 8 |
| | ATOM | 2761 | CB | LEU A 340 | 26.916 | 26.987 | 76.489 | 1.00 | 21.01 | 6 |

| ATOM | 2762 | CG | LEU A 340 | 26.161 | 27.034 | 77.864 | 1.00 | 22.85 | 6 |
| ATOM | 2763 | CD1 | LEU A 340 | 24.807 | 27.708 | 77.681 | 1.00 | 29.12 | 6 |
| ATOM | 2764 | CD2 | LEU A 340 | 25.934 | 25.631 | 78.372 | 1.00 | 20.86 | 6 |
| ATOM | 2765 | N | GLU A 341 | 30.410 | 26.644 | 75.257 | 1.00 | 15.17 | 7 |
| ATOM | 2766 | CA | GLU A 341 | 31.187 | 26.743 | 74.028 | 1.00 | 16.51 | 6 |
| ATOM | 2767 | C | GLU A 341 | 30.716 | 25.775 | 72.914 | 1.00 | 13.73 | 6 |
| ATOM | 2768 | O | GLU A 341 | 30.620 | 24.575 | 73.046 | 1.00 | 12.93 | 8 |
| ATOM | 2769 | CB | GLU A 341 | 32.678 | 26.615 | 74.252 | 1.00 | 15.92 | 6 |
| ATOM | 2770 | CG | GLU A 341 | 33.532 | 26.518 | 72.994 | 1.00 | 34.72 | 6 |
| ATOM | 2771 | CD | GLU A 341 | 35.022 | 26.565 | 73.226 | 1.00 | 38.23 | 6 |
| ATOM | 2772 | OE1 | GLU A 341 | 35.568 | 25.733 | 73.968 | 1.00 | 49.78 | 8 |
| ATOM | 2773 | OE2 | GLU A 341 | 35.730 | 27.429 | 72.683 | 1.00 | 51.54 | 8 |
| ATOM | 2774 | N | SER A 342 | 30.307 | 26.343 | 71.767 | 1.00 | 13.62 | 7 |
| ATOM | 2775 | CA | SER A 342 | 29.800 | 25.498 | 70.610 | 1.00 | 12.16 | 6 |
| ATOM | 2776 | C | SER A 342 | 29.630 | 26.518 | 69.453 | 1.00 | 9.95 | 6 |
| ATOM | 2777 | O | SER A 342 | 28.516 | 26.840 | 69.089 | 1.00 | 10.55 | 8 |
| ATOM | 2778 | CB | SER A 342 | 28.487 | 24.856 | 71.014 | 1.00 | 11.64 | 6 |
| ATOM | 2779 | OG | SER A 342 | 27.526 | 25.740 | 71.578 | 1.00 | 10.33 | 8 |
| ATOM | 2780 | N | PHE A 343 | 30.743 | 27.112 | 69.096 | 1.00 | 8.26 | 7 |
| ATOM | 2781 | CA | PHE A 343 | 30.845 | 28.273 | 68.243 | 1.00 | 14.28 | 6 |
| ATOM | 2782 | C | PHE A 343 | 30.727 | 27.865 | 66.752 | 1.00 | 14.09 | 6 |
| ATOM | 2783 | O | PHE A 343 | 31.490 | 26.977 | 66.427 | 1.00 | 15.10 | 8 |
| ATOM | 2784 | CB | PHE A 343 | 32.150 | 29.020 | 68.461 | 1.00 | 7.83 | 6 |
| ATOM | 2785 | CG | PHE A 343 | 32.130 | 30.489 | 68.111 | 1.00 | 18.35 | 6 |
| ATOM | 2786 | CD1 | PHE A 343 | 31.135 | 31.324 | 68.579 | 1.00 | 13.69 | 6 |
| ATOM | 2787 | CD2 | PHE A 343 | 33.124 | 31.041 | 67.314 | 1.00 | 15.40 | 6 |
| ATOM | 2788 | CE1 | PHE A 343 | 31.095 | 32.664 | 68.242 | 1.00 | 12.25 | 6 |
| ATOM | 2789 | CE2 | PHE A 343 | 33.113 | 32.400 | 67.009 | 1.00 | 10.93 | 6 |
| ATOM | 2790 | CZ | PHE A 343 | 32.119 | 33.211 | 67.491 | 1.00 | 10.68 | 6 |
| ATOM | 2791 | N | VAL A 344 | 29.802 | 28.461 | 66.025 | 1.00 | 15.94 | 7 |
| ATOM | 2792 | CA | VAL A 344 | 29.677 | 28.038 | 64.592 | 1.00 | 13.97 | 6 |
| ATOM | 2793 | C | VAL A 344 | 30.922 | 28.436 | 63.790 | 1.00 | 11.82 | 6 |
| ATOM | 2794 | O | VAL A 344 | 31.366 | 29.575 | 63.779 | 1.00 | 13.31 | 8 |
| ATOM | 2795 | CB | VAL A 344 | 28.406 | 28.592 | 63.990 | 1.00 | 17.29 | 6 |
| ATOM | 2796 | CG1 | VAL A 344 | 28.214 | 28.200 | 62.492 | 1.00 | 14.50 | 6 |
| ATOM | 2797 | CG2 | VAL A 344 | 27.178 | 28.056 | 64.744 | 1.00 | 4.23 | 6 |
| ATOM | 2798 | N | GLN A 345 | 31.557 | 27.472 | 63.108 | 1.00 | 11.93 | 7 |
| ATOM | 2799 | CA | GLN A 345 | 32.791 | 27.751 | 62.371 | 1.00 | 13.62 | 6 |
| ATOM | 2800 | C | GLN A 345 | 32.641 | 28.845 | 61.303 | 1.00 | 15.48 | 6 |
| ATOM | 2801 | O | GLN A 345 | 31.579 | 29.089 | 60.695 | 1.00 | 14.28 | 8 |
| ATOM | 2802 | CB | GLN A 345 | 33.410 | 26.543 | 61.726 | 1.00 | 16.29 | 6 |
| ATOM | 2803 | CG | GLN A 345 | 33.398 | 25.247 | 62.466 | 1.00 | 28.74 | 6 |
| ATOM | 2804 | CD | GLN A 345 | 34.757 | 24.688 | 62.741 | 1.00 | 41.22 | 6 |
| ATOM | 2805 | OE1 | GLN A 345 | 34.914 | 23.475 | 62.547 | 1.00 | 52.69 | 8 |
| ATOM | 2806 | NE2 | GLN A 345 | 35.721 | 25.561 | 62.976 | 1.00 | 49.90 | 7 |
| ATOM | 2807 | N | GLU A 346 | 33.742 | 29.587 | 61.162 | 1.00 | 12.40 | 7 |
| ATOM | 2808 | CA | GLU A 346 | 33.672 | 30.778 | 60.332 | 1.00 | 14.26 | 6 |
| ATOM | 2809 | C | GLU A 346 | 33.214 | 30.541 | 58.876 | 1.00 | 14.02 | 6 |
| ATOM | 2810 | O | GLU A 346 | 32.423 | 31.331 | 58.393 | 1.00 | 13.79 | 8 |
| ATOM | 2811 | CB | GLU A 346 | 35.068 | 31.404 | 60.394 | 1.00 | 14.25 | 6 |
| ATOM | 2812 | CG | GLU A 346 | 35.121 | 32.681 | 59.551 | 1.00 | 32.42 | 6 |
| ATOM | 2813 | CD | GLU A 346 | 36.535 | 33.237 | 59.460 | 1.00 | 48.94 | 6 |
| ATOM | 2814 | OE1 | GLU A 346 | 37.450 | 32.689 | 60.123 | 1.00 | 55.69 | 8 |
| ATOM | 2815 | OE2 | GLU A 346 | 36.723 | 34.230 | 58.719 | 1.00 | 52.71 | 8 |
| ATOM | 2816 | N | TRP A 347 | 33.609 | 29.456 | 58.224 | 1.00 | 12.79 | 7 |
| ATOM | 2817 | CA | TRP A 347 | 33.170 | 29.294 | 56.818 | 1.00 | 16.92 | 6 |
| ATOM | 2818 | C | TRP A 347 | 31.661 | 29.131 | 56.734 | 1.00 | 17.45 | 6 |
| ATOM | 2819 | O | TRP A 347 | 31.046 | 29.639 | 55.787 | 1.00 | 17.59 | 8 |
| ATOM | 2820 | CB | TRP A 347 | 33.884 | 28.078 | 56.211 | 1.00 | 8.52 | 6 |
| ATOM | 2821 | CG | TRP A 347 | 33.437 | 26.750 | 56.724 | 1.00 | 17.57 | 6 |
| ATOM | 2822 | CD1 | TRP A 347 | 33.897 | 26.140 | 57.885 | 1.00 | 16.50 | 6 |
| ATOM | 2823 | CD2 | TRP A 347 | 32.447 | 25.874 | 56.186 | 1.00 | 20.29 | 6 |
| ATOM | 2824 | NE1 | TRP A 347 | 33.231 | 24.958 | 58.076 | 1.00 | 15.01 | 7 |
| ATOM | 2825 | CE2 | TRP A 347 | 32.352 | 24.755 | 57.043 | 1.00 | 23.63 | 6 |
| ATOM | 2826 | CE3 | TRP A 347 | 31.625 | 25.925 | 55.052 | 1.00 | 25.23 | 6 |

| | ATOM | 2827 | CZ2 | TRP A 347 | 31.490 | 23.692 | 56.784 | 1.00 | 22.24 | 6 |
|---|---|---|---|---|---|---|---|---|---|---|
| | ATOM | 2828 | CZ3 | TRP A 347 | 30.765 | 24.880 | 54.811 | 1.00 | 18.80 | 6 |
| | ATOM | 2829 | CH2 | TRP A 347 | 30.708 | 23.754 | 55.639 | 1.00 | 19.24 | 6 |
| | ATOM | 2830 | N | PHE A 348 | 31.008 | 28.439 | 57.686 | 1.00 | 13.89 | 7 |
| 5 | ATOM | 2831 | CA | PHE A 348 | 29.580 | 28.185 | 57.685 | 1.00 | 12.21 | 6 |
| | ATOM | 2832 | C | PHE A 348 | 28.777 | 29.372 | 58.138 | 1.00 | 13.54 | 6 |
| | ATOM | 2833 | O | PHE A 348 | 27.569 | 29.424 | 57.920 | 1.00 | 15.25 | 8 |
| | ATOM | 2834 | CB | PHE A 348 | 29.253 | 26.982 | 58.612 | 1.00 | 13.35 | 6 |
| | ATOM | 2835 | CG | PHE A 348 | 27.920 | 26.338 | 58.393 | 1.00 | 17.24 | 6 |
| 10 | ATOM | 2836 | CD1 | PHE A 348 | 27.774 | 25.380 | 57.390 | 1.00 | 16.47 | 6 |
| | ATOM | 2837 | CD2 | PHE A 348 | 26.798 | 26.653 | 59.153 | 1.00 | 10.80 | 6 |
| | ATOM | 2838 | CE1 | PHE A 348 | 26.581 | 24.725 | 57.137 | 1.00 | 16.99 | 6 |
| | ATOM | 2839 | CE2 | PHE A 348 | 25.594 | 26.042 | 58.880 | 1.00 | 15.47 | 6 |
| | ATOM | 2840 | CZ | PHE A 348 | 25.468 | 25.067 | 57.898 | 1.00 | 17.41 | 6 |
| 15 | ATOM | 2841 | N | LYS A 349 | 29.441 | 30.318 | 58.853 | 1.00 | 12.58 | 7 |
| | ATOM | 2842 | CA | LYS A 349 | 28.736 | 31.427 | 59.451 | 1.00 | 14.41 | 6 |
| | ATOM | 2843 | C | LYS A 349 | 27.853 | 32.265 | 58.554 | 1.00 | 14.28 | 6 |
| | ATOM | 2844 | O | LYS A 349 | 26.689 | 32.562 | 58.876 | 1.00 | 13.07 | 8 |
| | ATOM | 2845 | CB | LYS A 349 | 29.685 | 32.253 | 60.351 | 1.00 | 11.83 | 6 |
| 20 | ATOM | 2846 | CG | LYS A 349 | 28.973 | 33.313 | 61.209 | 1.00 | 18.84 | 6 |
| | ATOM | 2847 | CD | LYS A 349 | 29.688 | 33.532 | 62.566 | 1.00 | 15.69 | 6 |
| | ATOM | 2848 | CE | LYS A 349 | 29.183 | 32.553 | 63.636 | 1.00 | 18.65 | 6 |
| | ATOM | 2849 | NZ | LYS A 349 | 30.124 | 32.604 | 64.865 | 1.00 | 14.15 | 7 |
| | ATOM | 2850 | N | PRO A 350 | 28.313 | 32.630 | 57.340 | 1.00 | 13.75 | 7 |
| 25 | ATOM | 2851 | CA | PRO A 350 | 27.479 | 33.386 | 56.384 | 1.00 | 9.95 | 6 |
| | ATOM | 2852 | C | PRO A 350 | 26.302 | 32.527 | 55.993 | 1.00 | 6.14 | 6 |
| | ATOM | 2853 | O | PRO A 350 | 25.181 | 33.057 | 55.892 | 1.00 | 9.02 | 8 |
| | ATOM | 2854 | CB | PRO A 350 | 28.425 | 33.760 | 55.209 | 1.00 | 11.63 | 6 |
| | ATOM | 2855 | CG | PRO A 350 | 29.789 | 33.521 | 55.791 | 1.00 | 13.93 | 6 |
| 30 | ATOM | 2856 | CD | PRO A 350 | 29.690 | 32.450 | 56.896 | 1.00 | 12.47 | 6 |
| | ATOM | 2857 | N | LEU A 351 | 26.423 | 31.209 | 55.890 | 1.00 | 5.76 | 7 |
| | ATOM | 2858 | CA | LEU A 351 | 25.254 | 30.399 | 55.544 | 1.00 | 7.58 | 6 |
| | ATOM | 2859 | C | LEU A 351 | 24.179 | 30.374 | 56.632 | 1.00 | 11.79 | 6 |
| | ATOM | 2860 | O | LEU A 351 | 22.931 | 30.395 | 56.432 | 1.00 | 8.84 | 8 |
| 35 | ATOM | 2861 | CB | LEU A 351 | 25.666 | 28.953 | 55.261 | 1.00 | 7.39 | 6 |
| | ATOM | 2862 | CG | LEU A 351 | 26.395 | 28.531 | 53.988 | 1.00 | 17.59 | 6 |
| | ATOM | 2863 | CD1 | LEU A 351 | 27.764 | 29.180 | 53.897 | 1.00 | 16.27 | 6 |
| | ATOM | 2864 | CD2 | LEU A 351 | 26.526 | 27.034 | 53.789 | 1.00 | 9.25 | 6 |
| | ATOM | 2865 | N | ALA A 352 | 24.724 | 30.316 | 57.908 | 1.00 | 9.34 | 7 |
| 40 | ATOM | 2866 | CA | ALA A 352 | 23.722 | 30.269 | 59.053 | 1.00 | 6.62 | 6 |
| | ATOM | 2867 | C | ALA A 352 | 23.055 | 31.607 | 59.170 | 1.00 | 2.63 | 6 |
| | ATOM | 2868 | O | ALA A 352 | 21.823 | 31.709 | 59.309 | 1.00 | 7.27 | 8 |
| | ATOM | 2869 | CB | ALA A 352 | 24.615 | 30.028 | 60.331 | 1.00 | 8.00 | 6 |
| | ATOM | 2870 | N | TYR A 353 | 23.733 | 32.721 | 58.894 | 1.00 | 4.31 | 7 |
| 45 | ATOM | 2871 | CA | TYR A 353 | 23.040 | 34.002 | 58.912 | 1.00 | 6.40 | 6 |
| | ATOM | 2872 | C | TYR A 353 | 21.981 | 34.202 | 57.823 | 1.00 | 10.05 | 6 |
| | ATOM | 2873 | O | TYR A 353 | 20.862 | 34.755 | 58.003 | 1.00 | 11.41 | 8 |
| | ATOM | 2874 | CB | TYR A 353 | 24.034 | 35.166 | 58.976 | 1.00 | 9.62 | 6 |
| | ATOM | 2875 | CG | TYR A 353 | 24.455 | 35.483 | 60.418 | 1.00 | 14.53 | 6 |
| 50 | ATOM | 2876 | CD1 | TYR A 353 | 23.589 | 36.097 | 61.305 | 1.00 | 18.62 | 6 |
| | ATOM | 2877 | CD2 | TYR A 353 | 25.726 | 35.177 | 60.886 | 1.00 | 17.29 | 6 |
| | ATOM | 2878 | CE1 | TYR A 353 | 23.950 | 36.375 | 62.629 | 1.00 | 17.02 | 6 |
| | ATOM | 2879 | CE2 | TYR A 353 | 26.111 | 35.447 | 62.213 | 1.00 | 19.57 | 6 |
| | ATOM | 2880 | CZ | TYR A 353 | 25.209 | 36.032 | 63.088 | 1.00 | 16.24 | 6 |
| 55 | ATOM | 2881 | OH | TYR A 353 | 25.568 | 36.289 | 64.398 | 1.00 | 12.95 | 8 |
| | ATOM | 2882 | N | ALA A 354 | 22.242 | 33.544 | 56.647 | 1.00 | 11.17 | 7 |
| | ATOM | 2883 | CA | ALA A 354 | 21.279 | 33.699 | 55.500 | 1.00 | 9.08 | 6 |
| | ATOM | 2884 | C | ALA A 354 | 20.072 | 32.896 | 55.874 | 1.00 | 5.76 | 6 |
| | ATOM | 2885 | O | ALA A 354 | 18.942 | 33.293 | 55.634 | 1.00 | 6.50 | 8 |
| 60 | ATOM | 2886 | CB | ALA A 354 | 21.964 | 33.141 | 54.255 | 1.00 | 8.32 | 6 |
| | ATOM | 2887 | N | LEU A 355 | 20.293 | 31.740 | 56.476 | 1.00 | 7.26 | 7 |
| | ATOM | 2888 | CA | LEU A 355 | 19.114 | 30.958 | 56.901 | 1.00 | 8.15 | 6 |
| | ATOM | 2889 | C | LEU A 355 | 18.208 | 31.687 | 57.869 | 1.00 | 13.11 | 6 |
| | ATOM | 2890 | O | LEU A 355 | 16.961 | 31.630 | 57.758 | 1.00 | 14.67 | 8 |
| 65 | ATOM | 2891 | CB | LEU A 355 | 19.670 | 29.630 | 57.456 | 1.00 | 11.74 | 6 |

| ATOM | 2892 | CG | LEU A 355 | 18.601 | 28.784 | 58.187 | 1.00 | 18.51 | 6 |
| ATOM | 2893 | CD1 | LEU A 355 | 17.767 | 28.021 | 57.175 | 1.00 | 23.46 | 6 |
| ATOM | 2894 | CD2 | LEU A 355 | 19.293 | 27.745 | 59.047 | 1.00 | 20.77 | 6 |
| ATOM | 2895 | N | ILE A 356 | 18.803 | 32.427 | 58.881 | 1.00 | 12.17 | 7 |
| ATOM | 2896 | CA | ILE A 356 | 17.858 | 33.039 | 59.827 | 1.00 | 12.67 | 6 |
| ATOM | 2897 | C | ILE A 356 | 17.463 | 34.402 | 59.307 | 1.00 | 13.33 | 6 |
| ATOM | 2898 | O | ILE A 356 | 16.406 | 34.878 | 59.760 | 1.00 | 14.98 | 8 |
| ATOM | 2899 | CB | ILE A 356 | 18.478 | 33.139 | 61.284 | 1.00 | 11.08 | 6 |
| ATOM | 2900 | CG1 | ILE A 356 | 19.683 | 34.049 | 61.369 | 1.00 | 11.75 | 6 |
| ATOM | 2901 | CG2 | ILE A 356 | 18.899 | 31.710 | 61.679 | 1.00 | 5.59 | 6 |
| ATOM | 2902 | CD1 | ILE A 356 | 20.169 | 34.327 | 62.846 | 1.00 | 12.46 | 6 |
| ATOM | 2903 | N | LEU A 357 | 18.239 | 35.098 | 58.466 | 1.00 | 9.14 | 7 |
| ATOM | 2904 | CA | LEU A 357 | 17.765 | 36.443 | 58.112 | 1.00 | 10.92 | 6 |
| ATOM | 2905 | C | LEU A 357 | 16.851 | 36.483 | 56.874 | 1.00 | 11.65 | 6 |
| ATOM | 2906 | O | LEU A 357 | 16.159 | 37.475 | 56.724 | 1.00 | 13.44 | 8 |
| ATOM | 2907 | CB | LEU A 357 | 18.970 | 37.362 | 57.908 | 1.00 | 15.64 | 6 |
| ATOM | 2908 | CG | LEU A 357 | 19.863 | 37.520 | 59.155 | 1.00 | 23.64 | 6 |
| ATOM | 2909 | CD1 | LEU A 357 | 21.206 | 38.149 | 58.863 | 1.00 | 9.34 | 6 |
| ATOM | 2910 | CD2 | LEU A 357 | 19.129 | 38.400 | 60.180 | 1.00 | 9.22 | 6 |
| ATOM | 2911 | N | THR A 358 | 16.853 | 35.476 | 56.009 | 1.00 | 13.41 | 7 |
| ATOM | 2912 | CA | THR A 358 | 16.047 | 35.618 | 54.767 | 1.00 | 15.69 | 6 |
| ATOM | 2913 | C | THR A 358 | 14.855 | 34.712 | 54.671 | 1.00 | 17.67 | 6 |
| ATOM | 2914 | O | THR A 358 | 14.114 | 34.871 | 53.669 | 1.00 | 18.83 | 8 |
| ATOM | 2915 | CB | THR A 358 | 16.892 | 35.503 | 53.488 | 1.00 | 6.92 | 6 |
| ATOM | 2916 | OG1 | THR A 358 | 17.493 | 34.198 | 53.338 | 1.00 | 9.85 | 8 |
| ATOM | 2917 | CG2 | THR A 358 | 18.016 | 36.551 | 53.490 | 1.00 | 6.29 | 6 |
| ATOM | 2918 | N | ARG A 359 | 14.629 | 33.807 | 55.632 | 1.00 | 15.05 | 7 |
| ATOM | 2919 | CA | ARG A 359 | 13.414 | 33.009 | 55.653 | 1.00 | 12.87 | 6 |
| ATOM | 2920 | C | ARG A 359 | 12.342 | 33.824 | 56.365 | 1.00 | 15.49 | 6 |
| ATOM | 2921 | O | ARG A 359 | 12.628 | 34.769 | 57.122 | 1.00 | 15.95 | 8 |
| ATOM | 2922 | CB | ARG A 359 | 13.597 | 31.645 | 56.291 | 1.00 | 14.00 | 6 |
| ATOM | 2923 | CG | ARG A 359 | 14.651 | 30.824 | 55.541 | 1.00 | 15.78 | 6 |
| ATOM | 2924 | CD | ARG A 359 | 14.643 | 29.396 | 56.080 | 1.00 | 11.69 | 6 |
| ATOM | 2925 | NE | ARG A 359 | 13.411 | 28.697 | 56.026 | 1.00 | 18.91 | 7 |
| ATOM | 2926 | CZ | ARG A 359 | 12.387 | 27.893 | 55.960 | 1.00 | 18.82 | 6 |
| ATOM | 2927 | NH1 | ARG A 359 | 12.470 | 26.638 | 55.555 | 1.00 | 37.09 | 7 |
| ATOM | 2928 | NH2 | ARG A 359 | 11.134 | 28.231 | 56.128 | 1.00 | 35.48 | 7 |
| ATOM | 2929 | N | GLU A 360 | 11.075 | 33.508 | 56.124 | 1.00 | 13.34 | 7 |
| ATOM | 2930 | CA | GLU A 360 | 10.009 | 34.272 | 56.766 | 1.00 | 16.87 | 6 |
| ATOM | 2931 | C | GLU A 360 | 9.797 | 33.905 | 58.272 | 1.00 | 17.41 | 6 |
| ATOM | 2932 | O | GLU A 360 | 9.164 | 34.657 | 58.978 | 1.00 | 17.91 | 8 |
| ATOM | 2933 | CB | GLU A 360 | 8.753 | 33.701 | 56.089 | 1.00 | 22.63 | 6 |
| ATOM | 2934 | CG | GLU A 360 | 7.507 | 34.543 | 56.320 | 1.00 | 43.72 | 6 |
| ATOM | 2935 | CD | GLU A 360 | 6.319 | 33.647 | 55.944 | 1.00 | 53.59 | 6 |
| ATOM | 2936 | OE1 | GLU A 360 | 6.476 | 32.823 | 55.022 | 1.00 | 33.23 | 8 |
| ATOM | 2937 | OE2 | GLU A 360 | 5.274 | 33.777 | 56.616 | 1.00 | 69.43 | 8 |
| ATOM | 2938 | N | GLN A 361 | 10.024 | 32.680 | 58.690 | 1.00 | 16.57 | 7 |
| ATOM | 2939 | CA | GLN A 361 | 9.823 | 32.228 | 60.052 | 1.00 | 20.85 | 6 |
| ATOM | 2940 | C | GLN A 361 | 10.894 | 32.729 | 61.033 | 1.00 | 18.61 | 6 |
| ATOM | 2941 | O | GLN A 361 | 12.109 | 32.718 | 60.781 | 1.00 | 15.15 | 8 |
| ATOM | 2942 | CB | GLN A 361 | 9.981 | 30.674 | 60.070 | 1.00 | 15.83 | 6 |
| ATOM | 2943 | CG | GLN A 361 | 8.810 | 30.118 | 59.253 | 1.00 | 20.02 | 6 |
| ATOM | 2944 | CD | GLN A 361 | 9.143 | 29.897 | 57.778 | 1.00 | 26.16 | 6 |
| ATOM | 2945 | OE1 | GLN A 361 | 10.184 | 30.238 | 57.224 | 1.00 | 15.02 | 8 |
| ATOM | 2946 | NE2 | GLN A 361 | 8.253 | 29.232 | 57.073 | 1.00 | 22.71 | 7 |
| ATOM | 2947 | N | GLY A 362 | 10.387 | 33.010 | 62.256 | 1.00 | 19.95 | 7 |
| ATOM | 2948 | CA | GLY A 362 | 11.266 | 33.294 | 63.385 | 1.00 | 16.72 | 6 |
| ATOM | 2949 | C | GLY A 362 | 11.673 | 34.720 | 63.504 | 1.00 | 19.34 | 6 |
| ATOM | 2950 | O | GLY A 362 | 11.589 | 35.495 | 62.537 | 1.00 | 19.82 | 8 |
| ATOM | 2951 | N | TYR A 363 | 12.132 | 35.159 | 64.678 | 1.00 | 17.12 | 7 |
| ATOM | 2952 | CA | TYR A 363 | 12.640 | 36.516 | 64.902 | 1.00 | 13.85 | 6 |
| ATOM | 2953 | C | TYR A 363 | 14.118 | 36.349 | 65.165 | 1.00 | 14.95 | 6 |
| ATOM | 2954 | O | TYR A 363 | 14.576 | 35.736 | 66.157 | 1.00 | 15.51 | 8 |
| ATOM | 2955 | CB | TYR A 363 | 11.833 | 37.074 | 66.067 | 1.00 | 16.66 | 6 |
| ATOM | 2956 | CG | TYR A 363 | 12.145 | 38.458 | 66.549 | 1.00 | 17.64 | 6 |

| ATOM | 2957 | CD1 | TYR A 363 | 12.827 | 39.352 | 65.739 | 1.00 | 18.51 | 6 |
|------|------|-----|-----------|--------|--------|--------|------|-------|---|
| ATOM | 2958 | CD2 | TYR A 363 | 11.702 | 38.910 | 67.805 | 1.00 | 18.47 | 6 |
| ATOM | 2959 | CE1 | TYR A 363 | 13.111 | 40.649 | 66.129 | 1.00 | 21.67 | 6 |
| ATOM | 2960 | CE2 | TYR A 363 | 11.970 | 40.197 | 68.233 | 1.00 | 19.85 | 6 |
| ATOM | 2961 | CZ  | TYR A 363 | 12.665 | 41.058 | 67.408 | 1.00 | 20.59 | 6 |
| ATOM | 2962 | OH  | TYR A 363 | 12.963 | 42.342 | 67.782 | 1.00 | 17.62 | 8 |
| ATOM | 2963 | N   | PRO A 364 | 14.971 | 36.846 | 64.285 | 1.00 | 14.44 | 7 |
| ATOM | 2964 | CA  | PRO A 364 | 16.376 | 36.602 | 64.232 | 1.00 | 12.94 | 6 |
| ATOM | 2965 | C   | PRO A 364 | 17.157 | 37.600 | 65.050 | 1.00 | 10.83 | 6 |
| ATOM | 2966 | O   | PRO A 364 | 16.828 | 38.782 | 65.173 | 1.00 | 12.01 | 8 |
| ATOM | 2967 | CB  | PRO A 364 | 16.861 | 36.777 | 62.728 | 1.00 | 12.52 | 6 |
| ATOM | 2968 | CG  | PRO A 364 | 15.821 | 37.780 | 62.253 | 1.00 | 13.06 | 6 |
| ATOM | 2969 | CD  | PRO A 364 | 14.522 | 37.501 | 63.016 | 1.00 | 17.02 | 6 |
| ATOM | 2970 | N   | SER A 365 | 18.303 | 37.060 | 65.467 | 1.00 | 12.81 | 7 |
| ATOM | 2971 | CA  | SER A 365 | 19.177 | 37.955 | 66.264 | 1.00 | 13.83 | 6 |
| ATOM | 2972 | C   | SER A 365 | 20.617 | 37.834 | 65.836 | 1.00 | 13.08 | 6 |
| ATOM | 2973 | O   | SER A 365 | 21.186 | 36.734 | 65.692 | 1.00 | 15.72 | 8 |
| ATOM | 2974 | CB  | SER A 365 | 19.016 | 37.409 | 67.724 | 1.00 | 19.64 | 6 |
| ATOM | 2975 | OG  | SER A 365 | 19.975 | 38.079 | 68.550 | 1.00 | 28.22 | 8 |
| ATOM | 2976 | N   | VAL A 366 | 21.271 | 38.967 | 65.698 | 1.00 | 12.55 | 7 |
| ATOM | 2977 | CA  | VAL A 366 | 22.671 | 38.974 | 65.280 | 1.00 | 13.77 | 6 |
| ATOM | 2978 | C   | VAL A 366 | 23.538 | 39.159 | 66.526 | 1.00 | 15.58 | 6 |
| ATOM | 2979 | O   | VAL A 366 | 23.215 | 40.017 | 67.353 | 1.00 | 14.42 | 8 |
| ATOM | 2980 | CB  | VAL A 366 | 22.890 | 40.239 | 64.373 | 1.00 | 17.08 | 6 |
| ATOM | 2981 | CG1 | VAL A 366 | 24.327 | 40.304 | 63.919 | 1.00 | 11.12 | 6 |
| ATOM | 2982 | CG2 | VAL A 366 | 21.942 | 40.159 | 63.185 | 1.00 | 23.07 | 6 |
| ATOM | 2983 | N   | PHE A 367 | 24.638 | 38.457 | 66.594 | 1.00 | 14.78 | 7 |
| ATOM | 2984 | CA  | PHE A 367 | 25.533 | 38.506 | 67.717 | 1.00 | 14.70 | 6 |
| ATOM | 2985 | C   | PHE A 367 | 26.613 | 39.550 | 67.502 | 1.00 | 17.61 | 6 |
| ATOM | 2986 | O   | PHE A 367 | 27.427 | 39.578 | 66.556 | 1.00 | 16.79 | 8 |
| ATOM | 2987 | CB  | PHE A 367 | 26.178 | 37.117 | 67.871 | 1.00 | 13.83 | 6 |
| ATOM | 2988 | CG  | PHE A 367 | 27.171 | 36.983 | 69.000 | 1.00 | 17.14 | 6 |
| ATOM | 2989 | CD1 | PHE A 367 | 26.912 | 37.575 | 70.245 | 1.00 | 21.47 | 6 |
| ATOM | 2990 | CD2 | PHE A 367 | 28.314 | 36.224 | 68.836 | 1.00 | 10.74 | 6 |
| ATOM | 2991 | CE1 | PHE A 367 | 27.811 | 37.426 | 71.295 | 1.00 | 17.03 | 6 |
| ATOM | 2992 | CE2 | PHE A 367 | 29.219 | 36.070 | 69.893 | 1.00 | 20.19 | 6 |
| ATOM | 2993 | CZ  | PHE A 367 | 28.970 | 36.675 | 71.138 | 1.00 | 11.94 | 6 |
| ATOM | 2994 | N   | TYR A 368 | 26.770 | 40.425 | 68.478 | 1.00 | 16.71 | 7 |
| ATOM | 2995 | CA  | TYR A 368 | 27.823 | 41.428 | 68.486 | 1.00 | 18.35 | 6 |
| ATOM | 2996 | C   | TYR A 368 | 29.182 | 40.803 | 68.219 | 1.00 | 19.12 | 6 |
| ATOM | 2997 | O   | TYR A 368 | 30.029 | 41.415 | 67.524 | 1.00 | 21.05 | 8 |
| ATOM | 2998 | CB  | TYR A 368 | 27.806 | 42.189 | 69.810 | 1.00 | 17.30 | 6 |
| ATOM | 2999 | CG  | TYR A 368 | 28.846 | 43.292 | 69.966 | 1.00 | 17.20 | 6 |
| ATOM | 3000 | CD1 | TYR A 368 | 30.183 | 43.012 | 70.185 | 1.00 | 14.16 | 6 |
| ATOM | 3001 | CD2 | TYR A 368 | 28.424 | 44.628 | 69.933 | 1.00 | 15.05 | 6 |
| ATOM | 3002 | CE1 | TYR A 368 | 31.098 | 44.049 | 70.329 | 1.00 | 16.57 | 6 |
| ATOM | 3003 | CE2 | TYR A 368 | 29.321 | 45.670 | 70.080 | 1.00 | 14.72 | 6 |
| ATOM | 3004 | CZ  | TYR A 368 | 30.641 | 45.354 | 70.276 | 1.00 | 18.79 | 6 |
| ATOM | 3005 | OH  | TYR A 368 | 31.554 | 46.387 | 70.443 | 1.00 | 24.91 | 8 |
| ATOM | 3006 | N   | GLY A 369 | 29.470 | 39.650 | 68.835 | 1.00 | 16.89 | 7 |
| ATOM | 3007 | CA  | GLY A 369 | 30.779 | 39.052 | 68.692 | 1.00 | 19.01 | 6 |
| ATOM | 3008 | C   | GLY A 369 | 31.071 | 38.607 | 67.249 | 1.00 | 21.56 | 6 |
| ATOM | 3009 | O   | GLY A 369 | 32.237 | 38.589 | 66.852 | 1.00 | 20.31 | 8 |
| ATOM | 3010 | N   | ASP A 370 | 30.001 | 38.233 | 66.530 | 1.00 | 20.90 | 7 |
| ATOM | 3011 | CA  | ASP A 370 | 30.203 | 37.856 | 65.119 | 1.00 | 21.19 | 6 |
| ATOM | 3012 | C   | ASP A 370 | 30.346 | 39.143 | 64.279 | 1.00 | 21.90 | 6 |
| ATOM | 3013 | O   | ASP A 370 | 31.190 | 39.176 | 63.390 | 1.00 | 20.14 | 8 |
| ATOM | 3014 | CB  | ASP A 370 | 29.024 | 37.062 | 64.591 | 1.00 | 15.54 | 6 |
| ATOM | 3015 | CG  | ASP A 370 | 28.821 | 35.687 | 65.177 | 1.00 | 11.32 | 6 |
| ATOM | 3016 | OD1 | ASP A 370 | 29.755 | 34.957 | 65.507 | 1.00 | 14.67 | 8 |
| ATOM | 3017 | OD2 | ASP A 370 | 27.644 | 35.274 | 65.227 | 1.00 | 14.90 | 8 |
| ATOM | 3018 | N   | TYR A 371 | 29.527 | 40.158 | 64.522 | 1.00 | 19.84 | 7 |
| ATOM | 3019 | CA  | TYR A 371 | 29.508 | 41.372 | 63.764 | 1.00 | 20.87 | 6 |
| ATOM | 3020 | C   | TYR A 371 | 30.777 | 42.214 | 63.872 | 1.00 | 24.06 | 6 |
| ATOM | 3021 | O   | TYR A 371 | 31.488 | 42.507 | 62.853 | 1.00 | 22.38 | 8 |

| | | | | | | | | | |
|---|---|---|---|---|---|---|---|---|---|
| ATOM | 3022 | CB | TYR | A 371 | 28.249 | 42.138 | 64.122 | 1.00 20.00 | 6 |
| ATOM | 3023 | CG | TYR | A 371 | 27.931 | 43.235 | 63.129 | 1.00 22.37 | 6 |
| ATOM | 3024 | CD1 | TYR | A 371 | 27.170 | 42.920 | 61.978 | 1.00 20.86 | 6 |
| ATOM | 3025 | CD2 | TYR | A 371 | 28.342 | 44.537 | 63.356 | 1.00 23.52 | 6 |
| ATOM | 3026 | CE1 | TYR | A 371 | 26.846 | 43.910 | 61.073 | 1.00 22.15 | 6 |
| ATOM | 3027 | CE2 | TYR | A 371 | 28.028 | 45.531 | 62.449 | 1.00 27.44 | 6 |
| ATOM | 3028 | CZ | TYR | A 371 | 27.291 | 45.201 | 61.302 | 1.00 26.41 | 6 |
| ATOM | 3029 | OH | TYR | A 371 | 27.020 | 46.192 | 60.406 | 1.00 25.92 | 8 |
| ATOM | 3030 | N | TYR | A 372 | 31.113 | 42.576 | 65.113 | 1.00 20.55 | 7 |
| ATOM | 3031 | CA | TYR | A 372 | 32.343 | 43.299 | 65.392 | 1.00 20.27 | 6 |
| ATOM | 3032 | C | TYR | A 372 | 33.540 | 42.457 | 65.762 | 1.00 19.46 | 6 |
| ATOM | 3033 | O | TYR | A 372 | 34.585 | 43.086 | 65.922 | 1.00 19.22 | 8 |
| ATOM | 3034 | CB | TYR | A 372 | 32.138 | 44.358 | 66.485 | 1.00 22.02 | 6 |
| ATOM | 3035 | CG | TYR | A 372 | 31.116 | 45.411 | 66.145 | 1.00 25.43 | 6 |
| ATOM | 3036 | CD1 | TYR | A 372 | 31.414 | 46.287 | 65.077 | 1.00 29.79 | 6 |
| ATOM | 3037 | CD2 | TYR | A 372 | 29.907 | 45.563 | 66.768 | 1.00 25.19 | 6 |
| ATOM | 3038 | CE1 | TYR | A 372 | 30.523 | 47.274 | 64.698 | 1.00 29.82 | 6 |
| ATOM | 3039 | CE2 | TYR | A 372 | 29.007 | 46.561 | 66.415 | 1.00 27.56 | 6 |
| ATOM | 3040 | CZ | TYR | A 372 | 29.335 | 47.410 | 65.383 | 1.00 30.90 | 6 |
| ATOM | 3041 | OH | TYR | A 372 | 28.494 | 48.412 | 64.971 | 1.00 33.96 | 8 |
| ATOM | 3042 | N | GLY | A 373 | 33.569 | 41.146 | 65.801 | 1.00 20.64 | 7 |
| ATOM | 3043 | CA | GLY | A 373 | 34.745 | 40.352 | 66.120 | 1.00 21.67 | 6 |
| ATOM | 3044 | C | GLY | A 373 | 34.897 | 40.097 | 67.649 | 1.00 23.24 | 6 |
| ATOM | 3045 | O | GLY | A 373 | 34.142 | 40.563 | 68.495 | 1.00 22.78 | 8 |
| ATOM | 3046 | N | ILE | A 374 | 35.796 | 39.198 | 68.001 | 1.00 21.63 | 7 |
| ATOM | 3047 | CA | ILE | A 374 | 36.132 | 38.841 | 69.367 | 1.00 23.49 | 6 |
| ATOM | 3048 | C | ILE | A 374 | 37.666 | 38.724 | 69.375 | 1.00 21.40 | 6 |
| ATOM | 3049 | O | ILE | A 374 | 38.398 | 37.741 | 69.231 | 1.00 19.77 | 8 |
| ATOM | 3050 | CB | ILE | A 374 | 35.265 | 37.898 | 70.159 | 1.00 31.39 | 6 |
| ATOM | 3051 | CG1 | ILE | A 374 | 36.097 | 36.914 | 71.011 | 1.00 30.19 | 6 |
| ATOM | 3052 | CG2 | ILE | A 374 | 34.048 | 37.123 | 69.642 | 1.00 20.15 | 6 |
| ATOM | 3053 | CD1 | ILE | A 374 | 35.843 | 37.222 | 72.468 | 1.00 43.36 | 6 |
| ATOM | 3054 | N | PRO | A 375 | 38.261 | 39.908 | 69.563 | 1.00 21.92 | 7 |
| ATOM | 3055 | CA | PRO | A 375 | 39.697 | 40.117 | 69.418 | 1.00 24.23 | 6 |
| ATOM | 3056 | C | PRO | A 375 | 40.527 | 39.315 | 70.387 | 1.00 28.10 | 6 |
| ATOM | 3057 | O | PRO | A 375 | 41.627 | 38.900 | 69.995 | 1.00 30.20 | 8 |
| ATOM | 3058 | CB | PRO | A 375 | 40.001 | 41.594 | 69.537 | 1.00 23.29 | 6 |
| ATOM | 3059 | CG | PRO | A 375 | 38.651 | 42.217 | 69.774 | 1.00 22.77 | 6 |
| ATOM | 3060 | CD | PRO | A 375 | 37.565 | 41.183 | 69.739 | 1.00 20.77 | 6 |
| ATOM | 3061 | N | THR | A 376 | 39.963 | 39.027 | 71.557 | 1.00 26.59 | 7 |
| ATOM | 3062 | CA | THR | A 376 | 40.694 | 38.305 | 72.571 | 1.00 29.38 | 6 |
| ATOM | 3063 | C | THR | A 376 | 40.912 | 36.901 | 72.077 | 1.00 31.17 | 6 |
| ATOM | 3064 | O | THR | A 376 | 41.922 | 36.294 | 72.423 | 1.00 32.53 | 8 |
| ATOM | 3065 | CB | THR | A 376 | 39.882 | 38.365 | 73.888 | 1.00 34.99 | 6 |
| ATOM | 3066 | OG1 | THR | A 376 | 38.559 | 37.905 | 73.570 | 1.00 33.12 | 8 |
| ATOM | 3067 | CG2 | THR | A 376 | 39.737 | 39.808 | 74.366 | 1.00 29.78 | 6 |
| ATOM | 3068 | N | HIS | A 377 | 39.924 | 36.317 | 71.381 | 1.00 31.46 | 7 |
| ATOM | 3069 | CA | HIS | A 377 | 40.107 | 34.949 | 70.876 | 1.00 32.11 | 6 |
| ATOM | 3070 | C | HIS | A 377 | 40.481 | 35.154 | 69.425 | 1.00 33.61 | 6 |
| ATOM | 3071 | O | HIS | A 377 | 40.760 | 36.367 | 69.170 | 1.00 35.65 | 8 |
| ATOM | 3072 | CB | HIS | A 377 | 38.872 | 34.112 | 71.176 | 1.00 27.76 | 6 |
| ATOM | 3073 | CG | HIS | A 377 | 38.794 | 33.981 | 72.680 | 1.00 31.06 | 6 |
| ATOM | 3074 | ND1 | HIS | A 377 | 38.521 | 35.079 | 73.472 | 1.00 34.60 | 7 |
| ATOM | 3075 | CD2 | HIS | A 377 | 38.993 | 32.924 | 73.497 | 1.00 36.91 | 6 |
| ATOM | 3076 | CE1 | HIS | A 377 | 38.556 | 34.685 | 74.739 | 1.00 45.06 | 6 |
| ATOM | 3077 | NE2 | HIS | A 377 | 38.832 | 33.386 | 74.790 | 1.00 43.40 | 7 |
| ATOM | 3078 | N | SER | A 378 | 40.550 | 34.303 | 68.425 | 1.00 34.63 | 7 |
| ATOM | 3079 | CA | SER | A 378 | 41.010 | 35.069 | 67.178 | 1.00 36.89 | 6 |
| ATOM | 3080 | C | SER | A 378 | 39.918 | 35.297 | 66.174 | 1.00 35.75 | 6 |
| ATOM | 3081 | O | SER | A 378 | 40.081 | 34.897 | 65.027 | 1.00 38.61 | 8 |
| ATOM | 3082 | CB | SER | A 378 | 42.341 | 34.526 | 66.711 | 1.00 43.48 | 6 |
| ATOM | 3083 | OG | SER | A 378 | 43.304 | 35.530 | 67.068 | 1.00 56.38 | 8 |
| ATOM | 3084 | N | VAL | A 379 | 38.787 | 35.882 | 66.582 | 1.00 34.79 | 7 |
| ATOM | 3085 | CA | VAL | A 379 | 37.590 | 36.026 | 65.778 | 1.00 32.09 | 6 |
| ATOM | 3086 | C | VAL | A 379 | 37.439 | 37.399 | 65.148 | 1.00 30.08 | 6 |

| ATOM | 3087 | O | VAL | A | 379 | 37.076 | 38.373 | 65.789 | 1.00 | 29.50 | 8 |
|------|------|-----|-----|---|-----|--------|--------|--------|------|-------|----|
| ATOM | 3088 | CB | VAL | A | 379 | 36.301 | 35.708 | 66.561 | 1.00 | 31.07 | 6 |
| ATOM | 3089 | CG1 | VAL | A | 379 | 35.102 | 35.593 | 65.619 | 1.00 | 22.44 | 6 |
| ATOM | 3090 | CG2 | VAL | A | 379 | 36.468 | 34.420 | 67.358 | 1.00 | 29.31 | 6 |
| ATOM | 3091 | N | PRO | A | 380 | 37.638 | 37.423 | 63.830 | 1.00 | 28.72 | 7 |
| ATOM | 3092 | CA | PRO | A | 380 | 37.614 | 38.627 | 63.017 | 1.00 | 25.27 | 6 |
| ATOM | 3093 | C | PRO | A | 380 | 36.213 | 39.177 | 62.905 | 1.00 | 20.31 | 6 |
| ATOM | 3094 | O | PRO | A | 380 | 35.288 | 38.402 | 63.071 | 1.00 | 21.62 | 8 |
| ATOM | 3095 | CB | PRO | A | 380 | 38.136 | 38.219 | 61.599 | 1.00 | 26.88 | 6 |
| ATOM | 3096 | CG | PRO | A | 380 | 37.929 | 36.723 | 61.630 | 1.00 | 28.41 | 6 |
| ATOM | 3097 | CD | PRO | A | 380 | 38.033 | 36.231 | 63.057 | 1.00 | 28.36 | 6 |
| ATOM | 3098 | N | ALA | A | 381 | 36.031 | 40.454 | 62.723 | 1.00 | 18.38 | 7 |
| ATOM | 3099 | CA | ALA | A | 381 | 34.731 | 41.051 | 62.525 | 1.00 | 21.39 | 6 |
| ATOM | 3100 | C | ALA | A | 381 | 34.134 | 40.531 | 61.198 | 1.00 | 23.08 | 6 |
| ATOM | 3101 | O | ALA | A | 381 | 34.852 | 40.306 | 60.231 | 1.00 | 21.90 | 8 |
| ATOM | 3102 | CB | ALA | A | 381 | 34.872 | 42.548 | 62.522 | 1.00 | 21.51 | 6 |
| ATOM | 3103 | N | MET | A | 382 | 32.870 | 40.142 | 61.151 | 1.00 | 20.95 | 7 |
| ATOM | 3104 | CA | MET | A | 382 | 32.283 | 39.562 | 59.957 | 1.00 | 19.68 | 6 |
| ATOM | 3105 | C | MET | A | 382 | 31.243 | 40.480 | 59.371 | 1.00 | 19.80 | 6 |
| ATOM | 3106 | O | MET | A | 382 | 30.361 | 40.117 | 58.575 | 1.00 | 20.42 | 8 |
| ATOM | 3107 | CB | MET | A | 382 | 31.720 | 38.171 | 60.316 | 1.00 | 12.09 | 6 |
| ATOM | 3108 | CG | MET | A | 382 | 32.901 | 37.210 | 60.460 | 1.00 | 22.27 | 6 |
| ATOM | 3109 | SD | MET | A | 382 | 32.198 | 35.595 | 60.910 | 1.00 | 34.94 | 16 |
| ATOM | 3110 | CE | MET | A | 382 | 33.716 | 34.885 | 61.572 | 1.00 | 45.83 | 6 |
| ATOM | 3111 | N | LYS | A | 383 | 31.326 | 41.739 | 59.837 | 1.00 | 17.95 | 7 |
| ATOM | 3112 | CA | LYS | A | 383 | 30.428 | 42.787 | 59.377 | 1.00 | 20.66 | 6 |
| ATOM | 3113 | C | LYS | A | 383 | 30.348 | 42.796 | 57.822 | 1.00 | 20.83 | 6 |
| ATOM | 3114 | O | LYS | A | 383 | 29.264 | 42.891 | 57.272 | 1.00 | 22.65 | 8 |
| ATOM | 3115 | CB | LYS | A | 383 | 31.099 | 44.109 | 59.793 | 1.00 | 15.20 | 6 |
| ATOM | 3116 | CG | LYS | A | 383 | 30.330 | 45.327 | 59.325 | 1.00 | 24.36 | 6 |
| ATOM | 3117 | CD | LYS | A | 383 | 30.986 | 46.580 | 59.956 | 1.00 | 30.19 | 6 |
| ATOM | 3118 | CE | LYS | A | 383 | 30.647 | 47.797 | 59.077 | 1.00 | 33.69 | 6 |
| ATOM | 3119 | NZ | LYS | A | 383 | 29.187 | 47.850 | 58.718 | 1.00 | 27.34 | 7 |
| ATOM | 3120 | N | ALA | A | 384 | 31.506 | 42.740 | 57.175 | 1.00 | 21.38 | 7 |
| ATOM | 3121 | CA | ALA | A | 384 | 31.504 | 42.788 | 55.685 | 1.00 | 24.86 | 6 |
| ATOM | 3122 | C | ALA | A | 384 | 30.684 | 41.650 | 55.106 | 1.00 | 21.91 | 6 |
| ATOM | 3123 | O | ALA | A | 384 | 29.954 | 41.867 | 54.128 | 1.00 | 23.76 | 8 |
| ATOM | 3124 | CB | ALA | A | 384 | 32.911 | 42.774 | 55.106 | 1.00 | 20.64 | 6 |
| ATOM | 3125 | N | LYS | A | 385 | 30.746 | 40.467 | 55.665 | 1.00 | 19.75 | 7 |
| ATOM | 3126 | CA | LYS | A | 385 | 29.909 | 39.379 | 55.191 | 1.00 | 19.30 | 6 |
| ATOM | 3127 | C | LYS | A | 385 | 28.495 | 39.409 | 55.687 | 1.00 | 18.88 | 6 |
| ATOM | 3128 | O | LYS | A | 385 | 27.640 | 38.802 | 55.031 | 1.00 | 21.08 | 8 |
| ATOM | 3129 | CB | LYS | A | 385 | 30.574 | 38.054 | 55.561 | 1.00 | 24.42 | 6 |
| ATOM | 3130 | CG | LYS | A | 385 | 31.939 | 38.084 | 54.864 | 1.00 | 38.35 | 6 |
| ATOM | 3131 | CD | LYS | A | 385 | 32.421 | 36.669 | 54.612 | 1.00 | 40.27 | 6 |
| ATOM | 3132 | CE | LYS | A | 385 | 33.732 | 36.479 | 55.365 | 1.00 | 50.29 | 6 |
| ATOM | 3133 | NZ | LYS | A | 385 | 34.643 | 35.513 | 54.703 | 1.00 | 54.83 | 7 |
| ATOM | 3134 | N | ILE | A | 386 | 28.190 | 40.107 | 56.801 | 1.00 | 17.18 | 7 |
| ATOM | 3135 | CA | ILE | A | 386 | 26.800 | 39.977 | 57.253 | 1.00 | 12.72 | 6 |
| ATOM | 3136 | C | ILE | A | 386 | 26.013 | 41.132 | 56.711 | 1.00 | 9.20 | 6 |
| ATOM | 3137 | O | ILE | A | 386 | 24.798 | 41.064 | 56.507 | 1.00 | 11.51 | 8 |
| ATOM | 3138 | CB | ILE | A | 386 | 26.814 | 40.000 | 58.848 | 1.00 | 16.85 | 6 |
| ATOM | 3139 | CG1 | ILE | A | 386 | 27.322 | 38.670 | 59.349 | 1.00 | 18.12 | 6 |
| ATOM | 3140 | CG2 | ILE | A | 386 | 25.402 | 40.258 | 59.352 | 1.00 | 9.70 | 6 |
| ATOM | 3141 | CD1 | ILE | A | 386 | 27.992 | 38.666 | 60.715 | 1.00 | 26.94 | 6 |
| ATOM | 3142 | N | ASP | A | 387 | 26.634 | 42.281 | 56.488 | 1.00 | 11.30 | 7 |
| ATOM | 3143 | CA | ASP | A | 387 | 25.911 | 43.440 | 55.965 | 1.00 | 12.22 | 6 |
| ATOM | 3144 | C | ASP | A | 387 | 25.032 | 43.227 | 54.750 | 1.00 | 14.02 | 6 |
| ATOM | 3145 | O | ASP | A | 387 | 23.879 | 43.635 | 54.731 | 1.00 | 14.95 | 8 |
| ATOM | 3146 | CB | ASP | A | 387 | 26.911 | 44.587 | 55.788 | 1.00 | 20.41 | 6 |
| ATOM | 3147 | CG | ASP | A | 387 | 26.987 | 45.457 | 57.041 | 1.00 | 23.19 | 6 |
| ATOM | 3148 | OD1 | ASP | A | 387 | 26.206 | 45.313 | 58.002 | 1.00 | 22.62 | 8 |
| ATOM | 3149 | OD2 | ASP | A | 387 | 27.865 | 46.315 | 57.094 | 1.00 | 20.44 | 8 |
| ATOM | 3150 | N | PRO | A | 388 | 25.495 | 42.550 | 53.702 | 1.00 | 16.26 | 7 |
| ATOM | 3151 | CA | PRO | A | 388 | 24.708 | 42.265 | 52.502 | 1.00 | 17.21 | 6 |

| | | | | | | | | | |
|---|---|---|---|---|---|---|---|---|---|
| ATOM | 3152 | C | PRO | A | 388 | 23.527 | 41.400 | 52.894 | 1.00 16.18 | 6 |
| ATOM | 3153 | O | PRO | A | 388 | 22.461 | 41.604 | 52.289 | 1.00 14.98 | 8 |
| ATOM | 3154 | CB | PRO | A | 388 | 25.603 | 41.521 | 51.492 | 1.00 17.18 | 6 |
| ATOM | 3155 | CG | PRO | A | 388 | 26.974 | 41.824 | 52.028 | 1.00 20.47 | 6 |
| ATOM | 3156 | CD | PRO | A | 388 | 26.869 | 42.092 | 53.538 | 1.00 16.83 | 6 |
| ATOM | 3157 | N | ILE | A | 389 | 23.678 | 40.499 | 53.878 | 1.00 15.35 | 7 |
| ATOM | 3158 | CA | ILE | A | 389 | 22.493 | 39.668 | 54.265 | 1.00 14.27 | 6 |
| ATOM | 3159 | C | ILE | A | 389 | 21.456 | 40.476 | 55.004 | 1.00 15.37 | 6 |
| ATOM | 3160 | O | ILE | A | 389 | 20.251 | 40.367 | 54.778 | 1.00 17.64 | 8 |
| ATOM | 3161 | CB | ILE | A | 389 | 22.904 | 38.411 | 55.012 | 1.00 13.28 | 6 |
| ATOM | 3162 | CG1 | ILE | A | 389 | 24.171 | 37.860 | 54.393 | 1.00 14.11 | 6 |
| ATOM | 3163 | CG2 | ILE | A | 389 | 21.798 | 37.398 | 55.185 | 1.00 10.66 | 6 |
| ATOM | 3164 | CD1 | ILE | A | 389 | 24.689 | 36.568 | 54.999 | 1.00 13.92 | 6 |
| ATOM | 3165 | N | LEU | A | 390 | 21.928 | 41.446 | 55.822 | 1.00 18.10 | 7 |
| ATOM | 3166 | CA | LEU | A | 390 | 20.977 | 42.349 | 56.488 | 1.00 18.21 | 6 |
| ATOM | 3167 | C | LEU | A | 390 | 20.268 | 43.216 | 55.426 | 1.00 18.49 | 6 |
| ATOM | 3168 | O | LEU | A | 390 | 19.086 | 43.509 | 55.556 | 1.00 16.37 | 8 |
| ATOM | 3169 | CB | LEU | A | 390 | 21.820 | 43.232 | 57.443 | 1.00 16.56 | 6 |
| ATOM | 3170 | CG | LEU | A | 390 | 22.135 | 42.516 | 58.799 | 1.00 19.93 | 6 |
| ATOM | 3171 | CD1 | LEU | A | 390 | 23.073 | 43.419 | 59.554 | 1.00 17.20 | 6 |
| ATOM | 3172 | CD2 | LEU | A | 390 | 20.845 | 42.259 | 59.575 | 1.00 16.58 | 6 |
| ATOM | 3173 | N | GLU | A | 391 | 21.007 | 43.665 | 54.386 | 1.00 16.17 | 7 |
| ATOM | 3174 | CA | GLU | A | 391 | 20.325 | 44.465 | 53.303 | 1.00 16.48 | 6 |
| ATOM | 3175 | C | GLU | A | 391 | 19.263 | 43.652 | 52.609 | 1.00 12.13 | 6 |
| ATOM | 3176 | O | GLU | A | 391 | 18.139 | 44.102 | 52.465 | 1.00 16.96 | 8 |
| ATOM | 3177 | CB | GLU | A | 391 | 21.446 | 44.917 | 52.361 | 1.00 25.49 | 6 |
| ATOM | 3178 | CG | GLU | A | 391 | 21.100 | 45.488 | 51.018 | 1.00 51.51 | 6 |
| ATOM | 3179 | CD | GLU | A | 391 | 20.006 | 46.533 | 51.042 | 1.00 69.83 | 6 |
| ATOM | 3180 | OE1 | GLU | A | 391 | 20.195 | 47.596 | 51.682 | 1.00 77.21 | 8 |
| ATOM | 3181 | OE2 | GLU | A | 391 | 18.946 | 46.275 | 50.422 | 1.00 80.47 | 8 |
| ATOM | 3182 | N | ALA | A | 392 | 19.503 | 42.363 | 52.322 | 1.00 12.95 | 7 |
| ATOM | 3183 | CA | ALA | A | 392 | 18.482 | 41.499 | 51.727 | 1.00 13.47 | 6 |
| ATOM | 3184 | C | ALA | A | 392 | 17.251 | 41.328 | 52.577 | 1.00 14.57 | 6 |
| ATOM | 3185 | O | ALA | A | 392 | 16.079 | 41.279 | 52.174 | 1.00 12.14 | 8 |
| ATOM | 3186 | CB | ALA | A | 392 | 19.080 | 40.082 | 51.469 | 1.00 5.69 | 6 |
| ATOM | 3187 | N | ARG | A | 393 | 17.527 | 41.153 | 53.924 | 1.00 16.57 | 7 |
| ATOM | 3188 | CA | ARG | A | 393 | 16.368 | 41.005 | 54.818 | 1.00 13.88 | 6 |
| ATOM | 3189 | C | ARG | A | 393 | 15.605 | 42.315 | 54.841 | 1.00 11.43 | 6 |
| ATOM | 3190 | O | ARG | A | 393 | 14.382 | 42.370 | 54.754 | 1.00 11.77 | 8 |
| ATOM | 3191 | CB | ARG | A | 393 | 16.836 | 40.691 | 56.266 | 1.00 24.03 | 6 |
| ATOM | 3192 | CG | ARG | A | 393 | 15.660 | 40.832 | 57.246 | 1.00 15.55 | 6 |
| ATOM | 3193 | CD | ARG | A | 393 | 16.104 | 40.214 | 58.625 | 1.00 20.25 | 6 |
| ATOM | 3194 | NE | ARG | A | 393 | 14.888 | 39.976 | 59.386 | 1.00 11.48 | 7 |
| ATOM | 3195 | CZ | ARG | A | 393 | 13.997 | 39.041 | 59.398 | 1.00 15.02 | 6 |
| ATOM | 3196 | NH1 | ARG | A | 393 | 14.119 | 37.965 | 58.629 | 1.00 12.91 | 7 |
| ATOM | 3197 | NH2 | ARG | A | 393 | 12.987 | 39.202 | 60.267 | 1.00 11.47 | 7 |
| ATOM | 3198 | N | GLN | A | 394 | 16.302 | 43.425 | 54.960 | 1.00 14.50 | 7 |
| ATOM | 3199 | CA | GLN | A | 394 | 15.572 | 44.692 | 55.025 | 1.00 18.94 | 6 |
| ATOM | 3200 | C | GLN | A | 394 | 14.768 | 45.107 | 53.787 | 1.00 20.87 | 6 |
| ATOM | 3201 | O | GLN | A | 394 | 13.698 | 45.710 | 53.936 | 1.00 21.23 | 8 |
| ATOM | 3202 | CB | GLN | A | 394 | 16.626 | 45.777 | 55.292 | 1.00 19.73 | 6 |
| ATOM | 3203 | CG | GLN | A | 394 | 15.997 | 47.166 | 55.327 | 1.00 34.13 | 6 |
| ATOM | 3204 | CD | GLN | A | 394 | 17.033 | 48.146 | 55.868 | 1.00 42.94 | 6 |
| ATOM | 3205 | OE1 | GLN | A | 394 | 18.211 | 48.045 | 55.527 | 1.00 48.00 | 8 |
| ATOM | 3206 | NE2 | GLN | A | 394 | 16.567 | 49.063 | 56.694 | 1.00 38.78 | 7 |
| ATOM | 3207 | N | ASN | A | 395 | 15.315 | 44.868 | 52.605 | 1.00 22.35 | 7 |
| ATOM | 3208 | CA | ASN | A | 395 | 14.704 | 45.340 | 51.349 | 1.00 22.62 | 6 |
| ATOM | 3209 | C | ASN | A | 395 | 14.155 | 44.303 | 50.380 | 1.00 22.55 | 6 |
| ATOM | 3210 | O | ASN | A | 395 | 13.227 | 44.631 | 49.640 | 1.00 22.44 | 8 |
| ATOM | 3211 | CB | ASN | A | 395 | 15.829 | 46.048 | 50.584 | 1.00 24.25 | 6 |
| ATOM | 3212 | CG | ASN | A | 395 | 15.991 | 47.421 | 51.208 | 1.00 29.25 | 6 |
| ATOM | 3213 | OD1 | ASN | A | 395 | 17.120 | 47.874 | 51.307 | 1.00 42.49 | 8 |
| ATOM | 3214 | ND2 | ASN | A | 395 | 14.890 | 48.003 | 51.618 | 1.00 34.43 | 7 |
| ATOM | 3215 | N | PHE | A | 396 | 14.625 | 43.069 | 50.419 | 1.00 20.24 | 7 |
| ATOM | 3216 | CA | PHE | A | 396 | 14.178 | 42.018 | 49.532 | 1.00 23.30 | 6 |

| ATOM | 3217 | C   | PHE A 396 | 13.431 | 40.810 | 50.076 | 1.00 | 25.23 | 6 |
| ATOM | 3218 | O   | PHE A 396 | 12.770 | 40.125 | 49.265 | 1.00 | 21.78 | 8 |
| ATOM | 3219 | CB  | PHE A 396 | 15.501 | 41.489 | 48.876 | 1.00 | 21.33 | 6 |
| ATOM | 3220 | CG  | PHE A 396 | 16.123 | 42.583 | 48.037 | 1.00 | 19.57 | 6 |
| ATOM | 3221 | CD1 | PHE A 396 | 15.499 | 42.952 | 46.846 | 1.00 | 26.52 | 6 |
| ATOM | 3222 | CD2 | PHE A 396 | 17.292 | 43.195 | 48.406 | 1.00 | 20.67 | 6 |
| ATOM | 3223 | CE1 | PHE A 396 | 16.057 | 43.949 | 46.042 | 1.00 | 22.29 | 6 |
| ATOM | 3224 | CE2 | PHE A 396 | 17.856 | 44.204 | 47.632 | 1.00 | 29.18 | 6 |
| ATOM | 3225 | CZ  | PHE A 396 | 17.230 | 44.580 | 46.437 | 1.00 | 24.68 | 6 |
| ATOM | 3226 | N   | ALA A 397 | 13.570 | 40.513 | 51.400 | 1.00 | 24.28 | 7 |
| ATOM | 3227 | CA  | ALA A 397 | 12.981 | 39.290 | 51.968 | 1.00 | 22.16 | 6 |
| ATOM | 3228 | C   | ALA A 397 | 11.557 | 39.399 | 52.386 | 1.00 | 21.58 | 6 |
| ATOM | 3229 | O   | ALA A 397 | 11.171 | 39.620 | 53.587 | 1.00 | 23.05 | 8 |
| ATOM | 3230 | CB  | ALA A 397 | 13.901 | 38.838 | 53.134 | 1.00 | 19.19 | 6 |
| ATOM | 3231 | N   | TYR A 398 | 10.619 | 39.421 | 51.435 | 1.00 | 18.06 | 7 |
| ATOM | 3232 | CA  | TYR A 398 | 9.191  | 39.615 | 51.630 | 1.00 | 17.56 | 6 |
| ATOM | 3233 | C   | TYR A 398 | 8.372  | 38.762 | 50.656 | 1.00 | 20.75 | 6 |
| ATOM | 3234 | O   | TYR A 398 | 8.866  | 38.357 | 49.598 | 1.00 | 20.32 | 8 |
| ATOM | 3235 | CB  | TYR A 398 | 8.789  | 41.079 | 51.316 | 1.00 | 19.32 | 6 |
| ATOM | 3236 | CG  | TYR A 398 | 9.471  | 42.075 | 52.213 | 1.00 | 23.94 | 6 |
| ATOM | 3237 | CD1 | TYR A 398 | 8.899  | 42.359 | 53.471 | 1.00 | 25.13 | 6 |
| ATOM | 3238 | CD2 | TYR A 398 | 10.683 | 42.646 | 51.885 | 1.00 | 23.28 | 6 |
| ATOM | 3239 | CE1 | TYR A 398 | 9.562  | 43.213 | 54.347 | 1.00 | 25.33 | 6 |
| ATOM | 3240 | CE2 | TYR A 398 | 11.333 | 43.489 | 52.764 | 1.00 | 25.72 | 6 |
| ATOM | 3241 | CZ  | TYR A 398 | 10.750 | 43.770 | 53.999 | 1.00 | 25.29 | 6 |
| ATOM | 3242 | OH  | TYR A 398 | 11.394 | 44.636 | 54.841 | 1.00 | 23.06 | 8 |
| ATOM | 3243 | N   | GLY A 399 | 7.142  | 38.444 | 50.960 | 1.00 | 19.46 | 7 |
| ATOM | 3244 | CA  | GLY A 399 | 6.211  | 37.716 | 50.120 | 1.00 | 18.92 | 6 |
| ATOM | 3245 | C   | GLY A 399 | 6.307  | 36.226 | 50.292 | 1.00 | 19.52 | 6 |
| ATOM | 3246 | O   | GLY A 399 | 7.169  | 35.751 | 51.061 | 1.00 | 18.13 | 8 |
| ATOM | 3247 | N   | THR A 400 | 5.450  | 35.527 | 49.577 | 1.00 | 15.63 | 7 |
| ATOM | 3248 | CA  | THR A 400 | 5.372  | 34.072 | 49.637 | 1.00 | 16.69 | 6 |
| ATOM | 3249 | C   | THR A 400 | 6.760  | 33.457 | 49.556 | 1.00 | 17.74 | 6 |
| ATOM | 3250 | O   | THR A 400 | 7.607  | 33.929 | 48.761 | 1.00 | 19.47 | 8 |
| ATOM | 3251 | CB  | THR A 400 | 4.500  | 33.578 | 48.455 | 1.00 | 20.78 | 6 |
| ATOM | 3252 | OG1 | THR A 400 | 3.266  | 34.312 | 48.565 | 1.00 | 26.31 | 8 |
| ATOM | 3253 | CG2 | THR A 400 | 4.170  | 32.117 | 48.502 | 1.00 | 18.82 | 6 |
| ATOM | 3254 | N   | GLN A 401 | 6.904  | 32.347 | 50.264 | 1.00 | 13.87 | 7 |
| ATOM | 3255 | CA  | GLN A 401 | 8.207  | 31.693 | 50.327 | 1.00 | 12.58 | 6 |
| ATOM | 3256 | C   | GLN A 401 | 8.072  | 30.316 | 49.725 | 1.00 | 10.72 | 6 |
| ATOM | 3257 | O   | GLN A 401 | 7.025  | 29.726 | 49.886 | 1.00 | 12.72 | 8 |
| ATOM | 3258 | CB  | GLN A 401 | 8.623  | 31.511 | 51.823 | 1.00 | 14.98 | 6 |
| ATOM | 3259 | CG  | GLN A 401 | 9.983  | 30.844 | 52.002 | 1.00 | 16.56 | 6 |
| ATOM | 3260 | CD  | GLN A 401 | 10.397 | 31.000 | 53.497 | 1.00 | 22.68 | 6 |
| ATOM | 3261 | OE1 | GLN A 401 | 10.340 | 30.068 | 54.312 | 1.00 | 15.75 | 8 |
| ATOM | 3262 | NE2 | GLN A 401 | 10.753 | 32.220 | 53.780 | 1.00 | 12.60 | 7 |
| ATOM | 3263 | N   | HIS A 402 | 9.083  | 29.893 | 48.969 | 1.00 | 10.91 | 7 |
| ATOM | 3264 | CA  | HIS A 402 | 9.047  | 28.533 | 48.421 | 1.00 | 11.66 | 6 |
| ATOM | 3265 | C   | HIS A 402 | 10.348 | 27.899 | 48.924 | 1.00 | 12.41 | 6 |
| ATOM | 3266 | O   | HIS A 402 | 11.410 | 28.518 | 48.690 | 1.00 | 14.47 | 8 |
| ATOM | 3267 | CB  | HIS A 402 | 9.181  | 28.627 | 46.865 | 1.00 | 16.44 | 6 |
| ATOM | 3268 | CG  | HIS A 402 | 7.932  | 29.307 | 46.340 | 1.00 | 11.10 | 6 |
| ATOM | 3269 | ND1 | HIS A 402 | 6.775  | 28.628 | 46.139 | 1.00 | 18.89 | 7 |
| ATOM | 3270 | CD2 | HIS A 402 | 7.695  | 30.590 | 46.062 | 1.00 | 20.41 | 6 |
| ATOM | 3271 | CE1 | HIS A 402 | 5.858  | 29.486 | 45.718 | 1.00 | 18.34 | 6 |
| ATOM | 3272 | NE2 | HIS A 402 | 6.396  | 30.678 | 45.646 | 1.00 | 20.72 | 7 |
| ATOM | 3273 | N   | ASP A 403 | 10.248 | 26.705 | 49.441 | 1.00 | 12.64 | 7 |
| ATOM | 3274 | CA  | ASP A 403 | 11.402 | 26.031 | 49.997 | 1.00 | 14.92 | 6 |
| ATOM | 3275 | C   | ASP A 403 | 11.920 | 24.881 | 49.174 | 1.00 | 14.87 | 6 |
| ATOM | 3276 | O   | ASP A 403 | 11.074 | 24.144 | 48.698 | 1.00 | 17.16 | 8 |
| ATOM | 3277 | CB  | ASP A 403 | 11.065 | 25.382 | 51.362 | 1.00 | 17.08 | 6 |
| ATOM | 3278 | CG  | ASP A 403 | 10.991 | 26.379 | 52.508 | 1.00 | 20.75 | 6 |
| ATOM | 3279 | OD1 | ASP A 403 | 11.378 | 27.559 | 52.450 | 1.00 | 25.42 | 8 |
| ATOM | 3280 | OD2 | ASP A 403 | 10.539 | 25.965 | 53.602 | 1.00 | 34.57 | 8 |
| ATOM | 3281 | N   | TYR A 404 | 13.246 | 24.771 | 49.068 | 1.00 | 14.04 | 7 |

| ATOM | 3282 | CA | TYR | A | 404 | 13.823 | 23.629 | 48.376 | 1.00 | 16.23 | 6 |
|------|------|----|-----|---|-----|--------|--------|--------|------|-------|---|
| ATOM | 3283 | C | TYR | A | 404 | 14.855 | 22.957 | 49.295 | 1.00 | 16.89 | 6 |
| ATOM | 3284 | O | TYR | A | 404 | 16.072 | 23.055 | 49.023 | 1.00 | 15.20 | 8 |
| ATOM | 3285 | CB | TYR | A | 404 | 14.474 | 24.048 | 47.005 | 1.00 | 15.62 | 6 |
| ATOM | 3286 | CG | TYR | A | 404 | 13.484 | 24.770 | 46.102 | 1.00 | 18.51 | 6 |
| ATOM | 3287 | CD1 | TYR | A | 404 | 13.259 | 26.145 | 46.273 | 1.00 | 18.46 | 6 |
| ATOM | 3288 | CD2 | TYR | A | 404 | 12.733 | 24.110 | 45.148 | 1.00 | 21.41 | 6 |
| ATOM | 3289 | CE1 | TYR | A | 404 | 12.335 | 26.804 | 45.500 | 1.00 | 22.55 | 6 |
| ATOM | 3290 | CE2 | TYR | A | 404 | 11.801 | 24.768 | 44.339 | 1.00 | 21.59 | 6 |
| ATOM | 3291 | CZ | TYR | A | 404 | 11.619 | 26.115 | 44.527 | 1.00 | 23.32 | 6 |
| ATOM | 3292 | OH | TYR | A | 404 | 10.723 | 26.830 | 43.779 | 1.00 | 23.96 | 8 |
| ATOM | 3293 | N | PHE | A | 405 | 14.372 | 22.256 | 50.326 | 1.00 | 17.74 | 7 |
| ATOM | 3294 | CA | PHE | A | 405 | 15.284 | 21.492 | 51.238 | 1.00 | 19.60 | 6 |
| ATOM | 3295 | C | PHE | A | 405 | 15.320 | 20.072 | 50.710 | 1.00 | 19.93 | 6 |
| ATOM | 3296 | O | PHE | A | 405 | 14.661 | 19.205 | 51.267 | 1.00 | 21.69 | 8 |
| ATOM | 3297 | CB | PHE | A | 405 | 14.731 | 21.454 | 52.680 | 1.00 | 17.01 | 6 |
| ATOM | 3298 | CG | PHE | A | 405 | 15.069 | 22.753 | 53.375 | 1.00 | 20.75 | 6 |
| ATOM | 3299 | CD1 | PHE | A | 405 | 14.317 | 23.873 | 53.178 | 1.00 | 22.73 | 6 |
| ATOM | 3300 | CD2 | PHE | A | 405 | 16.177 | 22.858 | 54.197 | 1.00 | 21.89 | 6 |
| ATOM | 3301 | CE1 | PHE | A | 405 | 14.612 | 25.070 | 53.790 | 1.00 | 21.02 | 6 |
| ATOM | 3302 | CE2 | PHE | A | 405 | 16.495 | 24.046 | 54.781 | 1.00 | 16.66 | 6 |
| ATOM | 3303 | CZ | PHE | A | 405 | 15.713 | 25.174 | 54.597 | 1.00 | 17.73 | 6 |
| ATOM | 3304 | N | ASP | A | 406 | 16.014 | 19.845 | 49.577 | 1.00 | 21.98 | 7 |
| ATOM | 3305 | CA | ASP | A | 406 | 15.832 | 18.590 | 48.897 | 1.00 | 21.63 | 6 |
| ATOM | 3306 | C | ASP | A | 406 | 17.093 | 17.945 | 48.411 | 1.00 | 22.94 | 6 |
| ATOM | 3307 | O | ASP | A | 406 | 16.984 | 17.020 | 47.609 | 1.00 | 24.02 | 8 |
| ATOM | 3308 | CB | ASP | A | 406 | 14.872 | 18.811 | 47.699 | 1.00 | 28.49 | 6 |
| ATOM | 3309 | CG | ASP | A | 406 | 15.357 | 19.804 | 46.665 | 1.00 | 32.06 | 6 |
| ATOM | 3310 | OD1 | ASP | A | 406 | 16.509 | 20.304 | 46.657 | 1.00 | 21.32 | 8 |
| ATOM | 3311 | OD2 | ASP | A | 406 | 14.537 | 20.124 | 45.779 | 1.00 | 37.10 | 8 |
| ATOM | 3312 | N | HIS | A | 407 | 18.235 | 18.336 | 48.921 | 1.00 | 20.46 | 7 |
| ATOM | 3313 | CA | HIS | A | 407 | 19.494 | 17.723 | 48.573 | 1.00 | 15.99 | 6 |
| ATOM | 3314 | C | HIS | A | 407 | 20.365 | 17.772 | 49.847 | 1.00 | 19.29 | 6 |
| ATOM | 3315 | O | HIS | A | 407 | 20.206 | 18.636 | 50.728 | 1.00 | 16.32 | 8 |
| ATOM | 3316 | CB | HIS | A | 407 | 20.180 | 18.592 | 47.501 | 1.00 | 21.88 | 6 |
| ATOM | 3317 | CG | HIS | A | 407 | 21.382 | 17.950 | 46.905 | 1.00 | 17.78 | 6 |
| ATOM | 3318 | ND1 | HIS | A | 407 | 22.682 | 18.370 | 47.145 | 1.00 | 14.44 | 7 |
| ATOM | 3319 | CD2 | HIS | A | 407 | 21.478 | 16.898 | 46.048 | 1.00 | 28.23 | 6 |
| ATOM | 3320 | CE1 | HIS | A | 407 | 23.533 | 17.609 | 46.464 | 1.00 | 25.92 | 6 |
| ATOM | 3321 | NE2 | HIS | A | 407 | 22.824 | 16.714 | 45.771 | 1.00 | 24.79 | 7 |
| ATOM | 3322 | N | HIS | A | 408 | 21.342 | 16.884 | 49.880 | 1.00 | 19.10 | 7 |
| ATOM | 3323 | CA | HIS | A | 408 | 22.188 | 16.822 | 51.064 | 1.00 | 21.16 | 6 |
| ATOM | 3324 | C | HIS | A | 408 | 23.186 | 17.947 | 51.022 | 1.00 | 21.67 | 6 |
| ATOM | 3325 | O | HIS | A | 408 | 23.680 | 18.158 | 52.121 | 1.00 | 19.33 | 8 |
| ATOM | 3326 | CB | HIS | A | 408 | 22.930 | 15.491 | 51.221 | 1.00 | 20.31 | 6 |
| ATOM | 3327 | CG | HIS | A | 408 | 23.579 | 15.023 | 49.970 | 1.00 | 26.72 | 6 |
| ATOM | 3328 | ND1 | HIS | A | 408 | 24.932 | 15.179 | 49.722 | 1.00 | 31.57 | 7 |
| ATOM | 3329 | CD2 | HIS | A | 408 | 23.034 | 14.426 | 48.883 | 1.00 | 26.74 | 6 |
| ATOM | 3330 | CE1 | HIS | A | 408 | 25.217 | 14.677 | 48.544 | 1.00 | 28.79 | 6 |
| ATOM | 3331 | NE2 | HIS | A | 408 | 24.084 | 14.213 | 48.021 | 1.00 | 30.92 | 7 |
| ATOM | 3332 | N | ASN | A | 409 | 23.506 | 18.620 | 49.903 | 1.00 | 19.79 | 7 |
| ATOM | 3333 | CA | ASN | A | 409 | 24.478 | 19.678 | 50.007 | 1.00 | 14.82 | 6 |
| ATOM | 3334 | C | ASN | A | 409 | 23.838 | 20.998 | 49.635 | 1.00 | 15.23 | 6 |
| ATOM | 3335 | O | ASN | A | 409 | 24.086 | 22.012 | 50.289 | 1.00 | 15.13 | 8 |
| ATOM | 3336 | CB | ASN | A | 409 | 25.696 | 19.563 | 49.120 | 1.00 | 13.46 | 6 |
| ATOM | 3337 | CG | ASN | A | 409 | 26.628 | 18.428 | 49.204 | 1.00 | 27.43 | 6 |
| ATOM | 3338 | OD1 | ASN | A | 409 | 27.478 | 17.977 | 48.416 | 1.00 | 28.86 | 8 |
| ATOM | 3339 | ND2 | ASN | A | 409 | 26.555 | 17.756 | 50.319 | 1.00 | 10.65 | 7 |
| ATOM | 3340 | N | ILE | A | 410 | 23.027 | 20.967 | 48.535 | 1.00 | 13.15 | 7 |
| ATOM | 3341 | CA | ILE | A | 410 | 22.604 | 22.283 | 48.031 | 1.00 | 9.70 | 6 |
| ATOM | 3342 | C | ILE | A | 410 | 21.166 | 22.552 | 48.400 | 1.00 | 7.63 | 6 |
| ATOM | 3343 | O | ILE | A | 410 | 20.320 | 21.757 | 48.041 | 1.00 | 11.50 | 8 |
| ATOM | 3344 | CB | ILE | A | 410 | 22.820 | 22.291 | 46.474 | 1.00 | 16.75 | 6 |
| ATOM | 3345 | CG1 | ILE | A | 410 | 24.299 | 22.086 | 46.177 | 1.00 | 22.85 | 6 |
| ATOM | 3346 | CG2 | ILE | A | 410 | 22.352 | 23.604 | 45.889 | 1.00 | 9.39 | 6 |

| ATOM | 3347 | CD1 | ILE A 410 | 24.632 | 21.694 | 44.755 | 1.00 | 31.95 | 6 |
|------|------|-----|-----------|--------|--------|--------|------|-------|---|
| ATOM | 3348 | N | ILE A 411 | 20.922 | 23.736 | 48.999 | 1.00 | 4.35 | 7 |
| ATOM | 3349 | CA | ILE A 411 | 19.476 | 23.883 | 49.370 | 1.00 | 7.35 | 6 |
| ATOM | 3350 | C | ILE A 411 | 19.118 | 25.312 | 49.101 | 1.00 | 6.74 | 6 |
| ATOM | 3351 | O | ILE A 411 | 20.055 | 26.094 | 48.964 | 1.00 | 10.01 | 8 |
| ATOM | 3352 | CB | ILE A 411 | 19.566 | 23.505 | 50.873 | 1.00 | 24.68 | 6 |
| ATOM | 3353 | CG1 | ILE A 411 | 18.497 | 22.504 | 51.187 | 1.00 | 28.54 | 6 |
| ATOM | 3354 | CG2 | ILE A 411 | 19.819 | 24.485 | 52.000 | 1.00 | 14.86 | 6 |
| ATOM | 3355 | CD1 | ILE A 411 | 19.176 | 21.170 | 51.304 | 1.00 | 29.46 | 6 |
| ATOM | 3356 | N | GLY A 412 | 17.853 | 25.708 | 49.136 | 1.00 | 10.56 | 7 |
| ATOM | 3357 | CA | GLY A 412 | 17.632 | 27.154 | 48.948 | 1.00 | 12.21 | 6 |
| ATOM | 3358 | C | GLY A 412 | 16.127 | 27.373 | 49.061 | 1.00 | 9.86 | 6 |
| ATOM | 3359 | O | GLY A 412 | 15.436 | 26.448 | 49.462 | 1.00 | 13.72 | 8 |
| ATOM | 3360 | N | TRP A 413 | 15.781 | 28.635 | 48.939 | 1.00 | 9.03 | 7 |
| ATOM | 3361 | CA | TRP A 413 | 14.392 | 29.000 | 49.050 | 1.00 | 11.26 | 6 |
| ATOM | 3362 | C | TRP A 413 | 14.236 | 30.311 | 48.290 | 1.00 | 10.42 | 6 |
| ATOM | 3363 | O | TRP A 413 | 15.203 | 31.062 | 48.143 | 1.00 | 12.22 | 8 |
| ATOM | 3364 | CB | TRP A 413 | 13.888 | 29.200 | 50.524 | 1.00 | 12.93 | 6 |
| ATOM | 3365 | CG | TRP A 413 | 14.834 | 30.062 | 51.320 | 1.00 | 5.97 | 6 |
| ATOM | 3366 | CD1 | TRP A 413 | 14.787 | 31.409 | 51.517 | 1.00 | 7.37 | 6 |
| ATOM | 3367 | CD2 | TRP A 413 | 15.978 | 29.574 | 52.035 | 1.00 | 8.67 | 6 |
| ATOM | 3368 | NE1 | TRP A 413 | 15.856 | 31.803 | 52.275 | 1.00 | 12.54 | 7 |
| ATOM | 3369 | CE2 | TRP A 413 | 16.582 | 30.676 | 52.625 | 1.00 | 4.92 | 6 |
| ATOM | 3370 | CE3 | TRP A 413 | 16.509 | 28.294 | 52.238 | 1.00 | 6.88 | 6 |
| ATOM | 3371 | CZ2 | TRP A 413 | 17.769 | 30.633 | 53.367 | 1.00 | 9.92 | 6 |
| ATOM | 3372 | CZ3 | TRP A 413 | 17.718 | 28.227 | 52.969 | 1.00 | 14.87 | 6 |
| ATOM | 3373 | CH2 | TRP A 413 | 18.292 | 29.378 | 53.503 | 1.00 | 5.74 | 6 |
| ATOM | 3374 | N | THR A 414 | 12.972 | 30.623 | 47.991 | 1.00 | 10.08 | 7 |
| ATOM | 3375 | CA | THR A 414 | 12.807 | 31.960 | 47.345 | 1.00 | 14.05 | 6 |
| ATOM | 3376 | C | THR A 414 | 11.677 | 32.691 | 48.030 | 1.00 | 14.13 | 6 |
| ATOM | 3377 | O | THR A 414 | 10.869 | 32.066 | 48.655 | 1.00 | 14.72 | 8 |
| ATOM | 3378 | CB | THR A 414 | 12.364 | 31.788 | 45.853 | 1.00 | 13.44 | 6 |
| ATOM | 3379 | OG1 | THR A 414 | 11.181 | 30.986 | 45.841 | 1.00 | 7.59 | 8 |
| ATOM | 3380 | CG2 | THR A 414 | 13.352 | 30.897 | 45.066 | 1.00 | 5.57 | 6 |
| ATOM | 3381 | N | ARG A 415 | 11.632 | 33.992 | 47.813 | 1.00 | 15.54 | 7 |
| ATOM | 3382 | CA | ARG A 415 | 10.563 | 34.849 | 48.279 | 1.00 | 16.88 | 6 |
| ATOM | 3383 | C | ARG A 415 | 10.036 | 35.572 | 47.003 | 1.00 | 17.79 | 6 |
| ATOM | 3384 | O | ARG A 415 | 10.822 | 36.251 | 46.335 | 1.00 | 17.94 | 8 |
| ATOM | 3385 | CB | ARG A 415 | 11.217 | 35.912 | 49.217 | 1.00 | 7.42 | 6 |
| ATOM | 3386 | CG | ARG A 415 | 11.958 | 35.313 | 50.482 | 1.00 | 8.31 | 6 |
| ATOM | 3387 | CD | ARG A 415 | 11.024 | 34.333 | 51.205 | 1.00 | 3.61 | 6 |
| ATOM | 3388 | NE | ARG A 415 | 9.971 | 35.182 | 51.854 | 1.00 | 13.50 | 7 |
| ATOM | 3389 | CZ | ARG A 415 | 10.214 | 35.932 | 52.957 | 1.00 | 19.07 | 6 |
| ATOM | 3390 | NH1 | ARG A 415 | 11.382 | 35.996 | 53.591 | 1.00 | 13.77 | 7 |
| ATOM | 3391 | NH2 | ARG A 415 | 9.241 | 36.682 | 53.478 | 1.00 | 12.34 | 7 |
| ATOM | 3392 | N | GLU A 416 | 8.749 | 35.703 | 46.821 | 1.00 | 19.68 | 7 |
| ATOM | 3393 | CA | GLU A 416 | 8.147 | 36.400 | 45.693 | 1.00 | 20.64 | 6 |
| ATOM | 3394 | C | GLU A 416 | 8.104 | 37.905 | 45.754 | 1.00 | 24.26 | 6 |
| ATOM | 3395 | O | GLU A 416 | 7.873 | 38.542 | 44.689 | 1.00 | 23.56 | 8 |
| ATOM | 3396 | CB | GLU A 416 | 6.754 | 35.864 | 45.394 | 1.00 | 16.78 | 6 |
| ATOM | 3397 | CG | GLU A 416 | 6.806 | 34.376 | 45.061 | 1.00 | 18.89 | 6 |
| ATOM | 3398 | CD | GLU A 416 | 5.452 | 33.880 | 44.567 | 1.00 | 27.96 | 6 |
| ATOM | 3399 | OE1 | GLU A 416 | 4.652 | 34.705 | 44.106 | 1.00 | 24.86 | 8 |
| ATOM | 3400 | OE2 | GLU A 416 | 5.116 | 32.685 | 44.620 | 1.00 | 21.51 | 8 |
| ATOM | 3401 | N | GLY A 417 | 8.319 | 38.515 | 46.930 | 1.00 | 20.79 | 7 |
| ATOM | 3402 | CA | GLY A 417 | 8.275 | 39.977 | 46.981 | 1.00 | 20.54 | 6 |
| ATOM | 3403 | C | GLY A 417 | 6.839 | 40.393 | 47.208 | 1.00 | 22.41 | 6 |
| ATOM | 3404 | O | GLY A 417 | 5.984 | 39.541 | 47.075 | 1.00 | 21.28 | 8 |
| ATOM | 3405 | N | ASN A 418 | 6.550 | 41.635 | 47.563 | 1.00 | 26.47 | 7 |
| ATOM | 3406 | CA | ASN A 418 | 5.170 | 42.093 | 47.674 | 1.00 | 31.49 | 6 |
| ATOM | 3407 | C | ASN A 418 | 5.114 | 43.539 | 47.163 | 1.00 | 34.80 | 6 |
| ATOM | 3408 | O | ASN A 418 | 6.155 | 44.146 | 46.924 | 1.00 | 34.09 | 8 |
| ATOM | 3409 | CB | ASN A 418 | 4.540 | 41.994 | 49.054 | 1.00 | 32.51 | 6 |
| ATOM | 3410 | CG | ASN A 418 | 5.325 | 42.721 | 50.118 | 1.00 | 40.02 | 6 |
| ATOM | 3411 | OD1 | ASN A 418 | 6.006 | 43.724 | 49.894 | 1.00 | 44.94 | 8 |

| | ATOM | 3412 | ND2 | ASN A 418 | 5.267 | 42.210 | 51.344 | 1.00 | 47.27 | 7 |
|---|---|---|---|---|---|---|---|---|---|---|
| | ATOM | 3413 | N | THR A 419 | 3.917 | 44.100 | 47.061 | 1.00 | 39.20 | 7 |
| | ATOM | 3414 | CA | THR A 419 | 3.754 | 45.468 | 46.536 | 1.00 | 43.25 | 6 |
| | ATOM | 3415 | C | THR A 419 | 4.284 | 46.547 | 47.442 | 1.00 | 44.75 | 6 |
| 5 | ATOM | 3416 | O | THR A 419 | 4.880 | 47.517 | 46.933 | 1.00 | 45.86 | 8 |
| | ATOM | 3417 | CB | THR A 419 | 2.342 | 45.731 | 46.006 | 1.00 | 54.57 | 6 |
| | ATOM | 3418 | OG1 | THR A 419 | 1.353 | 45.687 | 47.040 | 1.00 | 66.20 | 8 |
| | ATOM | 3419 | CG2 | THR A 419 | 2.009 | 44.626 | 44.988 | 1.00 | 55.68 | 6 |
| | ATOM | 3420 | N | THR A 420 | 4.186 | 46.410 | 48.760 | 1.00 | 45.25 | 7 |
| 10 | ATOM | 3421 | CA | THR A 420 | 4.927 | 47.405 | 49.604 | 1.00 | 46.78 | 6 |
| | ATOM | 3422 | C | THR A 420 | 6.370 | 47.026 | 49.328 | 1.00 | 46.84 | 6 |
| | ATOM | 3423 | O | THR A 420 | 6.524 | 45.824 | 48.976 | 1.00 | 48.22 | 8 |
| | ATOM | 3424 | CB | THR A 420 | 4.557 | 47.083 | 51.063 | 1.00 | 54.48 | 6 |
| | ATOM | 3425 | OG1 | THR A 420 | 3.747 | 45.884 | 51.075 | 1.00 | 58.03 | 8 |
| 15 | ATOM | 3426 | CG2 | THR A 420 | 3.719 | 48.205 | 51.647 | 1.00 | 60.68 | 6 |
| | ATOM | 3427 | N | HIS A 421 | 7.468 | 47.723 | 49.482 | 1.00 | 46.61 | 7 |
| | ATOM | 3428 | CA | HIS A 421 | 8.772 | 47.088 | 49.170 | 1.00 | 45.15 | 6 |
| | ATOM | 3429 | C | HIS A 421 | 8.861 | 46.701 | 47.695 | 1.00 | 44.34 | 6 |
| | ATOM | 3430 | O | HIS A 421 | 8.769 | 45.588 | 47.177 | 1.00 | 44.02 | 8 |
| 20 | ATOM | 3431 | CB | HIS A 421 | 9.116 | 45.866 | 50.038 | 1.00 | 41.65 | 6 |
| | ATOM | 3432 | CG | HIS A 421 | 8.945 | 46.140 | 51.499 | 1.00 | 45.00 | 6 |
| | ATOM | 3433 | ND1 | HIS A 421 | 7.822 | 45.690 | 52.166 | 1.00 | 46.28 | 7 |
| | ATOM | 3434 | CD2 | HIS A 421 | 9.669 | 46.858 | 52.383 | 1.00 | 49.53 | 6 |
| | ATOM | 3435 | CE1 | HIS A 421 | 7.885 | 46.115 | 53.419 | 1.00 | 49.03 | 6 |
| 25 | ATOM | 3436 | NE2 | HIS A 421 | 8.987 | 46.828 | 53.584 | 1.00 | 47.10 | 7 |
| | ATOM | 3437 | N | PRO A 422 | 9.168 | 47.720 | 46.916 | 1.00 | 44.15 | 7 |
| | ATOM | 3438 | CA | PRO A 422 | 9.307 | 47.609 | 45.461 | 1.00 | 42.61 | 6 |
| | ATOM | 3439 | C | PRO A 422 | 10.670 | 47.020 | 45.172 | 1.00 | 39.48 | 6 |
| | ATOM | 3440 | O | PRO A 422 | 11.684 | 47.306 | 45.824 | 1.00 | 39.30 | 8 |
| 30 | ATOM | 3441 | CB | PRO A 422 | 9.095 | 49.030 | 44.916 | 1.00 | 43.20 | 6 |
| | ATOM | 3442 | CG | PRO A 422 | 9.570 | 49.868 | 46.080 | 1.00 | 45.14 | 6 |
| | ATOM | 3443 | CD | PRO A 422 | 9.368 | 49.105 | 47.365 | 1.00 | 44.61 | 6 |
| | ATOM | 3444 | N | ASN A 423 | 10.745 | 46.110 | 44.209 | 1.00 | 36.22 | 7 |
| | ATOM | 3445 | CA | ASN A 423 | 11.996 | 45.473 | 43.830 | 1.00 | 32.97 | 6 |
| 35 | ATOM | 3446 | C | ASN A 423 | 12.315 | 44.285 | 44.718 | 1.00 | 29.70 | 6 |
| | ATOM | 3447 | O | ASN A 423 | 13.340 | 43.628 | 44.532 | 1.00 | 29.23 | 8 |
| | ATOM | 3448 | CB | ASN A 423 | 13.185 | 46.447 | 43.825 | 1.00 | 43.57 | 6 |
| | ATOM | 3449 | CG | ASN A 423 | 13.020 | 47.493 | 42.717 | 1.00 | 52.50 | 6 |
| | ATOM | 3450 | OD1 | ASN A 423 | 12.140 | 47.312 | 41.857 | 1.00 | 53.89 | 8 |
| 40 | ATOM | 3451 | ND2 | ASN A 423 | 13.817 | 48.550 | 42.776 | 1.00 | 51.34 | 7 |
| | ATOM | 3452 | N | SER A 424 | 11.384 | 43.991 | 45.601 | 1.00 | 27.55 | 7 |
| | ATOM | 3453 | CA | SER A 424 | 11.598 | 42.917 | 46.568 | 1.00 | 25.84 | 6 |
| | ATOM | 3454 | C | SER A 424 | 11.441 | 41.558 | 45.939 | 1.00 | 20.78 | 6 |
| | ATOM | 3455 | O | SER A 424 | 10.712 | 41.423 | 44.955 | 1.00 | 21.97 | 8 |
| 45 | ATOM | 3456 | CB | SER A 424 | 10.709 | 43.173 | 47.787 | 1.00 | 21.20 | 6 |
| | ATOM | 3457 | OG | SER A 424 | 9.338 | 42.983 | 47.528 | 1.00 | 26.10 | 8 |
| | ATOM | 3458 | N | GLY A 425 | 12.050 | 40.537 | 46.496 | 1.00 | 15.88 | 7 |
| | ATOM | 3459 | CA | GLY A 425 | 11.954 | 39.135 | 46.045 | 1.00 | 11.07 | 6 |
| | ATOM | 3460 | C | GLY A 425 | 13.381 | 38.628 | 46.051 | 1.00 | 9.56 | 6 |
| 50 | ATOM | 3461 | O | GLY A 425 | 14.252 | 39.481 | 45.929 | 1.00 | 12.58 | 8 |
| | ATOM | 3462 | N | LEU A 426 | 13.656 | 37.333 | 46.160 | 1.00 | 9.63 | 7 |
| | ATOM | 3463 | CA | LEU A 426 | 15.049 | 36.952 | 46.230 | 1.00 | 8.00 | 6 |
| | ATOM | 3464 | C | LEU A 426 | 15.075 | 35.433 | 46.125 | 1.00 | 6.59 | 6 |
| | ATOM | 3465 | O | LEU A 426 | 14.051 | 34.830 | 46.264 | 1.00 | 10.84 | 8 |
| 55 | ATOM | 3466 | CB | LEU A 426 | 15.766 | 37.454 | 47.493 | 1.00 | 12.80 | 6 |
| | ATOM | 3467 | CG | LEU A 426 | 15.217 | 36.918 | 48.855 | 1.00 | 17.04 | 6 |
| | ATOM | 3468 | CD1 | LEU A 426 | 15.485 | 35.433 | 49.028 | 1.00 | 8.16 | 6 |
| | ATOM | 3469 | CD2 | LEU A 426 | 15.896 | 37.682 | 50.019 | 1.00 | 14.54 | 6 |
| | ATOM | 3470 | N | ALA A 427 | 16.238 | 34.905 | 45.878 | 1.00 | 8.56 | 7 |
| 60 | ATOM | 3471 | CA | ALA A 427 | 16.470 | 33.494 | 45.795 | 1.00 | 9.40 | 6 |
| | ATOM | 3472 | C | ALA A 427 | 17.770 | 33.308 | 46.632 | 1.00 | 11.82 | 6 |
| | ATOM | 3473 | O | ALA A 427 | 18.790 | 33.846 | 46.230 | 1.00 | 11.64 | 8 |
| | ATOM | 3474 | CB | ALA A 427 | 16.694 | 32.989 | 44.389 | 1.00 | 12.17 | 6 |
| | ATOM | 3475 | N | THR A 428 | 17.618 | 32.535 | 47.755 | 1.00 | 12.60 | 7 |
| 65 | ATOM | 3476 | CA | THR A 428 | 18.847 | 32.242 | 48.520 | 1.00 | 7.12 | 6 |

| ATOM | 3477 | C   | THR A 428 | 19.337 | 30.874 | 48.149 | 1.00 | 5.21  | 6  |
|------|------|-----|-----------|--------|--------|--------|------|-------|----|
| ATOM | 3478 | O   | THR A 428 | 18.535 | 29.938 | 48.151 | 1.00 | 10.00 | 8  |
| ATOM | 3479 | CB  | THR A 428 | 18.458 | 32.190 | 50.076 | 1.00 | 14.89 | 6  |
| ATOM | 3480 | OG1 | THR A 428 | 18.370 | 33.536 | 50.538 | 1.00 | 9.37  | 8  |
| ATOM | 3481 | CG2 | THR A 428 | 19.732 | 31.683 | 50.770 | 1.00 | 7.45  | 6  |
| ATOM | 3482 | N   | ILE A 429 | 20.634 | 30.609 | 47.957 | 1.00 | 6.52  | 7  |
| ATOM | 3483 | CA  | ILE A 429 | 21.005 | 29.244 | 47.625 | 1.00 | 6.33  | 6  |
| ATOM | 3484 | C   | ILE A 429 | 22.335 | 28.967 | 48.333 | 1.00 | 6.38  | 6  |
| ATOM | 3485 | O   | ILE A 429 | 23.192 | 29.842 | 48.299 | 1.00 | 9.90  | 8  |
| ATOM | 3486 | CB  | ILE A 429 | 21.126 | 29.049 | 46.094 | 1.00 | 16.71 | 6  |
| ATOM | 3487 | CG1 | ILE A 429 | 21.745 | 27.675 | 45.805 | 1.00 | 13.81 | 6  |
| ATOM | 3488 | CG2 | ILE A 429 | 22.017 | 30.132 | 45.451 | 1.00 | 7.87  | 6  |
| ATOM | 3489 | CD1 | ILE A 429 | 21.400 | 27.207 | 44.377 | 1.00 | 29.66 | 6  |
| ATOM | 3490 | N   | MET A 430 | 22.515 | 27.739 | 48.867 | 1.00 | 6.66  | 7  |
| ATOM | 3491 | CA  | MET A 430 | 23.803 | 27.614 | 49.609 | 1.00 | 8.35  | 6  |
| ATOM | 3492 | C   | MET A 430 | 24.210 | 26.176 | 49.528 | 1.00 | 7.33  | 6  |
| ATOM | 3493 | O   | MET A 430 | 23.320 | 25.386 | 49.233 | 1.00 | 10.82 | 8  |
| ATOM | 3494 | CB  | MET A 430 | 23.491 | 28.031 | 51.114 | 1.00 | 12.61 | 6  |
| ATOM | 3495 | CG  | MET A 430 | 22.580 | 27.071 | 51.867 | 1.00 | 21.63 | 6  |
| ATOM | 3496 | SD  | MET A 430 | 22.237 | 27.588 | 53.648 | 1.00 | 20.92 | 16 |
| ATOM | 3497 | CE  | MET A 430 | 22.226 | 29.318 | 53.467 | 1.00 | 5.29  | 6  |
| ATOM | 3498 | N   | SER A 431 | 25.508 | 25.919 | 49.763 | 1.00 | 9.08  | 7  |
| ATOM | 3499 | CA  | SER A 431 | 25.931 | 24.524 | 49.765 | 1.00 | 9.29  | 6  |
| ATOM | 3500 | C   | SER A 431 | 26.997 | 24.353 | 50.879 | 1.00 | 11.18 | 6  |
| ATOM | 3501 | O   | SER A 431 | 27.888 | 25.180 | 51.006 | 1.00 | 10.71 | 8  |
| ATOM | 3502 | CB  | SER A 431 | 26.737 | 24.278 | 48.441 | 1.00 | 9.34  | 6  |
| ATOM | 3503 | OG  | SER A 431 | 27.031 | 22.880 | 48.398 | 1.00 | 10.03 | 8  |
| ATOM | 3504 | N   | ASP A 432 | 27.007 | 23.193 | 51.532 | 1.00 | 11.88 | 7  |
| ATOM | 3505 | CA  | ASP A 432 | 28.080 | 23.013 | 52.509 | 1.00 | 17.53 | 6  |
| ATOM | 3506 | C   | ASP A 432 | 29.128 | 22.106 | 51.888 | 1.00 | 18.48 | 6  |
| ATOM | 3507 | O   | ASP A 432 | 30.059 | 21.693 | 52.575 | 1.00 | 19.65 | 8  |
| ATOM | 3508 | CB  | ASP A 432 | 27.574 | 22.500 | 53.874 | 1.00 | 13.62 | 6  |
| ATOM | 3509 | CG  | ASP A 432 | 27.114 | 21.106 | 53.762 | 1.00 | 20.86 | 6  |
| ATOM | 3510 | OD1 | ASP A 432 | 26.632 | 20.741 | 52.631 | 1.00 | 25.08 | 8  |
| ATOM | 3511 | OD2 | ASP A 432 | 27.122 | 20.244 | 54.643 | 1.00 | 21.97 | 8  |
| ATOM | 3512 | N   | GLY A 433 | 28.965 | 21.728 | 50.636 | 1.00 | 18.06 | 7  |
| ATOM | 3513 | CA  | GLY A 433 | 29.942 | 20.908 | 49.901 | 1.00 | 17.93 | 6  |
| ATOM | 3514 | C   | GLY A 433 | 30.254 | 21.615 | 48.560 | 1.00 | 19.65 | 6  |
| ATOM | 3515 | O   | GLY A 433 | 30.256 | 22.837 | 48.415 | 1.00 | 18.59 | 8  |
| ATOM | 3516 | N   | PRO A 434 | 30.374 | 20.808 | 47.531 | 1.00 | 20.92 | 7  |
| ATOM | 3517 | CA  | PRO A 434 | 30.671 | 21.292 | 46.164 | 1.00 | 22.40 | 6  |
| ATOM | 3518 | C   | PRO A 434 | 29.579 | 22.204 | 45.633 | 1.00 | 19.51 | 6  |
| ATOM | 3519 | O   | PRO A 434 | 28.399 | 22.111 | 45.984 | 1.00 | 17.28 | 8  |
| ATOM | 3520 | CB  | PRO A 434 | 30.858 | 20.028 | 45.287 | 1.00 | 23.50 | 6  |
| ATOM | 3521 | CG  | PRO A 434 | 31.162 | 18.974 | 46.367 | 1.00 | 25.18 | 6  |
| ATOM | 3522 | CD  | PRO A 434 | 30.334 | 19.331 | 47.593 | 1.00 | 21.90 | 6  |
| ATOM | 3523 | N   | GLY A 435 | 29.977 | 23.221 | 44.899 | 1.00 | 21.46 | 7  |
| ATOM | 3524 | CA  | GLY A 435 | 29.117 | 24.193 | 44.213 | 1.00 | 22.25 | 6  |
| ATOM | 3525 | C   | GLY A 435 | 28.199 | 23.464 | 43.209 | 1.00 | 20.34 | 6  |
| ATOM | 3526 | O   | GLY A 435 | 28.357 | 22.297 | 42.932 | 1.00 | 18.28 | 8  |
| ATOM | 3527 | N   | GLY A 436 | 27.188 | 24.182 | 42.728 | 1.00 | 22.42 | 7  |
| ATOM | 3528 | CA  | GLY A 436 | 26.241 | 23.604 | 41.777 | 1.00 | 19.22 | 6  |
| ATOM | 3529 | C   | GLY A 436 | 25.110 | 24.613 | 41.533 | 1.00 | 15.97 | 6  |
| ATOM | 3530 | O   | GLY A 436 | 25.232 | 25.814 | 41.726 | 1.00 | 19.08 | 8  |
| ATOM | 3531 | N   | GLU A 437 | 23.947 | 24.068 | 41.202 | 1.00 | 15.44 | 7  |
| ATOM | 3532 | CA  | GLU A 437 | 22.879 | 24.987 | 40.862 | 1.00 | 17.39 | 6  |
| ATOM | 3533 | C   | GLU A 437 | 21.539 | 24.329 | 41.094 | 1.00 | 16.91 | 6  |
| ATOM | 3534 | O   | GLU A 437 | 21.473 | 23.132 | 41.287 | 1.00 | 19.16 | 8  |
| ATOM | 3535 | CB  | GLU A 437 | 23.088 | 25.476 | 39.401 | 1.00 | 37.35 | 6  |
| ATOM | 3536 | CG  | GLU A 437 | 22.561 | 24.488 | 38.402 | 1.00 | 48.60 | 6  |
| ATOM | 3537 | CD  | GLU A 437 | 23.271 | 24.417 | 37.059 | 1.00 | 63.89 | 6  |
| ATOM | 3538 | OE1 | GLU A 437 | 24.253 | 25.163 | 36.858 | 1.00 | 64.25 | 8  |
| ATOM | 3539 | OE2 | GLU A 437 | 22.760 | 23.611 | 36.220 | 1.00 | 61.31 | 8  |
| ATOM | 3540 | N   | LYS A 438 | 20.513 | 25.164 | 41.140 | 1.00 | 16.88 | 7  |
| ATOM | 3541 | CA  | LYS A 438 | 19.195 | 24.652 | 41.397 | 1.00 | 16.71 | 6  |

| | ATOM | 3542 | C | LYS | A | 438 | 18.197 | 25.538 | 40.661 | 1.00 | 15.03 | 6 |
|---|---|---|---|---|---|---|---|---|---|---|---|---|
| | ATOM | 3543 | O | LYS | A | 438 | 18.201 | 26.759 | 40.615 | 1.00 | 14.02 | 8 |
| | ATOM | 3544 | CB | LYS | A | 438 | 18.822 | 24.744 | 42.917 | 1.00 | 15.80 | 6 |
| | ATOM | 3545 | CG | LYS | A | 438 | 17.823 | 23.612 | 43.167 | 1.00 | 22.46 | 6 |
| 5 | ATOM | 3546 | CD | LYS | A | 438 | 17.118 | 23.747 | 44.517 | 1.00 | 27.63 | 6 |
| | ATOM | 3547 | CE | LYS | A | 438 | 18.087 | 23.399 | 45.659 | 1.00 | 14.39 | 6 |
| | ATOM | 3548 | NZ | LYS | A | 438 | 18.332 | 21.923 | 45.627 | 1.00 | 15.88 | 7 |
| | ATOM | 3549 | N | TRP | A | 439 | 17.179 | 24.852 | 40.212 | 1.00 | 17.22 | 7 |
| | ATOM | 3550 | CA | TRP | A | 439 | 16.073 | 25.457 | 39.455 | 1.00 | 20.48 | 6 |
| 10 | ATOM | 3551 | C | TRP | A | 439 | 15.022 | 25.892 | 40.475 | 1.00 | 19.48 | 6 |
| | ATOM | 3552 | O | TRP | A | 439 | 14.573 | 25.008 | 41.203 | 1.00 | 21.32 | 8 |
| | ATOM | 3553 | CB | TRP | A | 439 | 15.564 | 24.398 | 38.458 | 1.00 | 40.48 | 6 |
| | ATOM | 3554 | CG | TRP | A | 439 | 15.732 | 22.971 | 38.929 | 1.00 | 79.64 | 6 |
| | ATOM | 3555 | CD1 | TRP | A | 439 | 16.851 | 22.314 | 39.388 | 1.00 | 82.87 | 6 |
| 15 | ATOM | 3556 | CD2 | TRP | A | 439 | 14.689 | 21.975 | 38.972 | 1.00 | 92.39 | 6 |
| | ATOM | 3557 | NE1 | TRP | A | 439 | 16.577 | 21.027 | 39.732 | 1.00 | 88.68 | 7 |
| | ATOM | 3558 | CE2 | TRP | A | 439 | 15.250 | 20.786 | 39.478 | 1.00 | 94.65 | 6 |
| | ATOM | 3559 | CE3 | TRP | A | 439 | 13.328 | 21.982 | 38.640 | 1.00 | 99.81 | 6 |
| | ATOM | 3560 | CZ2 | TRP | A | 439 | 14.505 | 19.619 | 39.647 | 1.00 | 99.57 | 6 |
| 20 | ATOM | 3561 | CZ3 | TRP | A | 439 | 12.591 | 20.827 | 38.814 | 1.00 | 103.16 | 6 |
| | ATOM | 3562 | CH2 | TRP | A | 439 | 13.181 | 19.657 | 39.313 | 1.00 | 101.89 | 6 |
| | ATOM | 3563 | N | MET | A | 440 | 14.639 | 27.147 | 40.618 | 1.00 | 16.39 | 7 |
| | ATOM | 3564 | CA | MET | A | 440 | 13.662 | 27.556 | 41.601 | 1.00 | 20.47 | 6 |
| | ATOM | 3565 | C | MET | A | 440 | 12.726 | 28.644 | 41.097 | 1.00 | 19.37 | 6 |
| 25 | ATOM | 3566 | O | MET | A | 440 | 13.133 | 29.501 | 40.323 | 1.00 | 20.96 | 8 |
| | ATOM | 3567 | CB | MET | A | 440 | 14.393 | 28.185 | 42.862 | 1.00 | 14.92 | 6 |
| | ATOM | 3568 | CG | MET | A | 440 | 15.248 | 27.194 | 43.620 | 1.00 | 18.19 | 6 |
| | ATOM | 3569 | SD | MET | A | 440 | 16.016 | 27.776 | 45.176 | 1.00 | 23.71 | 16 |
| | ATOM | 3570 | CE | MET | A | 440 | 17.172 | 28.983 | 44.595 | 1.00 | 23.40 | 6 |
| 30 | ATOM | 3571 | N | TYR | A | 441 | 11.512 | 28.662 | 41.587 | 1.00 | 19.17 | 7 |
| | ATOM | 3572 | CA | TYR | A | 441 | 10.493 | 29.612 | 41.193 | 1.00 | 17.45 | 6 |
| | ATOM | 3573 | C | TYR | A | 441 | 10.491 | 30.925 | 41.911 | 1.00 | 19.37 | 6 |
| | ATOM | 3574 | O | TYR | A | 441 | 10.306 | 30.894 | 43.144 | 1.00 | 20.83 | 8 |
| | ATOM | 3575 | CB | TYR | A | 441 | 9.158 | 28.882 | 41.392 | 1.00 | 18.76 | 6 |
| 35 | ATOM | 3576 | CG | TYR | A | 441 | 7.946 | 29.700 | 41.019 | 1.00 | 23.90 | 6 |
| | ATOM | 3577 | CD1 | TYR | A | 441 | 7.714 | 30.003 | 39.663 | 1.00 | 24.83 | 6 |
| | ATOM | 3578 | CD2 | TYR | A | 441 | 7.035 | 30.174 | 41.929 | 1.00 | 26.10 | 6 |
| | ATOM | 3579 | CE1 | TYR | A | 441 | 6.622 | 30.734 | 39.268 | 1.00 | 22.74 | 6 |
| | ATOM | 3580 | CE2 | TYR | A | 441 | 5.936 | 30.926 | 41.560 | 1.00 | 26.92 | 6 |
| 40 | ATOM | 3581 | CZ | TYR | A | 441 | 5.735 | 31.181 | 40.213 | 1.00 | 26.49 | 6 |
| | ATOM | 3582 | OH | TYR | A | 441 | 4.644 | 31.921 | 39.817 | 1.00 | 27.24 | 8 |
| | ATOM | 3583 | N | VAL | A | 442 | 10.551 | 32.102 | 41.275 | 1.00 | 17.33 | 7 |
| | ATOM | 3584 | CA | VAL | A | 442 | 10.503 | 33.378 | 41.934 | 1.00 | 17.24 | 6 |
| | ATOM | 3585 | C | VAL | A | 442 | 9.215 | 34.147 | 41.685 | 1.00 | 19.14 | 6 |
| 45 | ATOM | 3586 | O | VAL | A | 442 | 8.989 | 35.223 | 42.261 | 1.00 | 18.47 | 8 |
| | ATOM | 3587 | CB | VAL | A | 442 | 11.711 | 34.267 | 41.631 | 1.00 | 21.08 | 6 |
| | ATOM | 3588 | CG1 | VAL | A | 442 | 12.950 | 33.529 | 42.117 | 1.00 | 12.81 | 6 |
| | ATOM | 3589 | CG2 | VAL | A | 442 | 11.819 | 34.555 | 40.118 | 1.00 | 17.82 | 6 |
| | ATOM | 3590 | N | GLY | A | 443 | 8.355 | 33.583 | 40.824 | 1.00 | 19.01 | 7 |
| 50 | ATOM | 3591 | CA | GLY | A | 443 | 7.106 | 34.258 | 40.520 | 1.00 | 20.35 | 6 |
| | ATOM | 3592 | C | GLY | A | 443 | 7.037 | 34.695 | 39.040 | 1.00 | 22.26 | 6 |
| | ATOM | 3593 | O | GLY | A | 443 | 7.945 | 35.338 | 38.527 | 1.00 | 22.27 | 8 |
| | ATOM | 3594 | N | GLN | A | 444 | 5.910 | 34.362 | 38.422 | 1.00 | 24.17 | 7 |
| | ATOM | 3595 | CA | GLN | A | 444 | 5.600 | 34.665 | 37.021 | 1.00 | 24.96 | 6 |
| 55 | ATOM | 3596 | C | GLN | A | 444 | 5.765 | 36.122 | 36.660 | 1.00 | 23.35 | 6 |
| | ATOM | 3597 | O | GLN | A | 444 | 6.399 | 36.407 | 35.636 | 1.00 | 27.45 | 8 |
| | ATOM | 3598 | CB | GLN | A | 444 | 4.162 | 34.299 | 36.663 | 1.00 | 29.53 | 6 |
| | ATOM | 3599 | CG | GLN | A | 444 | 3.900 | 32.806 | 36.803 | 1.00 | 46.12 | 6 |
| | ATOM | 3600 | CD | GLN | A | 444 | 2.592 | 32.427 | 36.120 | 1.00 | 62.67 | 6 |
| 60 | ATOM | 3601 | OE1 | GLN | A | 444 | 1.849 | 33.279 | 35.625 | 1.00 | 63.63 | 8 |
| | ATOM | 3602 | NE2 | GLN | A | 444 | 2.355 | 31.119 | 36.112 | 1.00 | 71.09 | 7 |
| | ATOM | 3603 | N | ASN | A | 445 | 5.375 | 37.067 | 37.464 | 1.00 | 21.45 | 7 |
| | ATOM | 3604 | CA | ASN | A | 445 | 5.605 | 38.469 | 37.254 | 1.00 | 21.23 | 6 |
| | ATOM | 3605 | C | ASN | A | 445 | 7.054 | 38.890 | 37.261 | 1.00 | 21.93 | 6 |
| 65 | ATOM | 3606 | O | ASN | A | 445 | 7.246 | 40.099 | 37.088 | 1.00 | 25.78 | 8 |

| | ATOM | 3607 | CB | ASN A 445 | 4.839 | 39.358 | 38.236 | 1.00 | 30.03 | 6 |
|---|---|---|---|---|---|---|---|---|---|---|
| | ATOM | 3608 | CG | ASN A 445 | 5.320 | 39.194 | 39.679 | 1.00 | 45.80 | 6 |
| | ATOM | 3609 | OD1 | ASN A 445 | 5.987 | 38.202 | 40.013 | 1.00 | 42.55 | 8 |
| | ATOM | 3610 | ND2 | ASN A 445 | 4.998 | 40.136 | 40.574 | 1.00 | 36.92 | 7 |
| 5 | ATOM | 3611 | N | LYS A 446 | 8.078 | 38.064 | 37.438 | 1.00 | 21.07 | 7 |
| | ATOM | 3612 | CA | LYS A 446 | 9.449 | 38.580 | 37.424 | 1.00 | 18.80 | 6 |
| | ATOM | 3613 | C | LYS A 446 | 10.117 | 38.163 | 36.087 | 1.00 | 16.42 | 6 |
| | ATOM | 3614 | O | LYS A 446 | 11.325 | 38.297 | 35.908 | 1.00 | 14.00 | 8 |
| | ATOM | 3615 | CB | LYS A 446 | 10.274 | 38.016 | 38.607 | 1.00 | 22.87 | 6 |
| 10 | ATOM | 3616 | CG | LYS A 446 | 9.714 | 38.055 | 40.045 | 1.00 | 20.43 | 6 |
| | ATOM | 3617 | CD | LYS A 446 | 9.144 | 39.421 | 40.333 | 1.00 | 19.39 | 6 |
| | ATOM | 3618 | CE | LYS A 446 | 8.549 | 39.569 | 41.735 | 1.00 | 33.48 | 6 |
| | ATOM | 3619 | NZ | LYS A 446 | 9.619 | 39.947 | 42.686 | 1.00 | 20.28 | 7 |
| | ATOM | 3620 | N | ALA A 447 | 9.313 | 37.561 | 35.214 | 1.00 | 18.69 | 7 |
| 15 | ATOM | 3621 | CA | ALA A 447 | 9.807 | 37.132 | 33.863 | 1.00 | 18.64 | 6 |
| | ATOM | 3622 | C | ALA A 447 | 10.638 | 38.198 | 33.169 | 1.00 | 16.44 | 6 |
| | ATOM | 3623 | O | ALA A 447 | 10.212 | 39.357 | 33.172 | 1.00 | 16.52 | 8 |
| | ATOM | 3624 | CB | ALA A 447 | 8.615 | 36.834 | 32.962 | 1.00 | 12.08 | 6 |
| | ATOM | 3625 | N | GLY A 448 | 11.828 | 37.822 | 32.725 | 1.00 | 18.95 | 7 |
| 20 | ATOM | 3626 | CA | GLY A 448 | 12.714 | 38.717 | 32.003 | 1.00 | 21.86 | 6 |
| | ATOM | 3627 | C | GLY A 448 | 13.580 | 39.636 | 32.844 | 1.00 | 25.00 | 6 |
| | ATOM | 3628 | O | GLY A 448 | 14.406 | 40.334 | 32.251 | 1.00 | 22.21 | 8 |
| | ATOM | 3629 | N | GLN A 449 | 13.460 | 39.625 | 34.209 | 1.00 | 23.94 | 7 |
| | ATOM | 3630 | CA | GLN A 449 | 14.356 | 40.485 | 35.002 | 1.00 | 20.19 | 6 |
| 25 | ATOM | 3631 | C | GLN A 449 | 15.726 | 39.824 | 35.110 | 1.00 | 19.28 | 6 |
| | ATOM | 3632 | O | GLN A 449 | 15.911 | 38.609 | 34.932 | 1.00 | 18.29 | 8 |
| | ATOM | 3633 | CB | GLN A 449 | 13.798 | 40.688 | 36.402 | 1.00 | 22.06 | 6 |
| | ATOM | 3634 | CG | GLN A 449 | 12.373 | 41.221 | 36.448 | 1.00 | 19.83 | 6 |
| | ATOM | 3635 | CD | GLN A 449 | 11.966 | 41.512 | 37.899 | 1.00 | 33.19 | 6 |
| 30 | ATOM | 3636 | OE1 | GLN A 449 | 10.960 | 42.166 | 38.157 | 1.00 | 27.87 | 8 |
| | ATOM | 3637 | NE2 | GLN A 449 | 12.776 | 41.029 | 38.836 | 1.00 | 18.13 | 7 |
| | ATOM | 3638 | N | VAL A 450 | 16.697 | 40.709 | 35.289 | 1.00 | 18.52 | 7 |
| | ATOM | 3639 | CA | VAL A 450 | 18.074 | 40.243 | 35.369 | 1.00 | 22.23 | 6 |
| | ATOM | 3640 | C | VAL A 450 | 18.481 | 40.412 | 36.875 | 1.00 | 21.59 | 6 |
| 35 | ATOM | 3641 | O | VAL A 450 | 18.406 | 41.522 | 37.392 | 1.00 | 19.00 | 8 |
| | ATOM | 3642 | CB | VAL A 450 | 19.009 | 41.180 | 34.587 | 1.00 | 21.38 | 6 |
| | ATOM | 3643 | CG1 | VAL A 450 | 20.465 | 40.804 | 34.829 | 1.00 | 18.85 | 6 |
| | ATOM | 3644 | CG2 | VAL A 450 | 18.645 | 41.095 | 33.101 | 1.00 | 25.37 | 6 |
| | ATOM | 3645 | N | TRP A 451 | 18.919 | 39.327 | 37.462 | 1.00 | 21.95 | 7 |
| 40 | ATOM | 3646 | CA | TRP A 451 | 19.269 | 39.345 | 38.893 | 1.00 | 22.78 | 6 |
| | ATOM | 3647 | C | TRP A 451 | 20.737 | 39.173 | 39.144 | 1.00 | 22.81 | 6 |
| | ATOM | 3648 | O | TRP A 451 | 21.421 | 38.496 | 38.371 | 1.00 | 24.18 | 8 |
| | ATOM | 3649 | CB | TRP A 451 | 18.473 | 38.191 | 39.545 | 1.00 | 18.72 | 6 |
| | ATOM | 3650 | CG | TRP A 451 | 17.006 | 38.481 | 39.743 | 1.00 | 15.12 | 6 |
| 45 | ATOM | 3651 | CD1 | TRP A 451 | 16.210 | 39.359 | 39.083 | 1.00 | 19.62 | 6 |
| | ATOM | 3652 | CD2 | TRP A 451 | 16.154 | 37.891 | 40.730 | 1.00 | 25.22 | 6 |
| | ATOM | 3653 | NE1 | TRP A 451 | 14.920 | 39.350 | 39.542 | 1.00 | 22.83 | 7 |
| | ATOM | 3654 | CE2 | TRP A 451 | 14.873 | 38.437 | 40.575 | 1.00 | 24.01 | 6 |
| | ATOM | 3655 | CE3 | TRP A 451 | 16.375 | 36.957 | 41.768 | 1.00 | 20.26 | 6 |
| 50 | ATOM | 3656 | CZ2 | TRP A 451 | 13.808 | 38.095 | 41.406 | 1.00 | 15.77 | 6 |
| | ATOM | 3657 | CZ3 | TRP A 451 | 15.302 | 36.589 | 42.552 | 1.00 | 16.21 | 6 |
| | ATOM | 3658 | CH2 | TRP A 451 | 14.060 | 37.165 | 42.384 | 1.00 | 11.49 | 6 |
| | ATOM | 3659 | N | HIS A 452 | 21.241 | 39.675 | 40.274 | 1.00 | 22.72 | 7 |
| | ATOM | 3660 | CA | HIS A 452 | 22.651 | 39.425 | 40.598 | 1.00 | 21.61 | 6 |
| 55 | ATOM | 3661 | C | HIS A 452 | 22.806 | 39.006 | 42.086 | 1.00 | 22.69 | 6 |
| | ATOM | 3662 | O | HIS A 452 | 21.833 | 38.928 | 42.854 | 1.00 | 22.08 | 8 |
| | ATOM | 3663 | CB | HIS A 452 | 23.469 | 40.648 | 40.251 | 1.00 | 19.24 | 6 |
| | ATOM | 3664 | CG | HIS A 452 | 23.193 | 41.764 | 41.225 | 1.00 | 37.38 | 6 |
| | ATOM | 3665 | ND1 | HIS A 452 | 24.209 | 42.528 | 41.757 | 1.00 | 43.93 | 7 |
| 60 | ATOM | 3666 | CD2 | HIS A 452 | 22.043 | 42.190 | 41.808 | 1.00 | 41.64 | 6 |
| | ATOM | 3667 | CE1 | HIS A 452 | 23.693 | 43.404 | 42.597 | 1.00 | 41.75 | 6 |
| | ATOM | 3668 | NE2 | HIS A 452 | 22.392 | 43.222 | 42.646 | 1.00 | 38.20 | 7 |
| | ATOM | 3669 | N | ASP A 453 | 24.007 | 38.542 | 42.389 | 1.00 | 21.14 | 7 |
| | ATOM | 3670 | CA | ASP A 453 | 24.298 | 37.985 | 43.727 | 1.00 | 21.43 | 6 |
| 65 | ATOM | 3671 | C | ASP A 453 | 24.675 | 39.145 | 44.647 | 1.00 | 20.48 | 6 |

| ATOM | 3672 | O | ASP A 453 | 25.785 | 39.620 | 44.557 | 1.00 | 19.57 | 8 |
| ATOM | 3673 | CB | ASP A 453 | 25.361 | 36.906 | 43.679 | 1.00 | 16.37 | 6 |
| ATOM | 3674 | CG | ASP A 453 | 25.748 | 36.255 | 45.020 | 1.00 | 30.12 | 6 |
| ATOM | 3675 | OD1 | ASP A 453 | 25.197 | 36.660 | 46.082 | 1.00 | 17.12 | 8 |
| ATOM | 3676 | OD2 | ASP A 453 | 26.600 | 35.324 | 45.079 | 1.00 | 13.59 | 8 |
| ATOM | 3677 | N | ILE A 454 | 23.768 | 39.576 | 45.504 | 1.00 | 21.42 | 7 |
| ATOM | 3678 | CA | ILE A 454 | 24.030 | 40.669 | 46.453 | 1.00 | 21.19 | 6 |
| ATOM | 3679 | C | ILE A 454 | 25.184 | 40.396 | 47.398 | 1.00 | 21.47 | 6 |
| ATOM | 3680 | O | ILE A 454 | 25.822 | 41.366 | 47.838 | 1.00 | 22.17 | 8 |
| ATOM | 3681 | CB | ILE A 454 | 22.786 | 41.083 | 47.230 | 1.00 | 21.21 | 6 |
| ATOM | 3682 | CG1 | ILE A 454 | 22.867 | 42.506 | 47.792 | 1.00 | 27.82 | 6 |
| ATOM | 3683 | CG2 | ILE A 454 | 22.392 | 40.067 | 48.293 | 1.00 | 12.48 | 6 |
| ATOM | 3684 | CD1 | ILE A 454 | 21.525 | 42.918 | 48.415 | 1.00 | 22.75 | 6 |
| ATOM | 3685 | N | THR A 455 | 25.652 | 39.166 | 47.580 | 1.00 | 21.33 | 7 |
| ATOM | 3686 | CA | THR A 455 | 26.806 | 38.928 | 48.418 | 1.00 | 24.19 | 6 |
| ATOM | 3687 | C | THR A 455 | 28.094 | 39.164 | 47.634 | 1.00 | 28.00 | 6 |
| ATOM | 3688 | O | THR A 455 | 29.175 | 39.281 | 48.243 | 1.00 | 25.46 | 8 |
| ATOM | 3689 | CB | THR A 455 | 26.869 | 37.516 | 48.996 | 1.00 | 20.94 | 6 |
| ATOM | 3690 | OG1 | THR A 455 | 27.101 | 36.595 | 47.918 | 1.00 | 13.03 | 8 |
| ATOM | 3691 | CG2 | THR A 455 | 25.576 | 37.131 | 49.723 | 1.00 | 11.73 | 6 |
| ATOM | 3692 | N | GLY A 456 | 27.936 | 39.109 | 46.284 | 1.00 | 26.42 | 7 |
| ATOM | 3693 | CA | GLY A 456 | 29.126 | 39.237 | 45.452 | 1.00 | 26.72 | 6 |
| ATOM | 3694 | C | GLY A 456 | 29.929 | 37.951 | 45.434 | 1.00 | 27.50 | 6 |
| ATOM | 3695 | O | GLY A 456 | 31.055 | 37.929 | 44.936 | 1.00 | 28.81 | 8 |
| ATOM | 3696 | N | ASN A 457 | 29.429 | 36.834 | 45.956 | 1.00 | 27.72 | 7 |
| ATOM | 3697 | CA | ASN A 457 | 30.161 | 35.582 | 45.935 | 1.00 | 28.88 | 6 |
| ATOM | 3698 | C | ASN A 457 | 30.186 | 35.037 | 44.505 | 1.00 | 30.88 | 6 |
| ATOM | 3699 | O | ASN A 457 | 31.208 | 34.478 | 44.116 | 1.00 | 32.05 | 8 |
| ATOM | 3700 | CB | ASN A 457 | 29.597 | 34.558 | 46.931 | 1.00 | 29.41 | 6 |
| ATOM | 3701 | CG | ASN A 457 | 29.776 | 34.897 | 48.411 | 1.00 | 35.69 | 6 |
| ATOM | 3702 | OD1 | ASN A 457 | 28.943 | 34.630 | 49.300 | 1.00 | 34.46 | 8 |
| ATOM | 3703 | ND2 | ASN A 457 | 30.905 | 35.518 | 48.721 | 1.00 | 20.50 | 7 |
| ATOM | 3704 | N | LYS A 458 | 29.078 | 35.062 | 43.779 | 1.00 | 31.28 | 7 |
| ATOM | 3705 | CA | LYS A 458 | 28.936 | 34.566 | 42.402 | 1.00 | 32.10 | 6 |
| ATOM | 3706 | C | LYS A 458 | 28.835 | 35.765 | 41.467 | 1.00 | 32.39 | 6 |
| ATOM | 3707 | O | LYS A 458 | 27.916 | 36.597 | 41.513 | 1.00 | 31.80 | 8 |
| ATOM | 3708 | CB | LYS A 458 | 27.586 | 33.853 | 42.246 | 1.00 | 30.51 | 6 |
| ATOM | 3709 | CG | LYS A 458 | 27.661 | 32.358 | 42.238 | 1.00 | 28.44 | 6 |
| ATOM | 3710 | CD | LYS A 458 | 28.557 | 31.874 | 41.120 | 1.00 | 30.75 | 6 |
| ATOM | 3711 | CE | LYS A 458 | 28.709 | 30.366 | 41.267 | 1.00 | 38.53 | 6 |
| ATOM | 3712 | NZ | LYS A 458 | 29.127 | 29.819 | 39.947 | 1.00 | 46.81 | 7 |
| ATOM | 3713 | N | PRO A 459 | 29.801 | 35.912 | 40.582 | 1.00 | 35.18 | 7 |
| ATOM | 3714 | CA | PRO A 459 | 29.929 | 37.091 | 39.739 | 1.00 | 35.47 | 6 |
| ATOM | 3715 | C | PRO A 459 | 28.953 | 37.258 | 38.602 | 1.00 | 37.23 | 6 |
| ATOM | 3716 | O | PRO A 459 | 28.746 | 38.445 | 38.202 | 1.00 | 40.65 | 8 |
| ATOM | 3717 | CB | PRO A 459 | 31.403 | 37.168 | 39.320 | 1.00 | 35.59 | 6 |
| ATOM | 3718 | CG | PRO A 459 | 31.844 | 35.739 | 39.467 | 1.00 | 35.76 | 6 |
| ATOM | 3719 | CD | PRO A 459 | 30.946 | 35.014 | 40.452 | 1.00 | 35.97 | 6 |
| ATOM | 3720 | N | GLY A 460 | 28.241 | 36.255 | 38.096 | 1.00 | 35.36 | 7 |
| ATOM | 3721 | CA | GLY A 460 | 27.370 | 36.618 | 36.959 | 1.00 | 33.99 | 6 |
| ATOM | 3722 | C | GLY A 460 | 26.079 | 37.355 | 37.124 | 1.00 | 31.39 | 6 |
| ATOM | 3723 | O | GLY A 460 | 25.723 | 38.162 | 37.987 | 1.00 | 31.32 | 8 |
| ATOM | 3724 | N | THR A 461 | 25.172 | 37.089 | 36.168 | 1.00 | 28.63 | 7 |
| ATOM | 3725 | CA | THR A 461 | 23.820 | 37.591 | 36.201 | 1.00 | 26.63 | 6 |
| ATOM | 3726 | C | THR A 461 | 22.977 | 36.365 | 35.857 | 1.00 | 26.19 | 6 |
| ATOM | 3727 | O | THR A 461 | 23.509 | 35.368 | 35.372 | 1.00 | 25.69 | 8 |
| ATOM | 3728 | CB | THR A 461 | 23.406 | 38.714 | 35.253 | 1.00 | 34.32 | 6 |
| ATOM | 3729 | OG1 | THR A 461 | 23.582 | 38.196 | 33.940 | 1.00 | 39.98 | 8 |
| ATOM | 3730 | CG2 | THR A 461 | 24.197 | 39.984 | 35.459 | 1.00 | 36.81 | 6 |
| ATOM | 3731 | N | VAL A 462 | 21.682 | 36.479 | 36.097 | 1.00 | 24.35 | 7 |
| ATOM | 3732 | CA | VAL A 462 | 20.801 | 35.342 | 35.840 | 1.00 | 24.97 | 6 |
| ATOM | 3733 | C | VAL A 462 | 19.525 | 36.061 | 35.394 | 1.00 | 25.20 | 6 |
| ATOM | 3734 | O | VAL A 462 | 19.129 | 37.029 | 36.059 | 1.00 | 26.38 | 8 |
| ATOM | 3735 | CB | VAL A 462 | 20.574 | 34.535 | 37.138 | 1.00 | 26.35 | 6 |
| ATOM | 3736 | CG1 | VAL A 462 | 19.170 | 34.009 | 37.299 | 1.00 | 27.37 | 6 |

| ATOM | 3737 | CG2 | VAL A 462 | 21.533 | 33.362 | 37.172 | 1.00 | 37.60 | 6 |
| --- | --- | --- | --- | --- | --- | --- | --- | --- | --- |
| ATOM | 3738 | N | THR A 463 | 18.932 | 35.524 | 34.343 | 1.00 | 24.53 | 7 |
| ATOM | 3739 | CA | THR A 463 | 17.720 | 36.194 | 33.827 | 1.00 | 22.54 | 6 |
| ATOM | 3740 | C | THR A 463 | 16.530 | 35.314 | 34.144 | 1.00 | 19.39 | 6 |
| ATOM | 3741 | O | THR A 463 | 16.687 | 34.104 | 33.936 | 1.00 | 18.11 | 8 |
| ATOM | 3742 | CB | THR A 463 | 17.799 | 36.326 | 32.270 | 1.00 | 27.00 | 6 |
| ATOM | 3743 | OG1 | THR A 463 | 18.933 | 37.127 | 31.946 | 1.00 | 25.69 | 8 |
| ATOM | 3744 | CG2 | THR A 463 | 16.563 | 37.080 | 31.786 | 1.00 | 21.84 | 6 |
| ATOM | 3745 | N | ILE A 464 | 15.443 | 35.905 | 34.620 | 1.00 | 18.98 | 7 |
| ATOM | 3746 | CA | ILE A 464 | 14.318 | 35.002 | 34.950 | 1.00 | 19.00 | 6 |
| ATOM | 3747 | C | ILE A 464 | 13.588 | 34.598 | 33.646 | 1.00 | 23.41 | 6 |
| ATOM | 3748 | O | ILE A 464 | 13.346 | 35.458 | 32.794 | 1.00 | 22.97 | 8 |
| ATOM | 3749 | CB | ILE A 464 | 13.345 | 35.759 | 35.871 | 1.00 | 23.33 | 6 |
| ATOM | 3750 | CG1 | ILE A 464 | 14.049 | 36.430 | 37.059 | 1.00 | 19.89 | 6 |
| ATOM | 3751 | CG2 | ILE A 464 | 12.261 | 34.806 | 36.345 | 1.00 | 23.29 | 6 |
| ATOM | 3752 | CD1 | ILE A 464 | 15.140 | 35.555 | 37.656 | 1.00 | 14.03 | 6 |
| ATOM | 3753 | N | ASN A 465 | 13.178 | 33.347 | 33.558 | 1.00 | 21.94 | 7 |
| ATOM | 3754 | CA | ASN A 465 | 12.516 | 32.846 | 32.387 | 1.00 | 22.42 | 6 |
| ATOM | 3755 | C | ASN A 465 | 11.097 | 33.333 | 32.280 | 1.00 | 23.26 | 6 |
| ATOM | 3756 | O | ASN A 465 | 10.512 | 33.991 | 33.139 | 1.00 | 23.81 | 8 |
| ATOM | 3757 | CB | ASN A 465 | 12.731 | 31.359 | 32.224 | 1.00 | 13.06 | 6 |
| ATOM | 3758 | CG | ASN A 465 | 11.672 | 30.476 | 32.848 | 1.00 | 24.11 | 6 |
| ATOM | 3759 | OD1 | ASN A 465 | 10.653 | 30.845 | 33.442 | 1.00 | 27.47 | 8 |
| ATOM | 3760 | ND2 | ASN A 465 | 11.913 | 29.185 | 32.652 | 1.00 | 26.50 | 7 |
| ATOM | 3761 | N | ALA A 466 | 10.436 | 32.919 | 31.184 | 1.00 | 22.42 | 7 |
| ATOM | 3762 | CA | ALA A 466 | 9.107 | 33.388 | 30.855 | 1.00 | 20.19 | 6 |
| ATOM | 3763 | C | ALA A 466 | 8.060 | 32.877 | 31.815 | 1.00 | 20.86 | 6 |
| ATOM | 3764 | O | ALA A 466 | 7.005 | 33.519 | 31.862 | 1.00 | 19.65 | 8 |
| ATOM | 3765 | CB | ALA A 466 | 8.720 | 32.927 | 29.440 | 1.00 | 27.57 | 6 |
| ATOM | 3766 | N | ASP A 467 | 8.339 | 31.758 | 32.472 | 1.00 | 20.43 | 7 |
| ATOM | 3767 | CA | ASP A 467 | 7.375 | 31.236 | 33.432 | 1.00 | 25.15 | 6 |
| ATOM | 3768 | C | ASP A 467 | 7.714 | 31.622 | 34.898 | 1.00 | 26.69 | 6 |
| ATOM | 3769 | O | ASP A 467 | 6.988 | 31.198 | 35.814 | 1.00 | 27.50 | 8 |
| ATOM | 3770 | CB | ASP A 467 | 7.280 | 29.718 | 33.419 | 1.00 | 35.94 | 6 |
| ATOM | 3771 | CG | ASP A 467 | 7.447 | 28.991 | 32.113 | 1.00 | 57.11 | 6 |
| ATOM | 3772 | OD1 | ASP A 467 | 6.618 | 29.149 | 31.191 | 1.00 | 55.73 | 8 |
| ATOM | 3773 | OD2 | ASP A 467 | 8.416 | 28.211 | 31.968 | 1.00 | 68.22 | 8 |
| ATOM | 3774 | N | GLY A 468 | 8.787 | 32.333 | 35.124 | 1.00 | 25.27 | 7 |
| ATOM | 3775 | CA | GLY A 468 | 9.169 | 32.772 | 36.449 | 1.00 | 25.94 | 6 |
| ATOM | 3776 | C | GLY A 468 | 10.173 | 31.846 | 37.129 | 1.00 | 26.60 | 6 |
| ATOM | 3777 | O | GLY A 468 | 10.379 | 31.937 | 38.329 | 1.00 | 23.74 | 8 |
| ATOM | 3778 | N | TRP A 469 | 10.857 | 30.984 | 36.384 | 1.00 | 26.03 | 7 |
| ATOM | 3779 | CA | TRP A 469 | 11.866 | 30.075 | 36.864 | 1.00 | 24.07 | 6 |
| ATOM | 3780 | C | TRP A 469 | 13.252 | 30.507 | 36.421 | 1.00 | 24.59 | 6 |
| ATOM | 3781 | O | TRP A 469 | 13.360 | 31.256 | 35.447 | 1.00 | 24.16 | 8 |
| ATOM | 3782 | CB | TRP A 469 | 11.711 | 28.639 | 36.344 | 1.00 | 24.41 | 6 |
| ATOM | 3783 | CG | TRP A 469 | 10.483 | 28.028 | 36.943 | 1.00 | 29.23 | 6 |
| ATOM | 3784 | CD1 | TRP A 469 | 9.187 | 28.305 | 36.618 | 1.00 | 34.11 | 6 |
| ATOM | 3785 | CD2 | TRP A 469 | 10.454 | 27.060 | 37.998 | 1.00 | 29.54 | 6 |
| ATOM | 3786 | NE1 | TRP A 469 | 8.336 | 27.562 | 37.415 | 1.00 | 33.70 | 7 |
| ATOM | 3787 | CE2 | TRP A 469 | 9.095 | 26.767 | 38.250 | 1.00 | 31.92 | 6 |
| ATOM | 3788 | CE3 | TRP A 469 | 11.426 | 26.377 | 38.726 | 1.00 | 30.77 | 6 |
| ATOM | 3789 | CZ2 | TRP A 469 | 8.709 | 25.856 | 39.233 | 1.00 | 35.82 | 6 |
| ATOM | 3790 | CZ3 | TRP A 469 | 11.040 | 25.474 | 39.697 | 1.00 | 30.23 | 6 |
| ATOM | 3791 | CH2 | TRP A 469 | 9.688 | 25.235 | 39.954 | 1.00 | 30.75 | 6 |
| ATOM | 3792 | N | ALA A 470 | 14.261 | 30.045 | 37.151 | 1.00 | 22.85 | 7 |
| ATOM | 3793 | CA | ALA A 470 | 15.628 | 30.383 | 36.788 | 1.00 | 21.53 | 6 |
| ATOM | 3794 | C | ALA A 470 | 16.546 | 29.352 | 37.431 | 1.00 | 23.57 | 6 |
| ATOM | 3795 | O | ALA A 470 | 16.167 | 28.716 | 38.421 | 1.00 | 23.74 | 8 |
| ATOM | 3796 | CB | ALA A 470 | 16.026 | 31.769 | 37.199 | 1.00 | 21.25 | 6 |
| ATOM | 3797 | N | ASN A 471 | 17.685 | 29.139 | 36.815 | 1.00 | 20.45 | 7 |
| ATOM | 3798 | CA | ASN A 471 | 18.653 | 28.210 | 37.305 | 1.00 | 22.12 | 6 |
| ATOM | 3799 | C | ASN A 471 | 19.645 | 29.034 | 38.152 | 1.00 | 22.93 | 6 |
| ATOM | 3800 | O | ASN A 471 | 20.502 | 29.705 | 37.574 | 1.00 | 23.29 | 8 |
| ATOM | 3801 | CB | ASN A 471 | 19.444 | 27.600 | 36.160 | 1.00 | 35.69 | 6 |

| ATOM | 3802 | CG  | ASN A 471 | 19.698 | 26.130 | 36.384 | 1.00 | 47.51 | 6 |
| ATOM | 3803 | OD1 | ASN A 471 | 20.841 | 25.728 | 36.333 | 1.00 | 50.34 | 8 |
| ATOM | 3804 | ND2 | ASN A 471 | 18.684 | 25.322 | 36.598 | 1.00 | 59.19 | 7 |
| ATOM | 3805 | N   | PHE A 472 | 19.494 | 28.961 | 39.468 | 1.00 | 19.79 | 7 |
| ATOM | 3806 | CA  | PHE A 472 | 20.419 | 29.796 | 40.310 | 1.00 | 16.18 | 6 |
| ATOM | 3807 | C   | PHE A 472 | 21.655 | 29.058 | 40.663 | 1.00 | 12.19 | 6 |
| ATOM | 3808 | O   | PHE A 472 | 21.623 | 27.815 | 40.786 | 1.00 | 17.32 | 8 |
| ATOM | 3809 | CB  | PHE A 472 | 19.541 | 30.196 | 41.489 | 1.00 | 13.15 | 6 |
| ATOM | 3810 | CG  | PHE A 472 | 18.432 | 31.150 | 41.246 | 1.00 |  6.63 | 6 |
| ATOM | 3811 | CD1 | PHE A 472 | 18.667 | 32.489 | 41.067 | 1.00 | 13.56 | 6 |
| ATOM | 3812 | CD2 | PHE A 472 | 17.122 | 30.703 | 41.236 | 1.00 |  7.40 | 6 |
| ATOM | 3813 | CE1 | PHE A 472 | 17.639 | 33.393 | 40.825 | 1.00 | 13.16 | 6 |
| ATOM | 3814 | CE2 | PHE A 472 | 16.099 | 31.585 | 40.959 | 1.00 | 12.05 | 6 |
| ATOM | 3815 | CZ  | PHE A 472 | 16.345 | 32.935 | 40.759 | 1.00 | 14.01 | 6 |
| ATOM | 3816 | N   | SER A 473 | 22.870 | 29.595 | 40.786 | 1.00 | 13.50 | 7 |
| ATOM | 3817 | CA  | SER A 473 | 23.961 | 28.697 | 41.169 | 1.00 | 14.11 | 6 |
| ATOM | 3818 | C   | SER A 473 | 24.726 | 29.176 | 42.424 | 1.00 | 12.54 | 6 |
| ATOM | 3819 | O   | SER A 473 | 24.490 | 30.293 | 42.846 | 1.00 | 13.13 | 8 |
| ATOM | 3820 | CB  | SER A 473 | 24.999 | 28.680 | 39.999 | 1.00 | 18.25 | 6 |
| ATOM | 3821 | OG  | SER A 473 | 25.372 | 30.054 | 39.899 | 1.00 | 20.56 | 8 |
| ATOM | 3822 | N   | VAL A 474 | 25.705 | 28.401 | 42.881 | 1.00 | 13.61 | 7 |
| ATOM | 3823 | CA  | VAL A 474 | 26.412 | 28.909 | 44.097 | 1.00 | 16.44 | 6 |
| ATOM | 3824 | C   | VAL A 474 | 27.764 | 28.251 | 44.127 | 1.00 | 15.20 | 6 |
| ATOM | 3825 | O   | VAL A 474 | 27.856 | 27.095 | 43.703 | 1.00 | 18.90 | 8 |
| ATOM | 3826 | CB  | VAL A 474 | 25.539 | 28.505 | 45.332 | 1.00 | 12.07 | 6 |
| ATOM | 3827 | CG1 | VAL A 474 | 25.307 | 26.998 | 45.341 | 1.00 |  4.17 | 6 |
| ATOM | 3828 | CG2 | VAL A 474 | 26.120 | 28.842 | 46.690 | 1.00 | 19.53 | 6 |
| ATOM | 3829 | N   | ASN A 475 | 28.761 | 28.905 | 44.681 | 1.00 | 16.23 | 7 |
| ATOM | 3830 | CA  | ASN A 475 | 30.069 | 28.301 | 44.876 | 1.00 | 17.52 | 6 |
| ATOM | 3831 | C   | ASN A 475 | 30.050 | 27.213 | 45.938 | 1.00 | 20.97 | 6 |
| ATOM | 3832 | O   | ASN A 475 | 29.049 | 27.130 | 46.676 | 1.00 | 20.95 | 8 |
| ATOM | 3833 | CB  | ASN A 475 | 31.046 | 29.414 | 45.253 | 1.00 | 21.99 | 6 |
| ATOM | 3834 | CG  | ASN A 475 | 31.374 | 30.221 | 43.978 | 1.00 | 30.21 | 6 |
| ATOM | 3835 | OD1 | ASN A 475 | 31.377 | 29.592 | 42.917 | 1.00 | 29.36 | 8 |
| ATOM | 3836 | ND2 | ASN A 475 | 31.631 | 31.510 | 44.084 | 1.00 | 26.76 | 7 |
| ATOM | 3837 | N   | GLY A 476 | 31.106 | 26.400 | 46.029 | 1.00 | 20.35 | 7 |
| ATOM | 3838 | CA  | GLY A 476 | 31.140 | 25.343 | 47.050 | 1.00 | 19.93 | 6 |
| ATOM | 3839 | C   | GLY A 476 | 31.348 | 25.970 | 48.453 | 1.00 | 19.53 | 6 |
| ATOM | 3840 | O   | GLY A 476 | 31.977 | 27.014 | 48.576 | 1.00 | 14.05 | 8 |
| ATOM | 3841 | N   | GLY A 477 | 30.658 | 25.410 | 49.493 | 1.00 | 19.68 | 7 |
| ATOM | 3842 | CA  | GLY A 477 | 30.888 | 25.911 | 50.867 | 1.00 | 17.22 | 6 |
| ATOM | 3843 | C   | GLY A 477 | 30.567 | 27.376 | 50.985 | 1.00 | 17.16 | 6 |
| ATOM | 3844 | O   | GLY A 477 | 31.300 | 28.184 | 51.538 | 1.00 | 16.37 | 8 |
| ATOM | 3845 | N   | SER A 478 | 29.413 | 27.756 | 50.402 | 1.00 | 15.45 | 7 |
| ATOM | 3846 | CA  | SER A 478 | 29.132 | 29.190 | 50.345 | 1.00 | 13.71 | 6 |
| ATOM | 3847 | C   | SER A 478 | 27.644 | 29.438 | 50.244 | 1.00 | 11.85 | 6 |
| ATOM | 3848 | O   | SER A 478 | 26.866 | 28.524 | 50.190 | 1.00 | 14.63 | 8 |
| ATOM | 3849 | CB  | SER A 478 | 29.720 | 29.555 | 48.930 | 1.00 | 14.86 | 6 |
| ATOM | 3850 | OG  | SER A 478 | 29.794 | 30.947 | 48.838 | 1.00 | 20.40 | 8 |
| ATOM | 3851 | N   | VAL A 479 | 27.275 | 30.697 | 50.221 | 1.00 | 11.60 | 7 |
| ATOM | 3852 | CA  | VAL A 479 | 25.905 | 31.087 | 49.998 | 1.00 | 12.55 | 6 |
| ATOM | 3853 | C   | VAL A 479 | 25.880 | 32.212 | 48.924 | 1.00 | 11.49 | 6 |
| ATOM | 3854 | O   | VAL A 479 | 26.741 | 33.083 | 48.864 | 1.00 | 11.55 | 8 |
| ATOM | 3855 | CB  | VAL A 479 | 25.273 | 31.623 | 51.311 | 1.00 | 12.79 | 6 |
| ATOM | 3856 | CG1 | VAL A 479 | 26.115 | 32.797 | 51.835 | 1.00 |  9.12 | 6 |
| ATOM | 3857 | CG2 | VAL A 479 | 23.817 | 32.055 | 51.166 | 1.00 |  4.71 | 6 |
| ATOM | 3858 | N   | SER A 480 | 24.780 | 32.237 | 48.166 | 1.00 | 13.81 | 7 |
| ATOM | 3859 | CA  | SER A 480 | 24.597 | 33.365 | 47.238 | 1.00 | 11.93 | 6 |
| ATOM | 3860 | C   | SER A 480 | 23.180 | 33.821 | 47.451 | 1.00 |  8.76 | 6 |
| ATOM | 3861 | O   | SER A 480 | 22.252 | 33.053 | 47.650 | 1.00 | 11.76 | 8 |
| ATOM | 3862 | CB  | SER A 480 | 24.856 | 32.914 | 45.765 | 1.00 | 20.36 | 6 |
| ATOM | 3863 | OG  | SER A 480 | 26.221 | 33.103 | 45.402 | 1.00 | 13.39 | 8 |
| ATOM | 3864 | N   | ILE A 481 | 22.897 | 35.104 | 47.407 | 1.00 | 11.45 | 7 |
| ATOM | 3865 | CA  | ILE A 481 | 21.517 | 35.554 | 47.543 | 1.00 | 13.32 | 6 |
| ATOM | 3866 | C   | ILE A 481 | 21.173 | 36.380 | 46.268 | 1.00 | 14.81 | 6 |

| ATOM | 3867 | O   | ILE A 481 | 21.643 | 37.490 | 46.094 | 1.00 | 13.00 | 8 |
| ATOM | 3868 | CB  | ILE A 481 | 21.369 | 36.401 | 48.839 | 1.00 | 12.79 | 6 |
| ATOM | 3869 | CG1 | ILE A 481 | 21.711 | 35.500 | 50.091 | 1.00 | 16.67 | 6 |
| ATOM | 3870 | CG2 | ILE A 481 | 19.939 | 36.934 | 48.878 | 1.00 | 6.58  | 6 |
| ATOM | 3871 | CD1 | ILE A 481 | 21.809 | 36.366 | 51.349 | 1.00 | 14.77 | 6 |
| ATOM | 3872 | N   | TRP A 482 | 20.266 | 35.842 | 45.450 | 1.00 | 16.67 | 7 |
| ATOM | 3873 | CA  | TRP A 482 | 19.996 | 36.529 | 44.159 | 1.00 | 16.84 | 6 |
| ATOM | 3874 | C   | TRP A 482 | 18.854 | 37.489 | 44.220 | 1.00 | 15.36 | 6 |
| ATOM | 3875 | O   | TRP A 482 | 17.773 | 37.074 | 44.690 | 1.00 | 16.15 | 8 |
| ATOM | 3876 | CB  | TRP A 482 | 19.791 | 35.479 | 43.055 | 1.00 | 11.32 | 6 |
| ATOM | 3877 | CG  | TRP A 482 | 20.966 | 34.610 | 42.832 | 1.00 | 13.31 | 6 |
| ATOM | 3878 | CD1 | TRP A 482 | 21.210 | 33.414 | 43.426 | 1.00 | 13.12 | 6 |
| ATOM | 3879 | CD2 | TRP A 482 | 22.055 | 34.820 | 41.906 | 1.00 | 20.71 | 6 |
| ATOM | 3880 | NE1 | TRP A 482 | 22.395 | 32.886 | 42.975 | 1.00 | 13.99 | 7 |
| ATOM | 3881 | CE2 | TRP A 482 | 22.923 | 33.727 | 42.033 | 1.00 | 17.34 | 6 |
| ATOM | 3882 | CE3 | TRP A 482 | 22.349 | 35.834 | 40.969 | 1.00 | 24.46 | 6 |
| ATOM | 3883 | CZ2 | TRP A 482 | 24.100 | 33.594 | 41.281 | 1.00 | 23.61 | 6 |
| ATOM | 3884 | CZ3 | TRP A 482 | 23.527 | 35.734 | 40.237 | 1.00 | 15.44 | 6 |
| ATOM | 3885 | CH2 | TRP A 482 | 24.375 | 34.608 | 40.391 | 1.00 | 15.55 | 6 |
| ATOM | 3886 | N   | VAL A 483 | 19.077 | 38.750 | 43.833 | 1.00 | 15.53 | 7 |
| ATOM | 3887 | CA  | VAL A 483 | 18.002 | 39.734 | 43.801 | 1.00 | 18.71 | 6 |
| ATOM | 3888 | C   | VAL A 483 | 18.016 | 40.540 | 42.454 | 1.00 | 18.89 | 6 |
| ATOM | 3889 | O   | VAL A 483 | 19.077 | 40.622 | 41.835 | 1.00 | 18.73 | 8 |
| ATOM | 3890 | CB  | VAL A 483 | 18.094 | 40.853 | 44.884 | 1.00 | 19.44 | 6 |
| ATOM | 3891 | CG1 | VAL A 483 | 18.117 | 40.240 | 46.286 | 1.00 | 24.26 | 6 |
| ATOM | 3892 | CG2 | VAL A 483 | 19.315 | 41.744 | 44.705 | 1.00 | 15.59 | 6 |
| ATOM | 3893 | N   | LYS A 484 | 16.913 | 41.189 | 42.139 | 1.00 | 19.32 | 7 |
| ATOM | 3894 | CA  | LYS A 484 | 16.841 | 42.076 | 40.980 | 1.00 | 21.09 | 6 |
| ATOM | 3895 | C   | LYS A 484 | 17.961 | 43.100 | 40.983 | 1.00 | 24.00 | 6 |
| ATOM | 3896 | O   | LYS A 484 | 18.192 | 43.826 | 41.973 | 1.00 | 23.05 | 8 |
| ATOM | 3897 | CB  | LYS A 484 | 15.530 | 42.867 | 40.958 | 1.00 | 28.12 | 6 |
| ATOM | 3898 | CG  | LYS A 484 | 15.350 | 43.773 | 39.739 | 1.00 | 32.20 | 6 |
| ATOM | 3899 | CD  | LYS A 484 | 14.045 | 44.535 | 39.852 | 1.00 | 44.02 | 6 |
| ATOM | 3900 | CE  | LYS A 484 | 13.718 | 45.239 | 38.534 | 1.00 | 55.99 | 6 |
| ATOM | 3901 | NZ  | LYS A 484 | 12.396 | 45.944 | 38.628 | 1.00 | 59.77 | 7 |
| ATOM | 3902 | N   | ARG A 485 | 18.719 | 43.105 | 39.867 | 1.00 | 24.97 | 7 |
| ATOM | 3903 | CA  | ARG A 485 | 19.804 | 44.080 | 39.768 | 1.00 | 29.19 | 6 |
| ATOM | 3904 | C   | ARG A 485 | 19.283 | 45.475 | 39.450 | 1.00 | 30.80 | 6 |
| ATOM | 3905 | O   | ARG A 485 | 19.850 | 46.446 | 39.999 | 1.00 | 33.55 | 8 |
| ATOM | 3906 | CB  | ARG A 485 | 20.903 | 43.779 | 38.748 | 1.00 | 40.45 | 6 |
| ATOM | 3907 | CG  | ARG A 485 | 22.106 | 44.686 | 39.037 | 1.00 | 59.45 | 6 |
| ATOM | 3908 | CD  | ARG A 485 | 23.403 | 43.990 | 38.638 | 1.00 | 78.70 | 6 |
| ATOM | 3909 | NE  | ARG A 485 | 23.356 | 43.672 | 37.209 | 1.00 | 93.35 | 7 |
| ATOM | 3910 | CZ  | ARG A 485 | 23.460 | 44.555 | 36.221 | 1.00 | 97.50 | 6 |
| ATOM | 3911 | NH1 | ARG A 485 | 23.646 | 45.839 | 36.505 | 1.00 | 99.91 | 7 |
| ATOM | 3912 | NH2 | ARG A 485 | 23.381 | 44.130 | 34.965 | 1.00 | 98.10 | 7 |
| ATOM | 3913 | OT  | ARG A 485 | 18.315 | 45.575 | 38.684 | 1.00 | 36.53 | 8 |
| ATOM | 3914 | CA  | IUM A 486 | 16.403 | 28.839 | 91.080 | 1.00 | 13.38 | 20 |
| ATOM | 3915 | CA  | IUM A 487 | 11.326 | 27.396 | 97.560 | 1.00 | 14.89 | 20 |
| ATOM | 3916 | CA  | IUM A 488 | 12.079 | 41.438 | 41.820 | 1.00 | 65.35 | 20 |
| ATOM | 3917 | CA  | IUM A 489 | 26.215 | 18.079 | 53.059 | 1.00 | 20.01 | 20 |
| ATOM | 3918 | NA  | IUM A 490 | 14.404 | 28.621 | 94.442 | 1.00 | 13.98 | 11 |
| ATOM | 3919 | OW0 | WAT W 1   | 15.331 | 30.924 | 91.968 | 1.00 | 8.40  | 8 |
| ATOM | 3920 | OW0 | WAT W 2   | 20.672 | 29.374 | 91.814 | 1.00 | 9.95  | 8 |
| ATOM | 3921 | OW0 | WAT W 3   | 10.621 | 27.443 | 100.167| 1.00 | 10.46 | 8 |
| ATOM | 3922 | OW0 | WAT W 4   | 28.869 | 20.050 | 56.659 | 1.00 | 11.85 | 8 |
| ATOM | 3923 | OW0 | WAT W 5   | 14.586 | 33.181 | 61.484 | 1.00 | 12.59 | 8 |
| ATOM | 3924 | OW0 | WAT W 6   | 18.392 | 34.544 | 86.249 | 1.00 | 13.31 | 8 |
| ATOM | 3925 | OW0 | WAT W 7   | 12.636 | 28.973 | 91.117 | 1.00 | 13.68 | 8 |
| ATOM | 3926 | OW0 | WAT W 8   | 15.634 | 35.829 | 85.277 | 1.00 | 13.76 | 8 |
| ATOM | 3927 | OW0 | WAT W 9   | 18.872 | 29.499 | 66.652 | 1.00 | 14.41 | 8 |
| ATOM | 3928 | OW0 | WAT W 10  | 15.541 | 28.877 | 74.819 | 1.00 | 14.80 | 8 |
| ATOM | 3929 | OW0 | WAT W 11  | 17.655 | 22.379 | 93.167 | 1.00 | 15.02 | 8 |
| ATOM | 3930 | OW0 | WAT W 12  | 10.694 | 30.117 | 84.366 | 1.00 | 15.45 | 8 |
| ATOM | 3931 | OW0 | WAT W 13  | 18.071 | 28.115 | 81.035 | 1.00 | 15.55 | 8 |

| ATOM | 3932 | OW0 | WAT | W | 14 | 26.048 | 15.607 | 52.885 | 1.00 | 15.91 | 8 |
| --- | --- | --- | --- | --- | --- | --- | --- | --- | --- | --- | --- |
| ATOM | 3933 | OW0 | WAT | W | 15 | 29.348 | 31.173 | 86.751 | 1.00 | 16.00 | 8 |
| ATOM | 3934 | OW0 | WAT | W | 16 | 10.192 | 22.022 | 80.509 | 1.00 | 16.03 | 8 |
| ATOM | 3935 | OW0 | WAT | W | 17 | 27.199 | 31.182 | 100.558 | 1.00 | 16.19 | 8 |
| ATOM | 3936 | OW0 | WAT | W | 18 | 29.018 | 45.155 | 85.220 | 1.00 | 16.88 | 8 |
| ATOM | 3937 | OW0 | WAT | W | 19 | 5.482 | 31.285 | 76.403 | 1.00 | 16.88 | 8 |
| ATOM | 3938 | OW0 | WAT | W | 20 | 26.381 | 45.012 | 84.704 | 1.00 | 17.27 | 8 |
| ATOM | 3939 | OW0 | WAT | W | 21 | 25.881 | 32.894 | 83.269 | 1.00 | 17.32 | 8 |
| ATOM | 3940 | OW0 | WAT | W | 22 | 25.409 | 35.676 | 97.523 | 1.00 | 17.35 | 8 |
| ATOM | 3941 | OW0 | WAT | W | 23 | 7.309 | 25.461 | 94.547 | 1.00 | 17.78 | 8 |
| ATOM | 3942 | OW0 | WAT | W | 24 | 20.157 | 53.017 | 89.490 | 1.00 | 18.71 | 8 |
| ATOM | 3943 | OW0 | WAT | W | 25 | 18.501 | 20.523 | 81.617 | 1.00 | 18.85 | 8 |
| ATOM | 3944 | OW0 | WAT | W | 26 | 30.763 | 42.059 | 78.813 | 1.00 | 18.95 | 8 |
| ATOM | 3945 | OW0 | WAT | W | 27 | 23.018 | 30.980 | 81.026 | 1.00 | 19.13 | 8 |
| ATOM | 3946 | OW0 | WAT | W | 28 | 18.707 | 38.961 | 91.110 | 1.00 | 19.60 | 8 |
| ATOM | 3947 | OW0 | WAT | W | 29 | 31.590 | 37.922 | 84.751 | 1.00 | 19.76 | 8 |
| ATOM | 3948 | OW0 | WAT | W | 30 | 28.452 | 29.435 | 92.663 | 1.00 | 19.87 | 8 |
| ATOM | 3949 | OW0 | WAT | W | 31 | 21.360 | 29.012 | 81.691 | 1.00 | 19.98 | 8 |
| ATOM | 3950 | OW0 | WAT | W | 32 | 25.513 | 33.621 | 80.784 | 1.00 | 20.06 | 8 |
| ATOM | 3951 | OW0 | WAT | W | 33 | 9.572 | 35.390 | 68.425 | 1.00 | 20.13 | 8 |
| ATOM | 3952 | OW0 | WAT | W | 34 | 6.621 | 38.273 | 73.833 | 1.00 | 20.26 | 8 |
| ATOM | 3953 | OW0 | WAT | W | 35 | 5.165 | 26.241 | 88.156 | 1.00 | 20.30 | 8 |
| ATOM | 3954 | OW0 | WAT | W | 36 | 23.265 | 33.446 | 79.934 | 1.00 | 20.36 | 8 |
| ATOM | 3955 | OW0 | WAT | W | 37 | 28.248 | 31.837 | 82.126 | 1.00 | 20.40 | 8 |
| ATOM | 3956 | OW0 | WAT | W | 38 | 23.025 | 15.287 | 58.844 | 1.00 | 20.72 | 8 |
| ATOM | 3957 | OW0 | WAT | W | 39 | 20.923 | 33.873 | 72.690 | 1.00 | 20.85 | 8 |
| ATOM | 3958 | OW0 | WAT | W | 40 | 12.290 | 35.963 | 59.757 | 1.00 | 20.91 | 8 |
| ATOM | 3959 | OW0 | WAT | W | 41 | 20.845 | 33.669 | 75.672 | 1.00 | 20.97 | 8 |
| ATOM | 3960 | OW0 | WAT | W | 42 | 22.075 | 21.682 | 81.126 | 1.00 | 21.31 | 8 |
| ATOM | 3961 | OW0 | WAT | W | 43 | 14.396 | 41.282 | 43.561 | 1.00 | 21.67 | 8 |
| ATOM | 3962 | OW0 | WAT | W | 44 | 26.359 | 38.541 | 40.833 | 1.00 | 21.93 | 8 |
| ATOM | 3963 | OW0 | WAT | W | 45 | 29.566 | 32.232 | 79.652 | 1.00 | 21.98 | 8 |
| ATOM | 3964 | OW0 | WAT | W | 46 | 23.283 | 35.309 | 65.908 | 1.00 | 22.07 | 8 |
| ATOM | 3965 | OW0 | WAT | W | 47 | 23.194 | 24.642 | 81.389 | 1.00 | 22.19 | 8 |
| ATOM | 3966 | OW0 | WAT | W | 48 | 31.442 | 30.641 | 53.232 | 1.00 | 22.24 | 8 |
| ATOM | 3967 | OW0 | WAT | W | 49 | 16.139 | 44.310 | 95.813 | 1.00 | 22.31 | 8 |
| ATOM | 3968 | OW0 | WAT | W | 50 | 29.098 | 45.750 | 88.021 | 1.00 | 22.46 | 8 |
| ATOM | 3969 | OW0 | WAT | W | 51 | 29.561 | 30.748 | 84.019 | 1.00 | 22.47 | 8 |
| ATOM | 3970 | OW0 | WAT | W | 52 | 27.980 | 37.414 | 52.564 | 1.00 | 22.67 | 8 |
| ATOM | 3971 | OW0 | WAT | W | 53 | 15.060 | 20.624 | 57.494 | 1.00 | 22.69 | 8 |
| ATOM | 3972 | OW0 | WAT | W | 54 | 35.494 | 34.127 | 73.318 | 1.00 | 23.02 | 8 |
| ATOM | 3973 | OW0 | WAT | W | 55 | 21.252 | 26.982 | 82.323 | 1.00 | 23.16 | 8 |
| ATOM | 3974 | OW0 | WAT | W | 56 | 8.169 | 23.595 | 96.531 | 1.00 | 23.42 | 8 |
| ATOM | 3975 | OW0 | WAT | W | 57 | 28.306 | 31.271 | 46.286 | 1.00 | 23.97 | 8 |
| ATOM | 3976 | OW0 | WAT | W | 58 | 4.904 | 32.005 | 52.469 | 1.00 | 24.08 | 8 |
| ATOM | 3977 | OW0 | WAT | W | 59 | 34.680 | 17.452 | 59.617 | 1.00 | 24.12 | 8 |
| ATOM | 3978 | OW0 | WAT | W | 60 | 33.674 | 21.421 | 58.909 | 1.00 | 24.14 | 8 |
| ATOM | 3979 | OW0 | WAT | W | 61 | 26.569 | 31.013 | 97.686 | 1.00 | 24.18 | 8 |
| ATOM | 3980 | OW0 | WAT | W | 62 | 20.007 | 44.821 | 80.894 | 1.00 | 24.42 | 8 |
| ATOM | 3981 | OW0 | WAT | W | 63 | 11.817 | 37.503 | 56.024 | 1.00 | 24.64 | 8 |
| ATOM | 3982 | OW0 | WAT | W | 64 | 29.823 | 54.365 | 78.471 | 1.00 | 24.84 | 8 |
| ATOM | 3983 | OW0 | WAT | W | 65 | 31.313 | 24.657 | 101.086 | 1.00 | 24.86 | 8 |
| ATOM | 3984 | OW0 | WAT | W | 66 | 21.188 | 24.062 | 81.773 | 1.00 | 25.00 | 8 |
| ATOM | 3985 | OW0 | WAT | W | 67 | 27.530 | 23.190 | 74.325 | 1.00 | 25.05 | 8 |
| ATOM | 3986 | OW0 | WAT | W | 68 | 24.237 | 27.662 | 82.417 | 1.00 | 25.21 | 8 |
| ATOM | 3987 | OW0 | WAT | W | 69 | 13.220 | 20.441 | 98.339 | 1.00 | 25.29 | 8 |
| ATOM | 3988 | OW0 | WAT | W | 70 | 9.835 | 20.463 | 84.092 | 1.00 | 25.33 | 8 |
| ATOM | 3989 | OW0 | WAT | W | 71 | 24.649 | 23.948 | 89.723 | 1.00 | 25.58 | 8 |
| ATOM | 3990 | OW0 | WAT | W | 72 | 5.014 | 36.356 | 89.453 | 1.00 | 25.65 | 8 |
| ATOM | 3991 | OW0 | WAT | W | 73 | 10.492 | 20.729 | 64.885 | 1.00 | 25.70 | 8 |
| ATOM | 3992 | OW0 | WAT | W | 74 | 32.733 | 31.987 | 63.454 | 1.00 | 25.93 | 8 |
| ATOM | 3993 | OW0 | WAT | W | 75 | 28.377 | 16.603 | 97.373 | 1.00 | 26.22 | 8 |
| ATOM | 3994 | OW0 | WAT | W | 76 | 26.237 | 18.558 | 98.847 | 1.00 | 26.31 | 8 |
| ATOM | 3995 | OW0 | WAT | W | 77 | 18.836 | 44.197 | 94.602 | 1.00 | 26.32 | 8 |
| ATOM | 3996 | OW0 | WAT | W | 78 | 30.554 | 38.651 | 99.023 | 1.00 | 26.53 | 8 |

| ATOM | 3997 | OW0 | WAT | W | 79 | 34.139 | 42.534 | 70.785 | 1.00 | 26.66 | 8 |
| --- | --- | --- | --- | --- | --- | --- | --- | --- | --- | --- | --- |
| ATOM | 3998 | OW0 | WAT | W | 80 | 19.699 | 41.304 | 95.115 | 1.00 | 26.70 | 8 |
| ATOM | 3999 | OW0 | WAT | W | 81 | 11.380 | 18.430 | 92.339 | 1.00 | 26.75 | 8 |
| ATOM | 4000 | OW0 | WAT | W | 82 | 33.445 | 25.595 | 69.634 | 1.00 | 26.97 | 8 |
| ATOM | 4001 | OW0 | WAT | W | 83 | 24.662 | 13.696 | 54.197 | 1.00 | 27.11 | 8 |
| ATOM | 4002 | OW0 | WAT | W | 84 | 28.266 | 31.003 | 94.890 | 1.00 | 27.29 | 8 |
| ATOM | 4003 | OW0 | WAT | W | 85 | 20.725 | 40.832 | 92.186 | 1.00 | 27.45 | 8 |
| ATOM | 4004 | OW0 | WAT | W | 86 | 25.146 | 50.544 | 83.841 | 1.00 | 27.48 | 8 |
| ATOM | 4005 | OW0 | WAT | W | 87 | 15.057 | 18.749 | 69.240 | 1.00 | 27.74 | 8 |
| ATOM | 4006 | OW0 | WAT | W | 88 | 13.048 | 28.893 | 58.627 | 1.00 | 27.83 | 8 |
| ATOM | 4007 | OW0 | WAT | W | 89 | 13.377 | 28.399 | 53.950 | 1.00 | 27.90 | 8 |
| ATOM | 4008 | OW0 | WAT | W | 90 | 5.299 | 31.836 | 93.231 | 1.00 | 27.96 | 8 |
| ATOM | 4009 | OW0 | WAT | W | 91 | 3.937 | 37.319 | 47.632 | 1.00 | 28.09 | 8 |
| ATOM | 4010 | OW0 | WAT | W | 92 | 23.639 | 21.750 | 78.833 | 1.00 | 28.09 | 8 |
| ATOM | 4011 | OW0 | WAT | W | 93 | 37.239 | 40.159 | 72.537 | 1.00 | 28.14 | 8 |
| ATOM | 4012 | OW0 | WAT | W | 94 | 23.345 | 33.695 | 85.122 | 1.00 | 28.24 | 8 |
| ATOM | 4013 | OW0 | WAT | W | 95 | 27.712 | 33.751 | 84.311 | 1.00 | 28.35 | 8 |
| ATOM | 4014 | OW0 | WAT | W | 96 | 29.746 | 32.309 | 51.898 | 1.00 | 28.37 | 8 |
| ATOM | 4015 | OW0 | WAT | W | 97 | 24.950 | 23.431 | 86.718 | 1.00 | 28.90 | 8 |
| ATOM | 4016 | OW0 | WAT | W | 98 | 30.172 | 32.741 | 97.140 | 1.00 | 28.98 | 8 |
| ATOM | 4017 | OW0 | WAT | W | 99 | 28.686 | 34.680 | 86.651 | 1.00 | 29.30 | 8 |
| ATOM | 4018 | OW0 | WAT | W | 100 | 29.828 | 22.276 | 104.713 | 1.00 | 29.31 | 8 |
| ATOM | 4019 | OW0 | WAT | W | 101 | 14.236 | 21.944 | 103.773 | 1.00 | 29.36 | 8 |
| ATOM | 4020 | OW0 | WAT | W | 102 | 23.731 | 32.676 | 83.036 | 1.00 | 30.10 | 8 |
| ATOM | 4021 | OW0 | WAT | W | 103 | 29.261 | 29.122 | 89.584 | 1.00 | 30.19 | 8 |
| ATOM | 4022 | OW0 | WAT | W | 104 | 27.892 | 34.046 | 96.695 | 1.00 | 30.42 | 8 |
| ATOM | 4023 | OW0 | WAT | W | 105 | 31.548 | 31.196 | 93.135 | 1.00 | 30.52 | 8 |
| ATOM | 4024 | OW0 | WAT | W | 106 | 29.180 | 35.694 | 97.563 | 1.00 | 30.65 | 8 |
| ATOM | 4025 | OW0 | WAT | W | 107 | 36.148 | 32.510 | 77.016 | 1.00 | 30.87 | 8 |
| ATOM | 4026 | OW0 | WAT | W | 108 | 19.500 | 19.810 | 67.860 | 1.00 | 30.97 | 8 |
| ATOM | 4027 | OW0 | WAT | W | 109 | 12.234 | 17.699 | 57.066 | 1.00 | 31.02 | 8 |
| ATOM | 4028 | OW0 | WAT | W | 110 | 30.140 | 30.959 | 90.861 | 1.00 | 31.02 | 8 |
| ATOM | 4029 | OW0 | WAT | W | 111 | 29.245 | 29.005 | 87.140 | 1.00 | 31.20 | 8 |
| ATOM | 4030 | OW0 | WAT | W | 112 | 8.712 | 44.931 | 98.058 | 1.00 | 31.25 | 8 |
| ATOM | 4031 | OW0 | WAT | W | 113 | 6.559 | 35.891 | 71.686 | 1.00 | 31.48 | 8 |
| ATOM | 4032 | OW0 | WAT | W | 114 | 16.096 | 46.682 | 97.419 | 1.00 | 31.49 | 8 |
| ATOM | 4033 | OW0 | WAT | W | 115 | 28.702 | 37.358 | 84.954 | 1.00 | 31.52 | 8 |
| ATOM | 4034 | OW0 | WAT | W | 116 | 23.269 | 36.298 | 69.635 | 1.00 | 31.73 | 8 |
| ATOM | 4035 | OW0 | WAT | W | 117 | 19.112 | 14.848 | 51.560 | 1.00 | 32.26 | 8 |
| ATOM | 4036 | OW0 | WAT | W | 118 | 34.859 | 46.381 | 91.799 | 1.00 | 32.30 | 8 |
| ATOM | 4037 | OW0 | WAT | W | 119 | 33.356 | 24.877 | 66.359 | 1.00 | 32.33 | 8 |
| ATOM | 4038 | OW0 | WAT | W | 120 | 36.212 | 28.332 | 58.979 | 1.00 | 32.66 | 8 |
| ATOM | 4039 | OW0 | WAT | W | 121 | 32.357 | 32.702 | 89.962 | 1.00 | 32.67 | 8 |
| ATOM | 4040 | OW0 | WAT | W | 122 | 15.791 | 18.309 | 98.565 | 1.00 | 32.94 | 8 |
| ATOM | 4041 | OW0 | WAT | W | 123 | 10.728 | 37.304 | 43.329 | 1.00 | 33.06 | 8 |
| ATOM | 4042 | OW0 | WAT | W | 124 | 9.424 | 44.511 | 70.118 | 1.00 | 33.07 | 8 |
| ATOM | 4043 | OW0 | WAT | W | 125 | 7.444 | 40.322 | 33.258 | 1.00 | 33.08 | 8 |
| ATOM | 4044 | OW0 | WAT | W | 126 | 26.139 | 24.623 | 81.599 | 1.00 | 33.35 | 8 |
| ATOM | 4045 | OW0 | WAT | W | 127 | 29.976 | 39.216 | 50.980 | 1.00 | 33.37 | 8 |
| ATOM | 4046 | OW0 | WAT | W | 128 | 12.352 | 20.468 | 101.408 | 1.00 | 33.41 | 8 |
| ATOM | 4047 | OW0 | WAT | W | 129 | 14.605 | 43.579 | 93.366 | 1.00 | 33.46 | 8 |
| ATOM | 4048 | OW0 | WAT | W | 130 | 14.568 | 25.226 | 100.442 | 1.00 | 33.95 | 8 |
| ATOM | 4049 | OW0 | WAT | W | 131 | 29.845 | 36.606 | 88.663 | 1.00 | 33.96 | 8 |
| ATOM | 4050 | OW0 | WAT | W | 132 | 29.315 | 35.203 | 52.245 | 1.00 | 34.39 | 8 |
| ATOM | 4051 | OW0 | WAT | W | 133 | 25.213 | 28.912 | 81.291 | 1.00 | 34.73 | 8 |
| ATOM | 4052 | OW0 | WAT | W | 134 | 4.056 | 25.026 | 86.078 | 1.00 | 34.75 | 8 |
| ATOM | 4053 | OW0 | WAT | W | 135 | 35.592 | 22.208 | 66.460 | 1.00 | 34.79 | 8 |
| ATOM | 4054 | OW0 | WAT | W | 136 | 30.056 | 32.499 | 94.980 | 1.00 | 35.03 | 8 |
| ATOM | 4055 | OW0 | WAT | W | 137 | 31.642 | 34.050 | 97.446 | 1.00 | 35.16 | 8 |
| ATOM | 4056 | OW0 | WAT | W | 138 | 6.399 | 39.252 | 53.656 | 1.00 | 35.16 | 8 |
| ATOM | 4057 | OW0 | WAT | W | 139 | 24.631 | 22.787 | 80.787 | 1.00 | 35.70 | 8 |
| ATOM | 4058 | OW0 | WAT | W | 140 | 17.164 | 40.603 | 93.345 | 1.00 | 35.88 | 8 |
| ATOM | 4059 | OW0 | WAT | W | 141 | 32.517 | 48.802 | 78.888 | 1.00 | 35.91 | 8 |
| ATOM | 4060 | OW0 | WAT | W | 142 | 12.605 | 47.246 | 48.871 | 1.00 | 36.06 | 8 |
| ATOM | 4061 | OW0 | WAT | W | 143 | 11.936 | 19.902 | 81.296 | 1.00 | 36.07 | 8 |

| ATOM | 4062 | OW0 | WAT | W | 144 | 14.511 | 30.434 | 59.331 | 1.00 | 36.46 | 8 |
|------|------|-----|-----|---|-----|--------|--------|--------|------|-------|---|
| ATOM | 4063 | OW0 | WAT | W | 145 | 24.904 | 20.322 | 90.078 | 1.00 | 36.46 | 8 |
| ATOM | 4064 | OW0 | WAT | W | 146 | 11.636 | 21.530 | 50.698 | 1.00 | 36.73 | 8 |
| ATOM | 4065 | OW0 | WAT | W | 147 | 19.239 | 17.437 | 61.534 | 1.00 | 36.95 | 8 |
| ATOM | 4066 | OW0 | WAT | W | 148 | 16.418 | 12.433 | 100.613 | 1.00 | 37.57 | 8 |
| ATOM | 4067 | OW0 | WAT | W | 149 | 36.156 | 29.107 | 62.733 | 1.00 | 37.66 | 8 |
| ATOM | 4068 | OW0 | WAT | W | 150 | 6.477 | 18.289 | 83.974 | 1.00 | 38.23 | 8 |
| ATOM | 4069 | OW0 | WAT | W | 151 | 26.962 | 19.421 | 46.014 | 1.00 | 38.28 | 8 |
| ATOM | 4070 | OW0 | WAT | W | 152 | 29.388 | 47.864 | 98.637 | 1.00 | 38.32 | 8 |
| ATOM | 4071 | OW0 | WAT | W | 153 | 26.646 | 55.807 | 96.596 | 1.00 | 38.49 | 8 |
| ATOM | 4072 | OW0 | WAT | W | 154 | 28.646 | 13.763 | 51.700 | 1.00 | 38.50 | 8 |
| ATOM | 4073 | OW0 | WAT | W | 155 | 8.410 | 25.455 | 43.443 | 1.00 | 38.68 | 8 |
| ATOM | 4074 | OW0 | WAT | W | 156 | 25.347 | 58.866 | 86.231 | 1.00 | 38.79 | 8 |
| ATOM | 4075 | OW0 | WAT | W | 157 | 31.258 | 40.850 | 95.798 | 1.00 | 38.83 | 8 |
| ATOM | 4076 | OW0 | WAT | W | 158 | 7.378 | 49.910 | 91.085 | 1.00 | 39.20 | 8 |
| ATOM | 4077 | OW0 | WAT | W | 159 | 9.042 | 38.586 | 56.053 | 1.00 | 39.25 | 8 |
| ATOM | 4078 | OW0 | WAT | W | 160 | 22.671 | 18.146 | 64.655 | 1.00 | 39.33 | 8 |
| ATOM | 4079 | OW0 | WAT | W | 161 | 26.367 | 57.488 | 76.515 | 1.00 | 39.61 | 8 |
| ATOM | 4080 | OW0 | WAT | W | 162 | 13.588 | 22.645 | 41.622 | 1.00 | 39.65 | 8 |
| ATOM | 4081 | OW0 | WAT | W | 163 | 22.142 | 20.782 | 77.722 | 1.00 | 39.83 | 8 |
| ATOM | 4082 | OW0 | WAT | W | 164 | 19.678 | 14.382 | 85.326 | 1.00 | 40.14 | 8 |
| ATOM | 4083 | OW0 | WAT | W | 165 | 0.073 | 38.203 | 87.061 | 1.00 | 40.22 | 8 |
| ATOM | 4084 | OW0 | WAT | W | 166 | 12.125 | 44.320 | 65.523 | 1.00 | 40.42 | 8 |
| ATOM | 4085 | OW0 | WAT | W | 167 | 33.005 | 23.458 | 44.185 | 1.00 | 40.49 | 8 |
| ATOM | 4086 | OW0 | WAT | W | 168 | 13.676 | 35.688 | 29.856 | 1.00 | 40.58 | 8 |
| ATOM | 4087 | OW0 | WAT | W | 169 | 7.713 | 34.066 | 62.308 | 1.00 | 41.00 | 8 |
| ATOM | 4088 | OW0 | WAT | W | 170 | 33.626 | 28.969 | 81.496 | 1.00 | 41.00 | 8 |
| ATOM | 4089 | OW0 | WAT | W | 171 | 34.640 | 39.088 | 81.088 | 1.00 | 41.27 | 8 |
| ATOM | 4090 | OW0 | WAT | W | 172 | 7.508 | 25.738 | 50.220 | 1.00 | 41.32 | 8 |
| ATOM | 4091 | OW0 | WAT | W | 173 | 27.507 | 32.995 | 78.641 | 1.00 | 41.44 | 8 |
| ATOM | 4092 | OW0 | WAT | W | 174 | 24.673 | 18.334 | 69.762 | 1.00 | 41.47 | 8 |
| ATOM | 4093 | OW0 | WAT | W | 175 | 23.738 | 57.783 | 66.442 | 1.00 | 41.59 | 8 |
| ATOM | 4094 | OW0 | WAT | W | 176 | 19.624 | 22.721 | 38.089 | 1.00 | 41.60 | 8 |
| ATOM | 4095 | OW0 | WAT | W | 177 | 27.605 | 34.431 | 110.231 | 1.00 | 41.68 | 8 |
| ATOM | 4096 | OW0 | WAT | W | 178 | 21.996 | 49.909 | 104.001 | 1.00 | 41.90 | 8 |
| ATOM | 4097 | OW0 | WAT | W | 179 | 39.172 | 40.763 | 66.149 | 1.00 | 41.90 | 8 |
| ATOM | 4098 | OW0 | WAT | W | 180 | 38.537 | 22.909 | 101.858 | 1.00 | 41.95 | 8 |
| ATOM | 4099 | OW0 | WAT | W | 181 | 23.698 | 34.735 | 111.561 | 1.00 | 42.12 | 8 |
| ATOM | 4100 | OW0 | WAT | W | 182 | 17.645 | 48.828 | 100.481 | 1.00 | 42.16 | 8 |
| ATOM | 4101 | OW0 | WAT | W | 183 | 30.615 | 32.188 | 88.694 | 1.00 | 42.29 | 8 |
| ATOM | 4102 | OW0 | WAT | W | 184 | 17.123 | 23.998 | 35.527 | 1.00 | 42.30 | 8 |
| ATOM | 4103 | OW0 | WAT | W | 185 | 2.539 | 26.609 | 84.787 | 1.00 | 42.40 | 8 |
| ATOM | 4104 | OW0 | WAT | W | 186 | 24.033 | 19.860 | 84.650 | 1.00 | 42.65 | 8 |
| ATOM | 4105 | OW0 | WAT | W | 187 | 31.887 | 40.293 | 98.414 | 1.00 | 42.89 | 8 |
| ATOM | 4106 | OW0 | WAT | W | 188 | 33.506 | 18.210 | 98.947 | 1.00 | 42.96 | 8 |
| ATOM | 4107 | OW0 | WAT | W | 189 | 2.974 | 18.178 | 83.400 | 1.00 | 43.15 | 8 |
| ATOM | 4108 | OW0 | WAT | W | 190 | 33.171 | 54.574 | 88.941 | 1.00 | 43.20 | 8 |
| ATOM | 4109 | OW0 | WAT | W | 191 | 3.299 | 33.009 | 41.931 | 1.00 | 43.24 | 8 |
| ATOM | 4110 | OW0 | WAT | W | 192 | 35.304 | 24.551 | 60.466 | 1.00 | 43.36 | 8 |
| ATOM | 4111 | OW0 | WAT | W | 193 | 34.043 | 42.579 | 58.374 | 1.00 | 43.48 | 8 |
| ATOM | 4112 | OW0 | WAT | W | 194 | 10.996 | 27.113 | 59.197 | 1.00 | 43.50 | 8 |
| ATOM | 4113 | OW0 | WAT | W | 195 | 15.166 | 18.417 | 80.762 | 1.00 | 43.54 | 8 |
| ATOM | 4114 | OW0 | WAT | W | 196 | 37.193 | 39.072 | 80.259 | 1.00 | 43.54 | 8 |
| ATOM | 4115 | OW0 | WAT | W | 197 | 12.438 | 18.505 | 96.190 | 1.00 | 43.72 | 8 |
| ATOM | 4116 | OW0 | WAT | W | 198 | 17.695 | 44.501 | 36.700 | 1.00 | 43.76 | 8 |
| ATOM | 4117 | OW0 | WAT | W | 199 | 24.143 | 20.985 | 40.867 | 1.00 | 44.18 | 8 |
| ATOM | 4118 | OW0 | WAT | W | 200 | 15.460 | 20.954 | 43.611 | 1.00 | 44.25 | 8 |
| ATOM | 4119 | OW0 | WAT | W | 201 | 4.001 | 35.301 | 72.707 | 1.00 | 44.35 | 8 |
| ATOM | 4120 | OW0 | WAT | W | 202 | 10.808 | 47.706 | 96.612 | 1.00 | 44.60 | 8 |
| ATOM | 4121 | OW0 | WAT | W | 203 | 2.700 | 27.115 | 67.478 | 1.00 | 44.62 | 8 |
| ATOM | 4122 | OW0 | WAT | W | 204 | 20.270 | 21.380 | 43.441 | 1.00 | 44.66 | 8 |
| ATOM | 4123 | OW0 | WAT | W | 205 | 34.265 | 41.303 | 81.840 | 1.00 | 44.75 | 8 |
| ATOM | 4124 | OW0 | WAT | W | 206 | 20.804 | 19.886 | 76.193 | 1.00 | 44.76 | 8 |
| ATOM | 4125 | OW0 | WAT | W | 207 | -1.913 | 32.845 | 78.176 | 1.00 | 44.88 | 8 |
| ATOM | 4126 | OW0 | WAT | W | 208 | 3.571 | 20.702 | 86.366 | 1.00 | 44.94 | 8 |

| ATOM | 4127 | OW0 | WAT | W | 209 | 21.880 | 36.365 | 32.858 | 1.00 | 44.94 | 8 |
|---|---|---|---|---|---|---|---|---|---|---|---|
| ATOM | 4128 | OW0 | WAT | W | 210 | 31.952 | 36.977 | 98.567 | 1.00 | 45.02 | 8 |
| ATOM | 4129 | OW0 | WAT | W | 211 | 33.791 | 22.964 | 69.030 | 1.00 | 45.06 | 8 |
| ATOM | 4130 | OW0 | WAT | W | 212 | 7.729 | 42.702 | 98.969 | 1.00 | 45.07 | 8 |
| ATOM | 4131 | OW0 | WAT | W | 213 | 37.694 | 42.784 | 73.625 | 1.00 | 45.22 | 8 |
| ATOM | 4132 | OW0 | WAT | W | 214 | 4.724 | 28.533 | 29.235 | 1.00 | 45.25 | 8 |
| ATOM | 4133 | OW0 | WAT | W | 215 | 21.892 | 60.975 | 73.720 | 1.00 | 45.41 | 8 |
| ATOM | 4134 | OW0 | WAT | W | 216 | 27.561 | 61.645 | 85.916 | 1.00 | 45.58 | 8 |
| ATOM | 4135 | OW0 | WAT | W | 217 | 3.363 | 20.188 | 78.686 | 1.00 | 45.61 | 8 |
| ATOM | 4136 | OW0 | WAT | W | 218 | 6.061 | 28.087 | 58.848 | 1.00 | 45.69 | 8 |
| ATOM | 4137 | OW0 | WAT | W | 219 | 28.536 | 22.771 | 93.894 | 1.00 | 45.79 | 8 |
| ATOM | 4138 | OW0 | WAT | W | 220 | 20.591 | 18.347 | 79.227 | 1.00 | 45.81 | 8 |
| ATOM | 4139 | OW0 | WAT | W | 221 | 30.557 | 17.389 | 50.458 | 1.00 | 45.89 | 8 |
| ATOM | 4140 | OW0 | WAT | W | 222 | 23.413 | 19.795 | 75.273 | 1.00 | 45.93 | 8 |
| ATOM | 4141 | OW0 | WAT | W | 223 | 15.330 | 26.238 | 35.832 | 1.00 | 46.01 | 8 |
| ATOM | 4142 | OW0 | WAT | W | 224 | 35.298 | 21.980 | 95.583 | 1.00 | 46.08 | 8 |
| ATOM | 4143 | OW0 | WAT | W | 225 | -0.227 | 45.804 | 77.922 | 1.00 | 46.08 | 8 |
| ATOM | 4144 | OW0 | WAT | W | 226 | 20.449 | 45.041 | 43.691 | 1.00 | 46.16 | 8 |
| ATOM | 4145 | OW0 | WAT | W | 227 | 36.625 | 44.442 | 71.826 | 1.00 | 46.29 | 8 |
| ATOM | 4146 | OW0 | WAT | W | 228 | -0.564 | 35.140 | 82.998 | 1.00 | 46.42 | 8 |
| ATOM | 4147 | OW0 | WAT | W | 229 | 30.786 | 30.184 | 87.592 | 1.00 | 46.52 | 8 |
| ATOM | 4148 | OW0 | WAT | W | 230 | 18.209 | 37.127 | 109.332 | 1.00 | 46.61 | 8 |
| ATOM | 4149 | OW0 | WAT | W | 231 | 5.290 | 35.674 | 32.713 | 1.00 | 46.73 | 8 |
| ATOM | 4150 | OW0 | WAT | W | 232 | 5.154 | 17.424 | 79.518 | 1.00 | 46.77 | 8 |
| ATOM | 4151 | OW0 | WAT | W | 233 | 32.476 | 32.647 | 94.155 | 1.00 | 46.78 | 8 |
| ATOM | 4152 | OW0 | WAT | W | 234 | 7.852 | 42.603 | 68.371 | 1.00 | 46.78 | 8 |
| ATOM | 4153 | OW0 | WAT | W | 235 | 25.458 | 20.989 | 77.688 | 1.00 | 46.83 | 8 |
| ATOM | 4154 | OW0 | WAT | W | 236 | 10.154 | 43.709 | 40.698 | 1.00 | 46.83 | 8 |
| ATOM | 4155 | OW0 | WAT | W | 237 | 17.064 | 27.389 | 108.176 | 1.00 | 47.00 | 8 |
| ATOM | 4156 | OW0 | WAT | W | 238 | 12.045 | 33.710 | 108.176 | 1.00 | 47.00 | 8 |
| ATOM | 4157 | OW0 | WAT | W | 239 | 21.079 | 35.817 | 70.824 | 1.00 | 47.00 | 8 |
| ATOM | 4158 | OW0 | WAT | W | 240 | 4.062 | 33.751 | 91.030 | 1.00 | 47.05 | 8 |
| ATOM | 4159 | OW0 | WAT | W | 241 | 12.236 | 21.901 | 56.733 | 1.00 | 47.06 | 8 |
| ATOM | 4160 | OW0 | WAT | W | 242 | 8.504 | 42.719 | 43.711 | 1.00 | 47.30 | 8 |
| ATOM | 4161 | OW0 | WAT | W | 243 | 16.036 | 14.646 | 61.411 | 1.00 | 47.31 | 8 |
| ATOM | 4162 | OW0 | WAT | W | 244 | 11.756 | 59.123 | 67.674 | 1.00 | 47.35 | 8 |
| ATOM | 4163 | OW0 | WAT | W | 245 | 13.009 | 42.732 | 103.719 | 1.00 | 47.60 | 8 |
| ATOM | 4164 | OW0 | WAT | W | 246 | 4.038 | 19.904 | 75.633 | 1.00 | 47.63 | 8 |
| ATOM | 4165 | OW0 | WAT | W | 247 | 18.647 | 28.978 | 110.196 | 1.00 | 47.69 | 8 |
| ATOM | 4166 | OW0 | WAT | W | 248 | 11.570 | 17.428 | 62.551 | 1.00 | 47.71 | 8 |
| ATOM | 4167 | OW0 | WAT | W | 249 | 28.148 | 15.319 | 92.300 | 1.00 | 47.72 | 8 |
| ATOM | 4168 | OW0 | WAT | W | 250 | 30.840 | 41.602 | 100.804 | 1.00 | 47.72 | 8 |
| ATOM | 4169 | OW0 | WAT | W | 251 | 14.520 | 13.079 | 91.654 | 1.00 | 47.75 | 8 |
| ATOM | 4170 | OW0 | WAT | W | 252 | 33.257 | 35.871 | 106.556 | 1.00 | 47.84 | 8 |
| ATOM | 4171 | OW0 | WAT | W | 253 | 1.506 | 20.542 | 67.428 | 1.00 | 48.00 | 8 |
| ATOM | 4172 | OW0 | WAT | W | 254 | 9.536 | 23.702 | 53.845 | 1.00 | 48.00 | 8 |
| ATOM | 4173 | OW0 | WAT | W | 255 | 28.105 | 14.221 | 96.049 | 1.00 | 48.00 | 8 |
| ATOM | 4174 | OW0 | WAT | W | 256 | 31.668 | 37.095 | 50.965 | 1.00 | 48.05 | 8 |
| ATOM | 4175 | OW0 | WAT | W | 257 | 31.136 | 23.241 | 93.584 | 1.00 | 48.09 | 8 |
| ATOM | 4176 | OW0 | WAT | W | 258 | 34.162 | 27.890 | 52.268 | 1.00 | 48.19 | 8 |
| ATOM | 4177 | OW0 | WAT | W | 259 | 28.257 | 59.913 | 83.794 | 1.00 | 48.22 | 8 |
| ATOM | 4178 | OW0 | WAT | W | 260 | 11.231 | 34.132 | 85.631 | 1.00 | 48.26 | 8 |
| ATOM | 4179 | OW0 | WAT | W | 261 | 28.468 | 26.940 | 40.649 | 1.00 | 48.28 | 8 |
| ATOM | 4180 | OW0 | WAT | W | 262 | 4.668 | 30.175 | 32.084 | 1.00 | 48.29 | 8 |
| ATOM | 4181 | OW0 | WAT | W | 263 | 33.486 | 33.217 | 55.794 | 1.00 | 48.30 | 8 |
| ATOM | 4182 | OW0 | WAT | W | 264 | 6.053 | 46.878 | 74.207 | 1.00 | 48.41 | 8 |
| ATOM | 4183 | OW0 | WAT | W | 265 | 16.402 | 26.298 | 33.796 | 1.00 | 48.49 | 8 |
| ATOM | 4184 | OW0 | WAT | W | 266 | 26.202 | 21.497 | 83.893 | 1.00 | 48.51 | 8 |
| ATOM | 4185 | OW0 | WAT | W | 267 | 20.785 | 36.028 | 111.236 | 1.00 | 48.54 | 8 |
| ATOM | 4186 | OW0 | WAT | W | 268 | 30.461 | 53.163 | 68.296 | 1.00 | 48.60 | 8 |
| ATOM | 4187 | OW0 | WAT | W | 269 | 0.696 | 21.394 | 79.805 | 1.00 | 48.82 | 8 |
| ATOM | 4188 | OW0 | WAT | W | 270 | 5.982 | 32.107 | 60.137 | 1.00 | 48.90 | 8 |
| ATOM | 4189 | OW0 | WAT | W | 271 | 13.998 | 16.761 | 78.562 | 1.00 | 48.92 | 8 |
| ATOM | 4190 | OW0 | WAT | W | 272 | 37.139 | 25.809 | 58.211 | 1.00 | 49.00 | 8 |
| ATOM | 4191 | OW0 | WAT | W | 273 | 24.090 | 56.359 | 101.385 | 1.00 | 49.00 | 8 |

| ATOM | 4192 | OW0 | WAT | W | 274 | 18.068 | 43.717 | 58.211 | 1.00 | 49.00 | 8 |
| ATOM | 4193 | OW0 | WAT | W | 275 | 5.008 | 30.008 | 59.014 | 1.00 | 49.03 | 8 |
| ATOM | 4194 | OW0 | WAT | W | 276 | 24.231 | 58.496 | 93.637 | 1.00 | 49.04 | 8 |
| ATOM | 4195 | OW0 | WAT | W | 277 | 25.516 | 55.866 | 63.971 | 1.00 | 49.05 | 8 |
| ATOM | 4196 | OW0 | WAT | W | 278 | 8.821 | 24.366 | 46.833 | 1.00 | 49.06 | 8 |
| ATOM | 4197 | OW0 | WAT | W | 279 | 18.557 | 30.050 | 34.351 | 1.00 | 49.07 | 8 |
| ATOM | 4198 | OW0 | WAT | W | 280 | 7.575 | 44.935 | 72.565 | 1.00 | 49.07 | 8 |
| ATOM | 4199 | OW0 | WAT | W | 281 | 32.725 | 15.893 | 52.239 | 1.00 | 49.18 | 8 |
| ATOM | 4200 | OW0 | WAT | W | 282 | 21.693 | 17.319 | 68.259 | 1.00 | 49.19 | 8 |
| ATOM | 4201 | OW0 | WAT | W | 283 | 31.079 | 23.166 | 75.579 | 1.00 | 49.30 | 8 |
| ATOM | 4202 | OW0 | WAT | W | 284 | 21.228 | 20.750 | 39.179 | 1.00 | 49.34 | 8 |
| ATOM | 4203 | OW0 | WAT | W | 285 | 19.380 | 17.588 | 77.097 | 1.00 | 49.37 | 8 |
| ATOM | 4204 | OW0 | WAT | W | 286 | 33.523 | 39.507 | 89.817 | 1.00 | 49.38 | 8 |
| ATOM | 4205 | OW0 | WAT | W | 287 | 15.676 | 43.664 | 35.502 | 1.00 | 49.41 | 8 |
| ATOM | 4206 | OW0 | WAT | W | 288 | 30.624 | 48.924 | 69.928 | 1.00 | 49.44 | 8 |
| ATOM | 4207 | OW0 | WAT | W | 289 | 20.158 | 44.944 | 34.473 | 1.00 | 49.44 | 8 |
| ATOM | 4208 | OW0 | WAT | W | 290 | 13.755 | 18.014 | 54.141 | 1.00 | 49.53 | 8 |
| ATOM | 4209 | OW0 | WAT | W | 291 | 22.712 | 56.885 | 98.458 | 1.00 | 49.55 | 8 |
| ATOM | 4210 | OW0 | WAT | W | 292 | 9.421 | 40.612 | 61.458 | 1.00 | 49.63 | 8 |
| ATOM | 4211 | OW0 | WAT | W | 293 | 10.544 | 38.205 | 62.017 | 1.00 | 49.65 | 8 |
| ATOM | 4212 | OW0 | WAT | W | 294 | 13.256 | 61.174 | 66.843 | 1.00 | 49.66 | 8 |
| ATOM | 4213 | OW0 | WAT | W | 295 | 7.047 | 28.393 | 101.031 | 1.00 | 49.76 | 8 |
| ATOM | 4214 | OW0 | WAT | W | 296 | 9.174 | 30.089 | 101.877 | 1.00 | 49.84 | 8 |
| ATOM | 4215 | OW0 | WAT | W | 297 | 23.631 | 10.416 | 92.206 | 1.00 | 49.86 | 8 |
| ATOM | 4216 | OW0 | WAT | W | 298 | 14.646 | 57.631 | 84.015 | 1.00 | 50.00 | 8 |
| ATOM | 4217 | OW0 | WAT | W | 299 | 13.679 | 27.889 | 30.169 | 1.00 | 50.03 | 8 |
| ATOM | 4218 | OW0 | WAT | W | 300 | 30.079 | 44.318 | 52.674 | 1.00 | 50.09 | 8 |
| ATOM | 4219 | OW0 | WAT | W | 301 | 36.058 | 24.067 | 95.389 | 1.00 | 50.27 | 8 |
| ATOM | 4220 | OW0 | WAT | W | 302 | 27.531 | 61.533 | 81.274 | 1.00 | 50.33 | 8 |
| ATOM | 4221 | OW0 | WAT | W | 303 | 2.018 | 19.978 | 73.415 | 1.00 | 50.40 | 8 |
| ATOM | 4222 | OW0 | WAT | W | 304 | 25.416 | 18.871 | 43.049 | 1.00 | 50.40 | 8 |
| ATOM | 4223 | OW0 | WAT | W | 305 | 24.002 | 61.548 | 72.183 | 1.00 | 50.45 | 8 |
| ATOM | 4224 | OW0 | WAT | W | 306 | 26.674 | 27.842 | 84.339 | 1.00 | 50.53 | 8 |
| ATOM | 4225 | OW0 | WAT | W | 307 | 10.414 | 26.991 | 32.858 | 1.00 | 50.68 | 8 |
| ATOM | 4226 | OW0 | WAT | W | 308 | 8.984 | 49.959 | 66.547 | 1.00 | 50.84 | 8 |
| ATOM | 4227 | OW0 | WAT | W | 309 | 31.052 | 26.170 | 92.925 | 1.00 | 50.84 | 8 |
| ATOM | 4228 | OW0 | WAT | W | 310 | 31.650 | 14.800 | 103.619 | 1.00 | 50.96 | 8 |
| ATOM | 4229 | OW0 | WAT | W | 311 | 4.552 | 44.172 | 94.195 | 1.00 | 51.18 | 8 |
| ATOM | 4230 | OW0 | WAT | W | 312 | 19.321 | 32.742 | 33.306 | 1.00 | 51.19 | 8 |
| ATOM | 4231 | OW0 | WAT | W | 313 | 39.664 | 44.974 | 80.079 | 1.00 | 51.34 | 8 |
| ATOM | 4232 | OW0 | WAT | W | 314 | 11.111 | 50.044 | 94.730 | 1.00 | 51.60 | 8 |
| ATOM | 4233 | OW0 | WAT | W | 315 | 41.633 | 35.268 | 62.507 | 1.00 | 51.64 | 8 |
| ATOM | 4234 | OW0 | WAT | W | 316 | 16.161 | 15.675 | 50.606 | 1.00 | 51.69 | 8 |
| ATOM | 4235 | OW0 | WAT | W | 317 | 17.076 | 13.663 | 54.383 | 1.00 | 52.35 | 8 |
| ATOM | 4236 | OW0 | WAT | W | 318 | -0.485 | 20.371 | 75.337 | 1.00 | 52.37 | 8 |
| ATOM | 4237 | OW0 | WAT | W | 319 | -1.074 | 32.905 | 75.009 | 1.00 | 52.93 | 8 |
| ATOM | 4238 | OW0 | WAT | W | 320 | 30.884 | 26.827 | 41.173 | 1.00 | 53.46 | 8 |
| ATOM | 4239 | OW0 | WAT | W | 321 | 34.249 | 25.468 | 77.767 | 1.00 | 54.80 | 8 |
| ATOM | 4240 | OW0 | WAT | W | 322 | 16.235 | 59.585 | 76.936 | 1.00 | 55.11 | 8 |

The invention claimed is:

1. A purified variant of a parent alpha-amylase, said variant comprising a substitution of a K at an amino acid position corresponding to an amino acid selected from the group consisting of 118, 320 and 458 in the amino acid sequence shown in SEQ ID NO:12, wherein the variant has alpha-amylase activity, and wherein the variant has at least 95% homology to the amino acid sequence shown in SEQ ID NO:12.

2. The variant of claim 1, comprising a substitution of R118K.

3. The variant of claim 1, comprising a substitution of R320K.

4. The variant of claim 1, comprising a substitution of R458K.

5. The variant of claim 1, wherein the parent alpha-amylase is *Bacillus* sp. DSMZ no. 12649 alpha-amylase.

6. The variant of claim 1, wherein the variant has at least 97% homology with the amino acid sequence shown in SEQ ID NO:12.

7. A purified variant of a parent alpha-amylase, said variant comprising a substitution of a K at an amino acid position corresponding to amino acid 118, 320 or 458 in the amino acid sequence shown in SEQ ID NO:12, wherein the substitution at position 118 is further characterized as R188K, wherein the variant has alpha-amylase activity, and wherein the variant has at least 95% homology to the amino acid sequence shown in SEQ ID NO:12.

* * * * *